US012096688B2

(12) United States Patent
Kang et al.

(10) Patent No.: US 12,096,688 B2
(45) Date of Patent: Sep. 17, 2024

(54) COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Dong Min Kang, Suwon-si (KR); Jiyun Kwon, Suwon-si (KR); Byungku Kim, Suwon-si (KR); Junmo Park, Suwon-si (KR); Eunjeong Choi, Suwon-si (KR); Jin Sook Kim, Suwon-si (KR); Sangil Lee, Suwon-si (KR); Kipo Jang, Suwon-si (KR); Sung-Hyun Jung, Suwon-si (KR); Ho Kuk Jung, Suwon-si (KR); Youngkyoung Jo, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 695 days.

(21) Appl. No.: 17/363,540

(22) Filed: Jun. 30, 2021

(65) Prior Publication Data

US 2022/0013732 A1 Jan. 13, 2022

(30) Foreign Application Priority Data

Jul. 3, 2020 (KR) ........................ 10-2020-0082247

(51) Int. Cl.
*H01L 51/50* (2006.01)
*C07D 307/77* (2006.01)
(Continued)

(52) U.S. Cl.
CPC ....... *H10K 85/6574* (2023.02); *C07D 307/77* (2013.01); *C07D 307/91* (2013.01);
(Continued)

(58) Field of Classification Search
None
See application file for complete search history.

(56) References Cited

U.S. PATENT DOCUMENTS 5,061,569 A 10/1991 Vanslyke et al.
2020/0075866 A1 3/2020 Lee et al.
(Continued)

FOREIGN PATENT DOCUMENTS

CN 110872511 A 3/2020
CN 111162185 A 5/2020
(Continued)

OTHER PUBLICATIONS

Korean Office Action dated Nov. 27, 2023, of the corresponding Korean Patent Application No. 10-2020-0082247.
(Continued)

*Primary Examiner* — Gregory D Clark
(74) *Attorney, Agent, or Firm* — Lee IP Law, P.C.

(57) ABSTRACT

A composition for an organic optoelectronic device, an organic optoelectronic device including the same, and a display device, the composition including a first compound represented by Chemical Formula 1, and a second compound represented by a combination of Chemical Formula 2 and Chemical Formula 3:
(Continued)

[Chemical Formula 1]

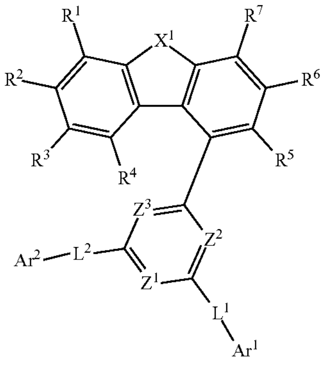

[Chemical Formula 2]

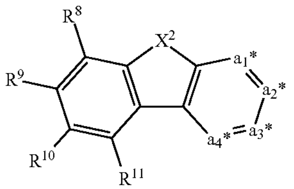

[Chemical Formula 3]

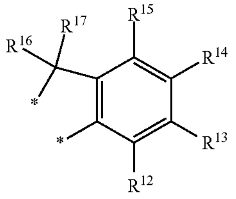

15 Claims, 1 Drawing Sheet

(51) Int. Cl.

| | |
|---|---|
| *C07D 307/91* | (2006.01) |
| *C07D 405/04* | (2006.01) |
| *C07D 405/12* | (2006.01) |
| *C07D 405/14* | (2006.01) |
| *C09K 11/02* | (2006.01) |
| *H10K 85/60* | (2023.01) |
| *H10K 50/11* | (2023.01) |
| *H10K 101/00* | (2023.01) |
| *H10K 101/10* | (2023.01) |

(52) U.S. Cl.

CPC ......... *C07D 405/04* (2013.01); *C07D 405/12* (2013.01); *C07D 405/14* (2013.01); *C09K 11/02* (2013.01); *H10K 85/615* (2023.02); *H10K 85/633* (2023.02); *H10K 85/636* (2023.02); *H10K 85/654* (2023.02); *H10K 50/11* (2023.02); *H10K 85/6572* (2023.02); *H10K 2101/10* (2023.02); *H10K 2101/90* (2023.02)

(56) References Cited

U.S. PATENT DOCUMENTS

| | | | | |
|---|---|---|---|---|
| 2020/0144510 | A1 | 5/2020 | Kim et al. | |
| 2020/0203623 | A1 | 6/2020 | Lee et al. | |
| 2022/0037594 | A1 | 2/2022 | Lee et al. | |
| 2022/0199911 | A1 * | 6/2022 | Lee .................... | H10K 85/6572 |

FOREIGN PATENT DOCUMENTS

| | | | |
|---|---|---|---|
| CN | 111354873 | A | 6/2020 |
| JP | 1993-009471 | A | 1/1993 |
| JP | 1995-126615 | A | 5/1995 |
| JP | 1998-095973 | A | 4/1998 |
| KR | 10-1399636 | B1 | 5/2014 |
| KR | 10-1423173 | B1 | 7/2014 |
| KR | 10-1814875 | B1 | 1/2018 |
| KR | 10-2018-0022574 | A | 3/2018 |
| KR | 10-2018-0038834 | A | 4/2018 |
| KR | 10-2019-0013353 | A | 2/2019 |
| KR | 10-2021294 | B1 | 9/2019 |
| KR | 10-2019-0140732 | A | 12/2019 |
| KR | 10-2020-0052702 | A | 5/2020 |
| KR | 10-2020-0070462 | A | 6/2020 |
| WO | WO 1995/009147 | A1 | 4/1995 |
| WO | WO 2013/077352 | A1 | 5/2013 |

OTHER PUBLICATIONS

Chinese Office Action (including a search report) dated Feb. 7, 2024, of the corresponding Chinese Patent Application No. 202110749597.X.

* cited by examiner

COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2020-0082247, filed on Jul. 3, 2020, in the Korean Intellectual Property Office, and entitled: "Composition for Organic Optoelectronic Device, Organic Optoelectronic Device and Display Device," is incorporated by reference herein in its entirety.

BACKGROUND

1. Field

Embodiments relate to a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a composition for an organic optoelectronic device, the composition including a first compound represented by Chemical Formula 1, and a second compound represented by a combination of Chemical Formula 2 and Chemical Formula 3:

[Chemical Formula 1]

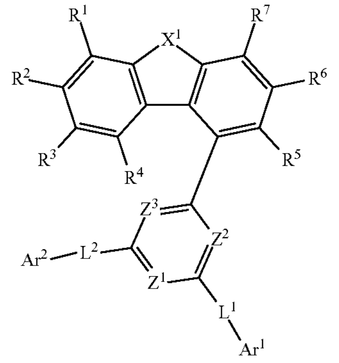

wherein, in Chemical Formula 1, $X^1$ is O or S, $Z^1$ to $Z^3$ are each independently N or $CR^a$, at least two of $Z^1$ to $Z^3$ being N, $L^1$ and $L^2$ are each independently a single bond, a substituted or unsubstituted C6 to C20 arylene group, a substituted or unsubstituted C2 to C20 heterocyclic group, or a combination thereof, $Ar^1$ and $Ar^2$ are each independently a substituted or unsubstituted C6 to C30 aryl group or a substituted or unsubstituted C2 to C30 heterocyclic group, $R^a$ and $R^1$ to $R^7$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and at least one pair of $R^1$ and $R^2$; $R^2$ and $R^3$; $R^3$ and $R^4$; $R^5$ and $R^6$; and $R^6$ and $R^7$ are linked to each other to provide a substituted or unsubstituted aromatic ring or a substituted or unsubstituted heteroaromatic ring,

[Chemical Formula 2]

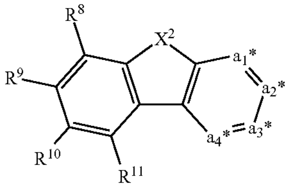

[Chemical Formula 3]

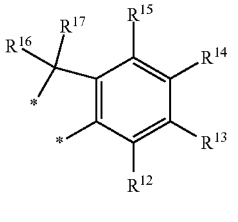

wherein, in Chemical Formula 2 and Chemical Formula 3, $X^2$ is O or S, two adjacent ones of a1* to a4* of Chemical Formula 2 are linking carbons linked at * of Chemical Formula 3, the remaining two of a1* to a4* of Chemical Formula 2, not linked at * of Chemical Formula 3, are $CR^b$, $R^b$ and $R^8$ to $R^{15}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, at least one of $R^8$ to $R^{15}$ being a group represented by Chemical Formula A, and $R^{16}$ and $R^{17}$ are each independently a substituted or unsubstituted C1 to C30 alkyl group or a substituted or unsubstituted C6 to C30 aryl group,

[Chemical Formula A]

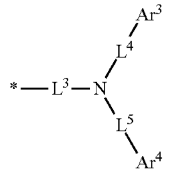

wherein, in Chemical Formula A, $L^3$ to $L^5$ are each independently a single bond or a substituted or unsubstituted C6 to C30 arylene group, $Ar^3$ and $Ar^4$ are each independently a substituted or unsubstituted C6 to C30 aryl group or a substituted or unsubstituted C2 to C30 heterocyclic group, and * is linking point.

The embodiments may be realized by providing an organic optoelectronic device including an anode and a cathode facing each other, and at least one organic layer between the anode and the cathode, wherein the at least one organic layer includes a light emitting layer, and the light emitting layer includes the composition for an organic optoelectronic device according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
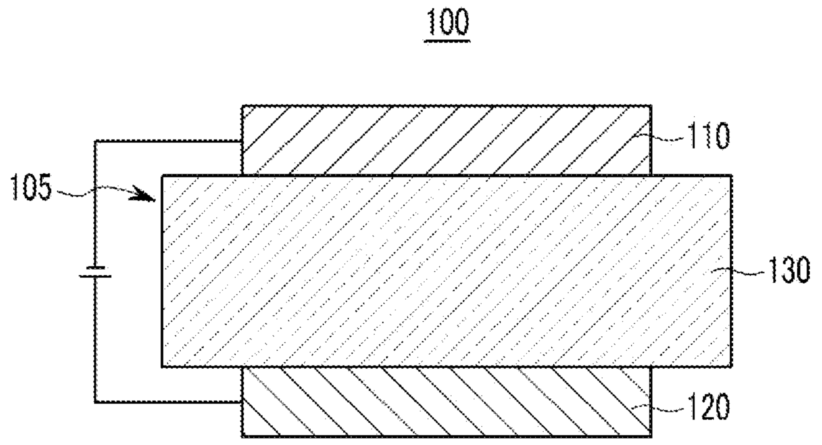
FIGS. 1 and 2 are cross-sectional views each illustrating an organic light emitting diode according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In one example of the present disclosure, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof. As used herein, the term "or" is not an exclusive term, e.g., "A or B" would include A, B, or A and B.

In specific example of the present disclosure, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example of the present disclosure, "substituted" refers to replacement of at least one hydrogen of a substituent or a compound by deuterium, a C1 to C20 alkyl group, a C6 to C30 aryl group, or a cyano group. In specific example of the present disclosure, "substituted" refers to replacement of at least one hydrogen of a substituent or a compound by deuterium, a C1 to C5 alkyl group, a C6 to C18 aryl group, or a cyano group. In specific example of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment may include, e.g., a first compound represented by Chemical Formula 1, and a second compound represented by a combination of Chemical Formula 2 and Chemical Formula 3.

[Chemical Formula 1]

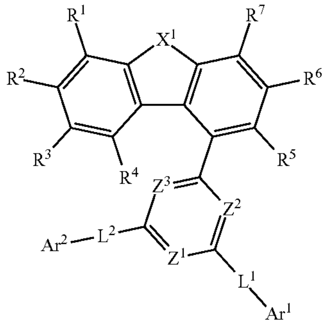

In Chemical Formula 1, $X^1$ may be, e.g., O or S.

$Z^1$ to $Z^3$ may each independently be, e.g., N or $CR^a$. In an implementation, at least two of $Z^1$ to $Z^3$ may be N.

$L^1$ and $L^2$ may each independently be or include, e.g., a single bond, a substituted or unsubstituted C6 to C20 arylene group, a substituted or unsubstituted C2 to C20 heterocyclic group, or a combination thereof.

$Ar^1$ and $Ar^2$ may each independently be or include, e.g., a substituted or unsubstituted C6 to C30 aryl group or a substituted or unsubstituted C2 to C30 heterocyclic group.

$R^a$ and $R^1$ to $R^7$ may each independently be or include, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an implementation, at least one pair of $R^1$ and $R^2$; $R^2$ and $R^3$; $R^3$ and $R^4$; $R^5$ and $R^6$; and $R^6$ and $R^7$ may be linked to each other to provide a substituted or unsubstituted aromatic (e.g., fused) ring or a substituted or unsubstituted heteroaromatic (e.g., fused) ring.

[Chemical Formula 2]

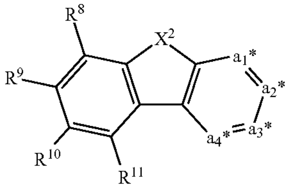

[Chemical Formula 3]

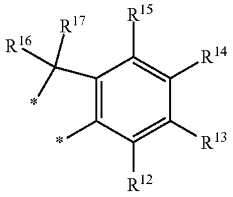

In Chemical Formula 2 and Chemical Formula 3, $X^2$ may be, e.g., O or S.

Two adjacent ones of a1* to a4* of Chemical Formula 2 may be linking carbons linked at * of Chemical Formula 3. The remaining two of a1* to a4* of Chemical Formula 2, not linked at * of Chemical Formula 3, may be, e.g., $CR^b$. As used herein, the term "linking carbon" refers to a shared carbon at which fused rings are linked.

$R^b$ and $R^8$ to $R^{15}$ may each independently be or include, e.g., hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

$R^{16}$ and $R^{17}$ may each independently be or include, e.g., a substituted or unsubstituted C1 to C30 alkyl group or a substituted or unsubstituted C6 to C30 aryl group.

In an implementation, at least one of $R^8$ to $R^{15}$ may be, e.g., a group (e.g., substituted amine group) represented by Chemical Formula A.

[Chemical Formula A]

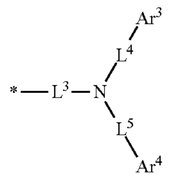

In Chemical Formula A, $L^3$ to $L^5$ may each independently be or include, e.g., a single bond or a substituted or unsubstituted C6 to C30 arylene group.

$Ar^3$ and $Ar^4$ may each independently be or include, e.g., a substituted or unsubstituted C6 to C30 aryl group, or a substituted or unsubstituted C2 to C30 heterocyclic group.

* is linking point.

The first compound represented by Chemical Formula 1 may have a skeletal structure in which a dibenzofuran or dibenzothiophene are further fused (e.g., include an additional ring fused thereto), and a nitrogen-containing 6-membered ring may be substituted or bonded at a specific position of the dibenzofuran or dibenzothiophene.

The first compound having such a structure may have a stabilized T1 energy level (which is advantageous in realizing a device having a long life-span), compared with a compound having a dibenzofuran and dibenzothiophene skeleton that is not further fused.

In addition, the nitrogen-containing 6-membered ring may be directly substituted, and a faster electron mobility may be implemented compared with a compound including a linker, so that a device having a low driving may be implemented.

The second compound represented by the combination of Chemical Formula 2 and Chemical Formula 3 may have a structure in which an additionally fused dibenzofuran (or an additionally fused dibenzothiophene) is substituted with an amine group.

The second compound having such a structure may have a high glass transition temperature and may be deposited at a relatively low temperature, and the second compound has improved thermal stability.

The second compound may be included together with the aforementioned first compound (e.g., as a mixture) to help increase the balance between holes and electrons, thereby greatly improving life-span characteristics of a device including the second compound.

In an implementation, at least one pair of $R^1$ and $R^2$; $R^2$ and $R^3$; $R^3$ and $R^4$; $R^5$ and $R^6$; and $R^6$ and $R^7$ in Chemical Formula 1 may be linked to each other to provide a substituted or unsubstituted aromatic ring.

In an implementation, at least one pair of $R^1$ and $R^2$; $R^2$ and $R^3$; $R^3$ and $R^4$; $R^5$ and $R^6$; and $R^6$ and $R^7$ in Chemical Formula 1 may be linked to each other to provide a substituted or unsubstituted phenyl ring.

In an implementation, the first compound may be represented by, e.g., one of Chemical Formula 1-I to Chemical Formula 1-XI.

[Chemical Formula 1-I]

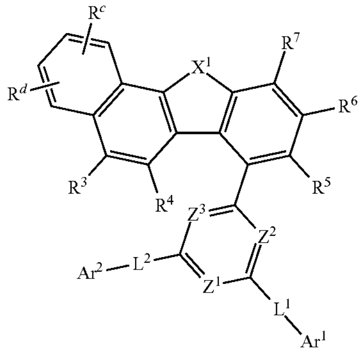

[Chemical Formula 1-II]

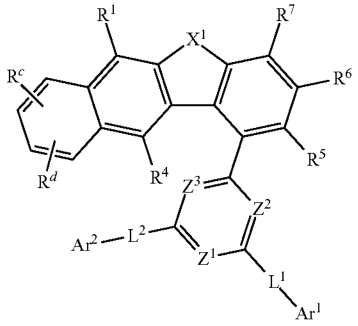

[Chemical Formula 1-III]

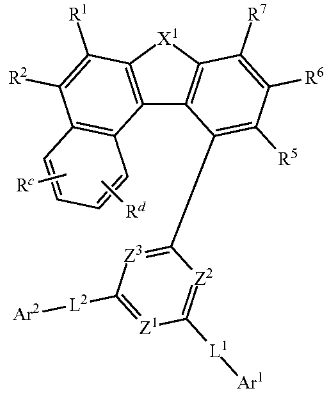

[Chemical Formula 1-IV]

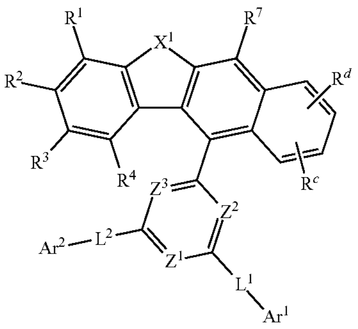

-continued

[Chemical Formula 1-V]

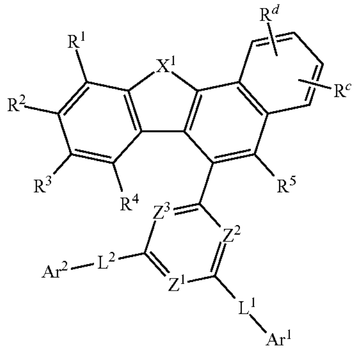

[Chemical Formula 1-VI]

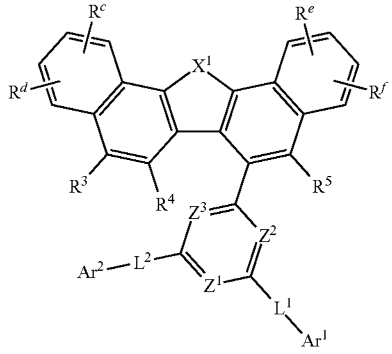

[Chemical Formula 1-VII]

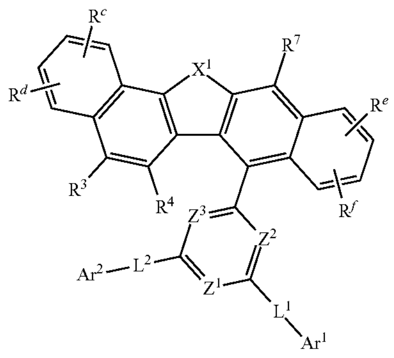

[Chemical Formula 1-VIII]

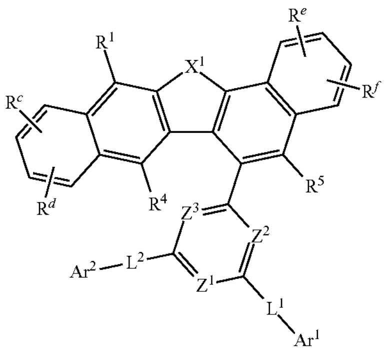

-continued

[Chemical Formula 1-IX]

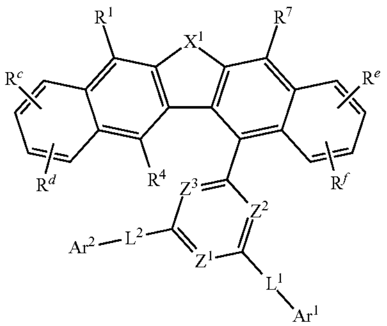

[Chemical Formula 1-X]

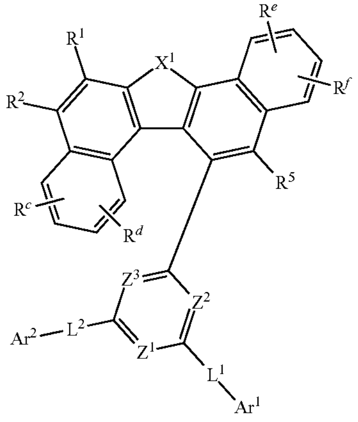

[Chemical Formula 1-XI]

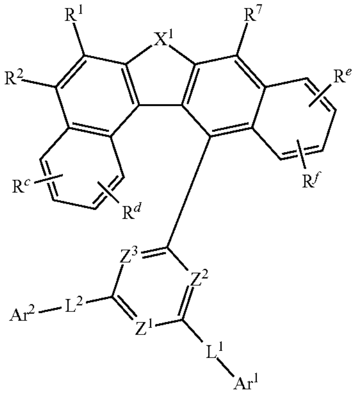

In Chemical Formula 1-I to Chemical Formula 1-XI, $X^1$, $Z^1$ to $Z^3$, $L^1$ and $L^2$, $Ar^1$, and $Ar^2$ may be defined the same as those described above.

$R^c$, $R^d$, $R^e$, $R^f$, and $R^1$ to $R^7$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group or a combination thereof.

In an implementation, in Chemical Formula 1, $Z^1$ and $Z^2$ may be N, and $Z^3$ may be $CR^a$.

In an implementation, in Chemical Formula 1, $Z^2$ and $Z^3$ may be N, and $Z^1$ may be $CR^a$.

$R^a$ may be, e.g., hydrogen, deuterium, a substituted or unsubstituted C1 to C10 alkyl group, or a substituted or unsubstituted C6 to C12 aryl group.

In an implementation, each of $Z^1$ to $Z^3$ in Chemical Formula 1 may be N.

In an implementation, $L^1$ and $L^2$ may each independently be, e.g., a single bond, a substituted or unsubstituted phenylene group, a substituted or unsubstituted biphenylene group, or a substituted or unsubstituted naphthylene group.

In an implementation, $L^1$ and $L^2$ may each independently be, e.g., a single bond or a substituted or unsubstituted phenylene group.

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuran, or a substituted or unsubstituted benzonaphthothiophene.

In an implementation, $Ar^1$ and $Ar^2$ may each independently be, e.g., a group of Group I.

[Group I]

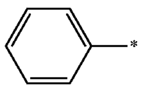
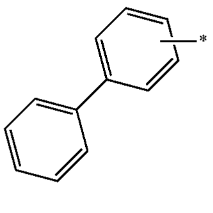
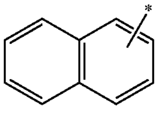

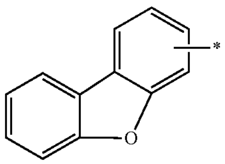
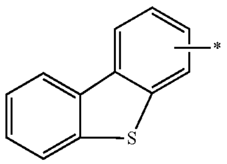

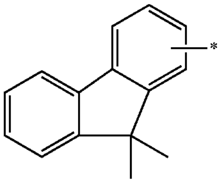
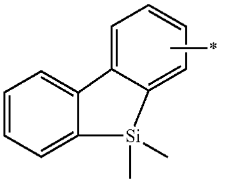

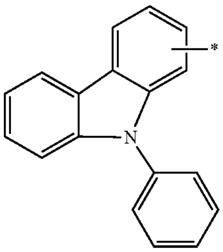
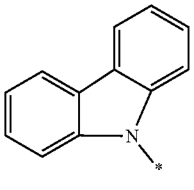

-continued

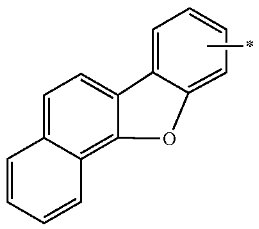
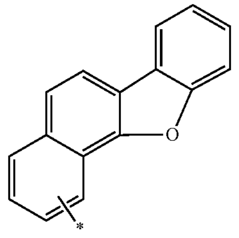

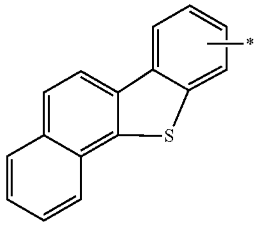
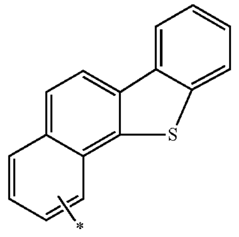

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted dibenzofuranyl group, a substituted or unsubstituted dibenzothiophenyl group, or a substituted or unsubstituted dibenzosilolyl group.

In an implementation, $R^c$, $R^d$, $R^e$, $R^f$, and $R^1$ to $R^7$ may each independently be, e.g., hydrogen, deuterium, a substituted or unsubstituted C1 to C5 alkyl group, a substituted or unsubstituted phenyl group, a substituted or unsubstituted biphenyl group, or a substituted or unsubstituted naphthyl group.

In an implementation, each of $R^c$, $R^d$, $R^e$, $R^f$, and $R^1$ to $R^7$ may be hydrogen.

In an implementation, the first compound may be represented by, e.g., Chemical Formula 1-I, Chemical Formula 1-II, Chemical Formula 1-III, Chemical Formula 1-VI, Chemical Formula 1-VII, Chemical Formula 1-VIII, or Chemical Formula 1-X.

In an implementation, the first compound may be represented by Chemical Formula 1-I.

In an implementation, the first compound may be a compound of Group 1.

[Group 1]

[1-1]

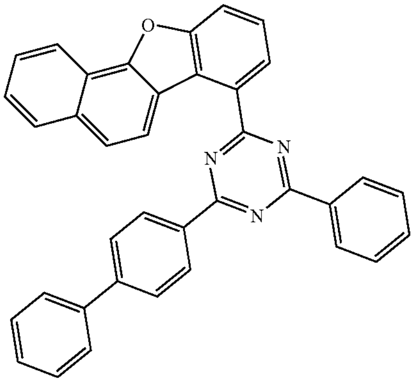

-continued
[1-2]
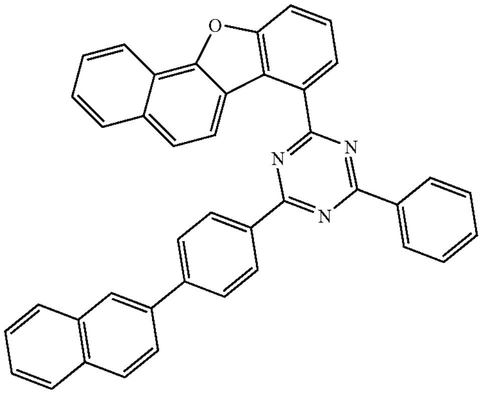
[1-3]
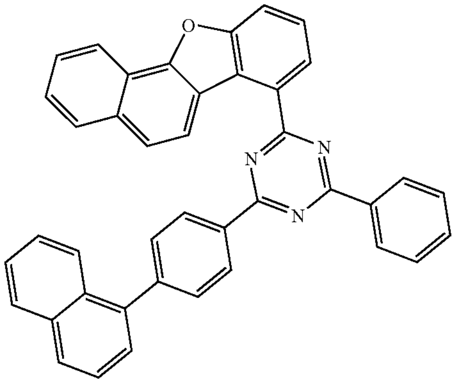
[1-4]
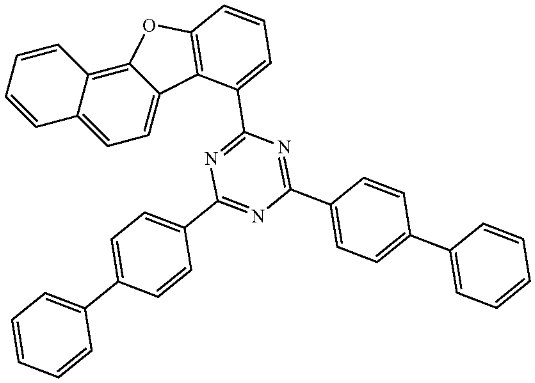
[1-5]
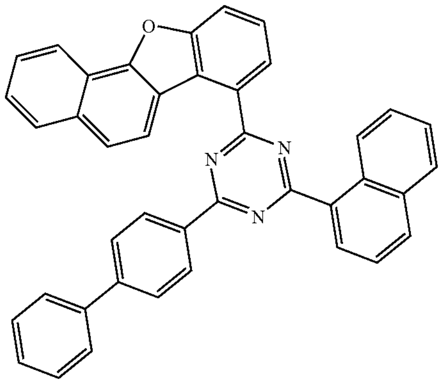
-continued
[1-6]
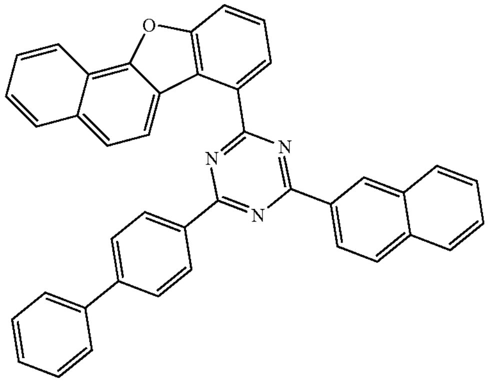
[1-7]
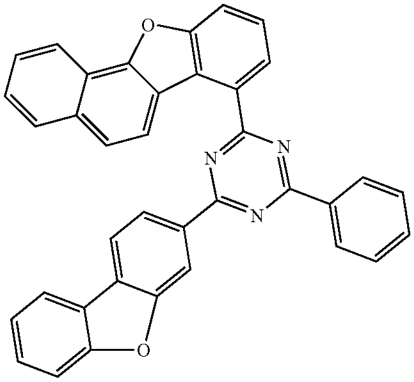
[1-8]
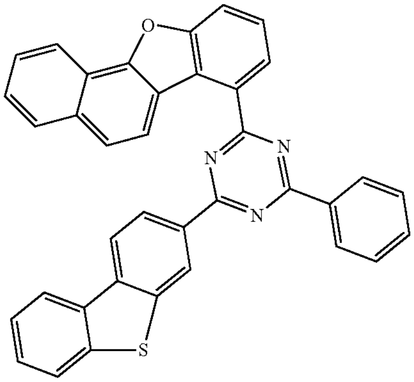
[1-9]
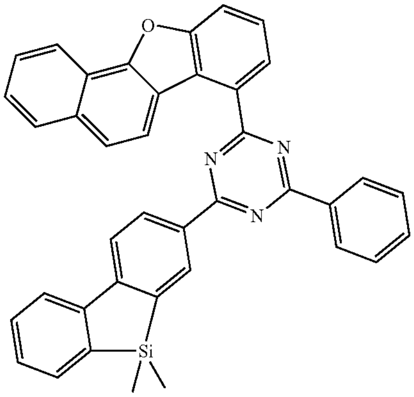

-continued
[1-10]
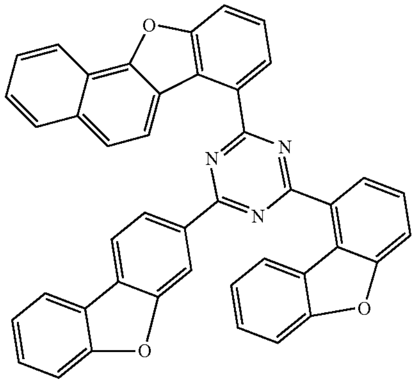
[1-11]
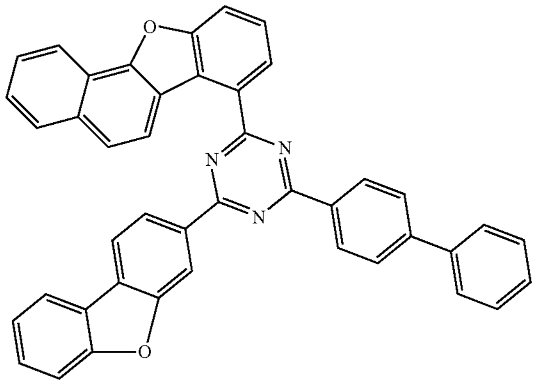
[1-12]
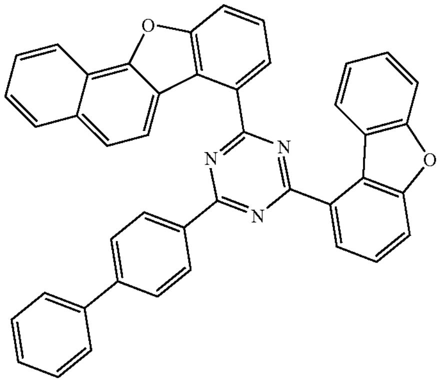
[1-13]
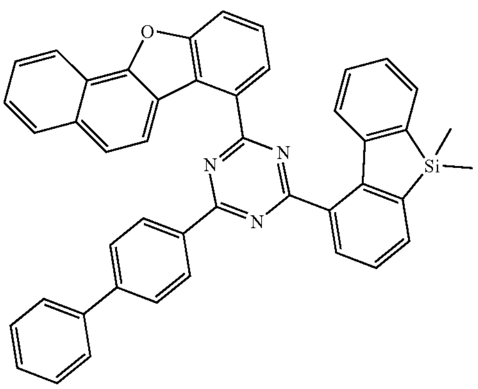
-continued
[1-14]
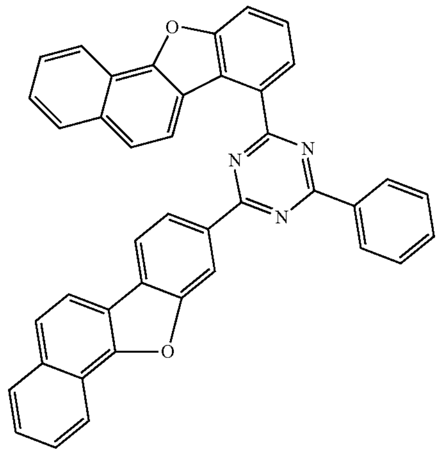
[1-15]
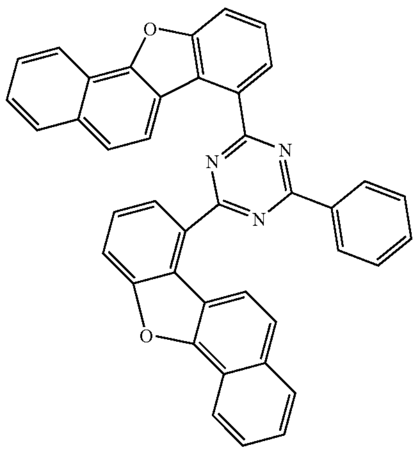
[1-16]
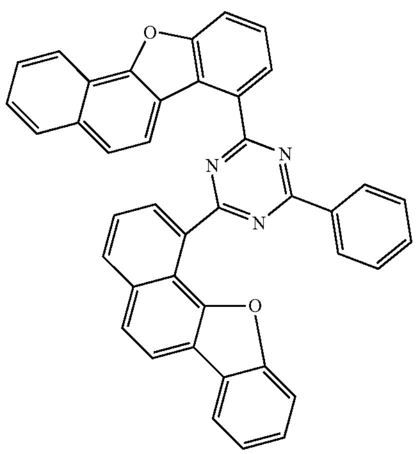

-continued
[1-17]
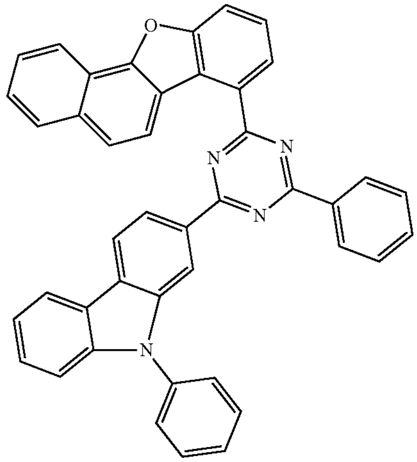
[1-18]
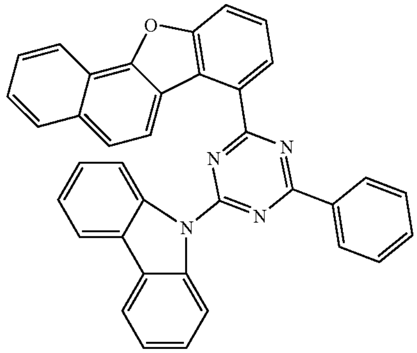
[1-19]
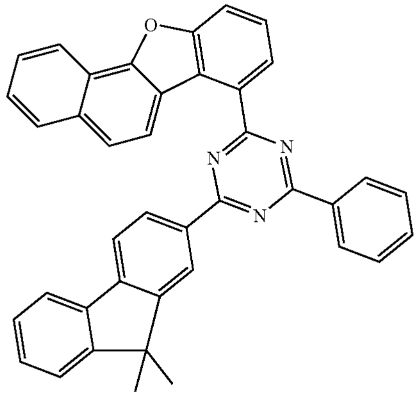
[1-20]
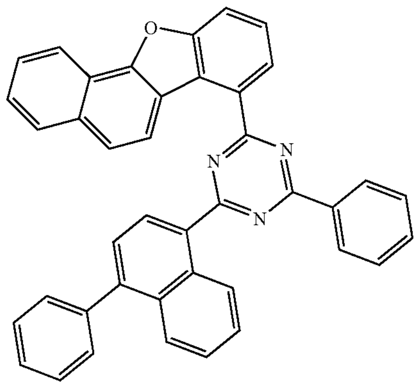
-continued
[1-21]
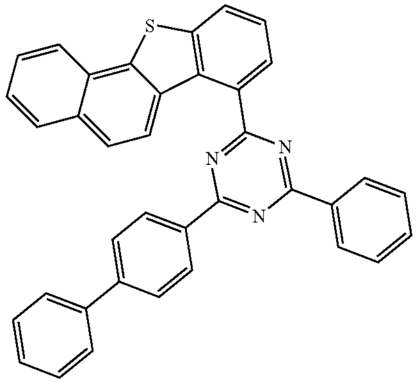
[1-22]
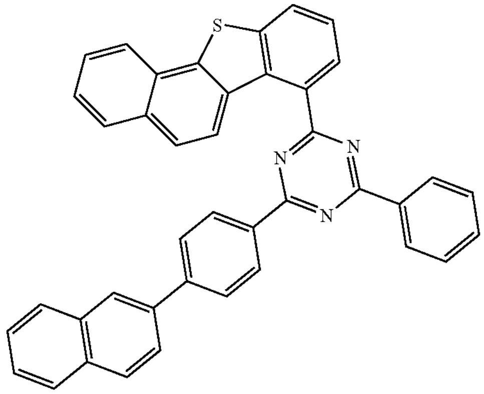
[1-23]
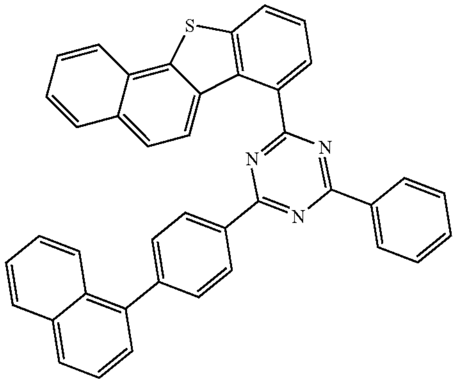
[1-24]
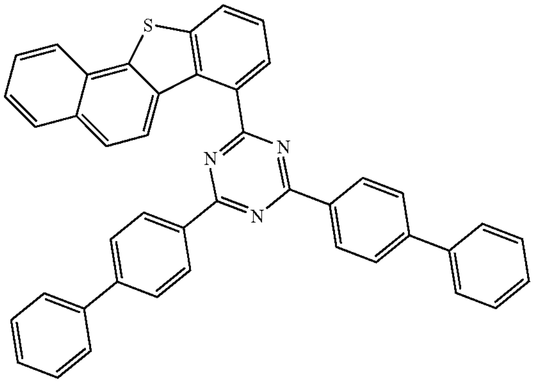

[1-25]
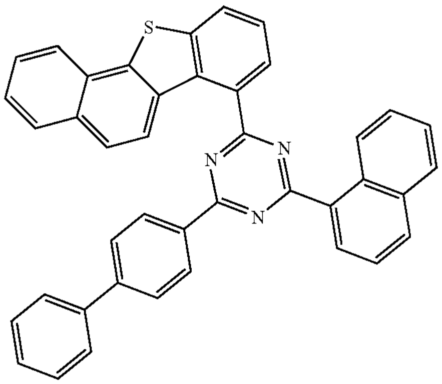
[1-26]
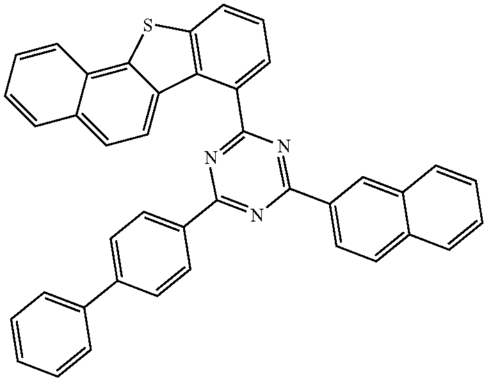
[1-27]
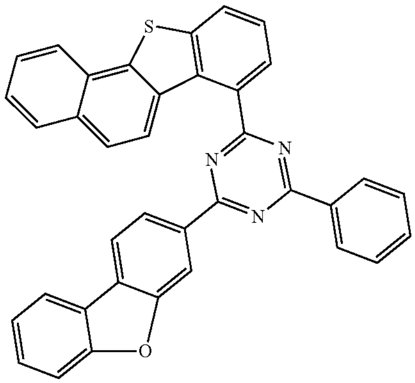
[1-28]
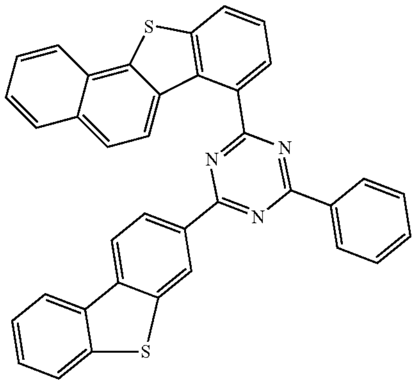
[1-29]
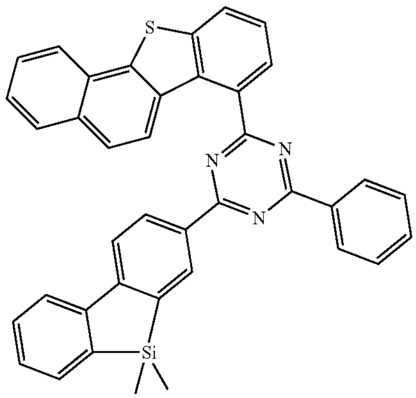
[1-30]
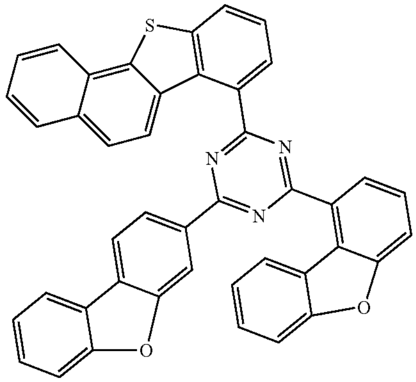
[1-31]
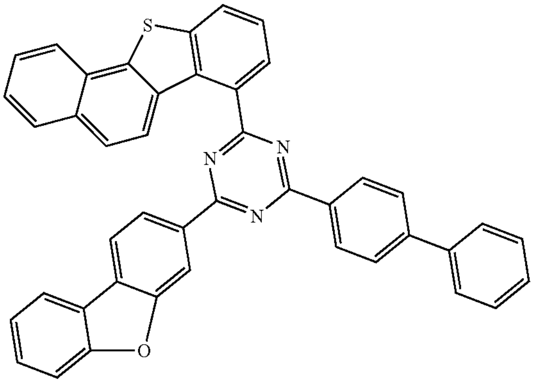
[1-32]
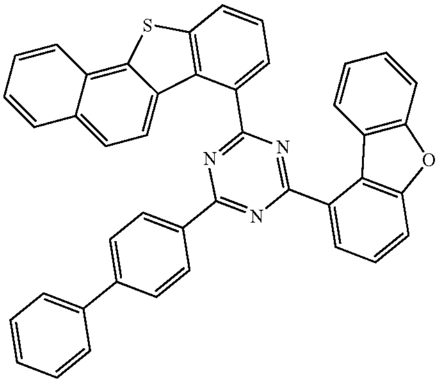

-continued
[1-33]
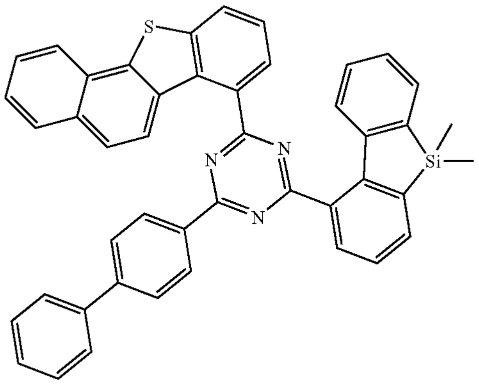
[1-34]
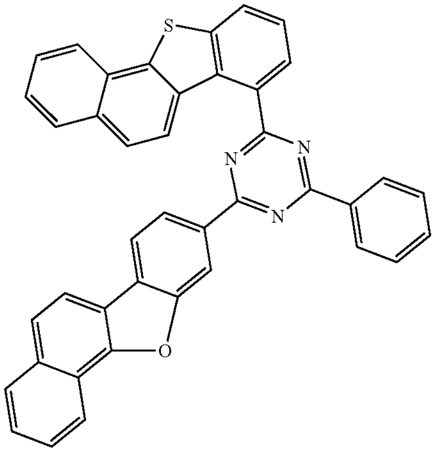
[1-35]
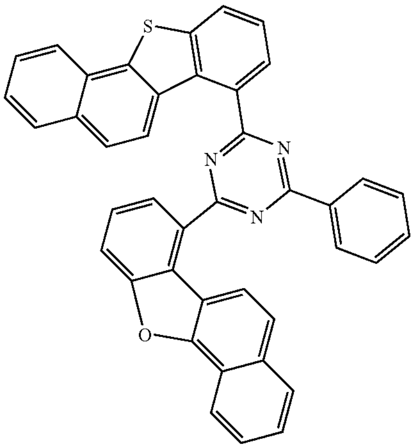
-continued
[1-36]
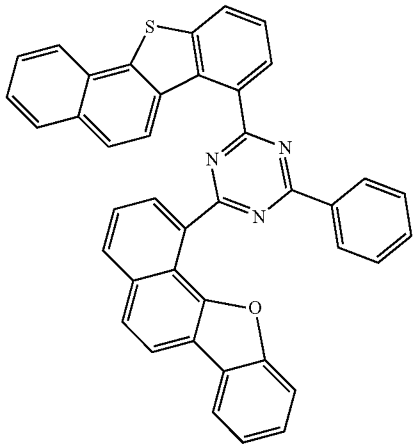
[1-37]
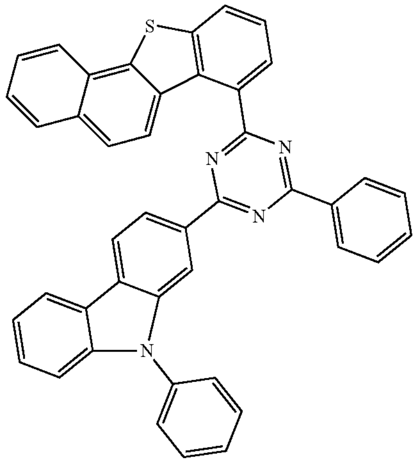
[1-38]
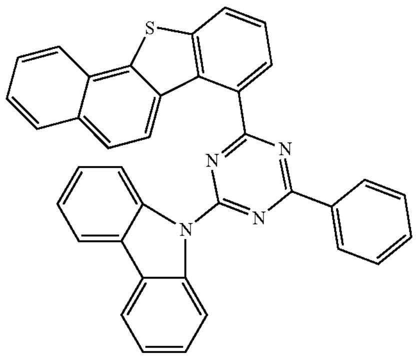

-continued
[1-39]
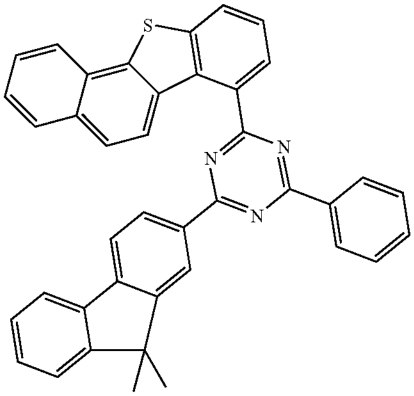
[1-40]
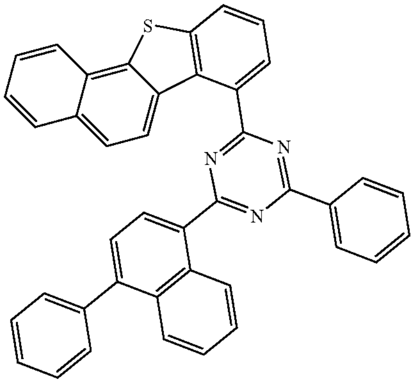
[1-41]
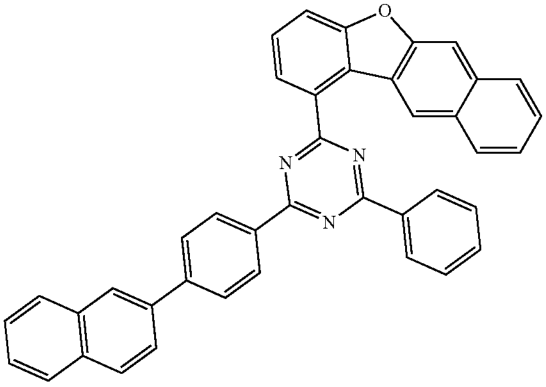
[1-42]
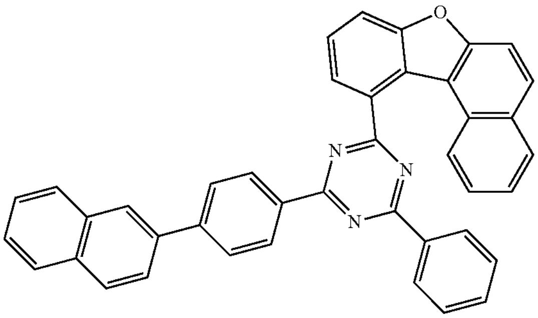
-continued
[1-43]
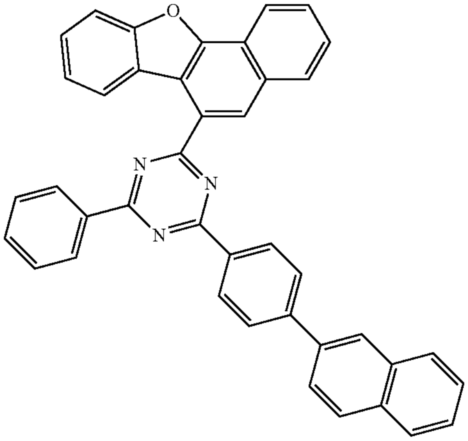
[1-44]
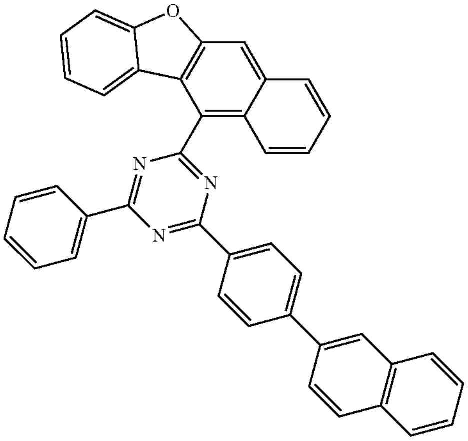
[1-45]
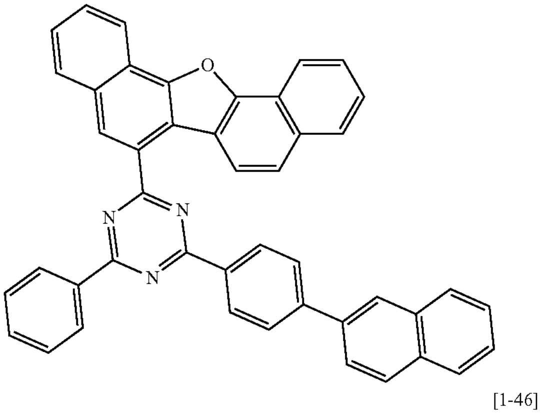
[1-46]
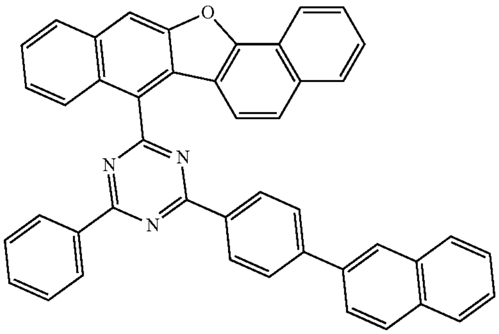

-continued
[1-47]
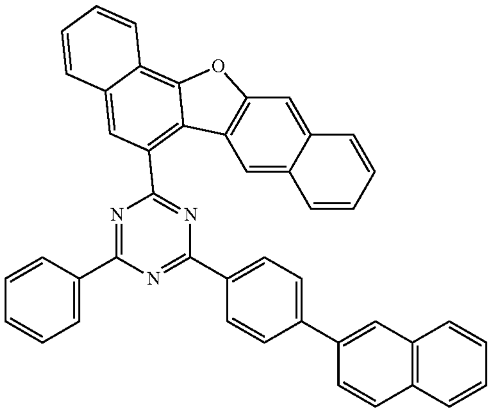
[1-48]
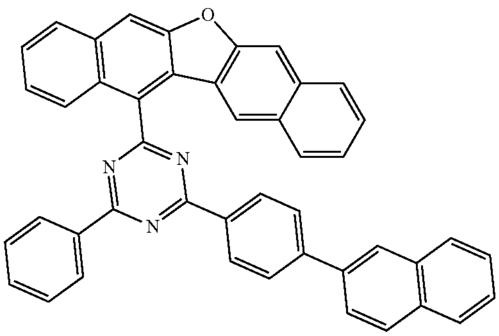
[1-49]
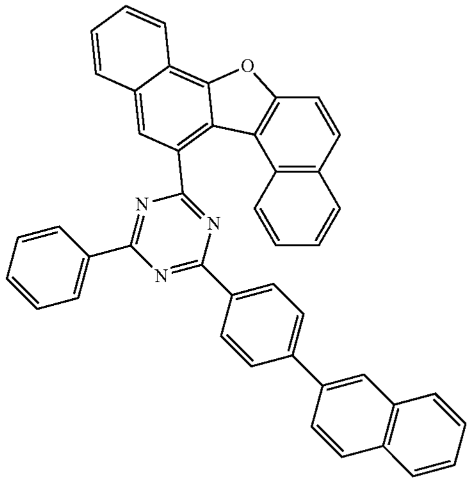
[1-50]
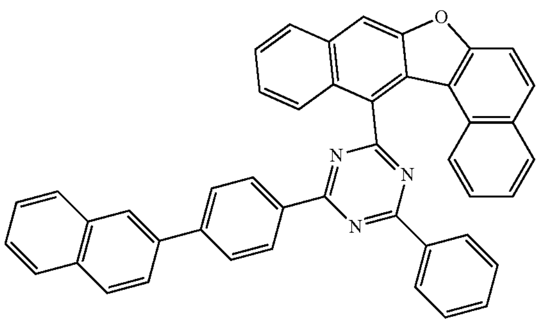
-continued
[1-51]
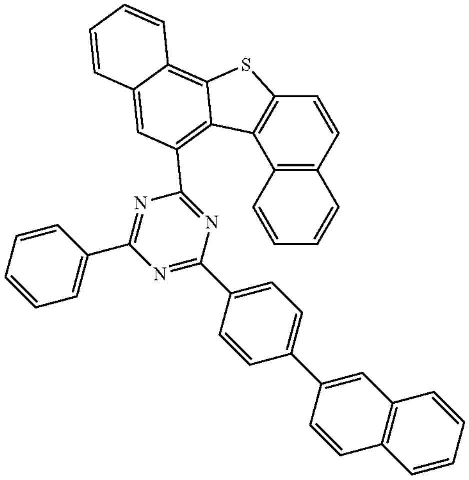
[1-52]
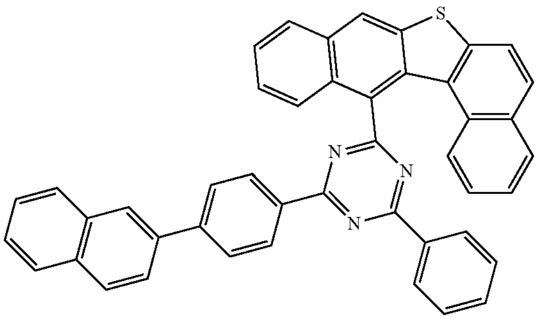
[1-53]
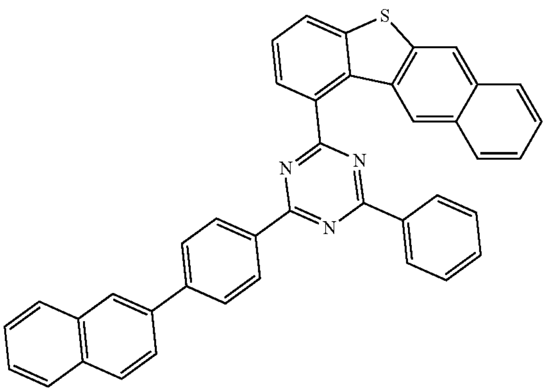
[1-54]
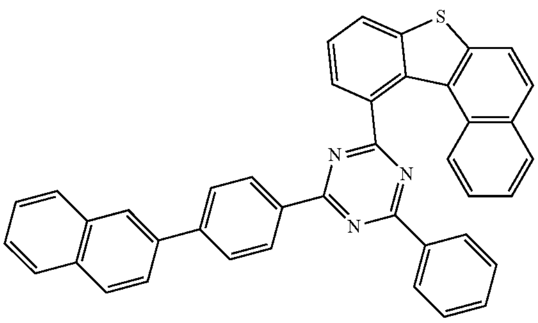

-continued
[1-55]
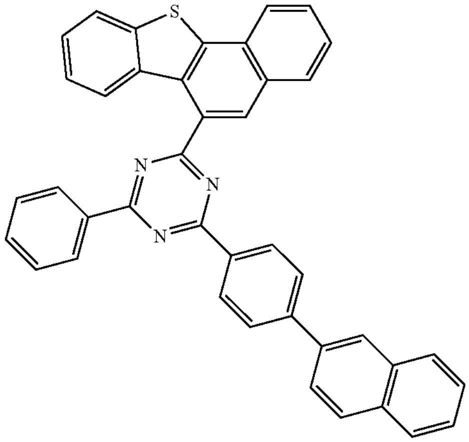
[1-56]
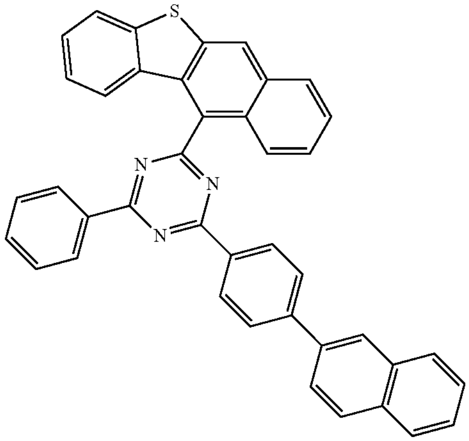
[1-57]
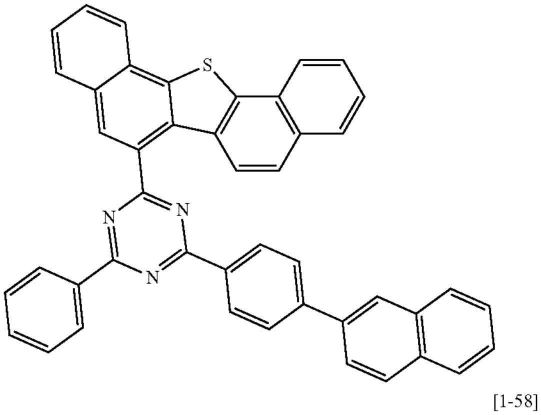
[1-58]
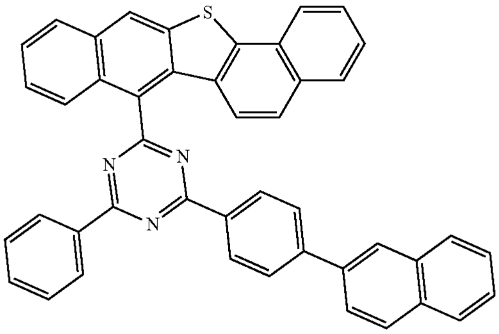
-continued
[1-59]
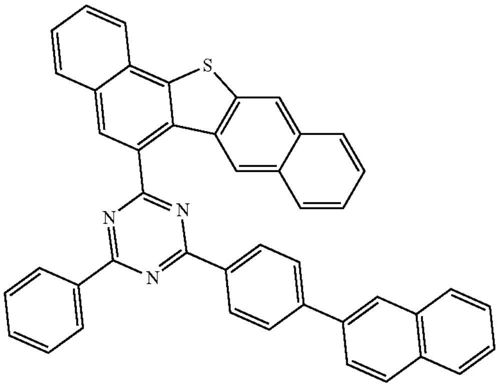
[1-60]
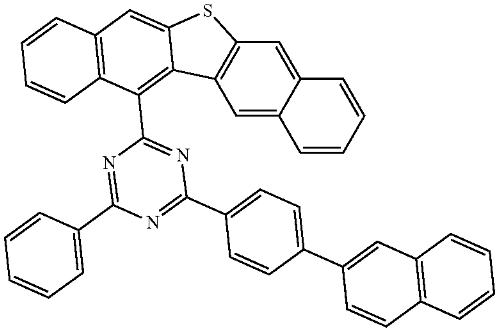
In an implementation, the second compound may be represented by, e.g., one of Chemical Formulae 2-IA to 2-IF and 2-IIA to 2-IIF depending on a fusion position of an additional fused ring and a substituted position of an amine group.
[Chemical Formula 2-IA]
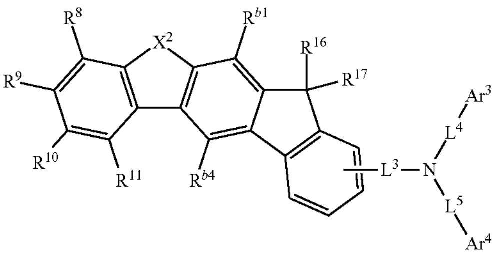
[Chemical Formula 2-IB]
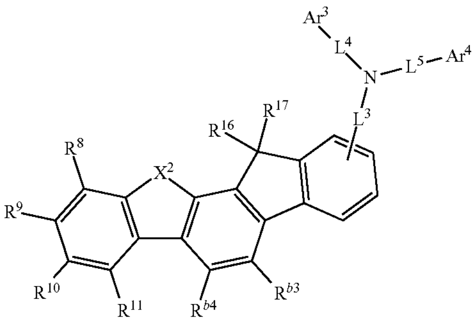

-continued
[Chemical Formula 2-IC]
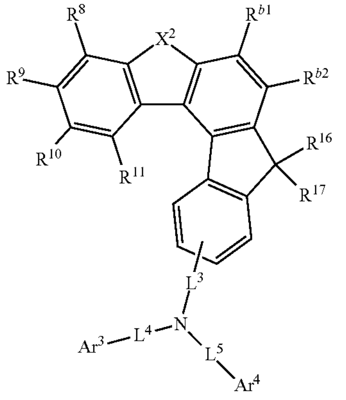
[Chemical Formula 2-ID]
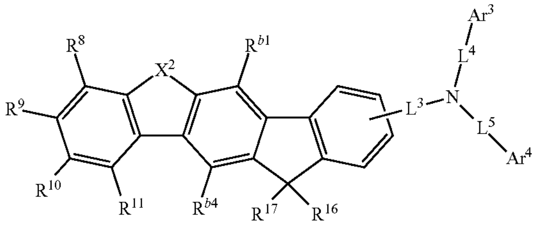
[Chemical Formula 2-IE]
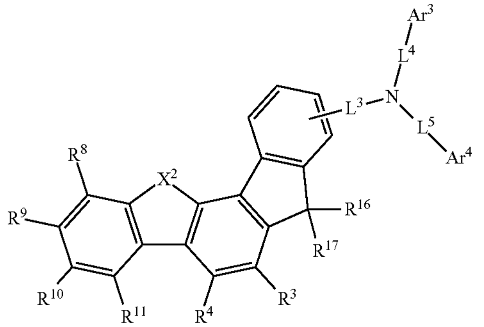
[Chemical Formula 2-IF]
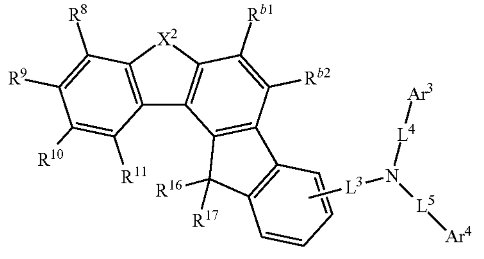
[Chemical Formula 2-IIA]
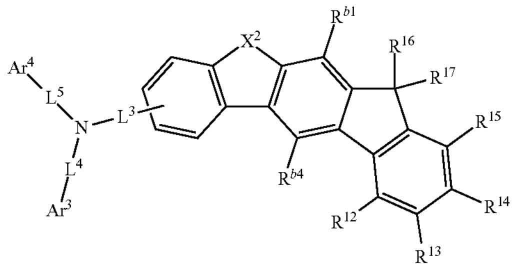
-continued
[Chemical Formula 2-IIB]
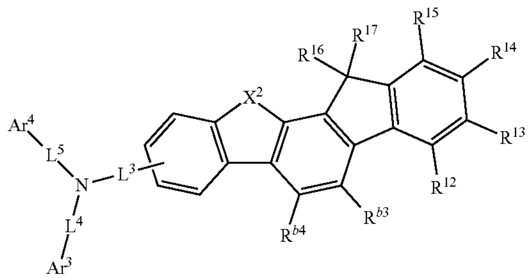
[Chemical Formula 2-IIC]
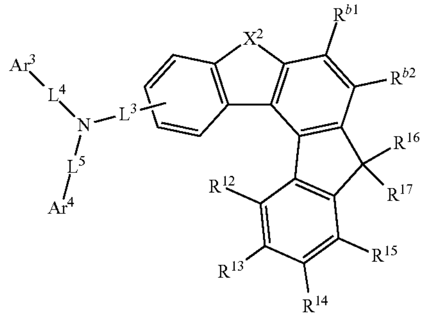
[Chemical Formula 2-IID]
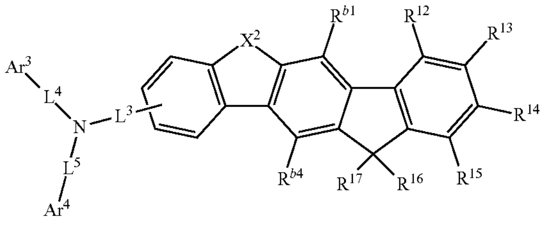
[Chemical Formula 2-IIE]
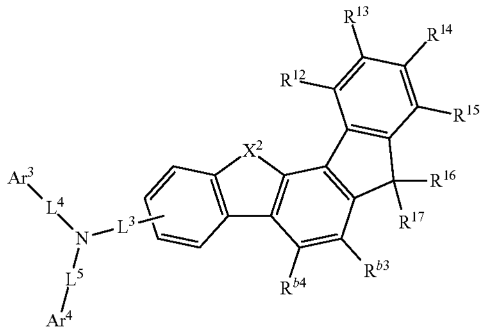
[Chemical Formula 2-IIF]
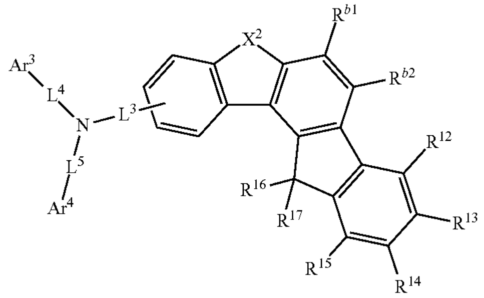

In Chemical Formula 2-IA to Chemical Formula 2-IF, and Chemical Formula 2-IIA to Chemical Formula 2-IIF, $X^2$, $Ar^3$, $Ar^4$, $L^3$ to $L^5$, $R^8$ to $R^{17}$ may be defined the same as those described above.

$R^{b1}$ to $R^4$ may each independently be defined the same as $R^b$ described above.

Chemical Formula 2-IA to Chemical Formula 2-IF, and Chemical Formula 2-IIA to Chemical Formula 2-IIF may be represented by one of Chemical Formula 2-IA-1 to Chemical Formula 2-IA-4, Chemical Formula 2-IB-1 to Chemical Formula 2-IB-4, Chemical Formula 2-IC-1 to Chemical Formula 2-IC-4, Chemical Formula 2-ID-1 to Chemical Formula 2-ID-4, Chemical Formula 2-IE-I to Chemical Formula 2-IE-4, Chemical Formula 2-IF-1 to Chemical Formula 2-IF-1, Chemical Formula 2-IIA-I to Chemical Formula 2-IIA-4, Chemical Formula 2-IIB-1 to Chemical Formula 2-IIB-4, Chemical Formula 2-IIC-1 to Chemical Formula 2-IIC-4, Chemical Formula 2-II-1 to Chemical Formula 2-IID-4, Chemical Formula 2-IIE-1 to Chemical Formula 2-IIE-4, and Chemical Formula 2-IIF-1 to Chemical Formula 2-IIF-4, according to the specific substitution position of the amine group.

[Chemical Formula 2-IA-1]

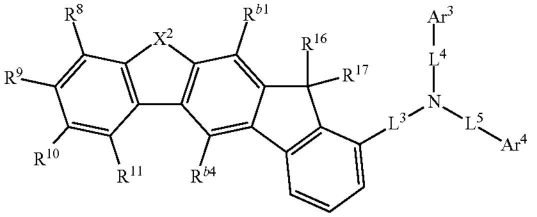

[Chemical Formula 2-IA-2]

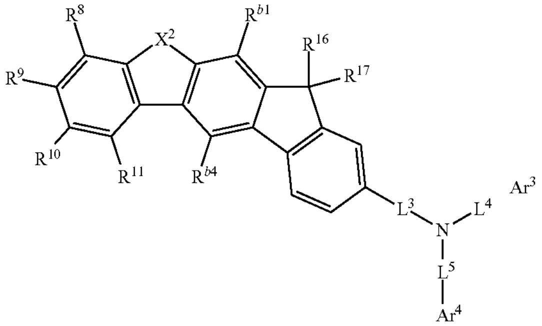

[Chemical Formula 2-IA-3]

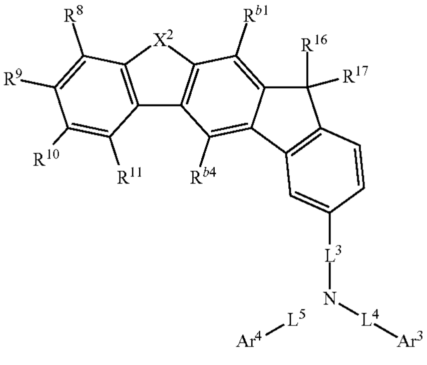

-continued

[Chemical Formula 2-IA-4]

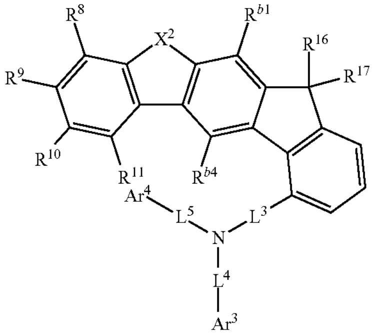

[Chemical Formula 2-IB-1]

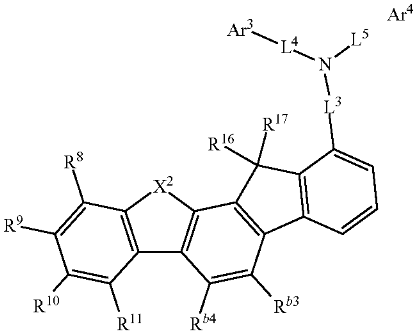

[Chemical Formula 2-IB-2]

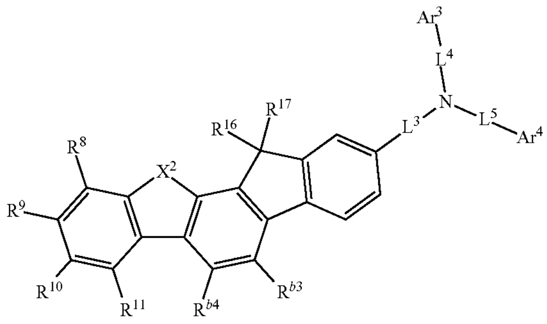

[Chemical Formula 2-IB-3]

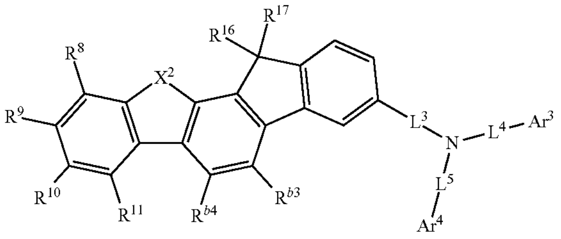

[Chemical Formula 2-IB-4]

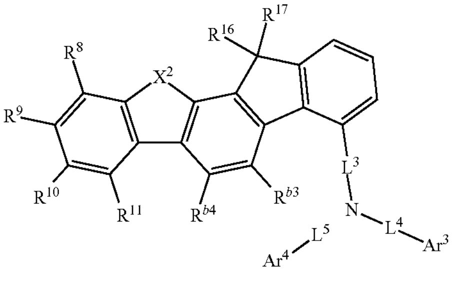

-continued
[Chemical Formula 2-IC-1]
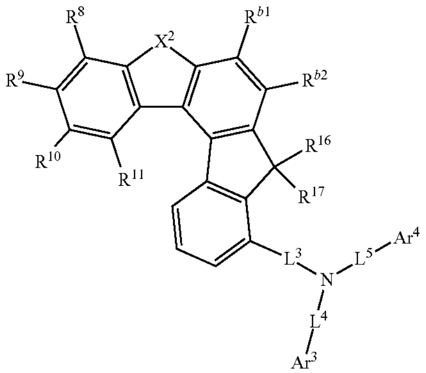
[Chemical Formula 2-IC-2]
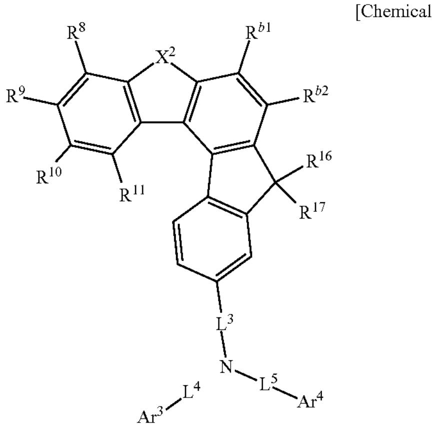
[Chemical Formula 2-IC-3]
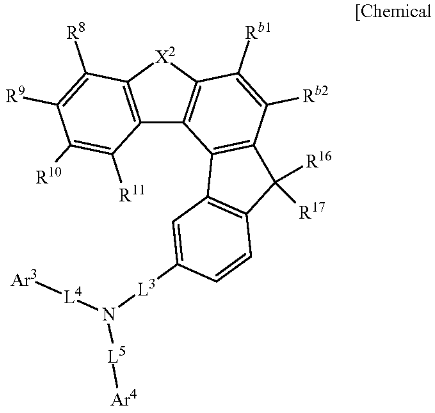
[Chemical Formula 2-IC-4]
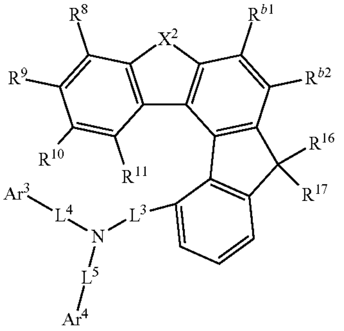
-continued
[Chemical Formula 2-ID-1]
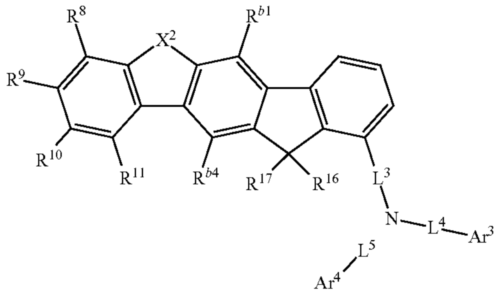
[Chemical Formula 2-ID-2]
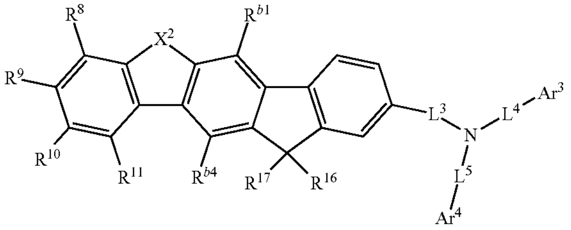
[Chemical Formula 2-ID-3]
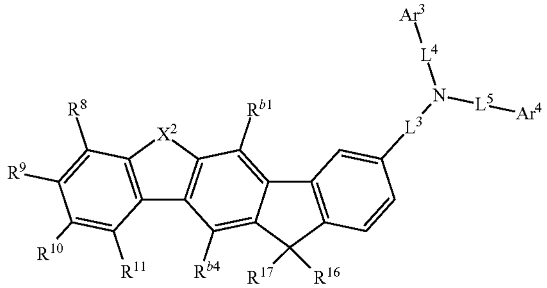
[Chemical Formula 2-ID-4]
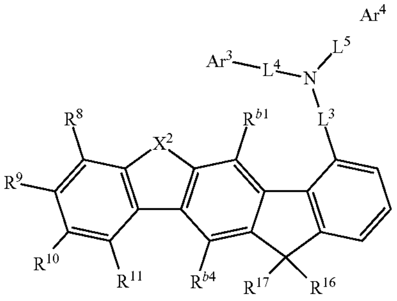
[Chemical Formula 2-IE-1]
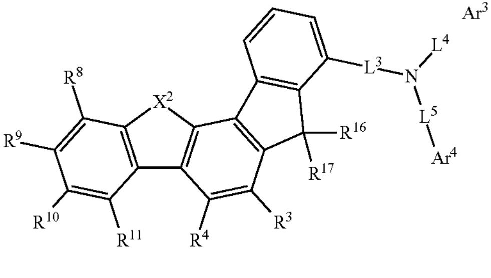

-continued
[Chemical Formula 2-IE-2]
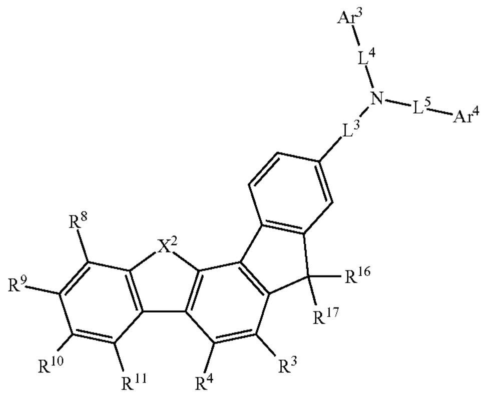
[Chemical Formula 2-IE-3]
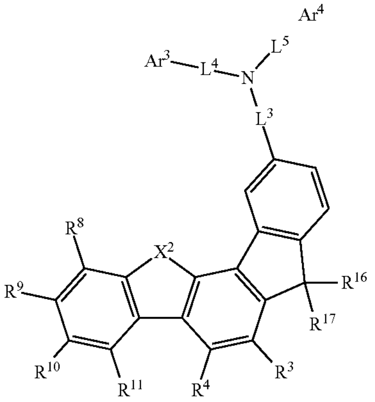
[Chemical Formula 2-IE-4]
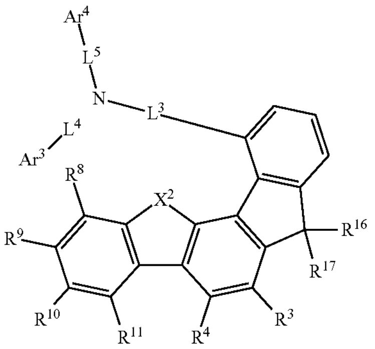
[Chemical Formula 2-IF-1]
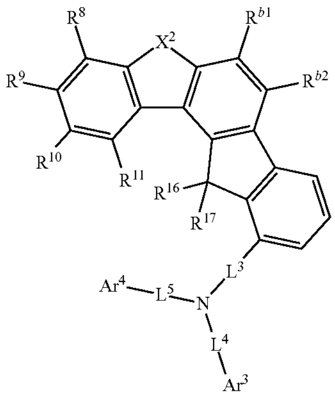
-continued
[Chemical Formula 2-IF-2]
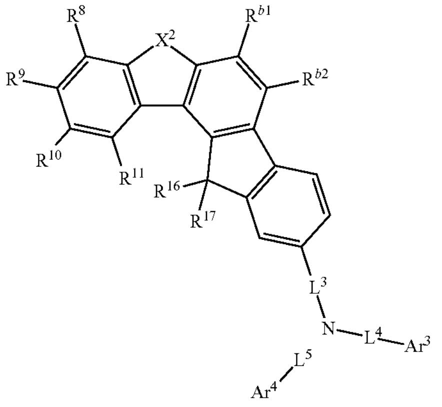
[Chemical Formula 2-IF-3]
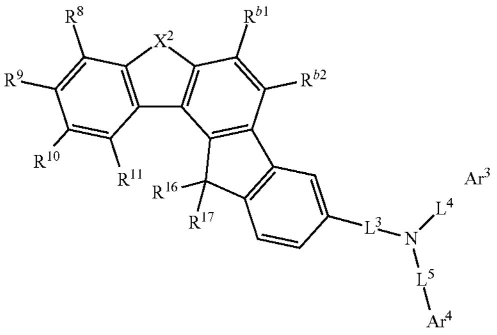
[Chemical Formula 2-IF-4]
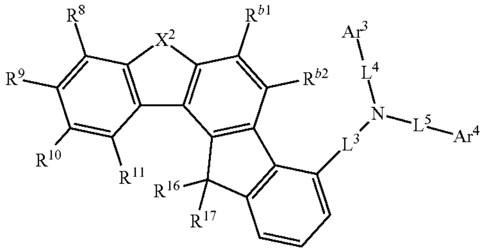
[Chemical Formula 2-IIA-1]
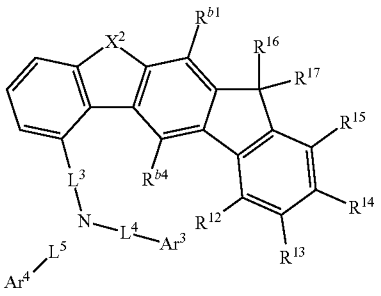

-continued
[Chemical Formula 2-IIA-2]
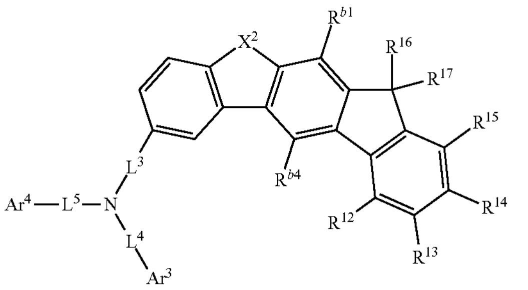
[Chemical Formula 2-IIA-3]
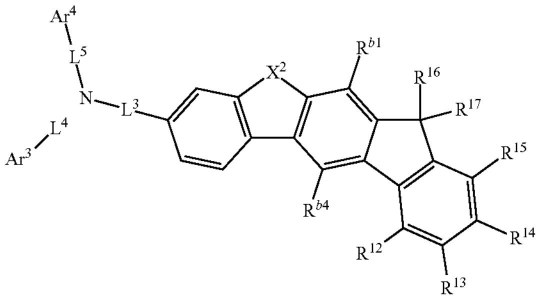
[Chemical Formula 2-IIA-4]
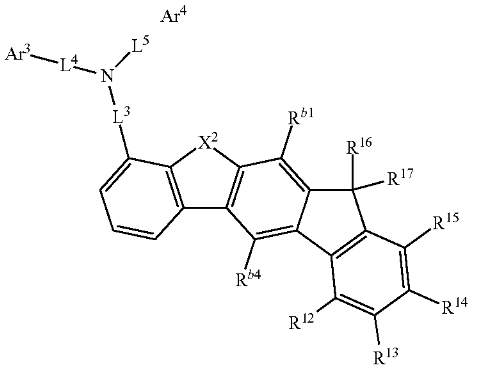
[Chemical Formula 2-IIB-1]
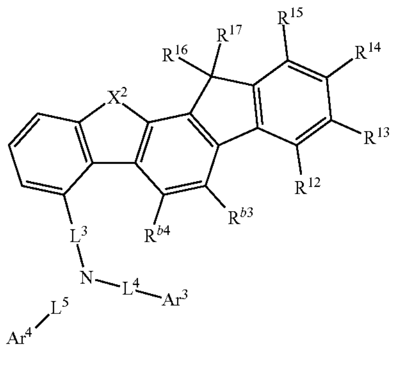
-continued
[Chemical Formula 2-IIB-2]
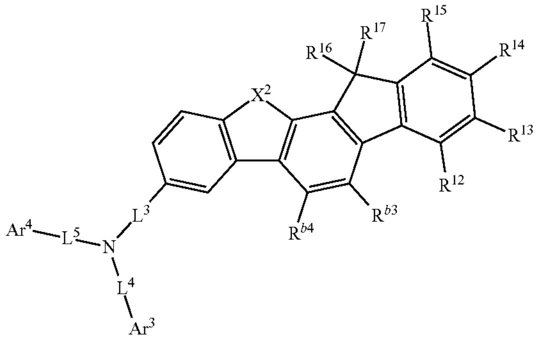
[Chemical Formula 2-IIB-3]
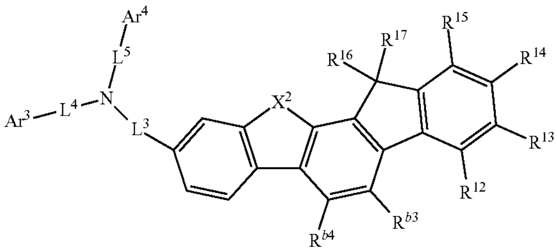
[Chemical Formula 2-IIB-4]
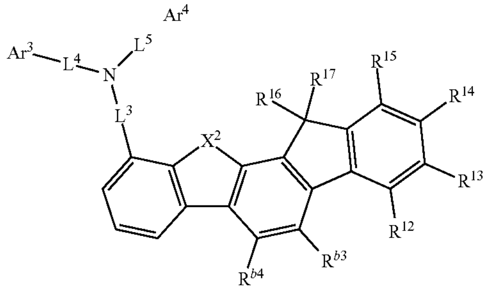
[Chemical Formula 2-IIC-1]
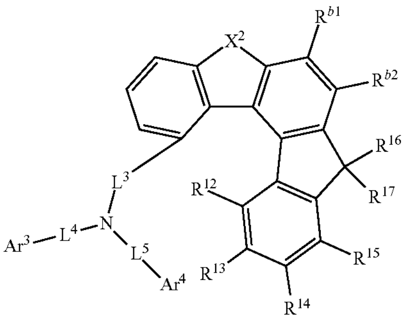
[Chemical Formula 2-IIC-2]
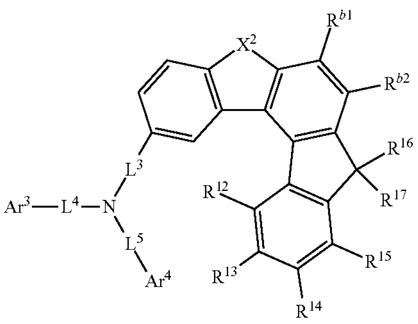

-continued
[Chemical Formula 2-IIC-3]
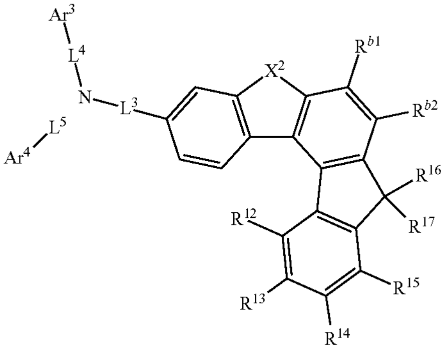
[Chemical Formula 2-IIC-4]
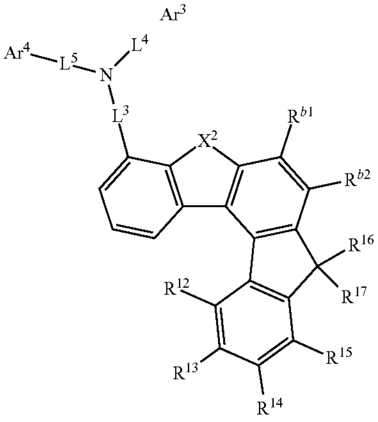
[Chemical Formula 2-IID-1]
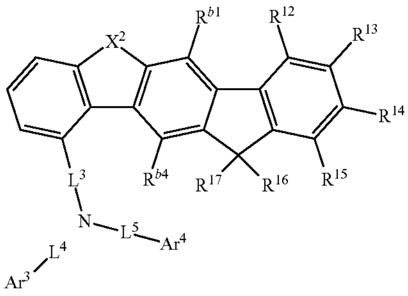
[Chemical Formula 2-IID-2]
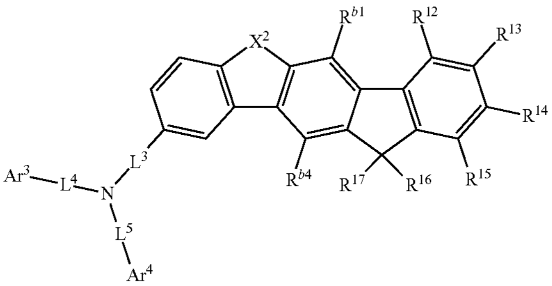
-continued
[Chemical Formula 2-IID-3]
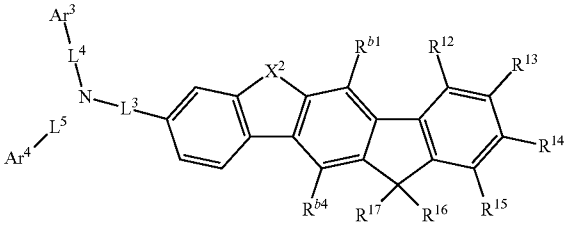
[Chemical Formula 2-IID-4]
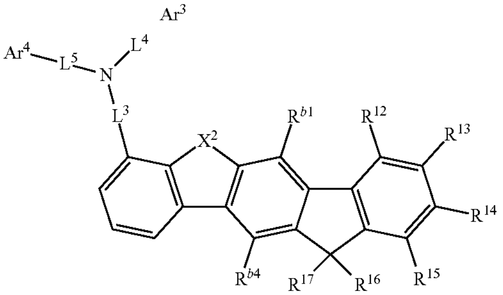
[Chemical Formula 2-IIE-1]
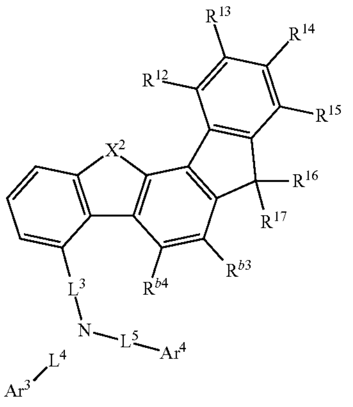
[Chemical Formula 2-IIE-2]
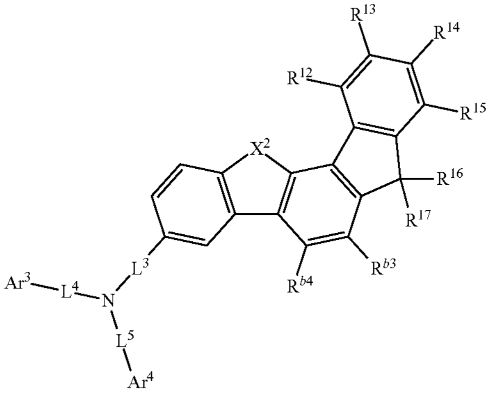

-continued

[Chemical Formula 2-IIE-3]

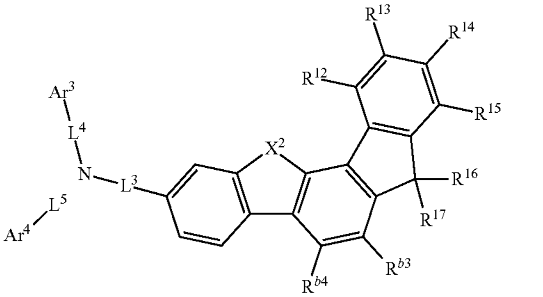

[Chemical Formula 2-IIE-4]

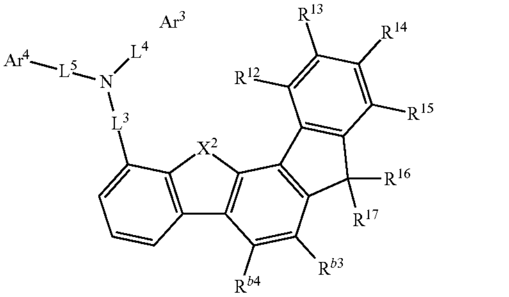

[Chemical Formula 2-IIF-1]

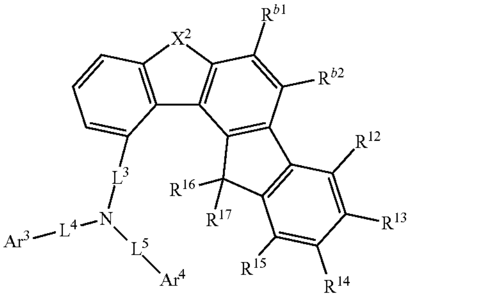

[Chemical Formula 2-IIF-2]

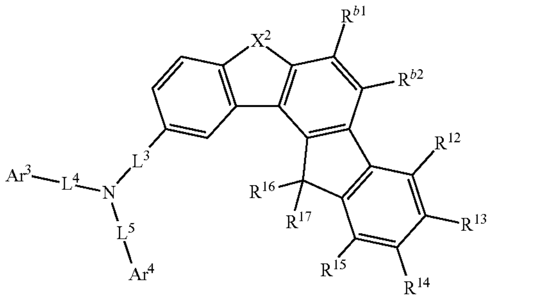

[Chemical Formula 2-IIF-3]

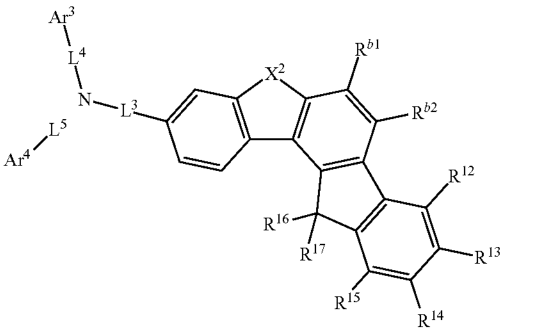

-continued

[Chemical Formula 2-IIF-4]

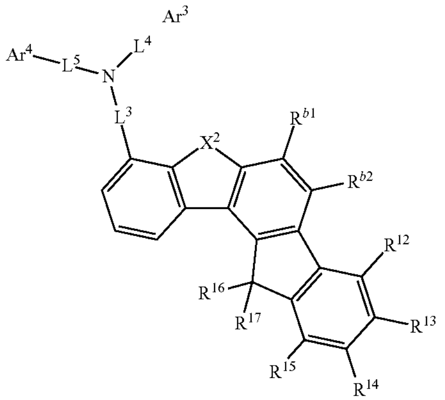

In Chemical Formula 2-IA-1 to Chemical Formula 2-IA-4, Chemical Formula 2-IB-1 to Chemical Formula 2-IB-4, Chemical Formula 2-IC-1 to Chemical Formula 2-IC-4, Chemical Formula 2-ID-1 to Chemical Formula 2-ID-4, Chemical Formula 2-IE-1 to Chemical Formula 2-IE-4, Chemical Formula 2-IF-1 to Chemical Formula 2-IF-1, Chemical Formula 2-IIA-1 to Chemical Formula 2-IIA-4, Chemical Formula 2-IIB-1 to Chemical Formula 2-IIB-4, Chemical Formula 2-IIC-1 to Chemical Formula 2-IIC-4, Chemical Formula 2-II-1 to Chemical Formula 2-IID-4, Chemical Formula 2-IIE-1 to Chemical Formula 2-IIE-4, and Chemical Formula 2-IIF-1 to Chemical Formula 2-IIF-4, $X^2$, $Ar^3$, $Ar^4$, $L^3$ to $L^5$, $R^8$ to $R^{17}$ and $R^{b1}$ to $R^4$ may be defined the same as those described above.

In an implementation, the second compound may be represented by, e.g., Chemical Formula 2-IA-2, Chemical Formula 2-IA-3, Chemical Formula 2-IB-2, Chemical Formula 2-IB-3, Chemical Formula 2-IC-2, Chemical Formula 2-IC-3, Chemical Formula 2-ID-2, Chemical Formula 2-ID-3, Chemical Formula 2-IE-1, Chemical Formula 2-IE-2, Chemical Formula 2-IE-3, Chemical Formula 2-IE-4, Chemical Formula 2-IF-2, Chemical Formula 2-IF-3, Chemical Formula 2-IIA-4, Chemical Formula 2-IIB-4, Chemical Formula 2-IIC-4, Chemical Formula 2-IID-4, Chemical Formula 2-IIE-1, Chemical Formula 2-IIE-2, Chemical Formula 2-IIE-3, Chemical Formula 2-IIE-4, or Chemical Formula 2-IIF-4.

In an implementation, the second compound may be represented by, e.g., Chemical Formula 2-IE-2 or Chemical Formula 2-IIE-4.

In an implementation, $Ar^3$ and $Ar^4$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group.

In an implementation, $Ar^3$ to $Ar^5$ may each independently be, e.g., a substituted or unsubstituted biphenyl group, a substituted or unsubstituted naphthyl group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group.

In an implementation, $L^3$ to $L^5$ may each independently be, e.g., a single bond, a substituted or unsubstituted phenylene group, or a substituted or unsubstituted biphenylene group.

In an implementation, $L^3$ to $L^5$ may each independently be, e.g., a single bond or a substituted or unsubstituted phenylene group.

In an implementation, $R^{b1}$ to $R^4$ and $R^8$ to $R^{15}$ may each independently be, e.g., hydrogen, deuterium, a substituted or unsubstituted C1 to C10 alkyl group, or a substituted or unsubstituted C6 to C12 aryl group.

In an implementation, each of $R^{b1}$ to $R^{b4}$, and $R^8$ to $R^{15}$ may be hydrogen.

In an implementation, $R^{16}$ and $R^{17}$ may each independently be, e.g., a substituted or unsubstituted C1 to C10 alkyl group or a substituted or unsubstituted C6 to C10 aryl group.

In an implementation, $R^{16}$ and $R^{17}$ may each independently be, e.g., a substituted or unsubstituted methyl group or a substituted or unsubstituted phenyl group.

In an implementation, the second compound may be a compound of Group 2.

[Group 2]

[A-1]

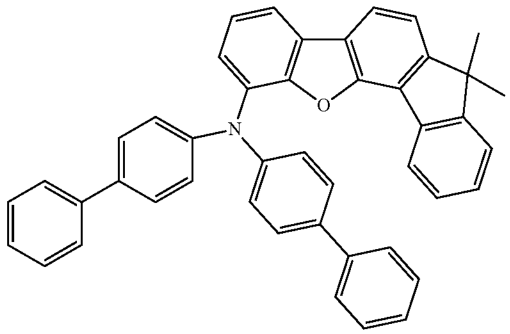

[A-2]

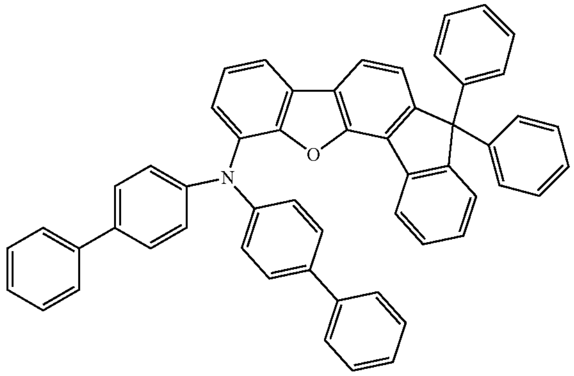

-continued

[A-3]

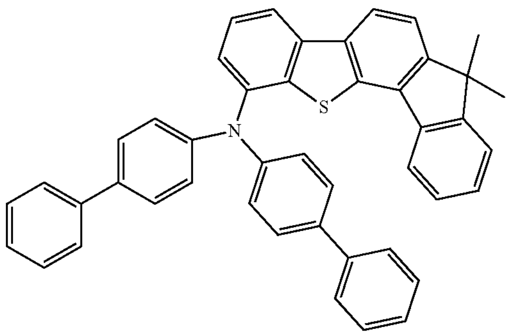

[A-4]

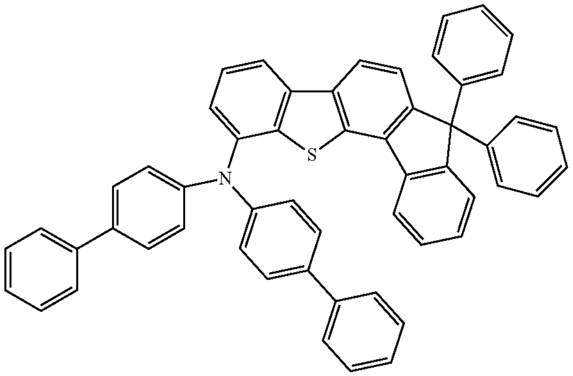

[A-5]

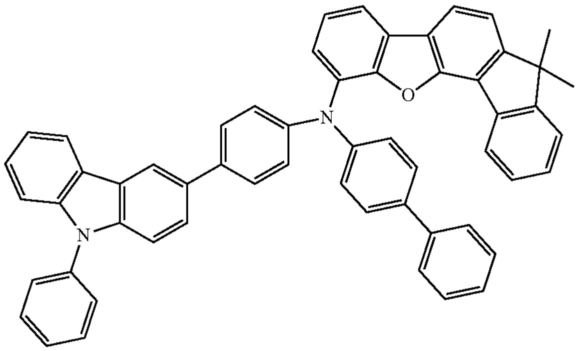

[A-6]

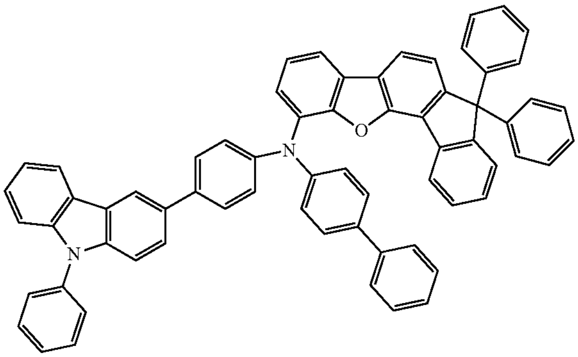

-continued
[A-7]
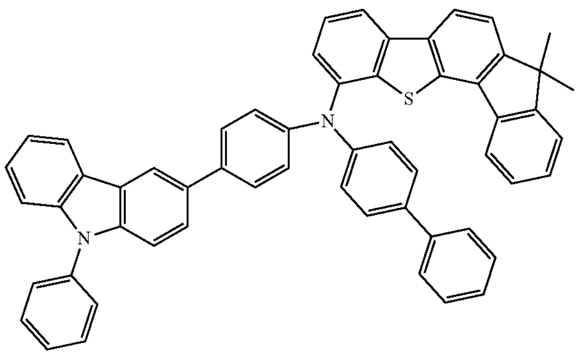
[A-8]
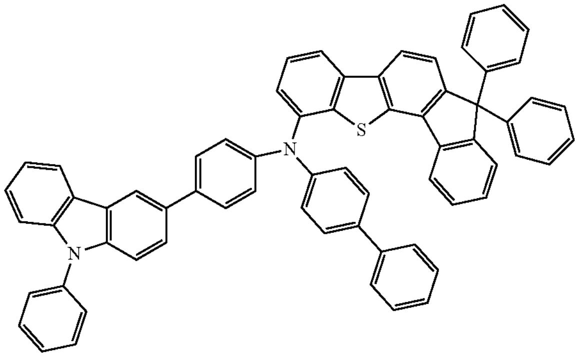
[A-9]
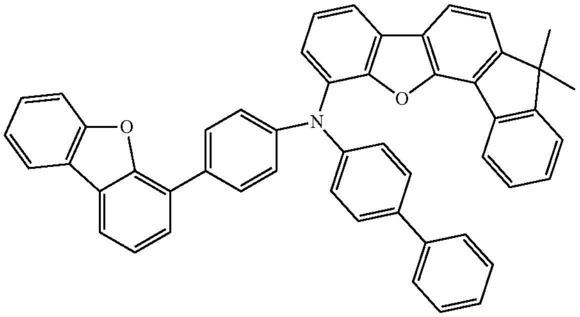
[A-10]
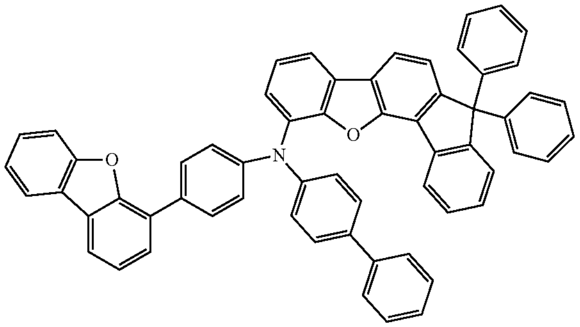
-continued
[A-11]
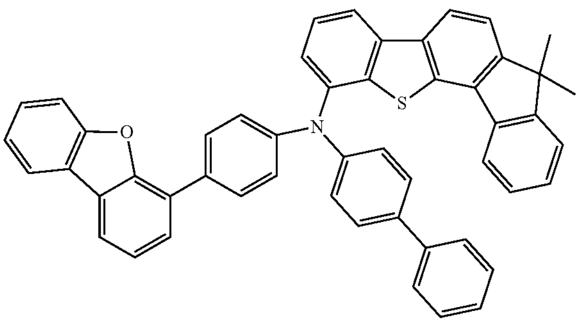
[A-12]
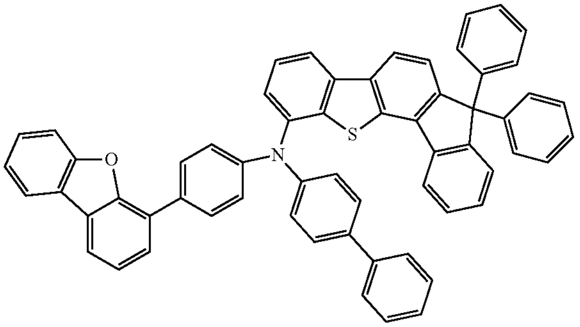
[A-13]
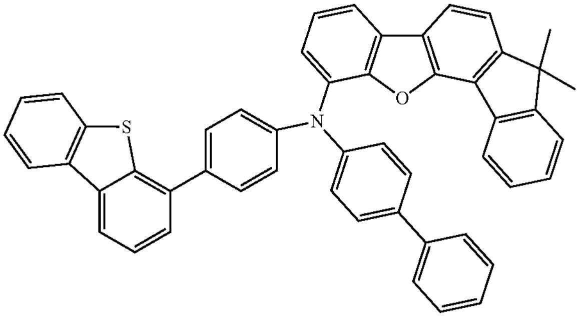
[A-14]
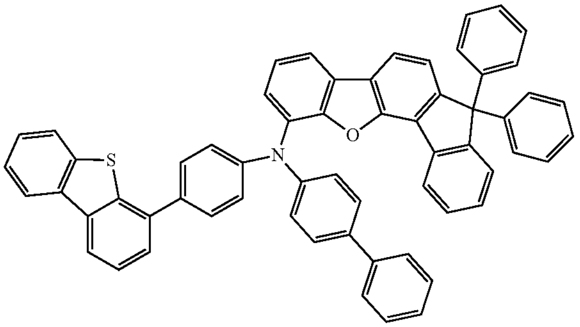

-continued
[A-15]
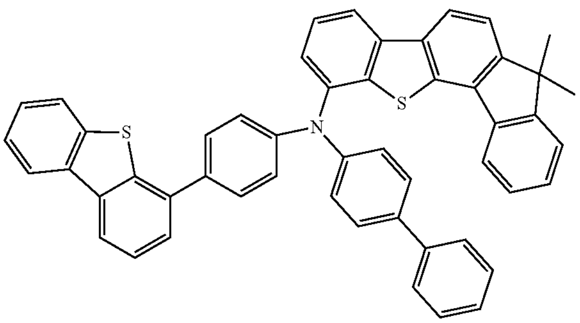
[A-16]
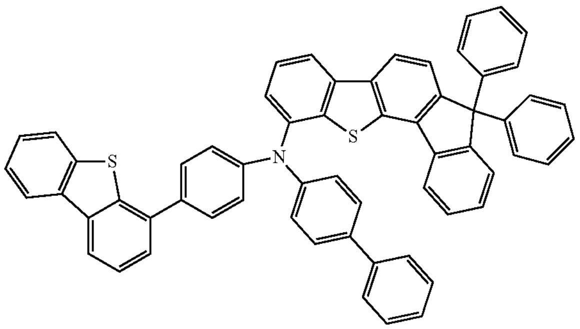
[A-17]
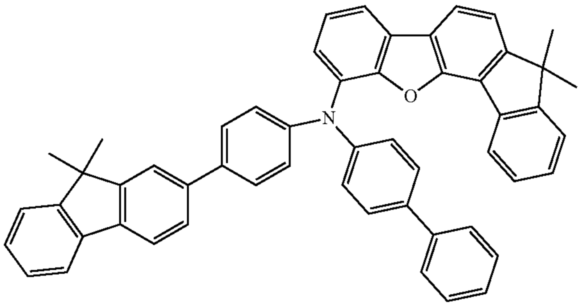
[A-18]
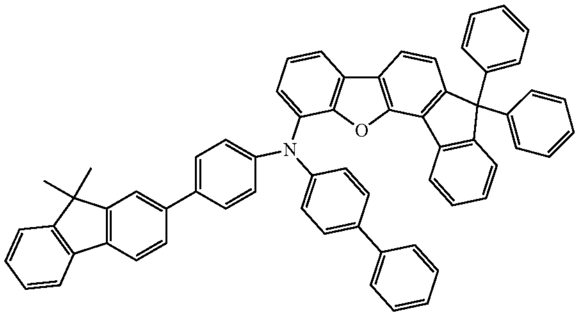
-continued
[A-19]
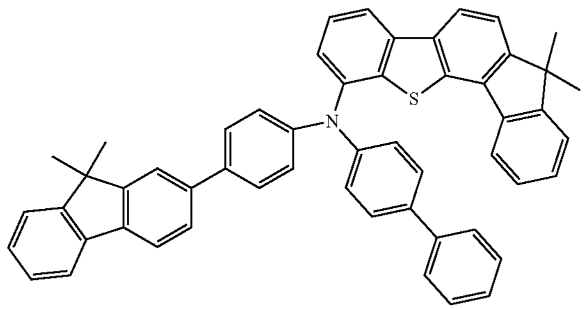
[A-20]
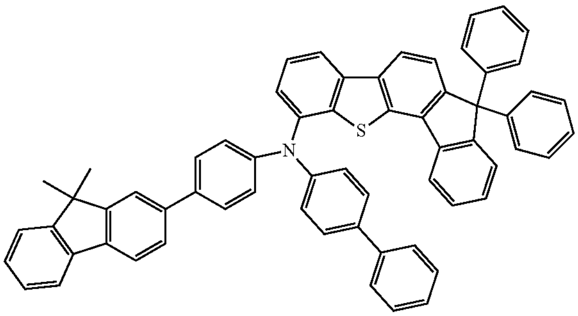
[A-21]
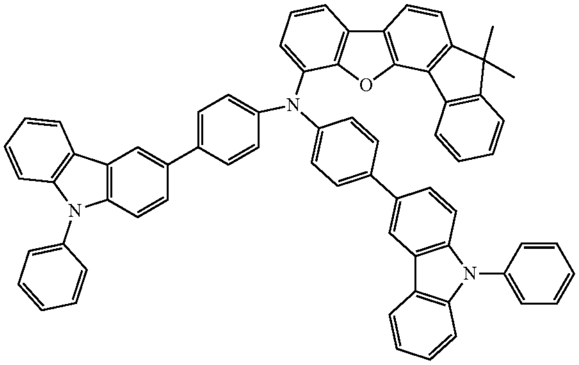
[A-22]
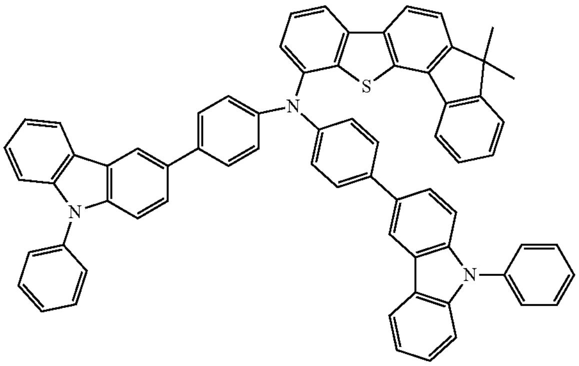

-continued
[A-23]
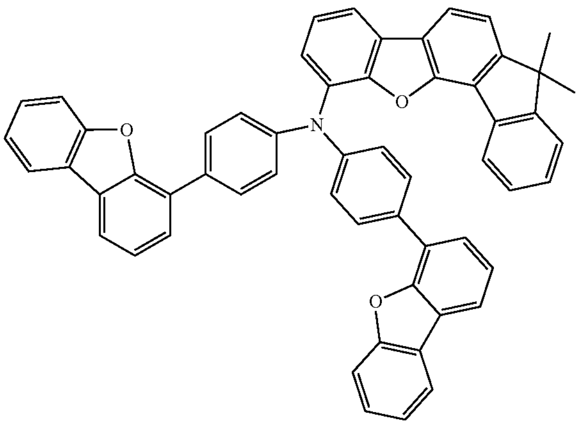
[A-24]
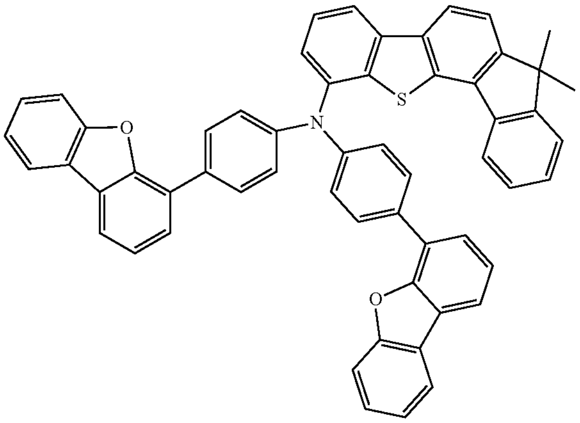
[A-25]
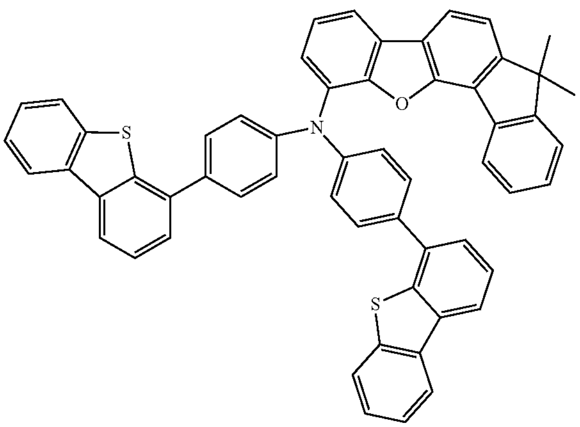
-continued
[A-26]
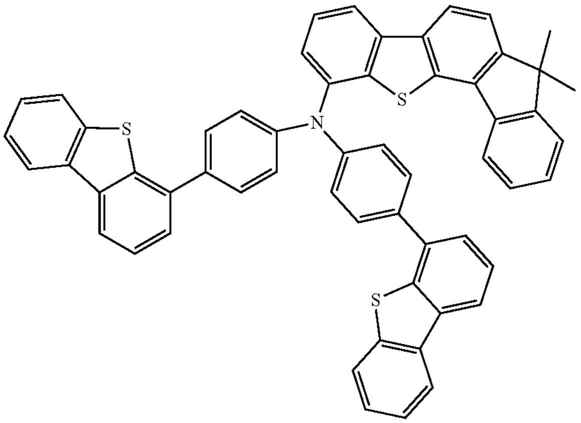
[A-27]
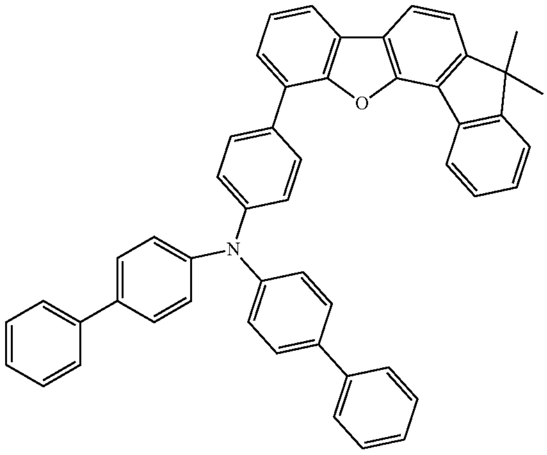
[A-28]
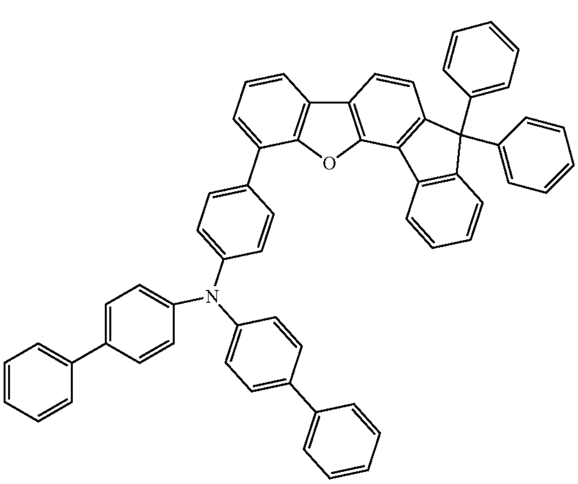

-continued
[A-29]
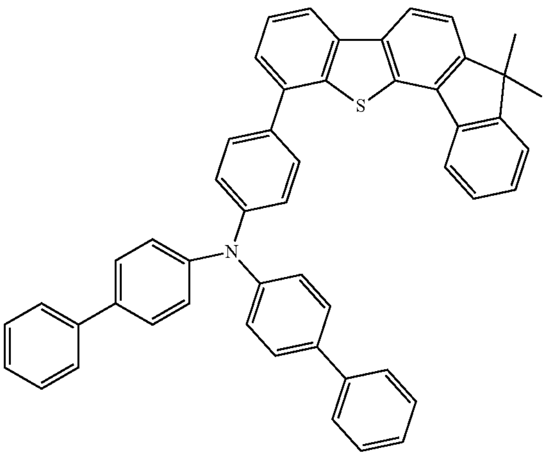
[A-30]
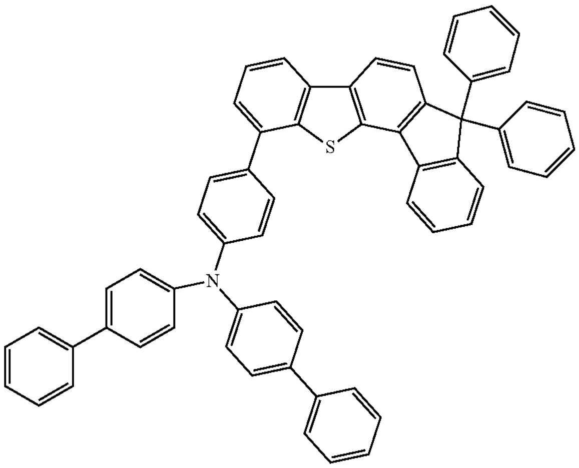
[A-31]
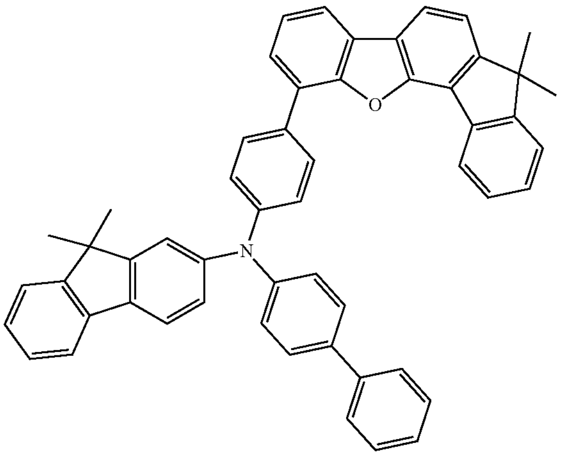
-continued
[A-32]
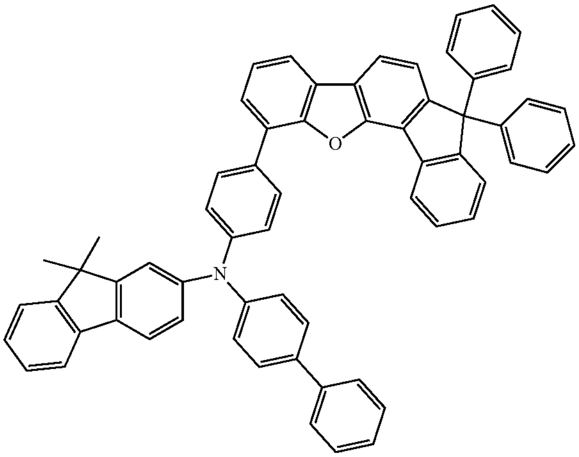
[A-33]
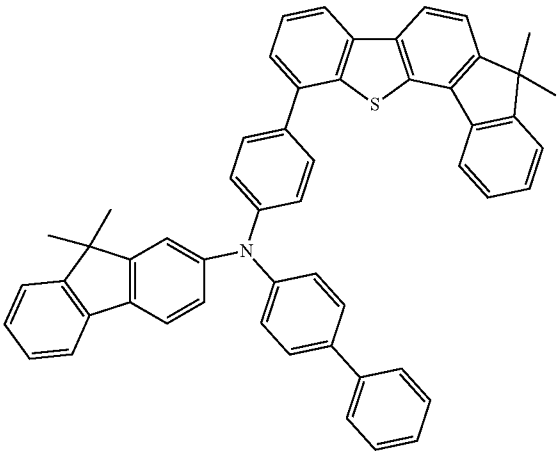
[A-34]
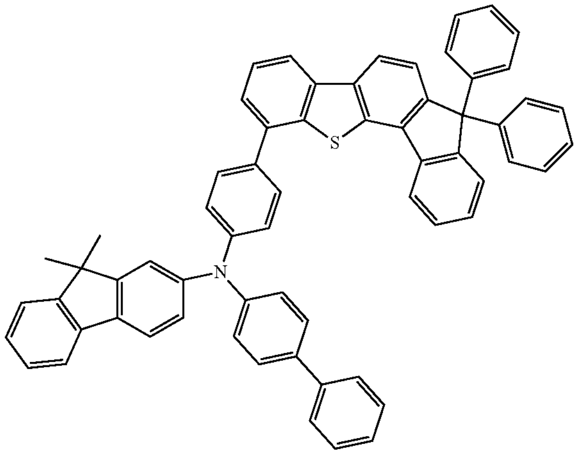

-continued
[A-35]
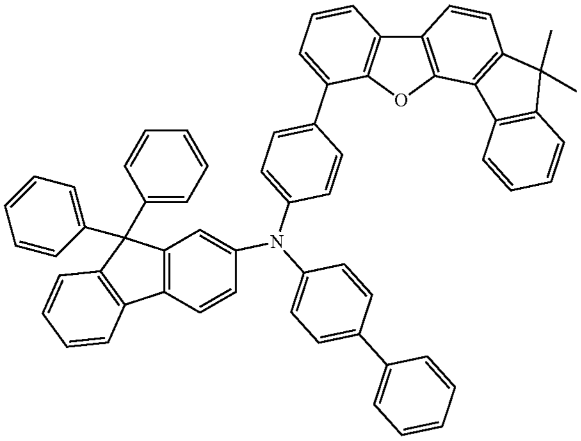
[A-36]
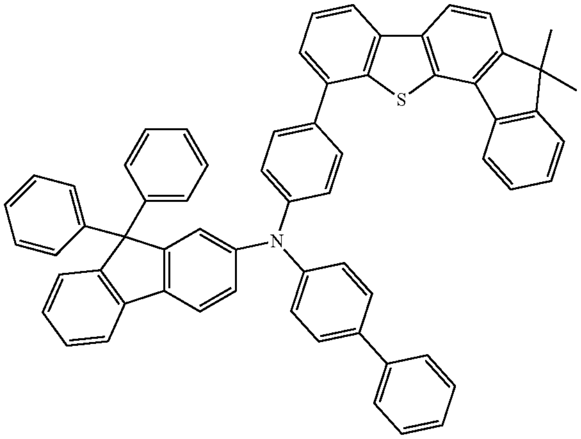
[A-37]
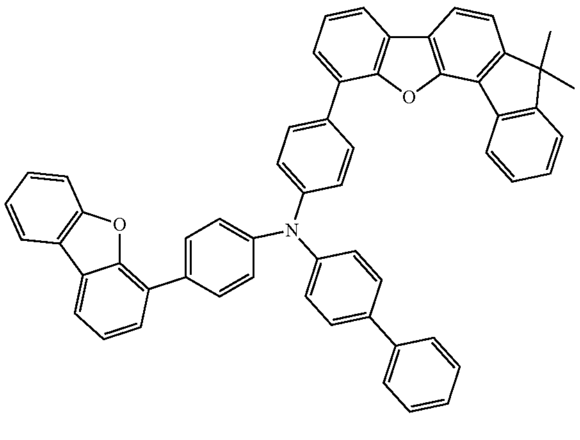
-continued
[A-38]
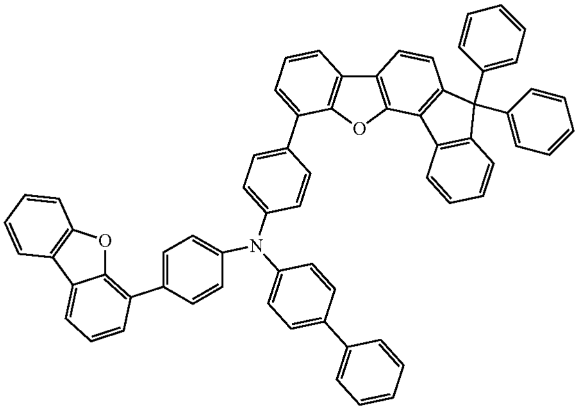
[A-39]
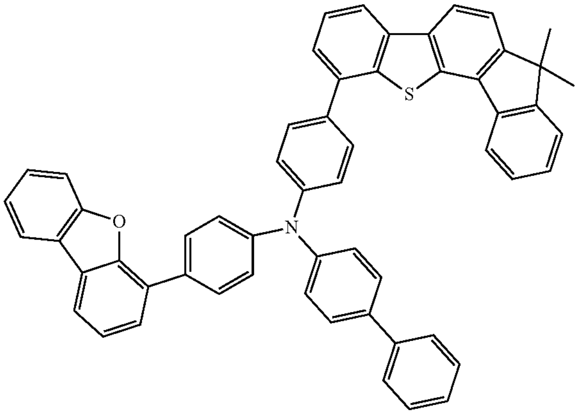
[A-40]
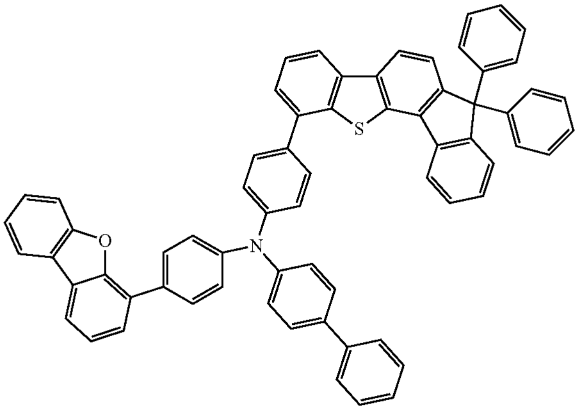

-continued
[A-41]
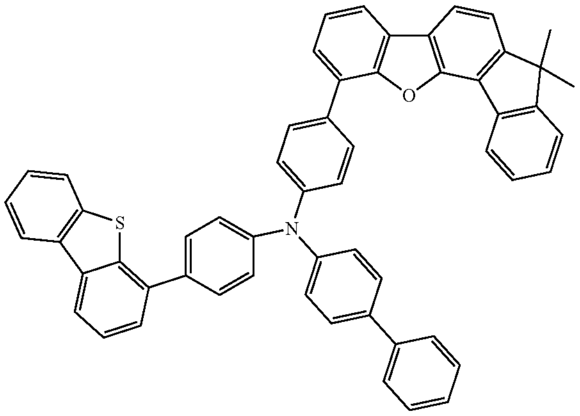
[A-42]
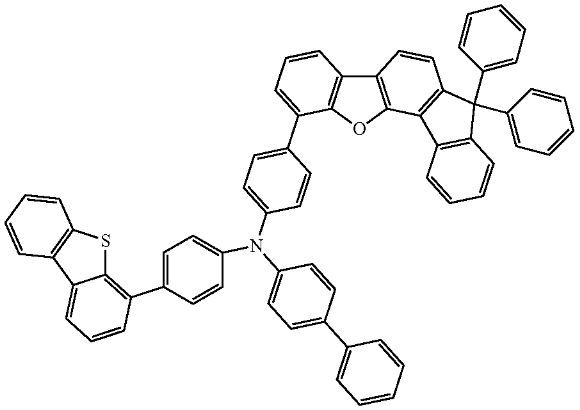
[A-43]
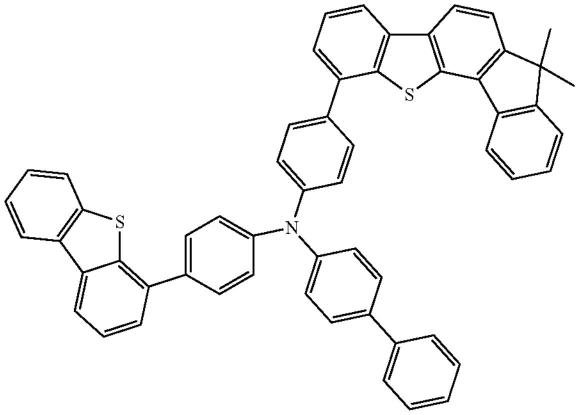
-continued
[A-44]
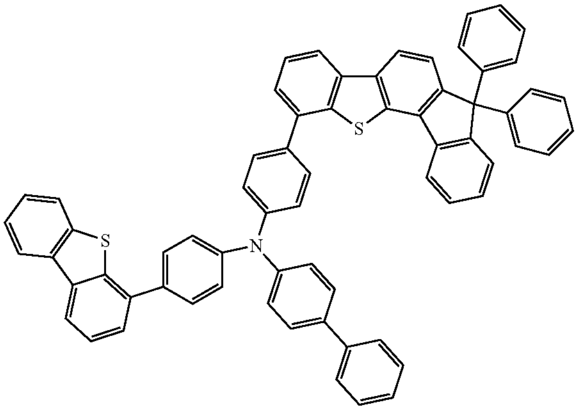
[A-45]
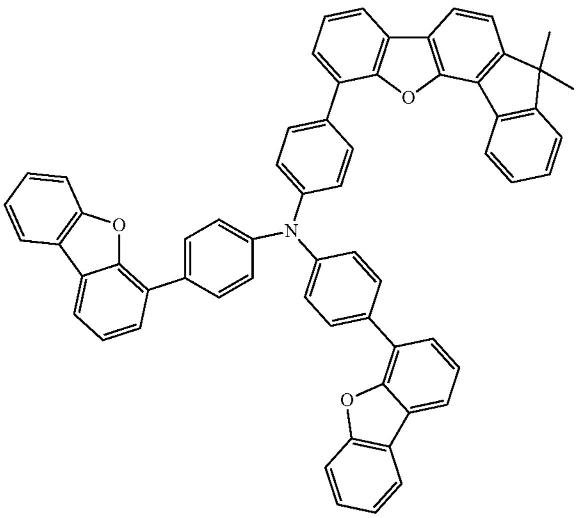
[A-46]
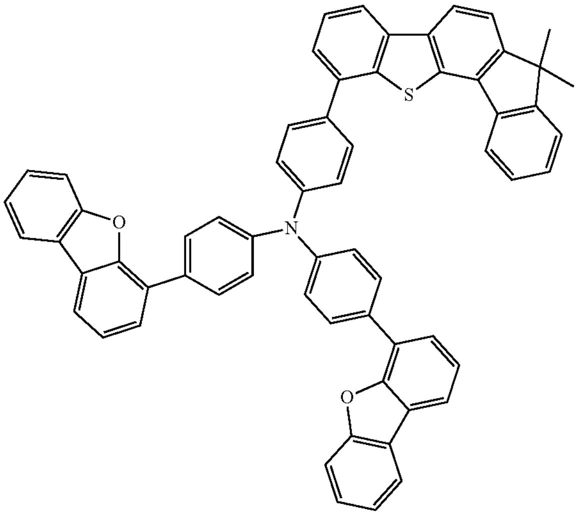

-continued
[A-47]
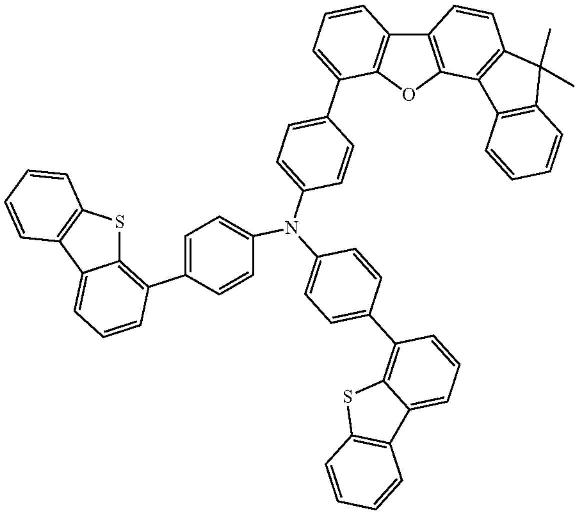
[A-48]
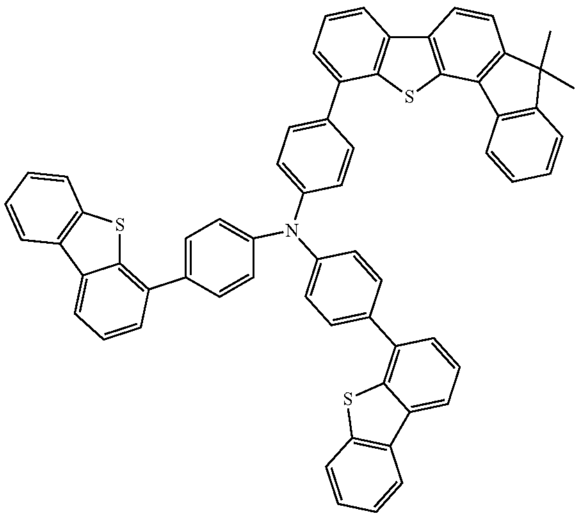
[A-49]
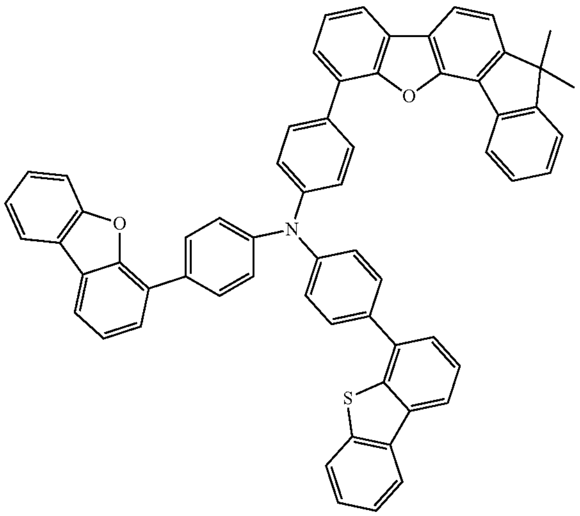
-continued
[A-50]
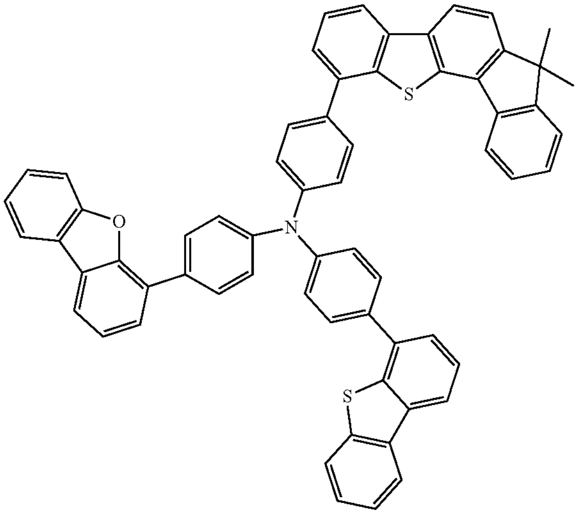
[A-51]
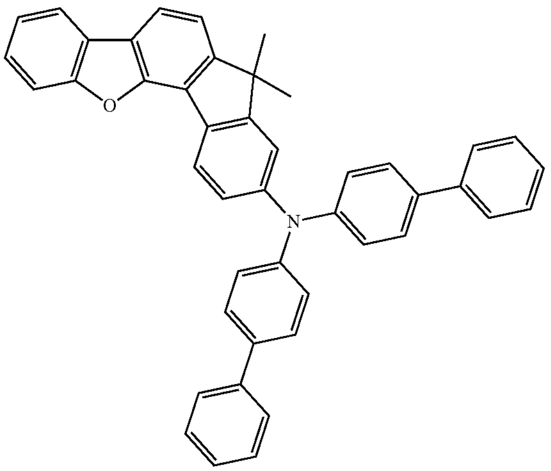
[A-52]
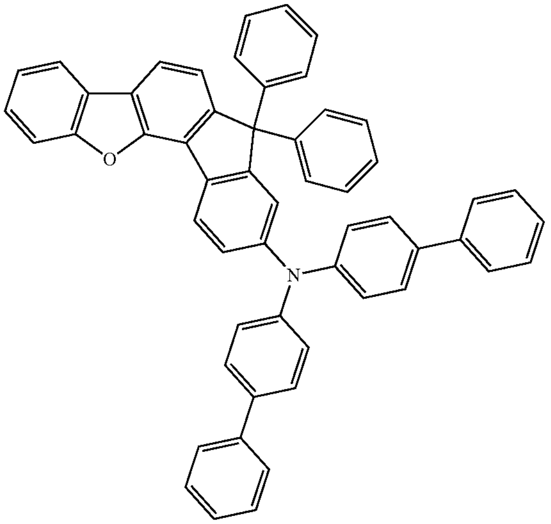

-continued
[A-53]
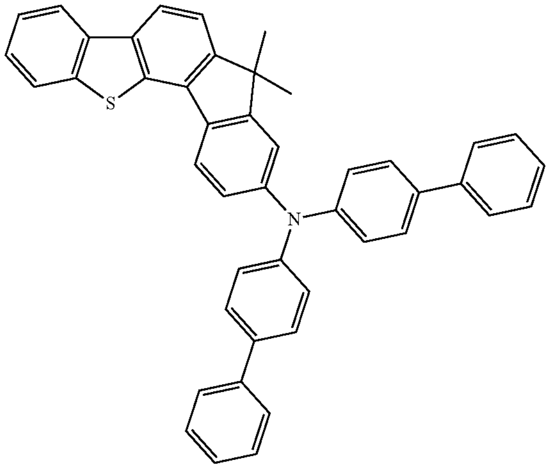
[A-54]
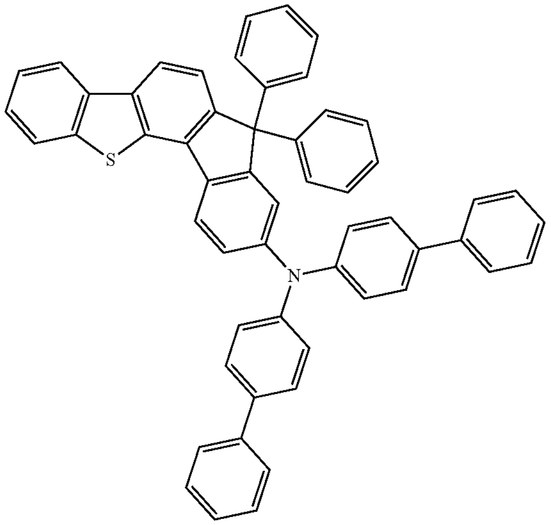
[A-55]
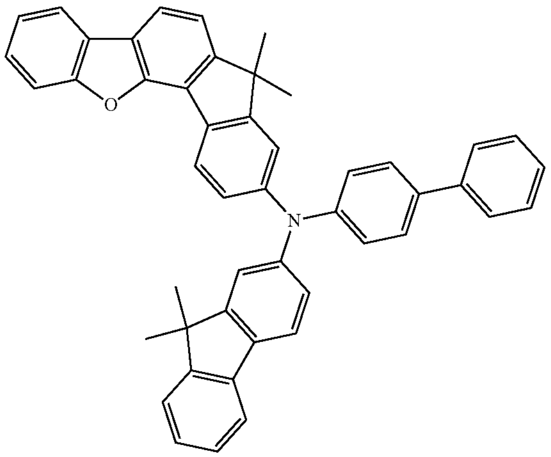
-continued
[A-56]
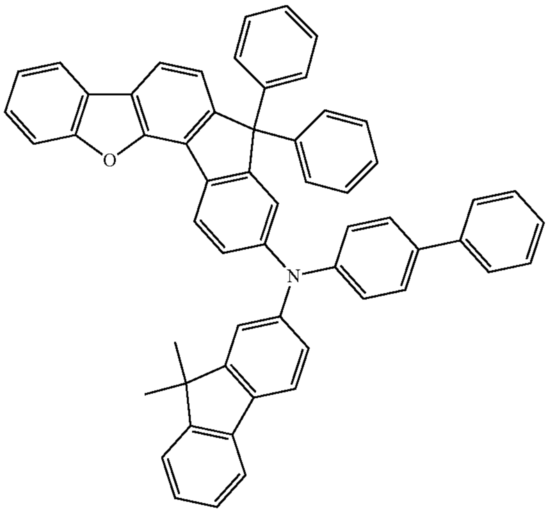
[A-57]
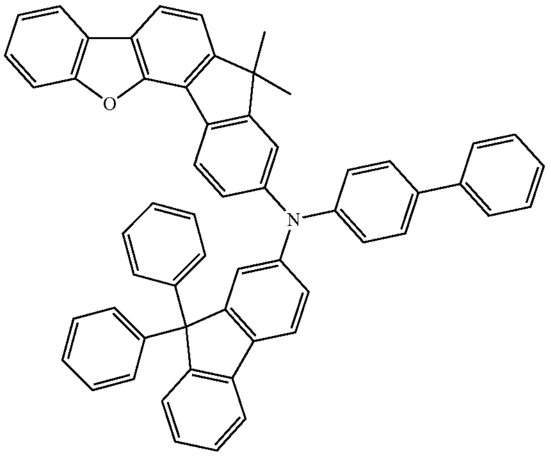
[A-58]
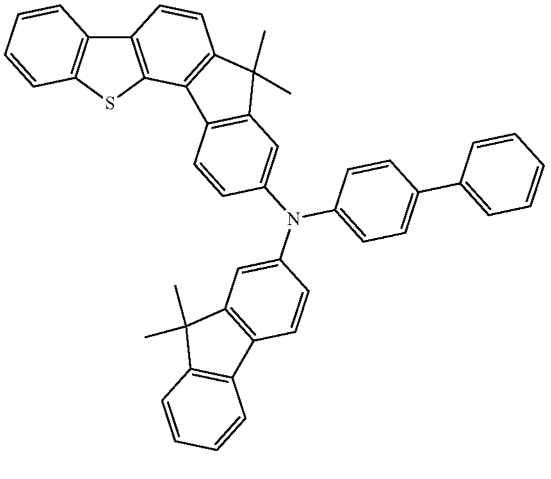

[A-59]
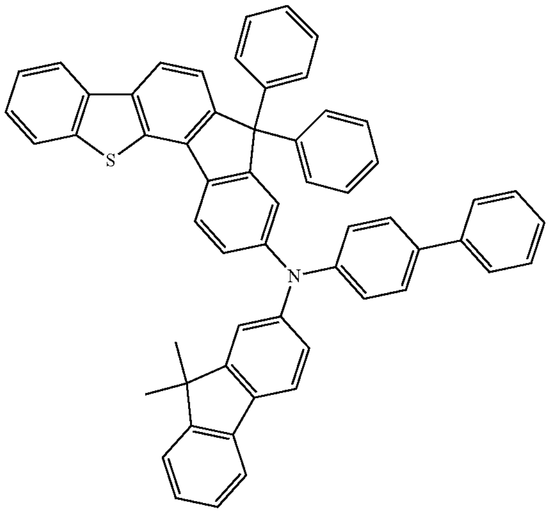
[A-60]
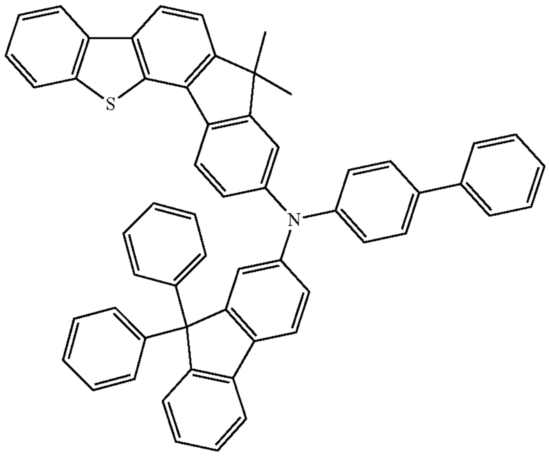
[A-61]
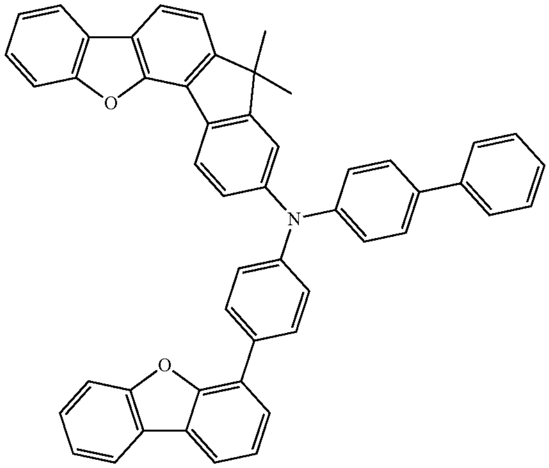
[A-62]
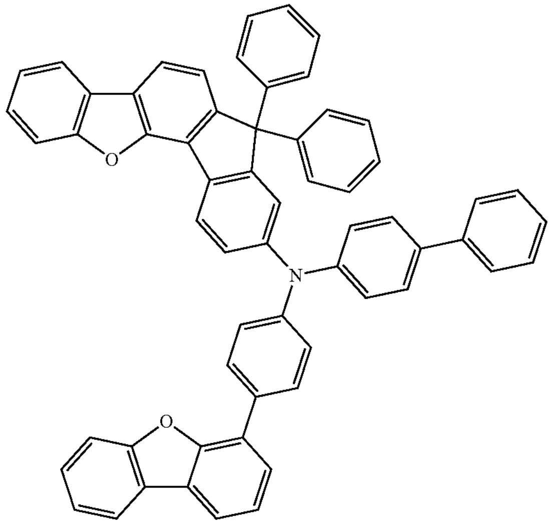
[A-63]
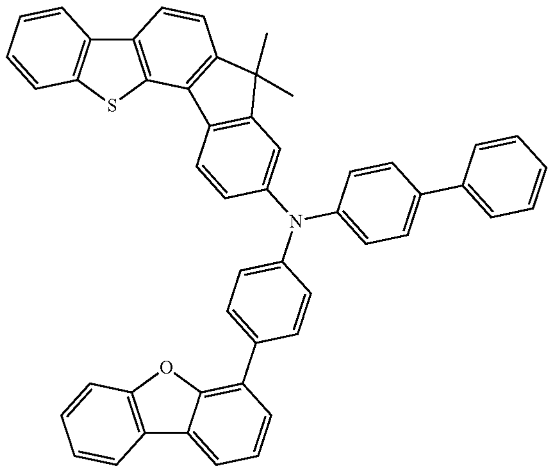
[A-64]
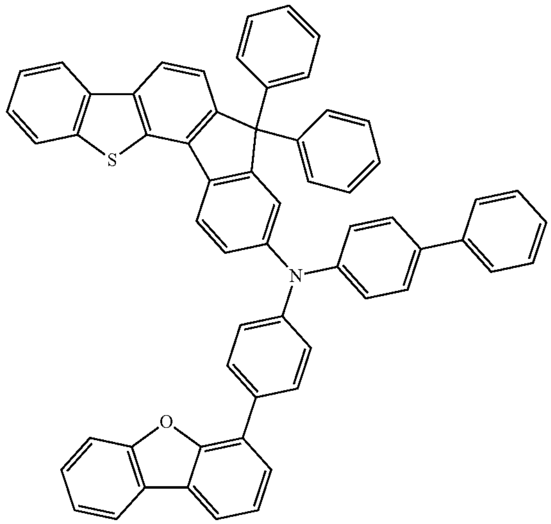

-continued
[A-65]
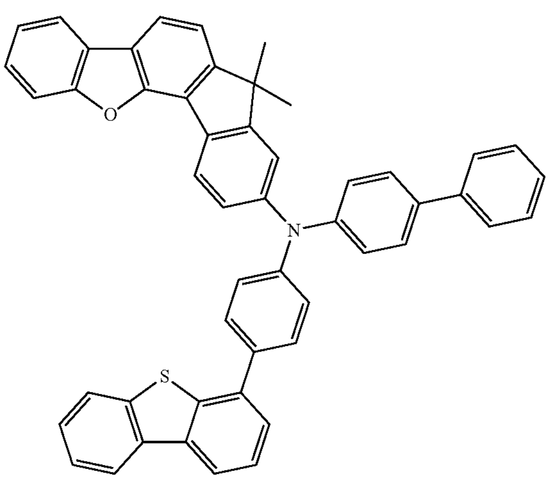
[A-66]
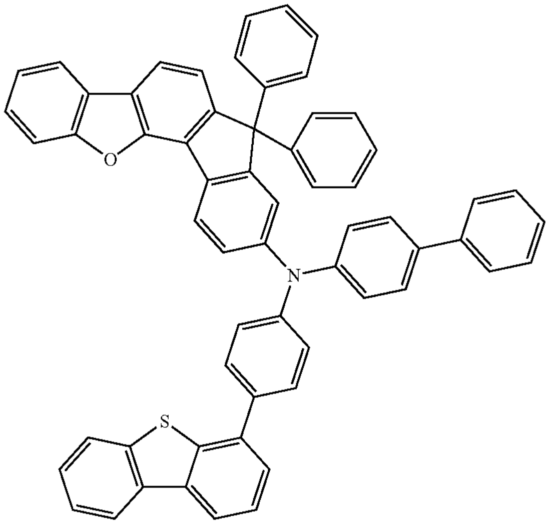
[A-67]
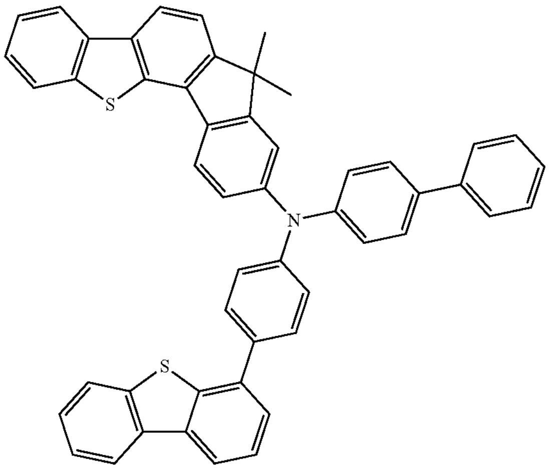
-continued
[A-68]
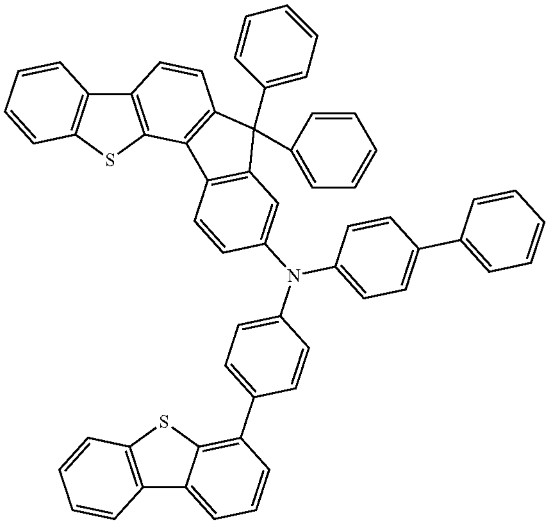
[A-69]
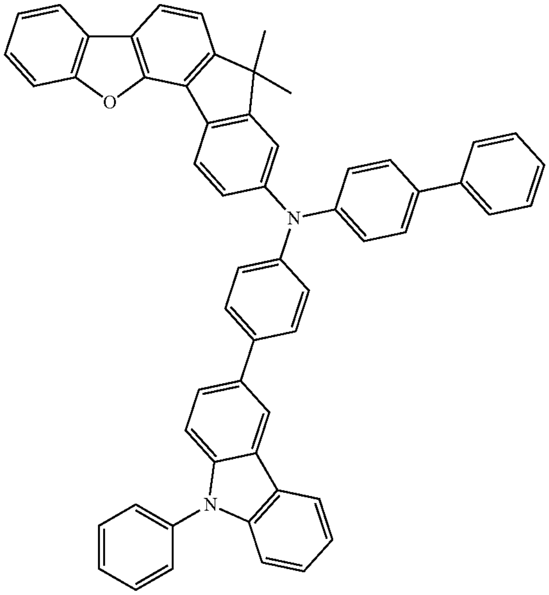

-continued
[A-70]
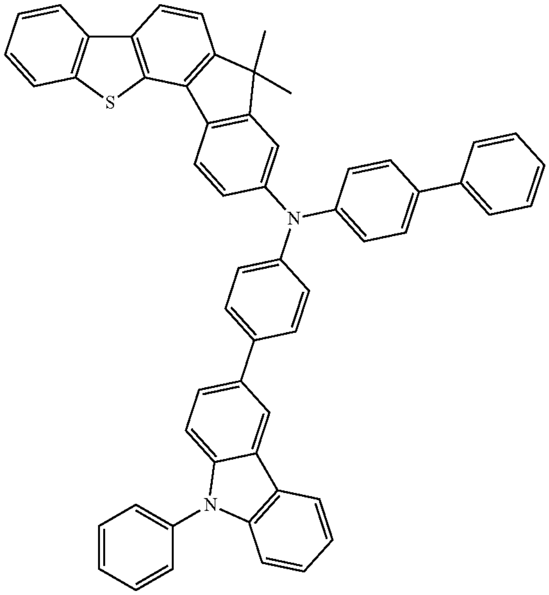
[A-71]
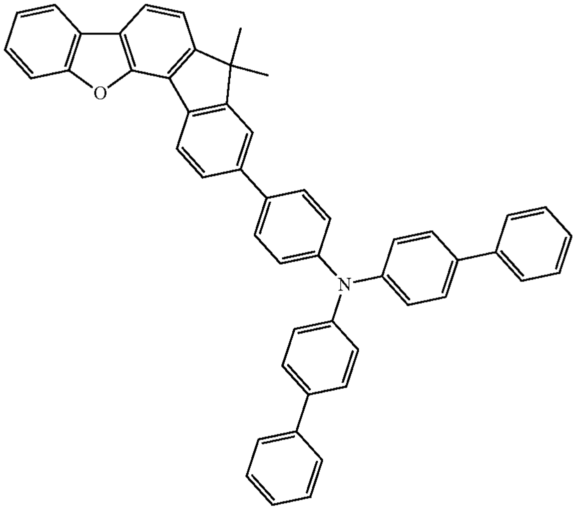
-continued
[A-72]
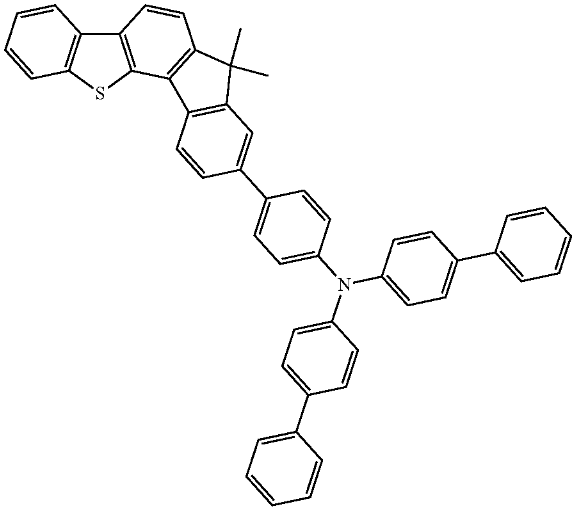
[A-73]
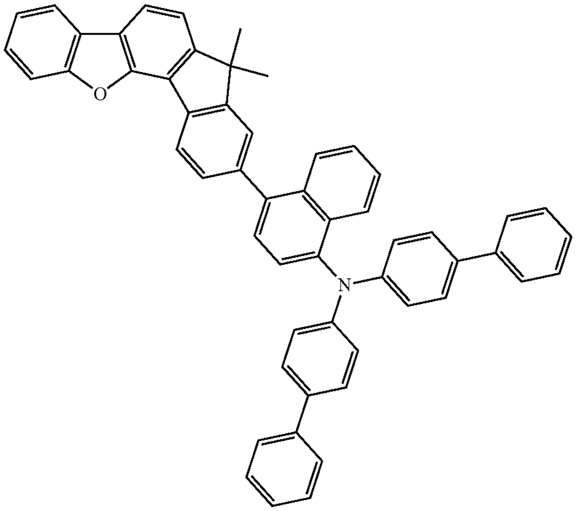
[A-74]
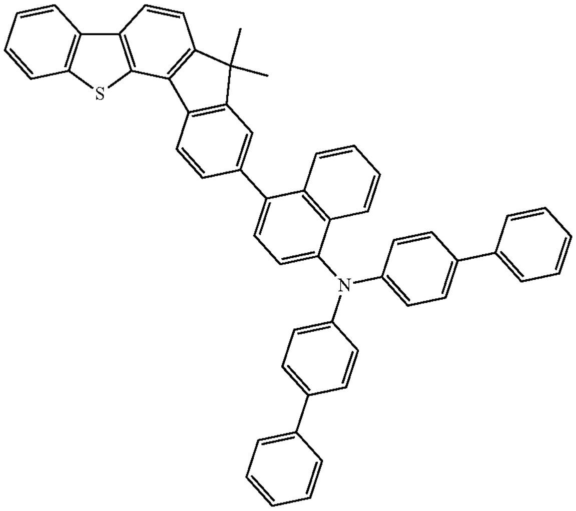

-continued
[A-75]
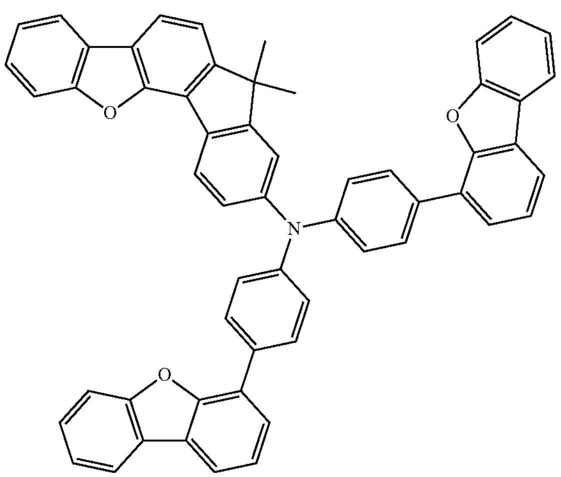
[A-76]
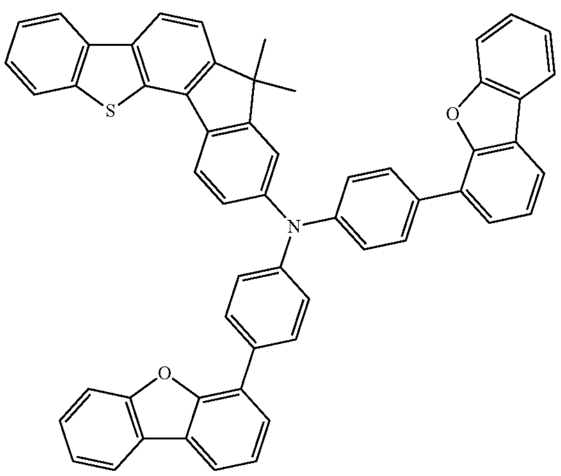
[A-77]
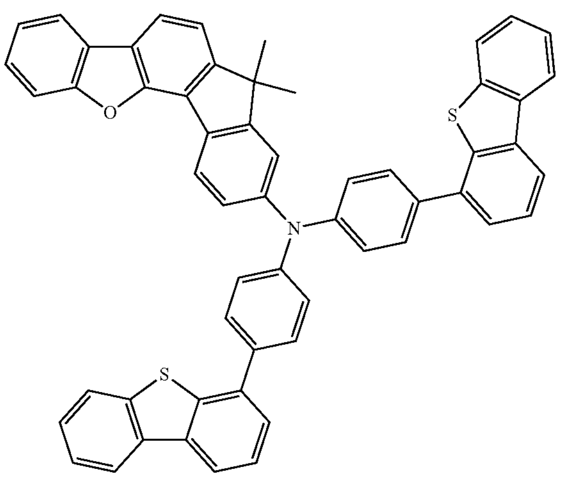
-continued
[A-78]
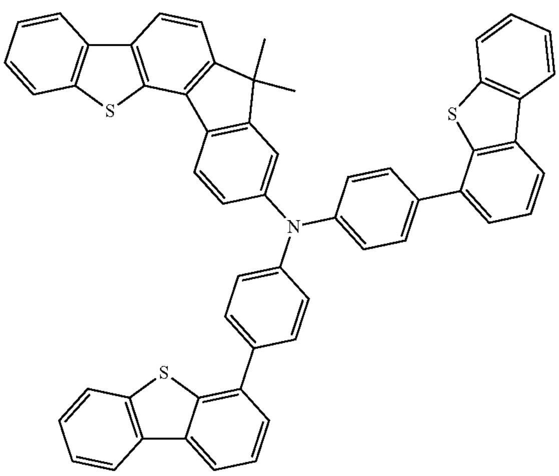
[A-79]
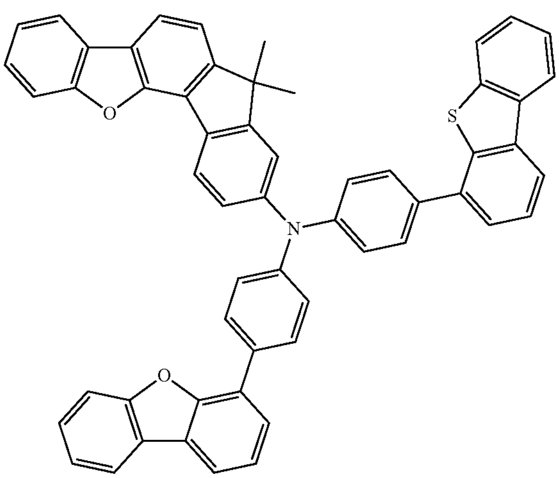
[A-80]
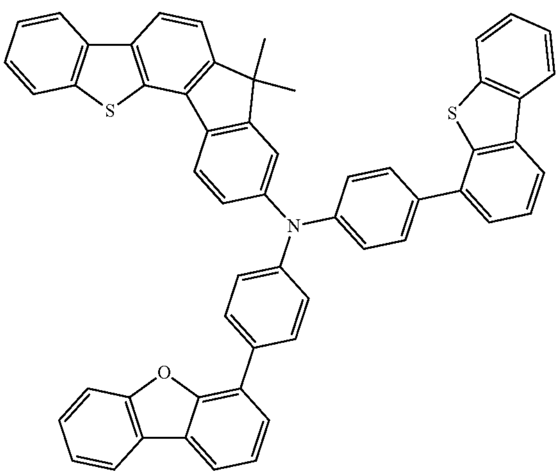

-continued
[A-81]
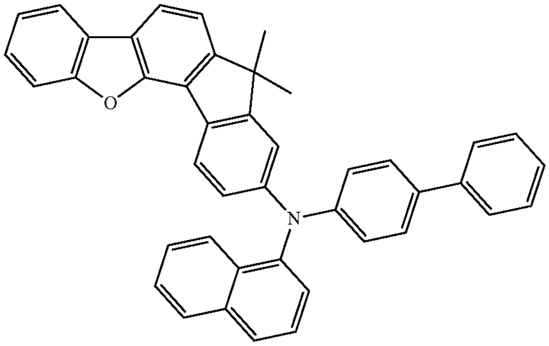
[A-82]
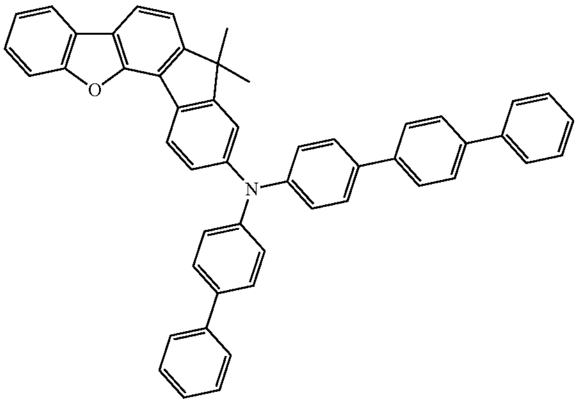
[A-83]
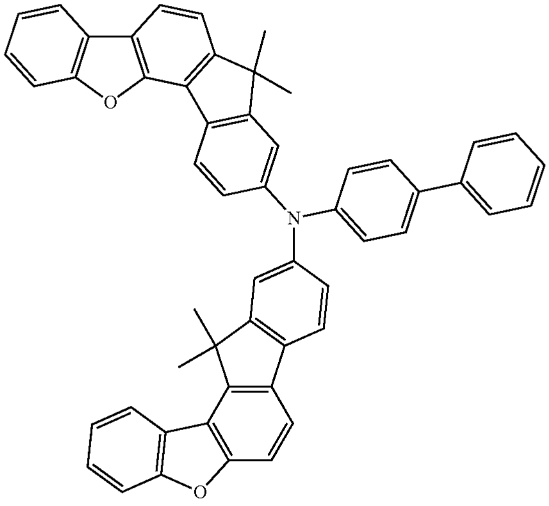
-continued
[A-84]
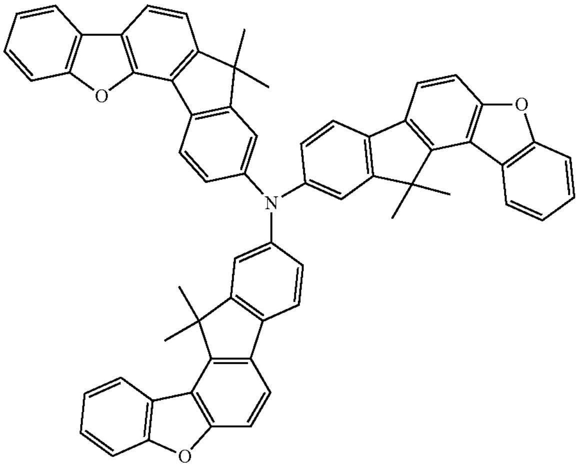
[A-85]
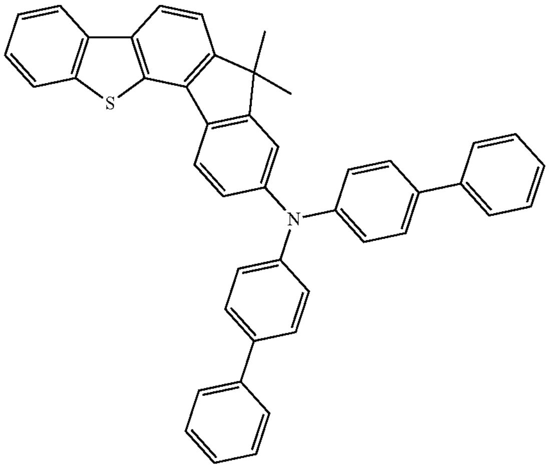
[A-86]
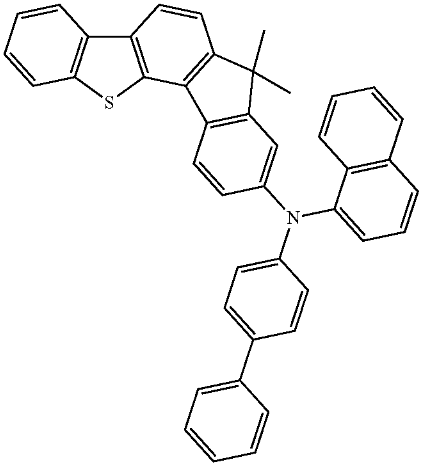

[A-87]
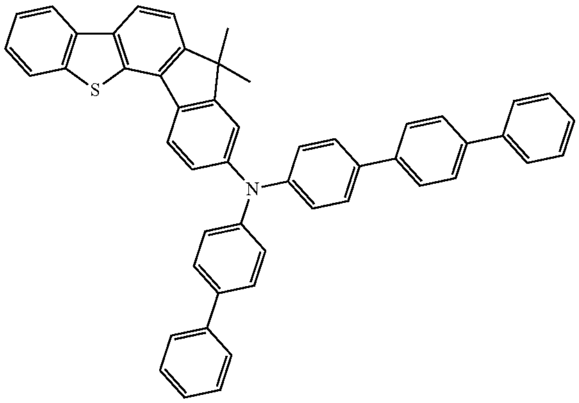
[A-88]
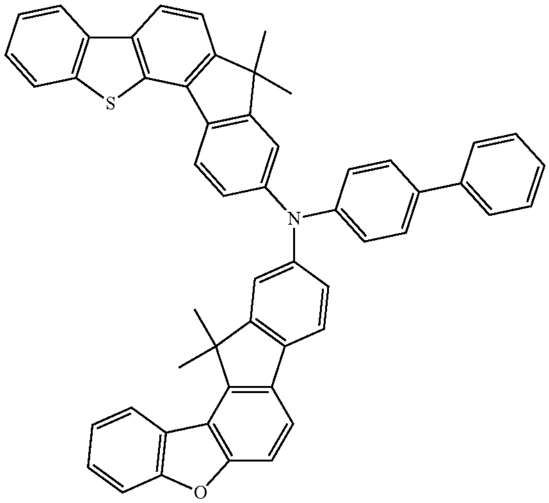
[A-89]
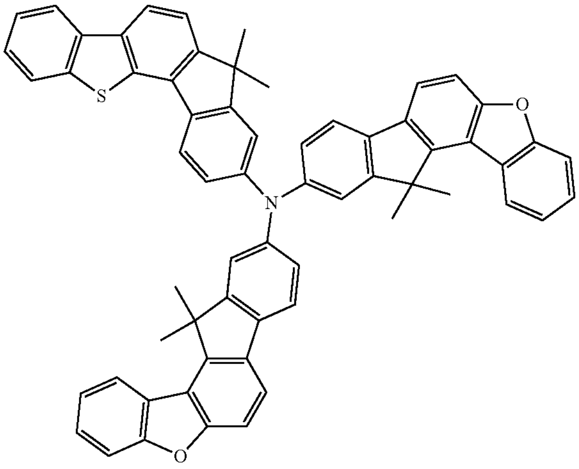
[A-90]
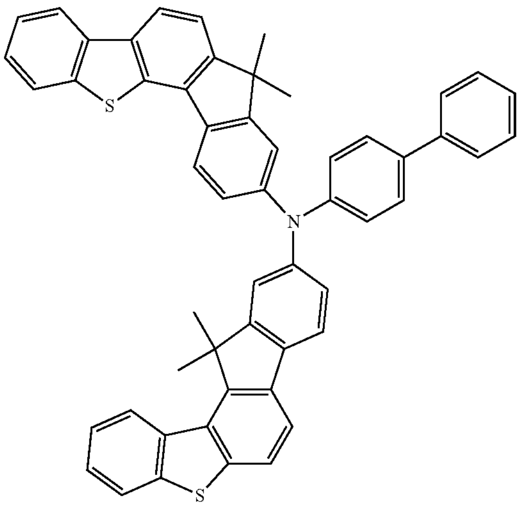
[A-91]
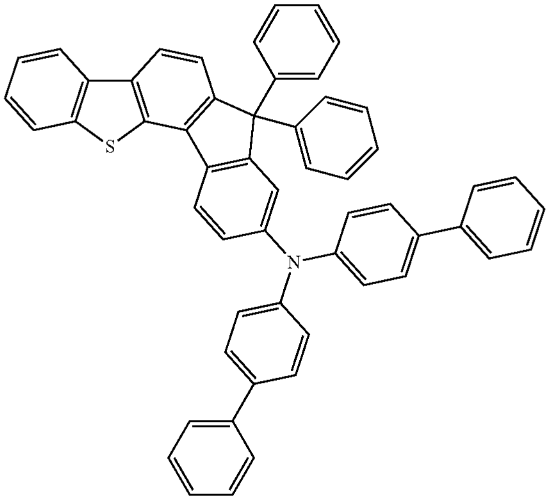
[A-92]
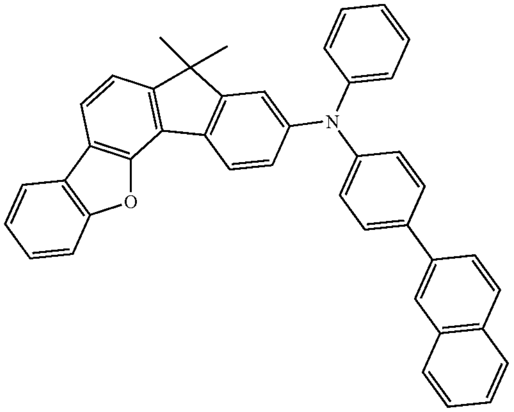

-continued
[A-93]
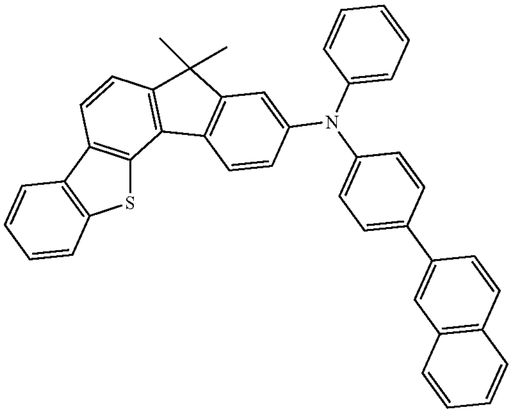
[A-94]
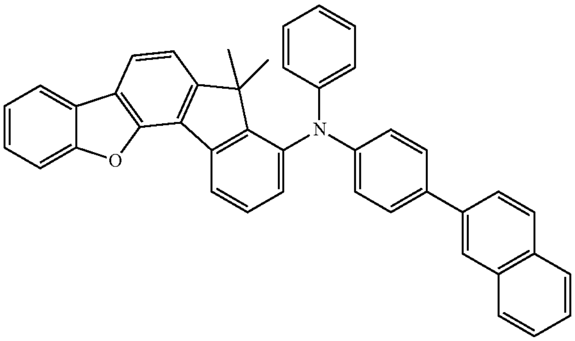
[A-95]
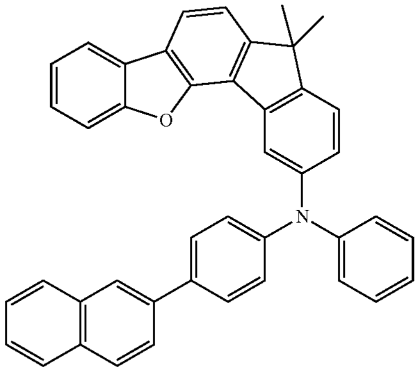
[A-96]
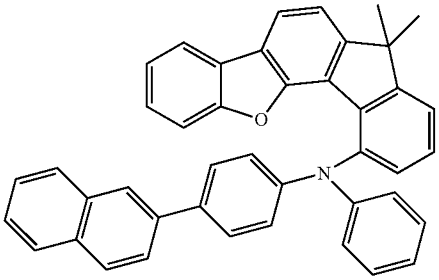
-continued
[A-97]
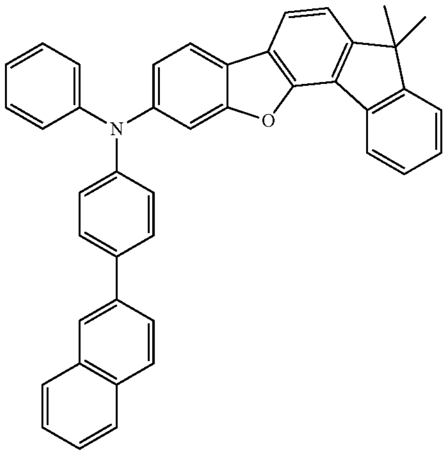
[A-98]
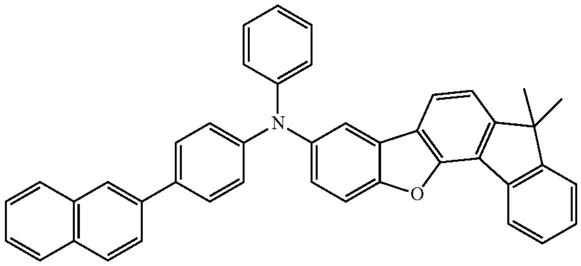
[A-99]
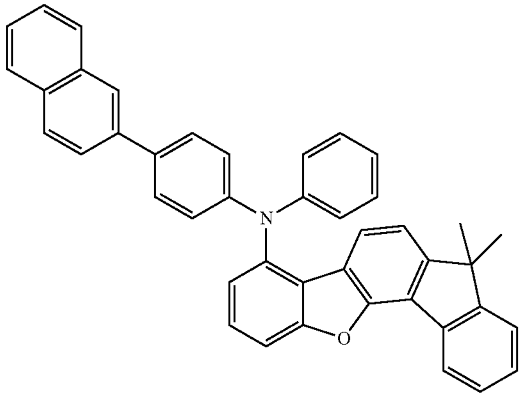
[A-100]
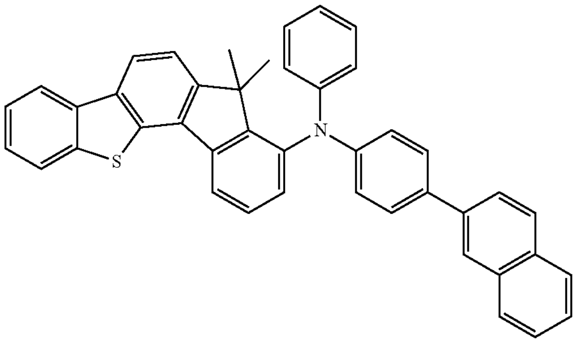

-continued
[A-101]
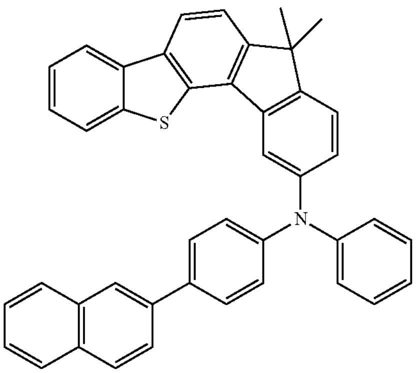
[A-102]
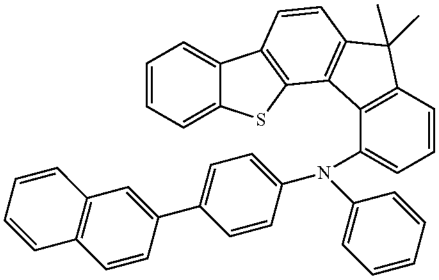
[A-103]
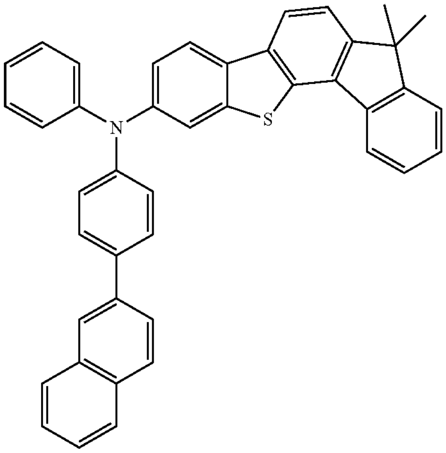
[A-104]
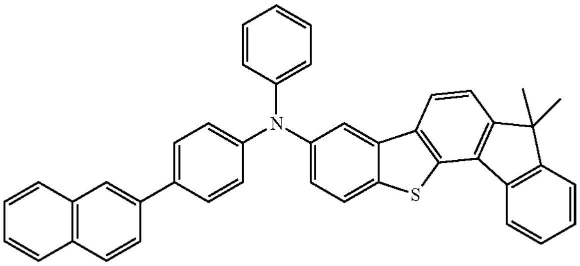
-continued
[A-105]
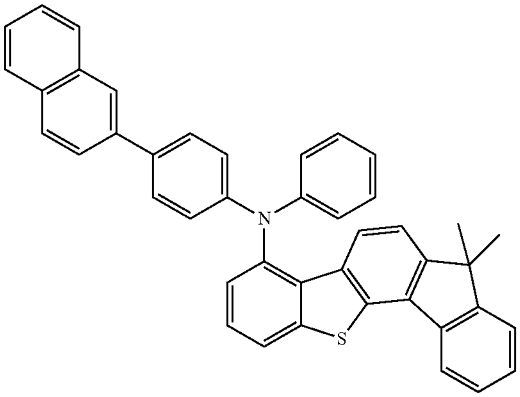
[A-106]
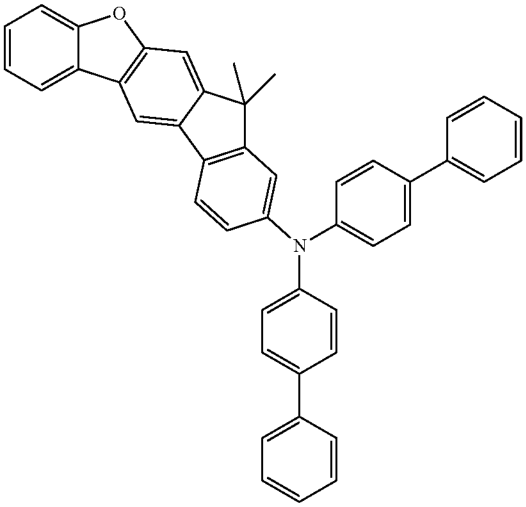
[A-107]
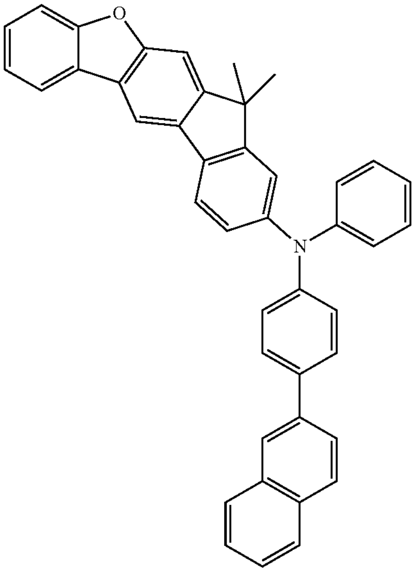

-continued
[A-108]
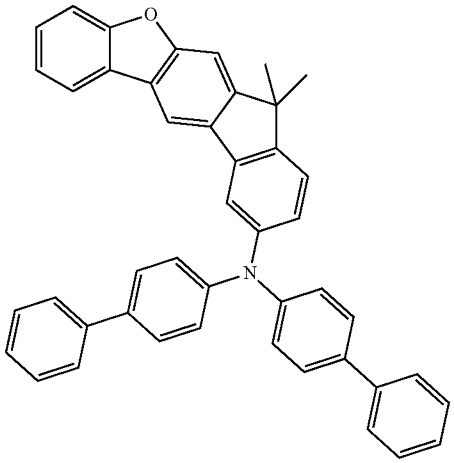
[A-109]
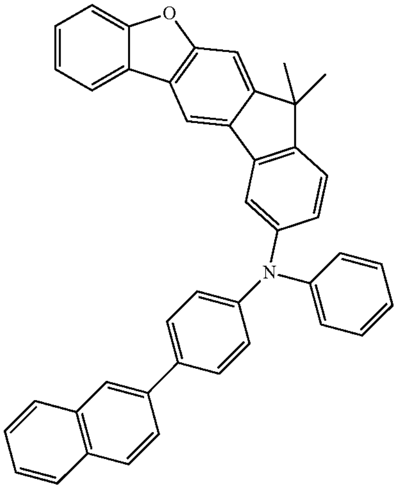
[A-110]
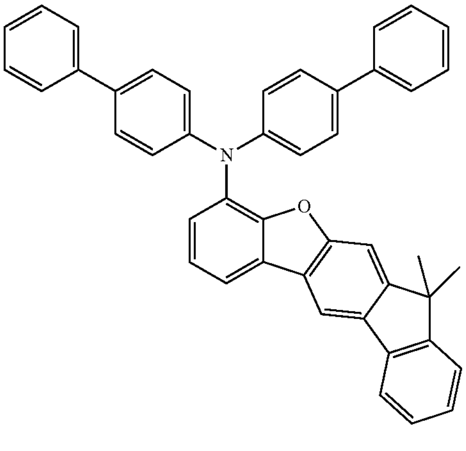
-continued
[A-111]
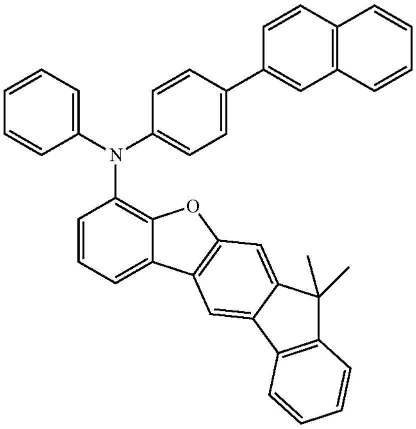
[A-112]
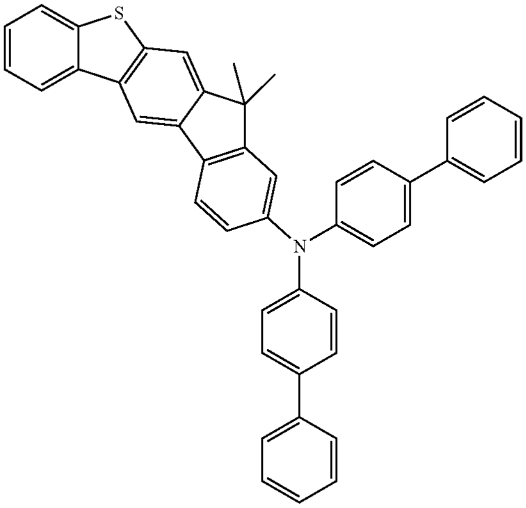
[A-113]
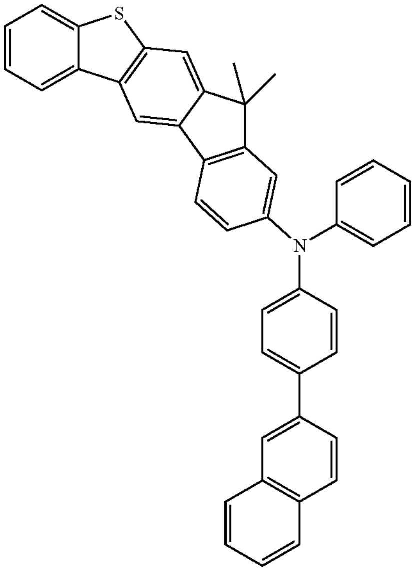

-continued
[A-114]
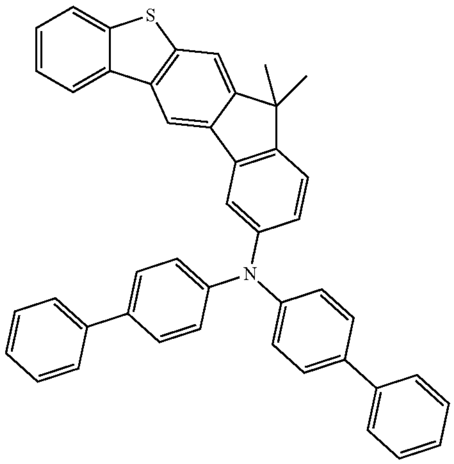
[A-115]
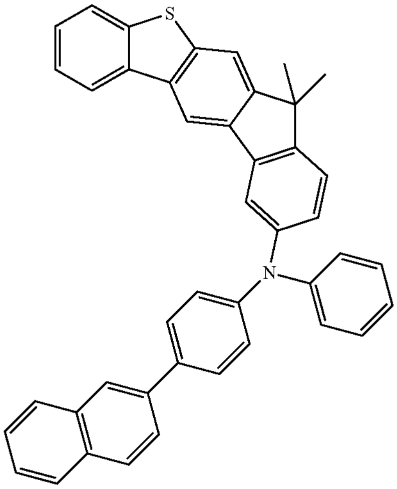
[A-116]
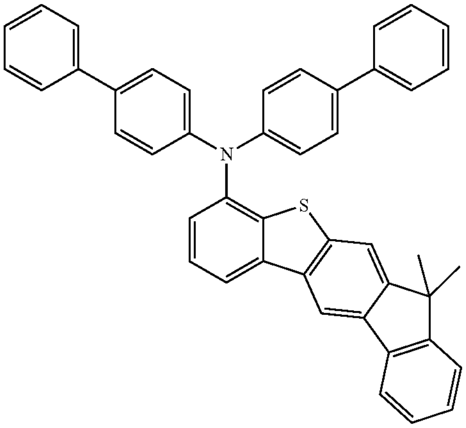
-continued
[A-117]
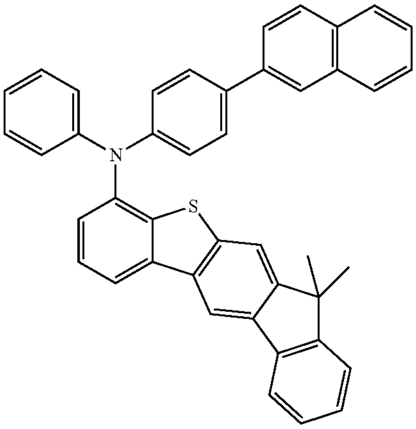
[A-118]
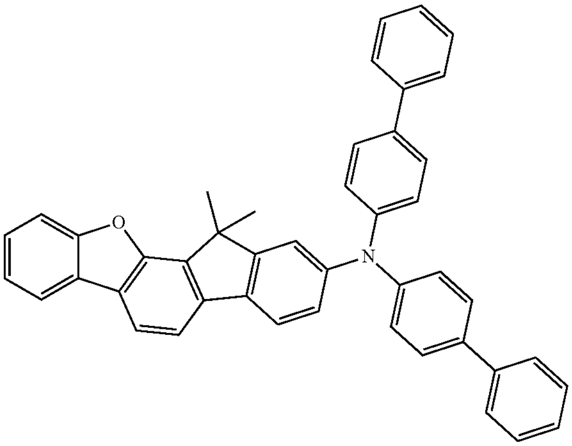
[A-119]
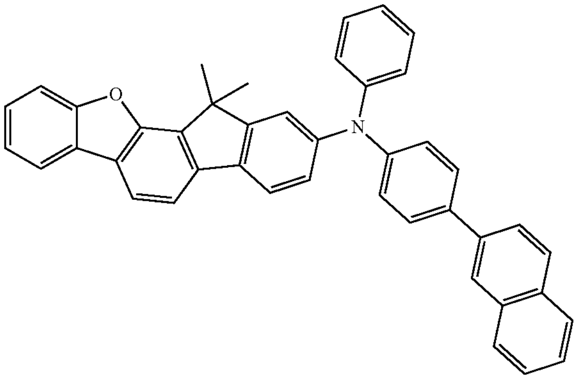

-continued
[A-120]
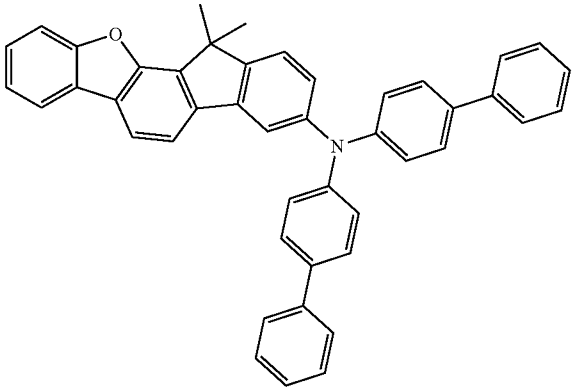
[A-121]
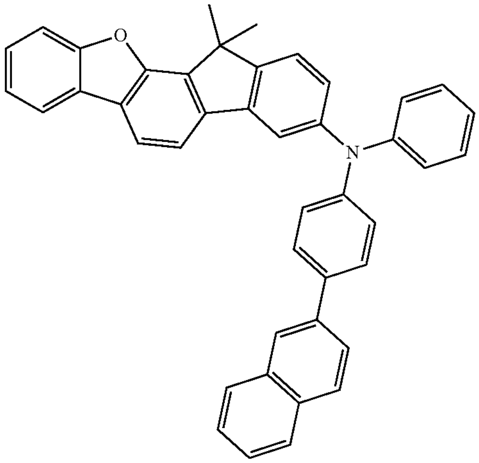
[A-122]
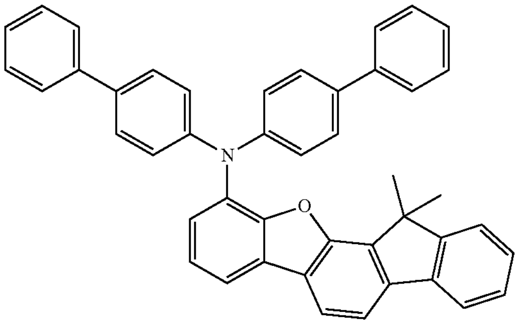
[A-123]
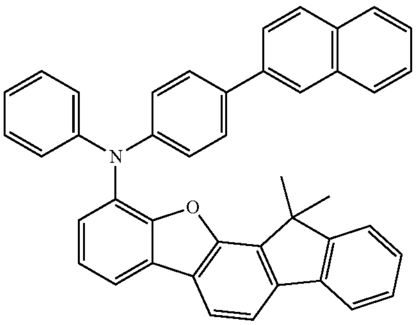
-continued
[A-124]
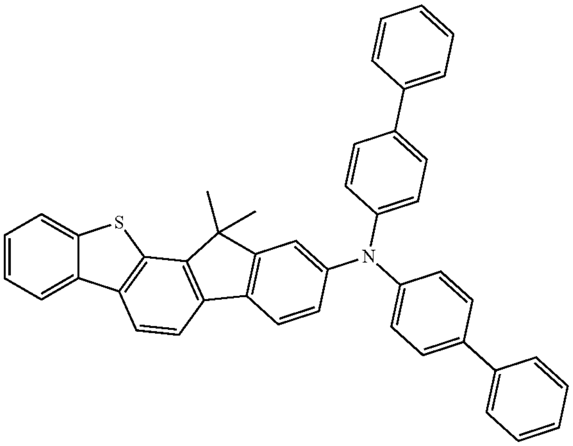
[A-125]
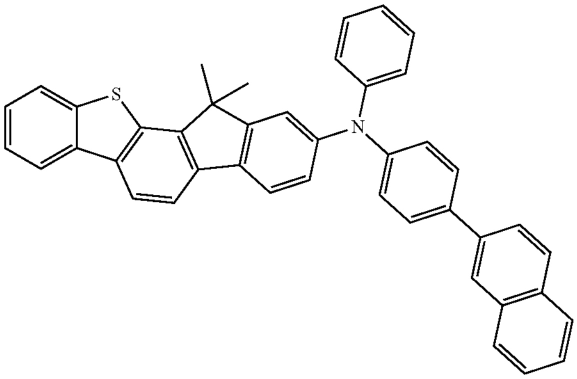
[A-126]
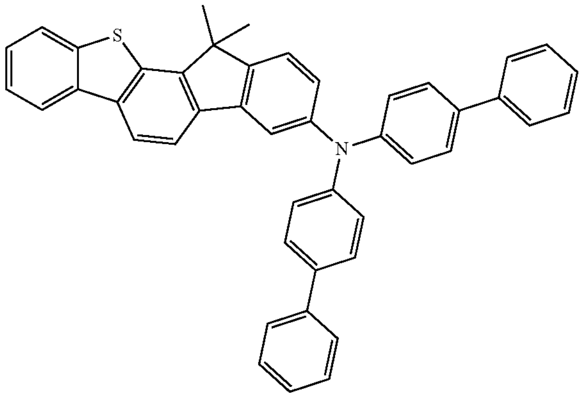

-continued
[A-127]
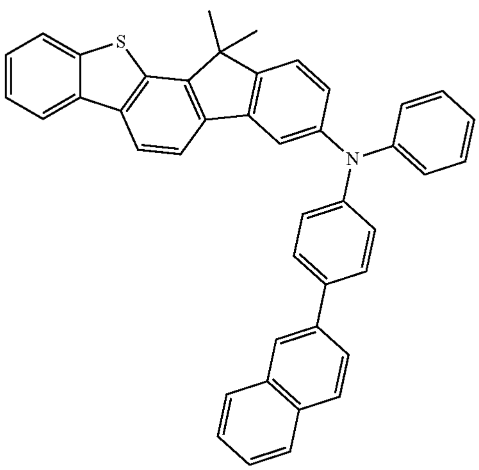
[A-128]
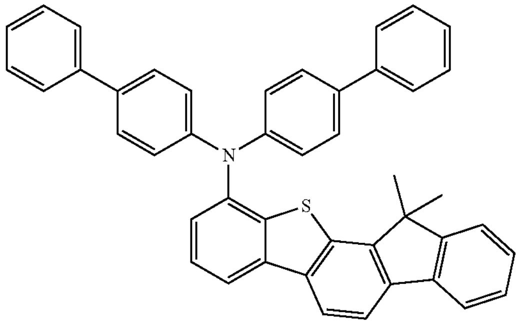
[A-129]
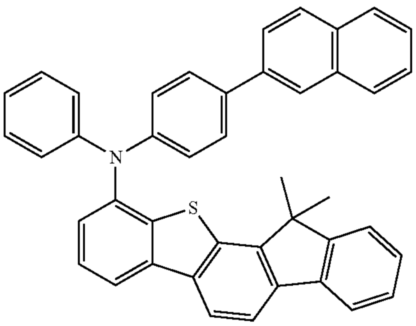
[A-130]
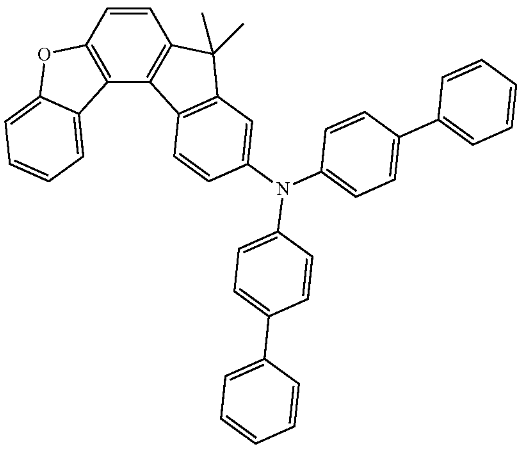
-continued
[A-131]
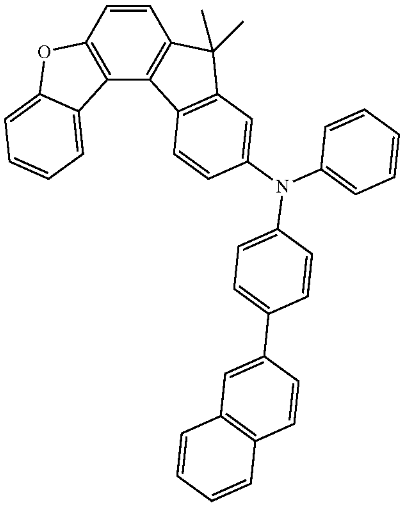
[A-132]
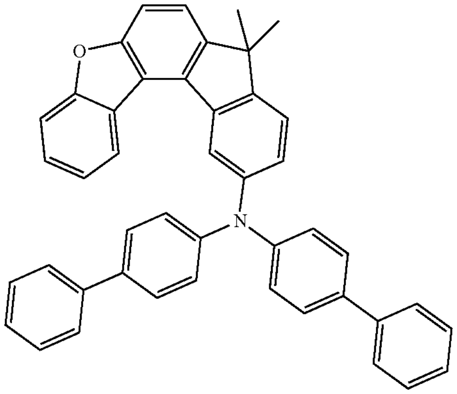
[A-133]
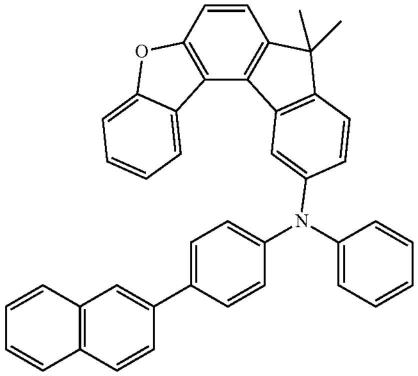

-continued
[A-134]
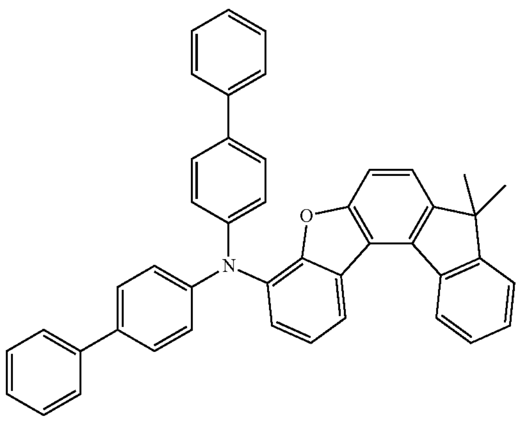
[A-135]
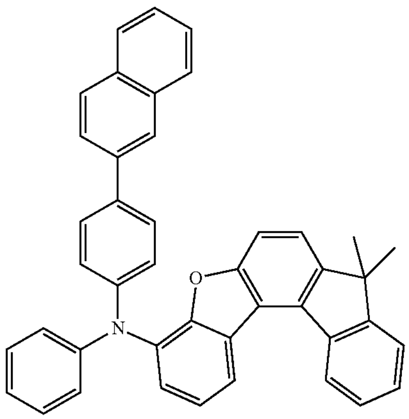
[A-136]
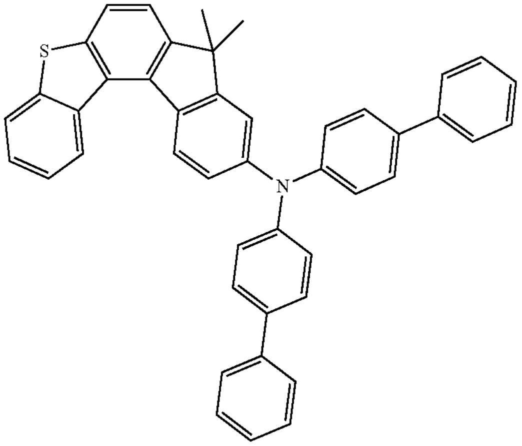
-continued
[A-137]
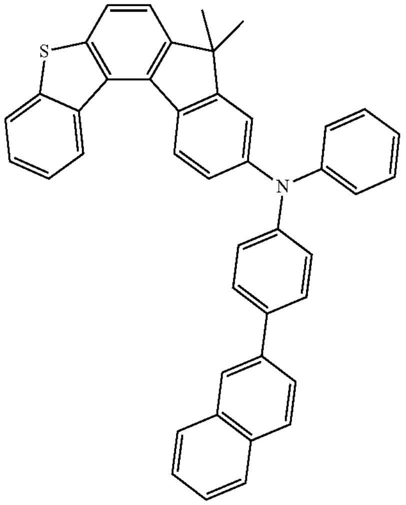
[A-138]
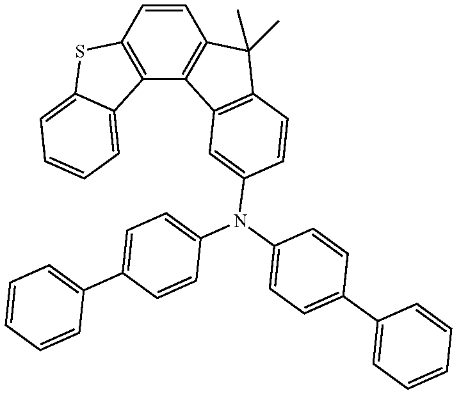
[A-139]
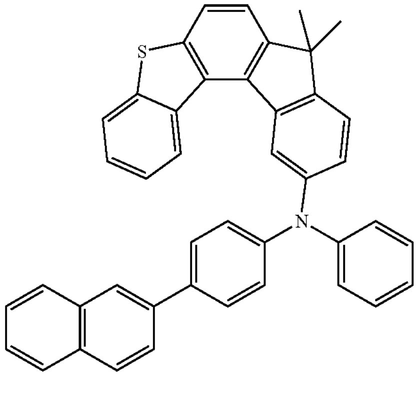

-continued
[A-140]
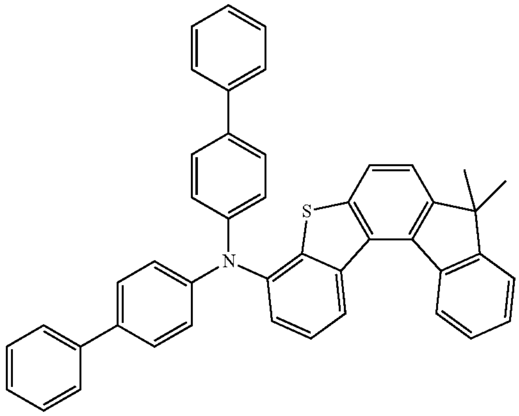
[A-141]
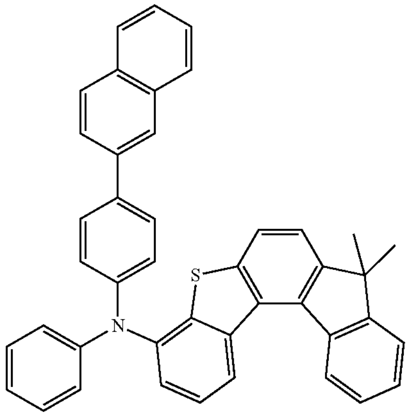
[A-142]
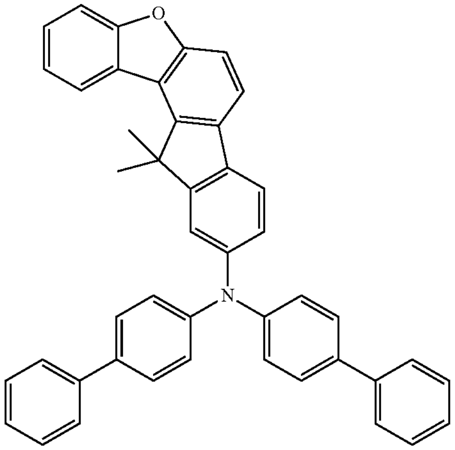
-continued
[A-143]
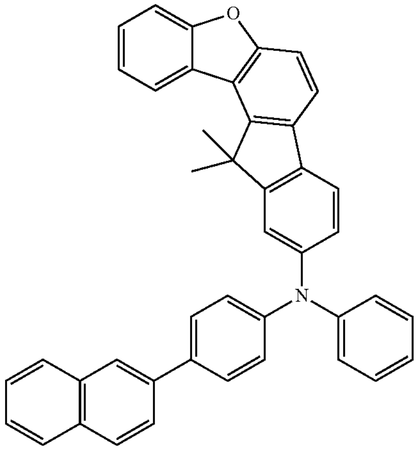
[A-144]
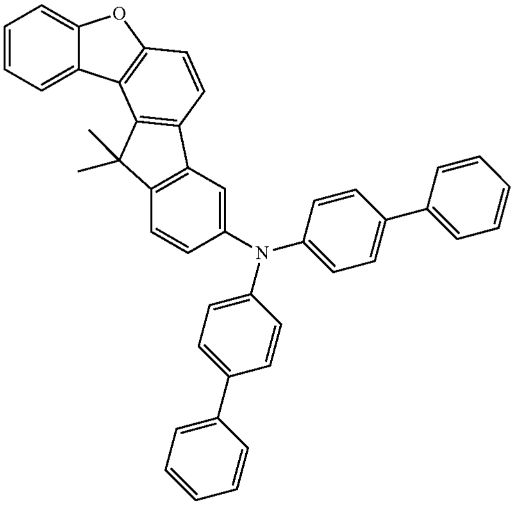
[A-145]
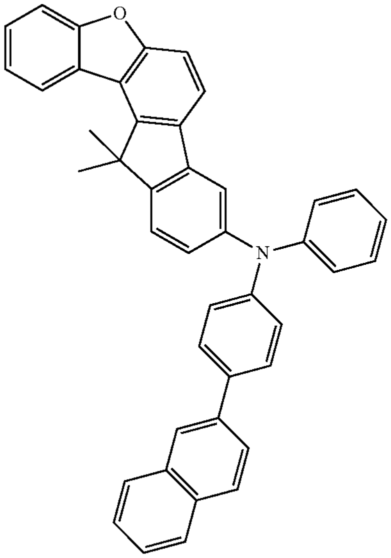

-continued
[A-146]
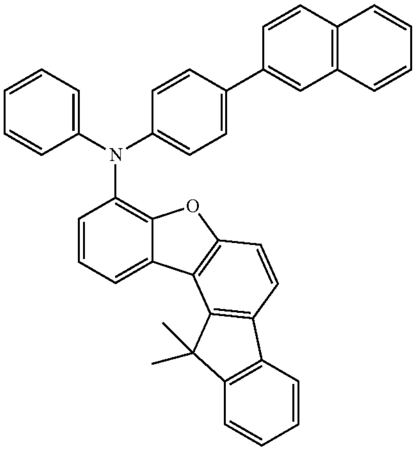
[A-147]
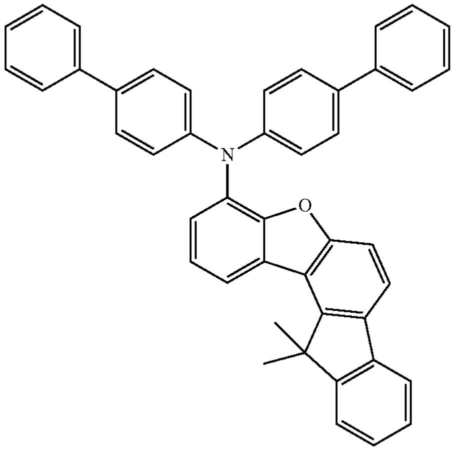
[A-148]
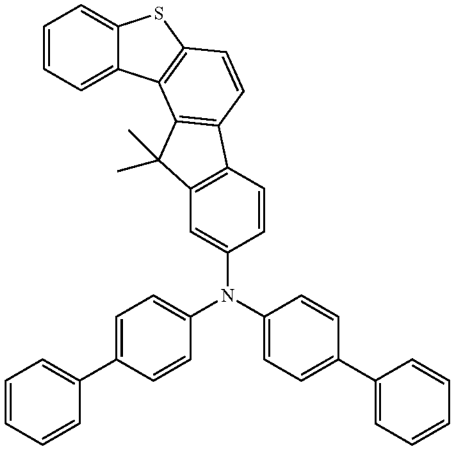
-continued
[A-149]
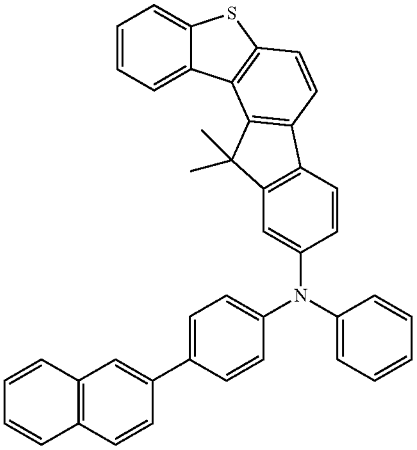
[A-150]
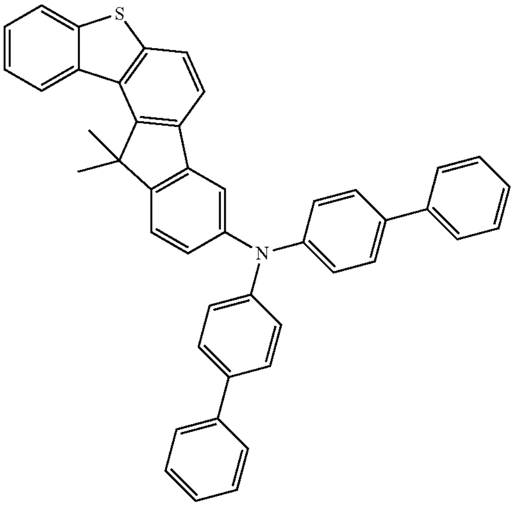
[A-151]
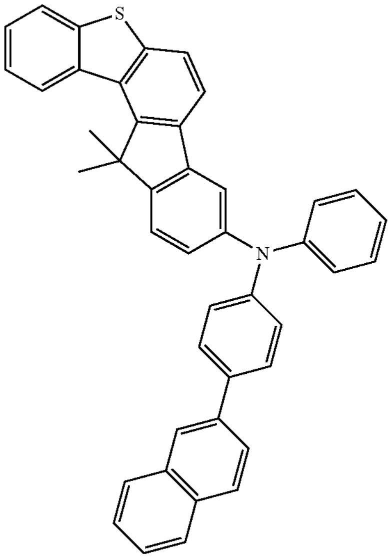

-continued
[A-152]
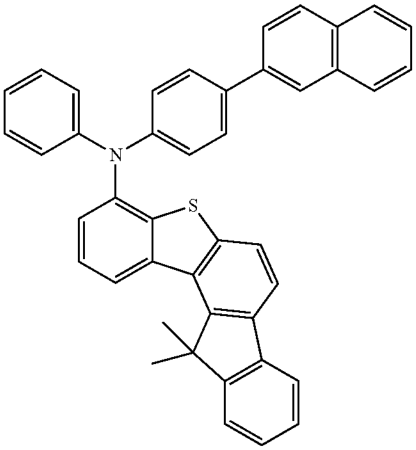
[A-153]
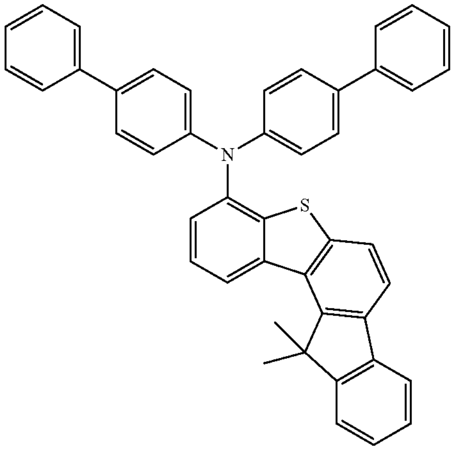
[A-154]
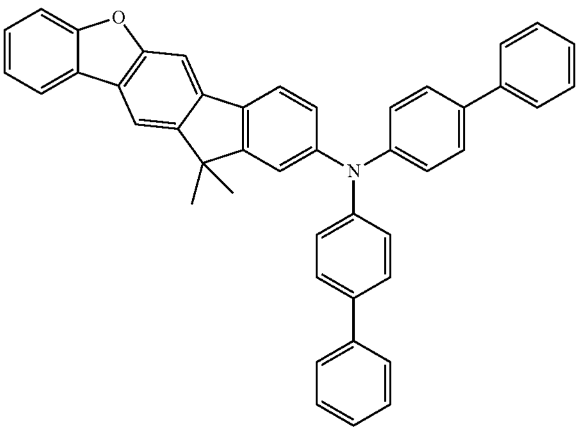
-continued
[A-155]
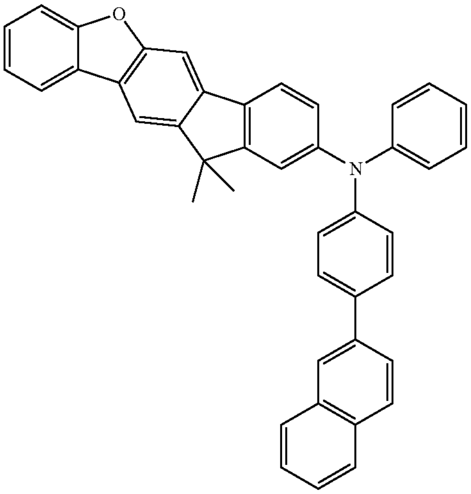
[A-156]
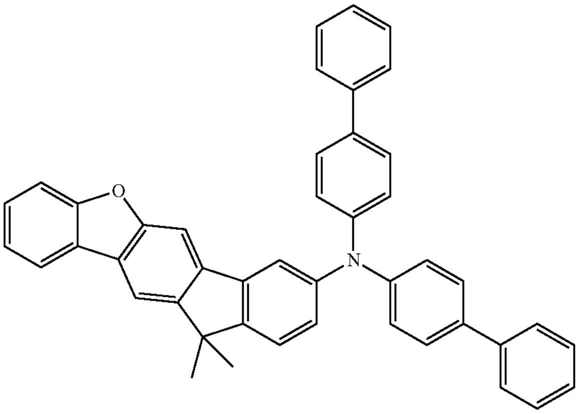
[A-157]
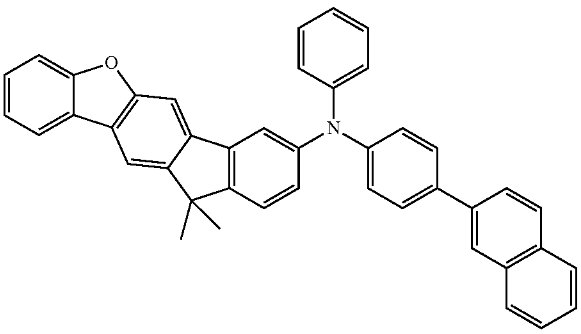

-continued
[A-158]
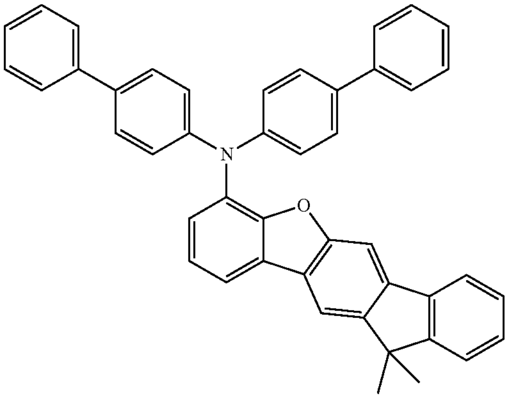
[A-159]
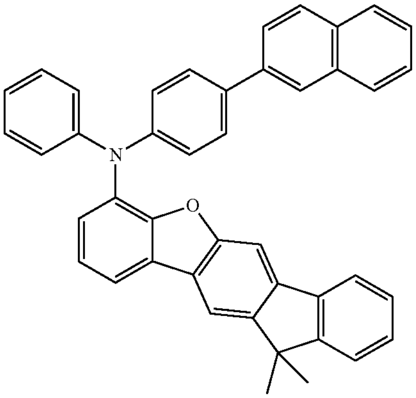
[A-160]
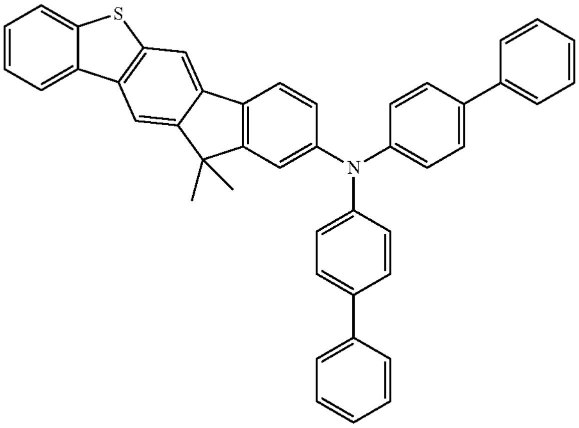
-continued
[A-161]
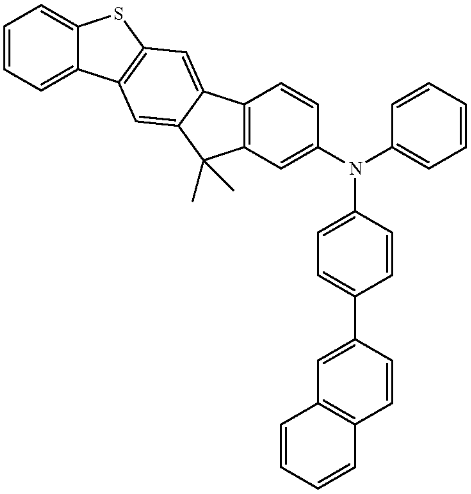
[A-162]
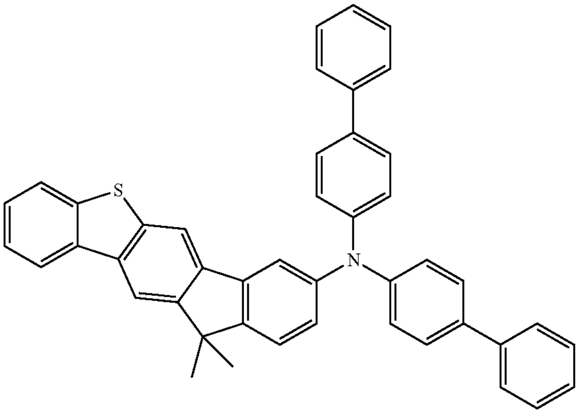
[A-163]
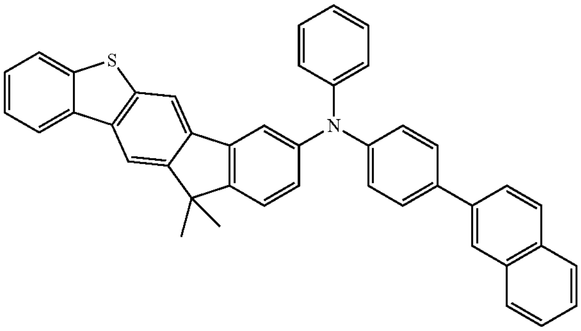

-continued

[A-164]

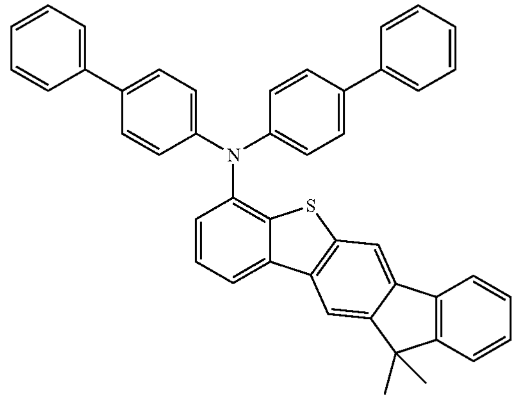

[A-165]

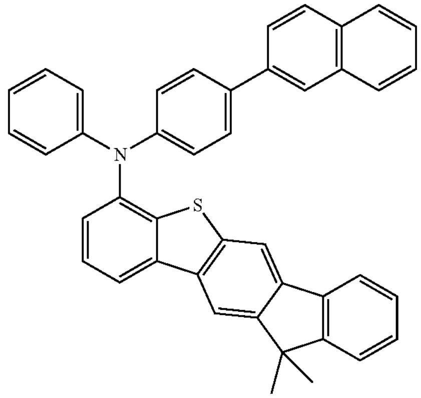

The first compound and the second compound may be included in the composition (e.g., mixed in) a weight ratio of, e.g., about 1:99 to about 99:1. Within the above range, bipolar characteristics may be implemented by adjusting an appropriate weight ratio using the electron transport capability of the first compound and the hole transport capability of the second compound, so that efficiency and life-span may be improved. Within the above range, the first compound and the second compound may be, e.g., included in a weight ratio of about 90:10 to 10:90, about 90:10 to 20:80, about 90:10 to 30:70, about 80:20 to 30:70, or about 70:30 to 30:70. In an implementation, the first compound and the second compound may be included in a weight ratio of about 60:40 to about 50:50, e.g., about 50:50.

In an implementation, the first compound and the second compound (e.g., the composition) may be a host of a light emitting layer, e.g., a phosphorescent host.

The aforementioned composition for an organic optoelectronic device may be formed into a film by a dry film forming method such as chemical vapor deposition.

Hereinafter, an organic optoelectronic device including the aforementioned composition for an organic optoelectronic device is described.

The organic optoelectronic device may be a suitable device to convert electrical energy into photoenergy and vice versa, e.g., an organic photoelectric device, an organic light emitting diode, an organic solar cell, or an organic photoconductor drum.

Herein, an organic light emitting diode as one example of an organic optoelectronic device is described referring to drawings.

Figure 2:
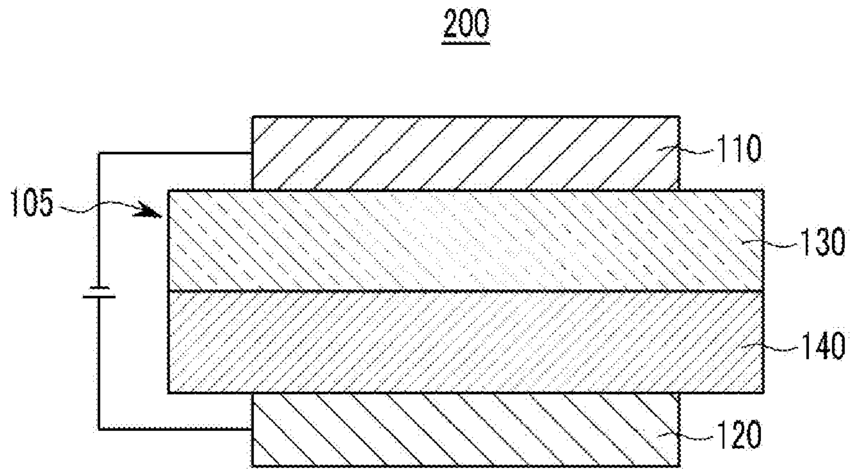

FIGS. 1 and 2 are cross-sectional views showing organic light emitting diodes according to embodiments.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; or a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; or a multi-layer structure material such as LiF/Al, $LiO_2$/Al, LiF/Ca or $BaF_2$/Ca.

The organic layer 105 may include the aforementioned composition for an organic optoelectronic device.

The organic layer 105 may include, e.g., a light emitting layer 130, and the light emitting layer 130 may include, e.g., the aforementioned composition for an organic optoelectronic device.

The light emitting layer 130 may include, e.g., the aforementioned composition for an organic optoelectronic device as a phosphorescent host.

In addition to the aforementioned host, the light emitting layer may further include one or more compounds.

The light emitting layer may further include a dopant. The dopant may be, e.g., a phosphorescent dopant. In an implementation, the dopant may be, e.g., a red, green or blue phosphorescent dopant. In an implementation, the dopant may be, e.g., a red phosphorescent dopant.

The composition for an organic optoelectronic device further including a dopant may be, e.g., a red light emitting composition.

A dopant is a material that emits light by being mixed in a small amount with a compound or composition for an organic optoelectronic device. The dopant may be a material such as a metal complex that emits light by multiple excitation into a triplet or more. The dopant may be, e.g., an inorganic, organic, or organic-inorganic compound, and may include one or two or more.

An example of the dopant may be a phosphorescent dopant, and examples of the phosphorescent dopant may include an organometallic compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$L^6MX^3$ [Chemical Formula Z]

In Chemical Formula Z, M may be, e.g., a metal, and $L^6$ and $X^3$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd or a combination thereof and $L^6$ and $X^3$ may be, e.g., a bidendate ligand.

In an implementation, the organic layer may further include an auxiliary layer in addition to the light emitting layer.

The auxiliary layer may be, e.g., a hole auxiliary layer 140.

Referring to FIG. 2, an organic light emitting diode 200 may further include a hole auxiliary layer 140 in addition to the light emitting layer 130. The hole auxiliary layer 140 may help further increase hole injection and/or hole mobility, and may help block electrons between the anode 120 and the light emitting layer 130.

The hole auxiliary layer 140 may include, e.g., a compound of Group A.

In an implementation, the hole auxiliary layer 140 may include a hole transport layer between the anode 120 and the light emitting layer 130 and a hole transport auxiliary layer between the light emitting layer 130 and the hole transport layer, and a compound of Group A may be included in the hole transport auxiliary layer.

[Group A]

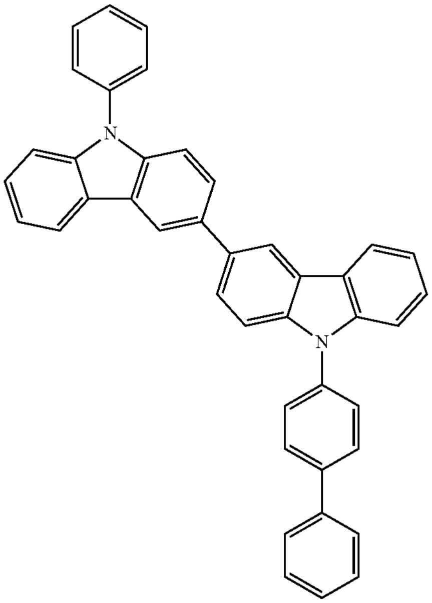

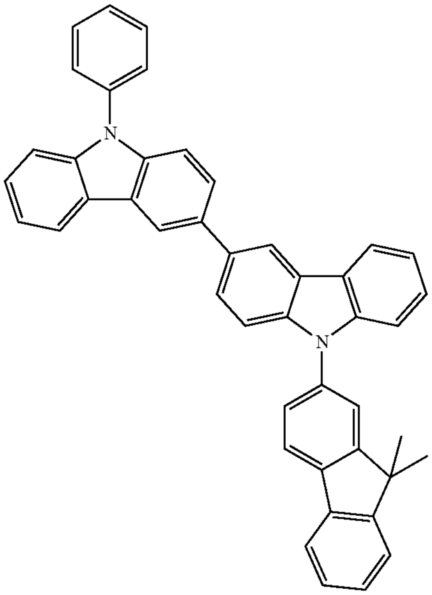

-continued

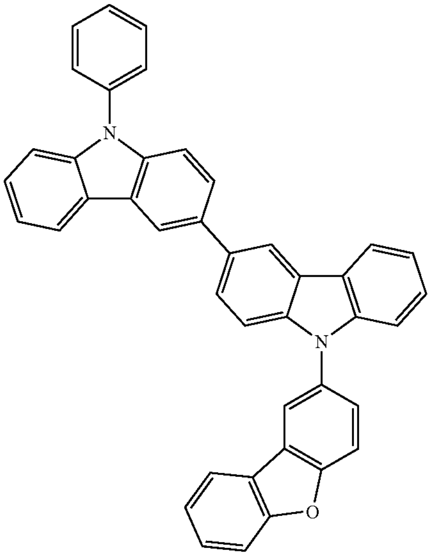

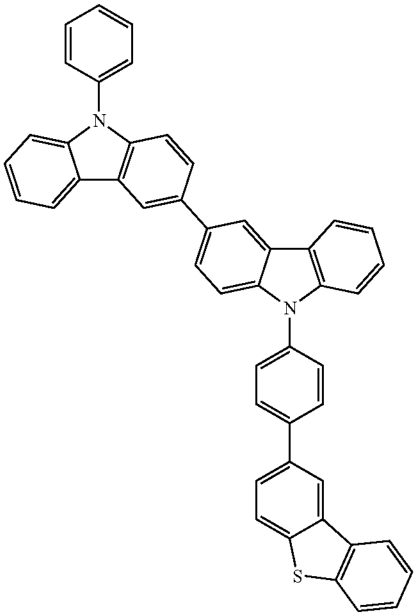

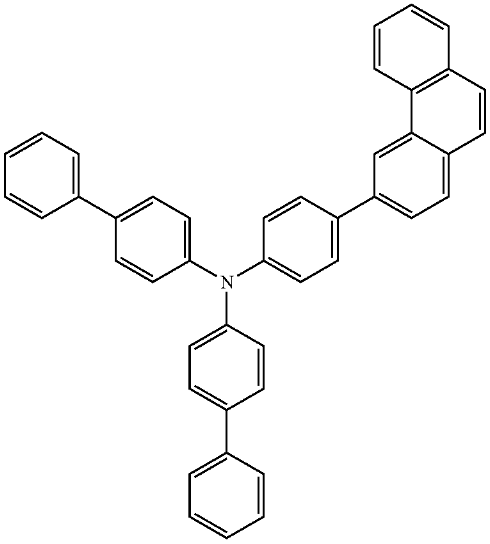

-continued
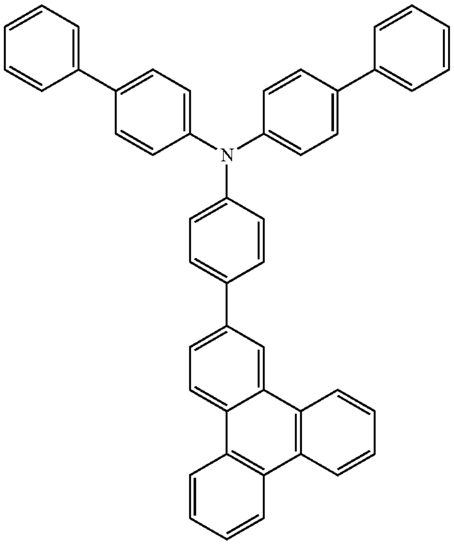
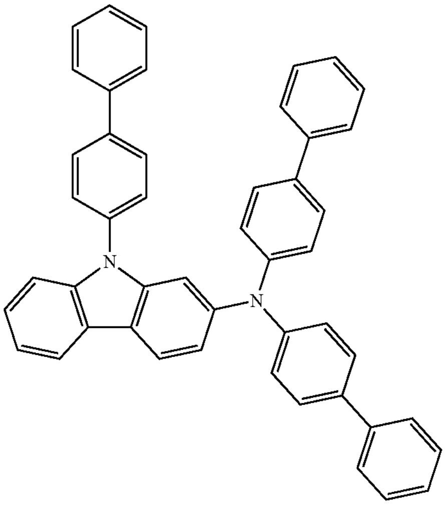
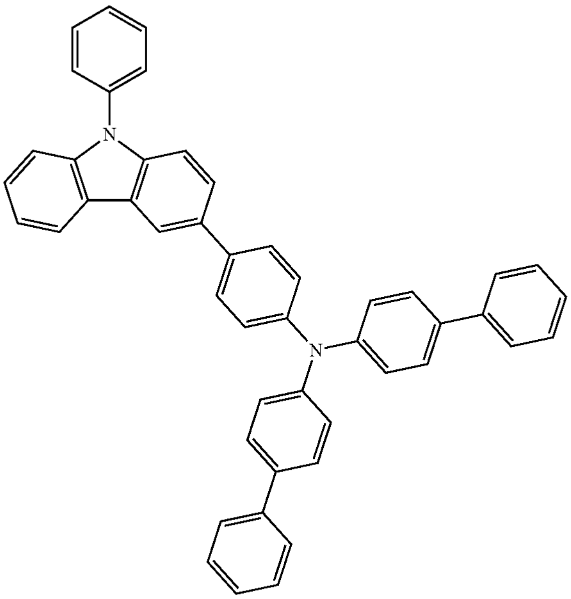
-continued
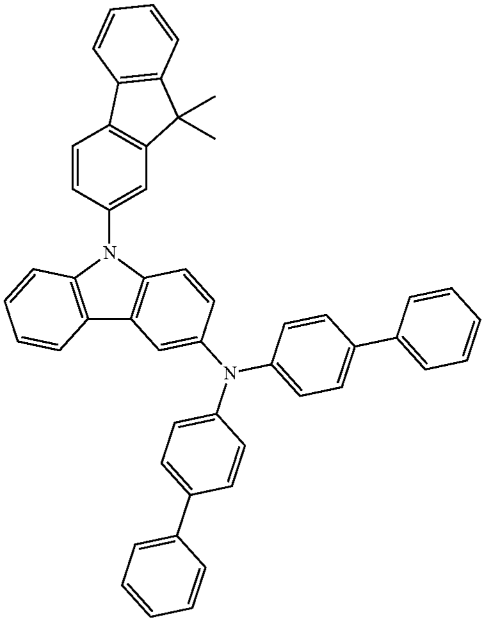
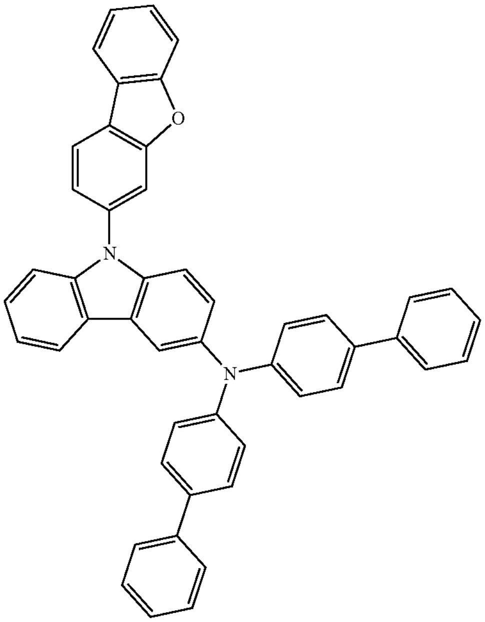

-continued
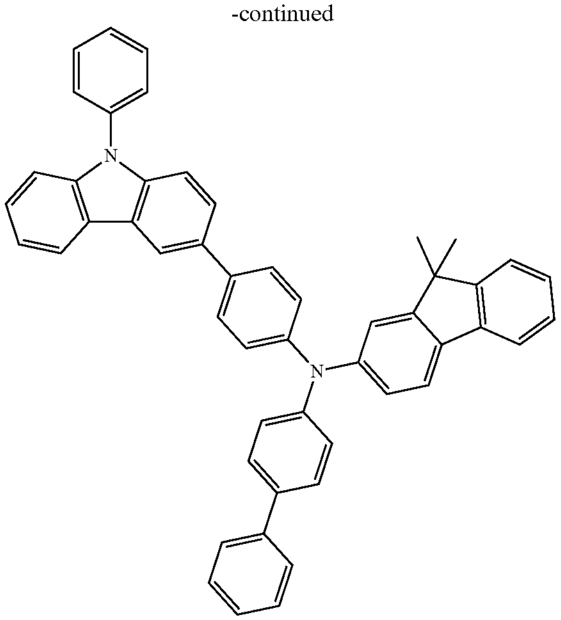
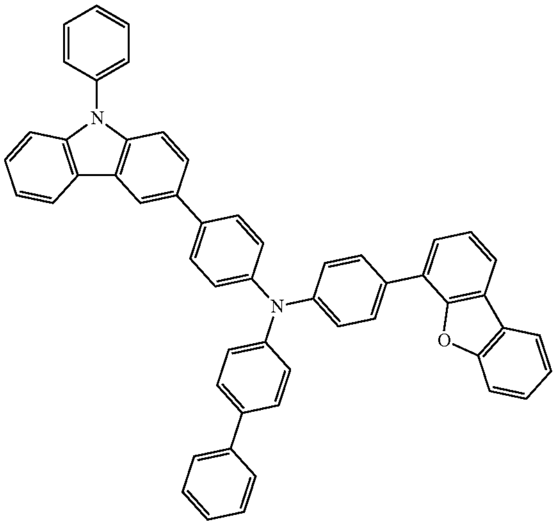
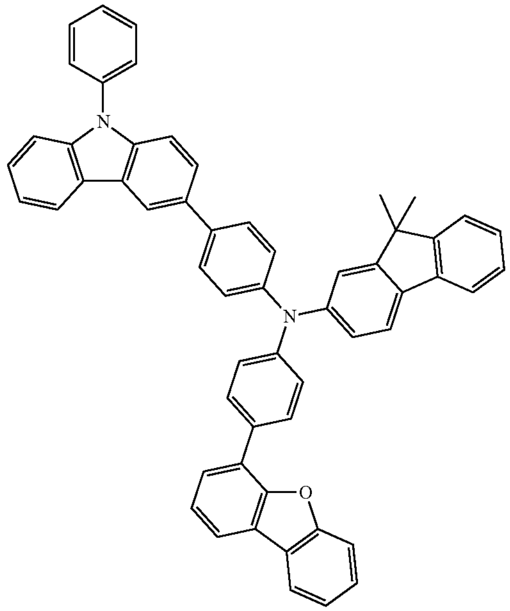
-continued
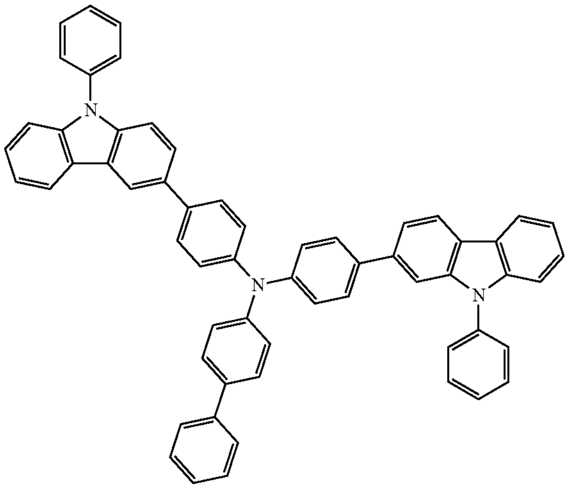
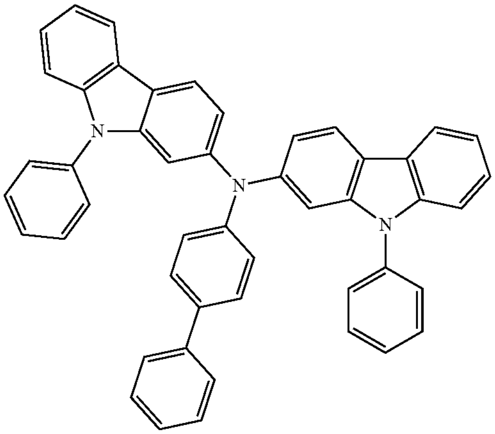
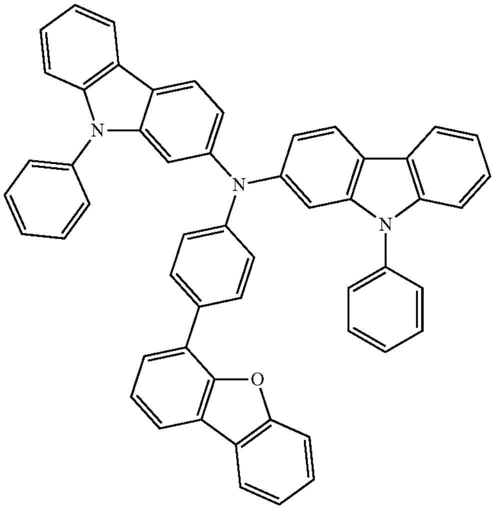

-continued
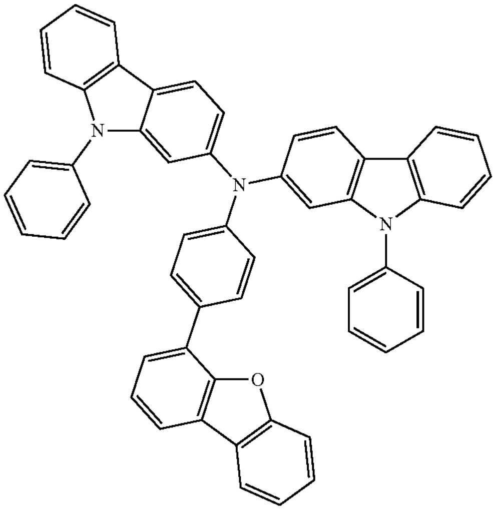
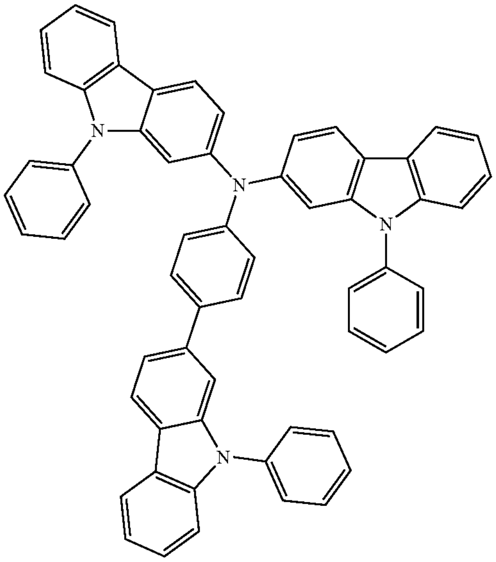
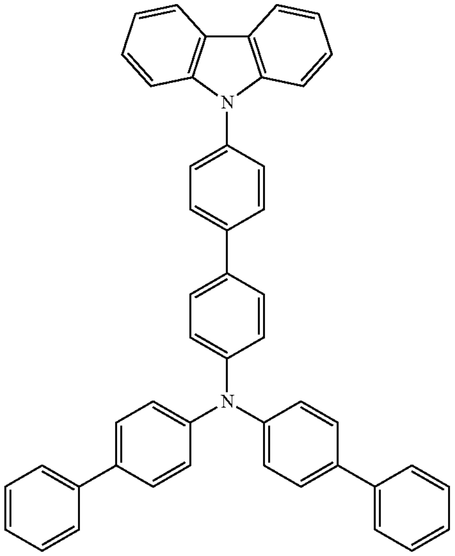
-continued
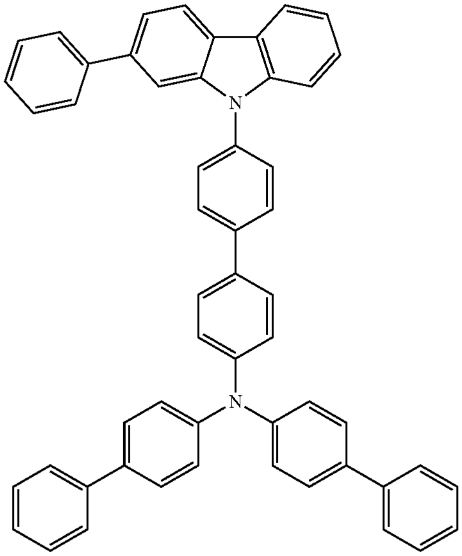
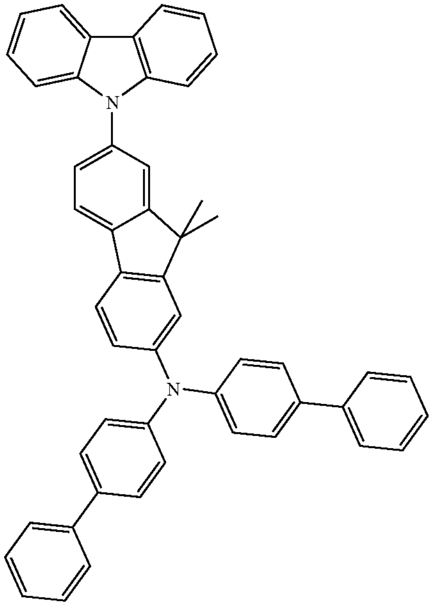
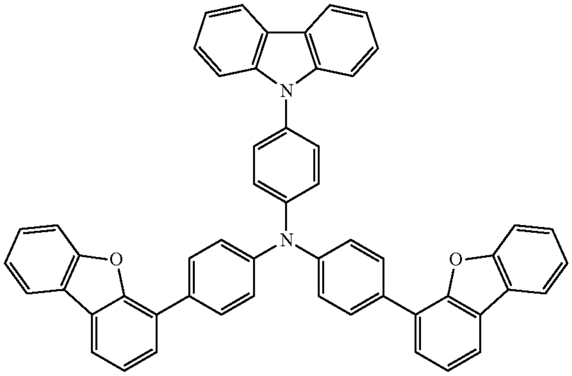

-continued
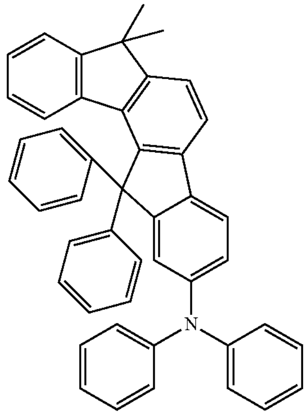
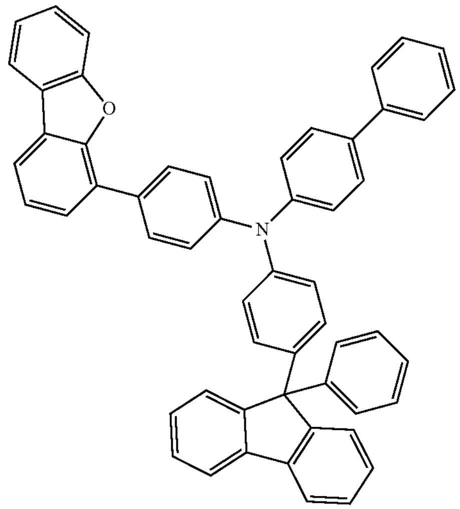
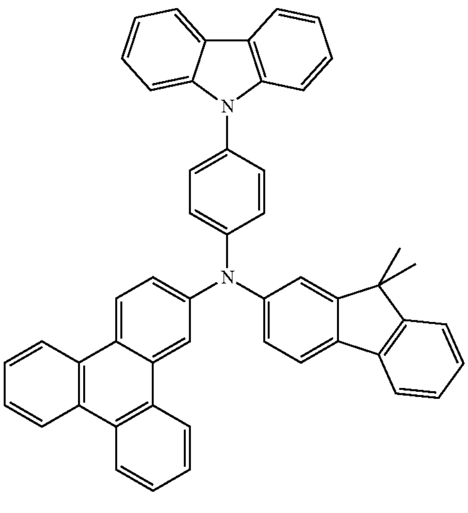
-continued
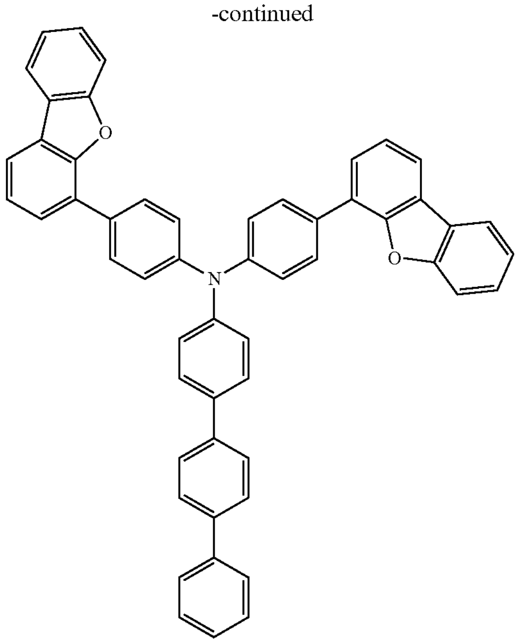
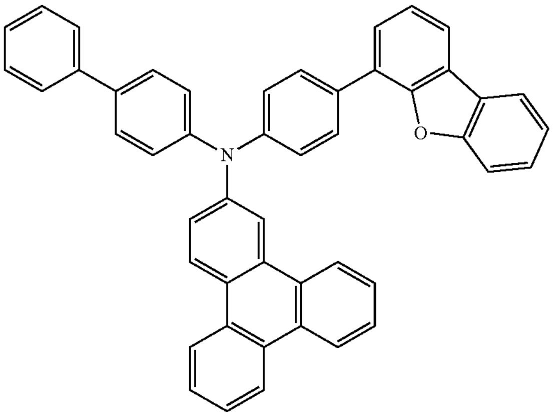
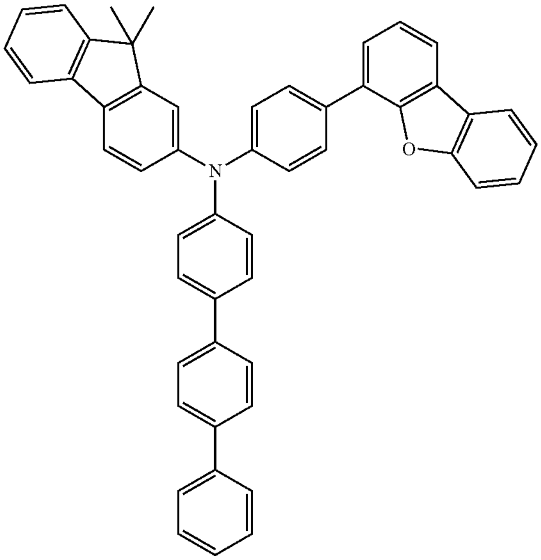

-continued
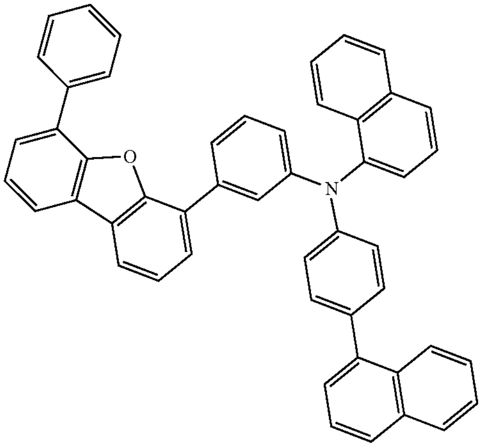
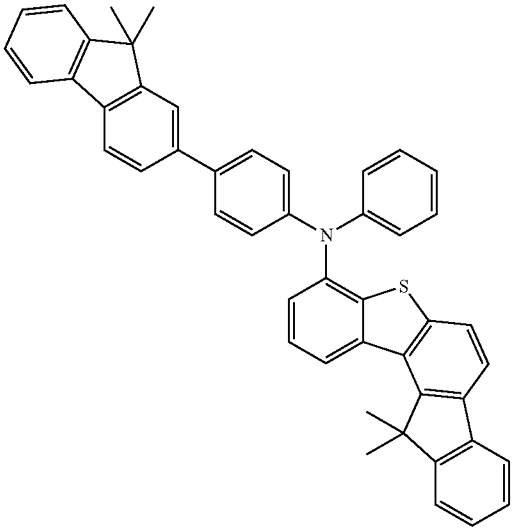
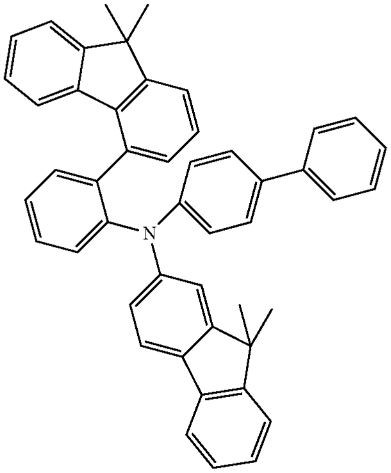
-continued
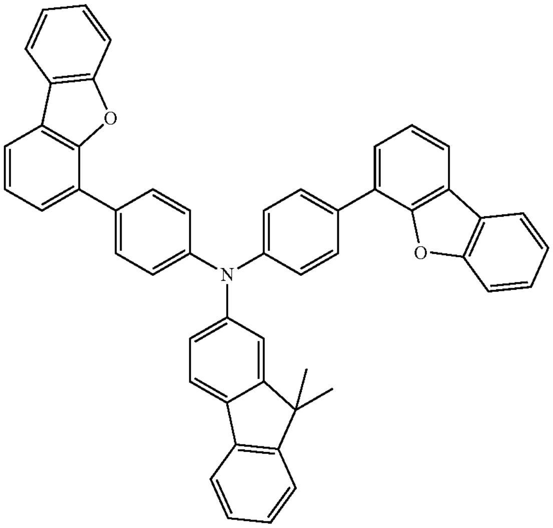
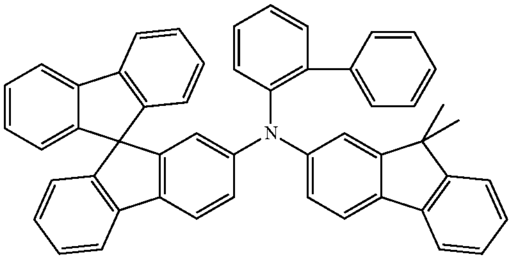
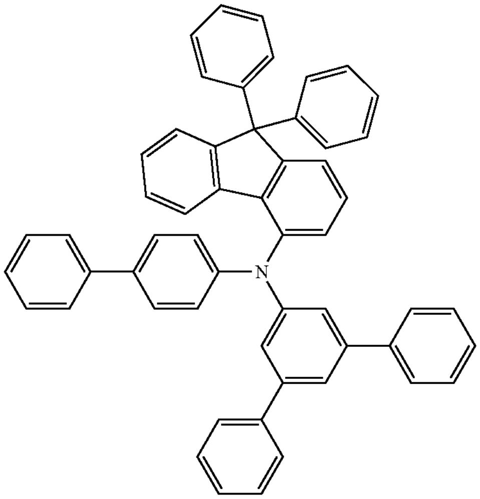
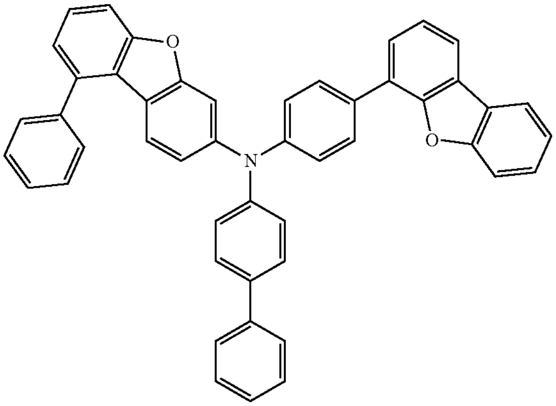

-continued
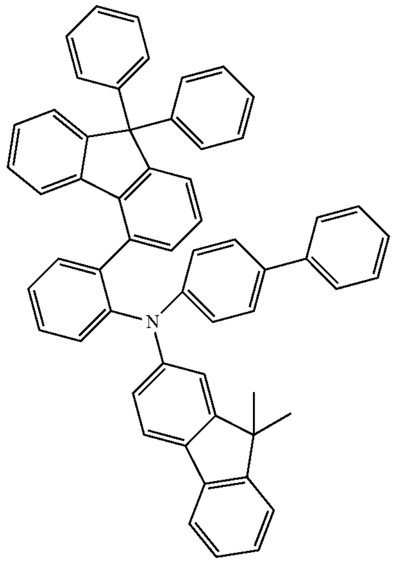
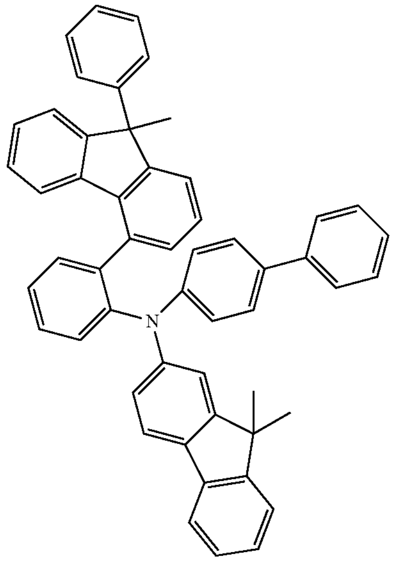
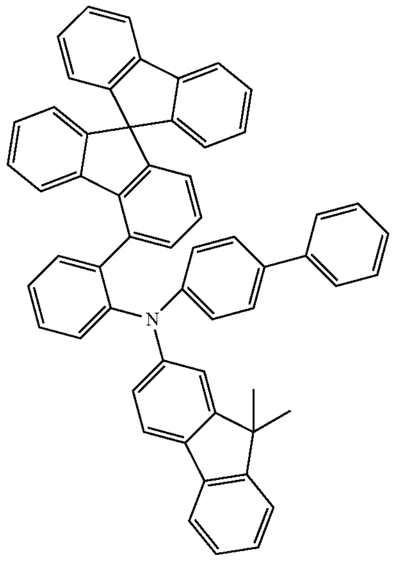
-continued
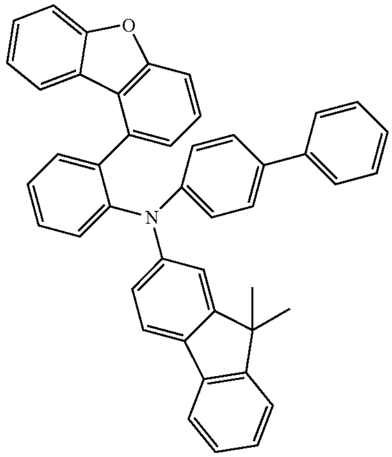
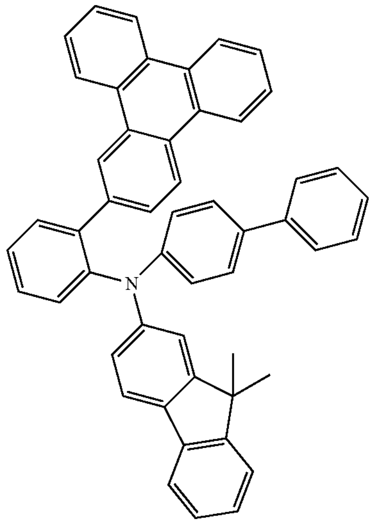
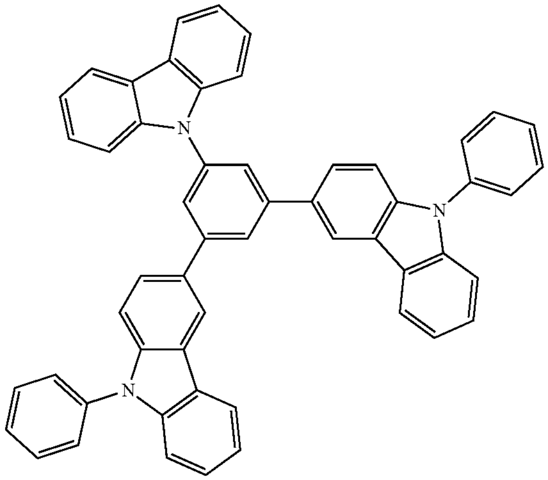

-continued
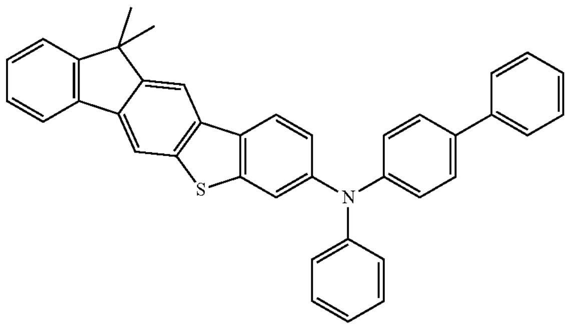
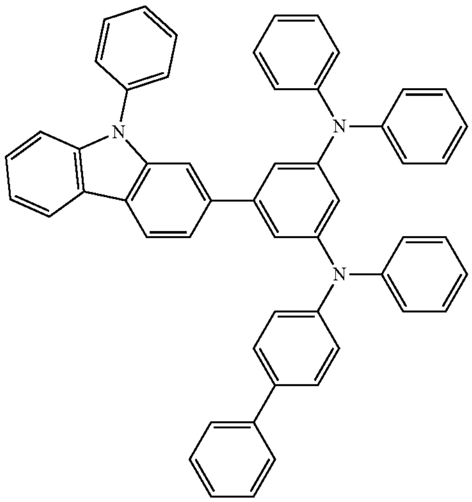
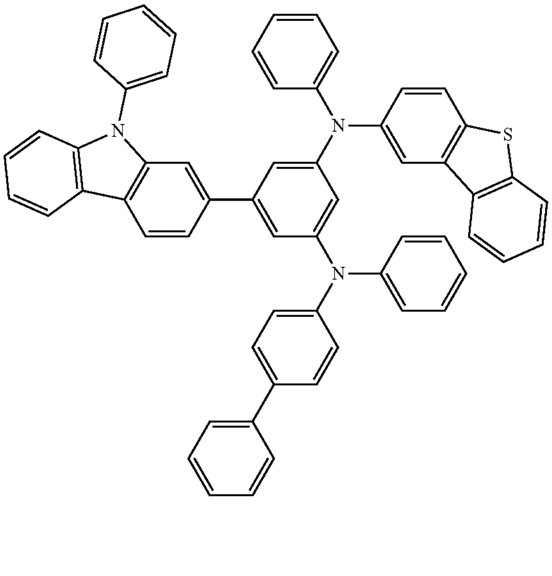
-continued
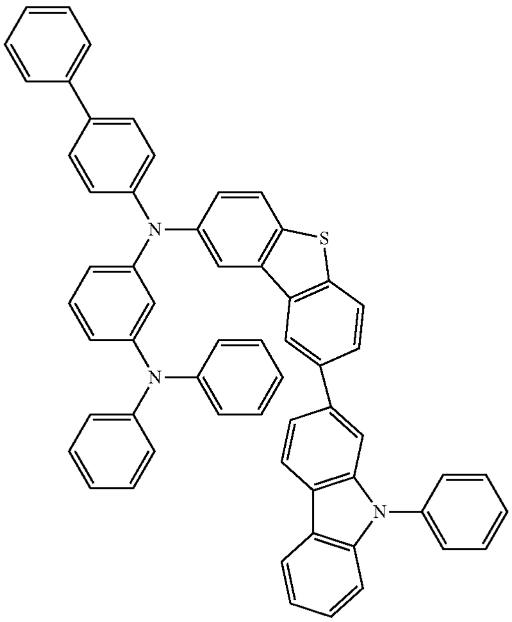
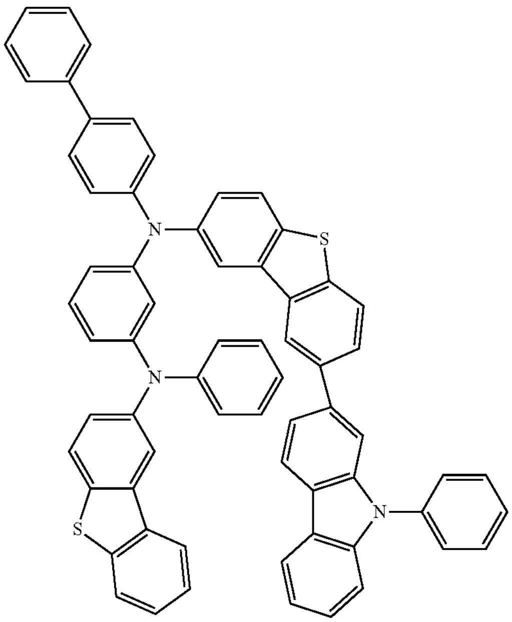
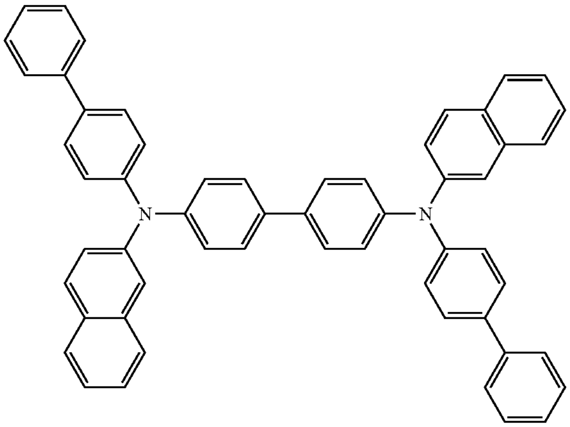

-continued
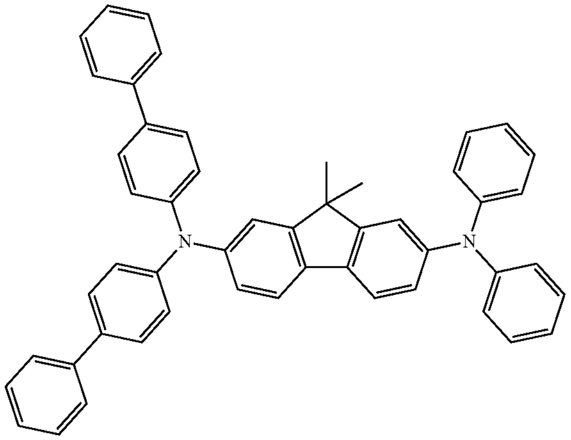
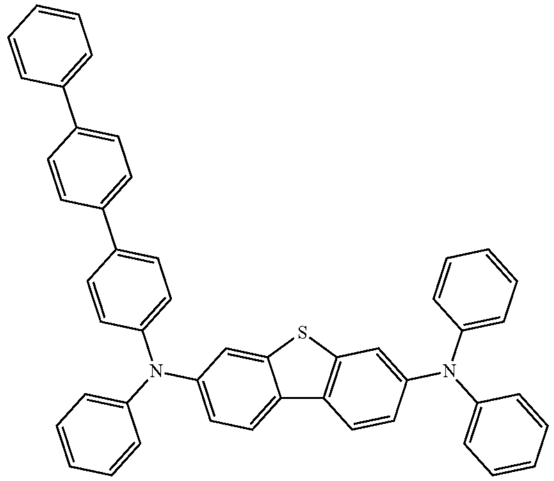
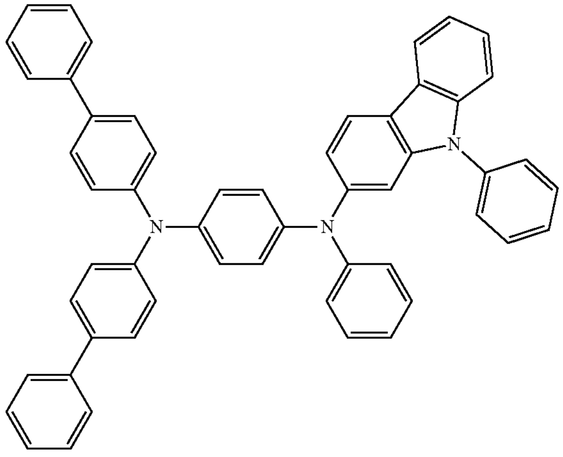
-continued
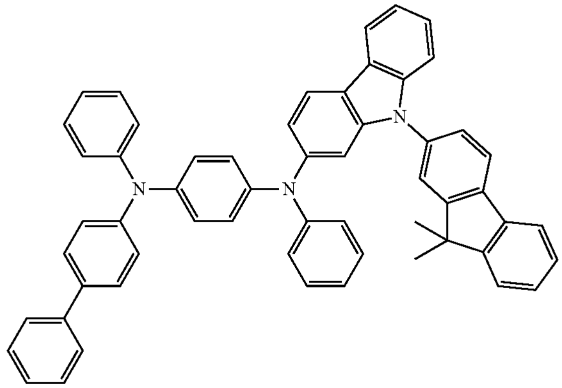
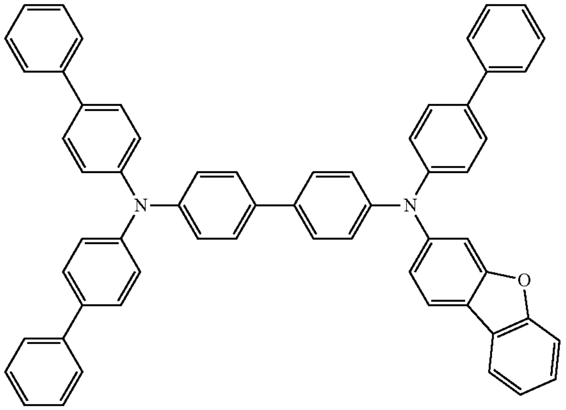
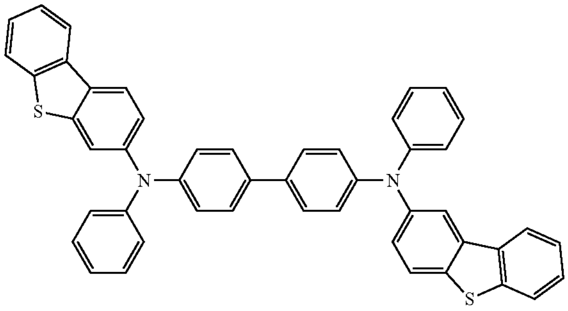
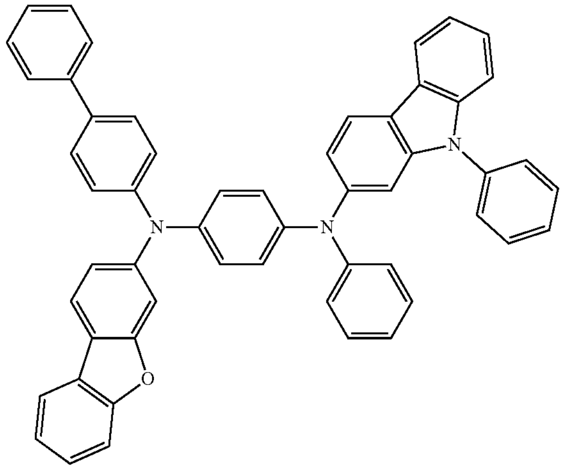

-continued
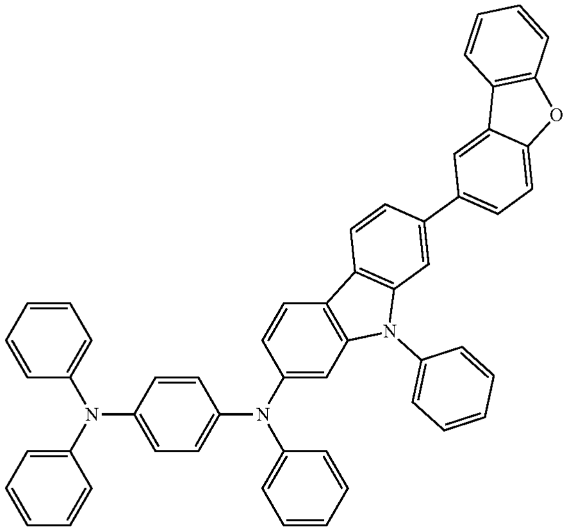
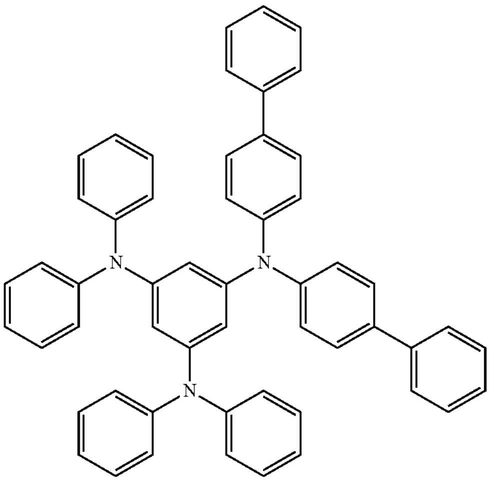
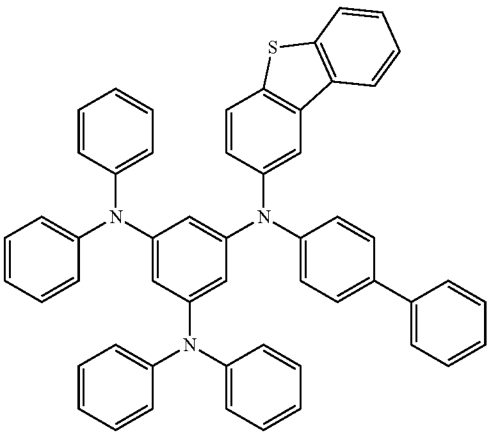
-continued
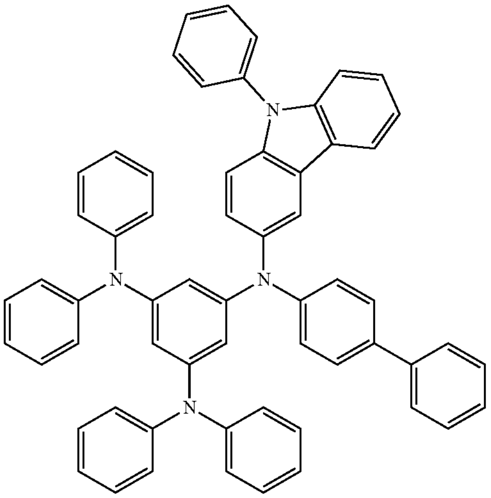
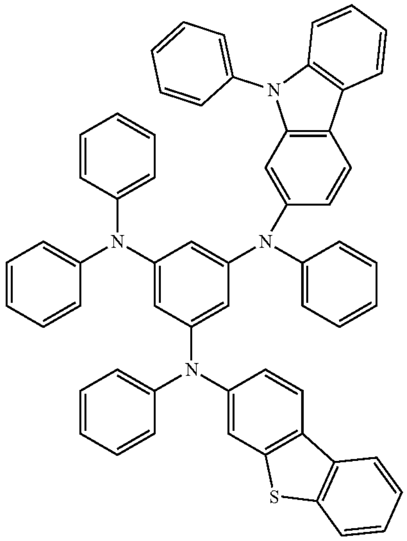
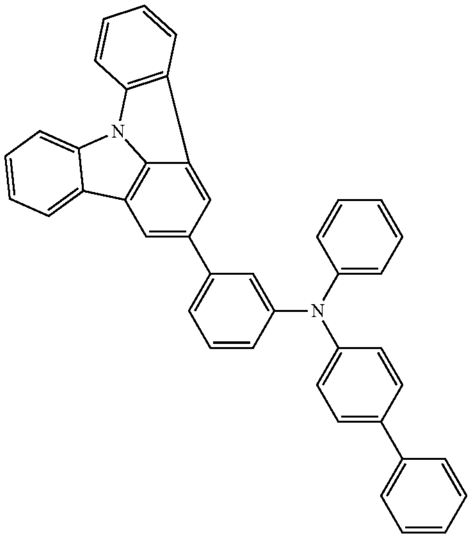

-continued
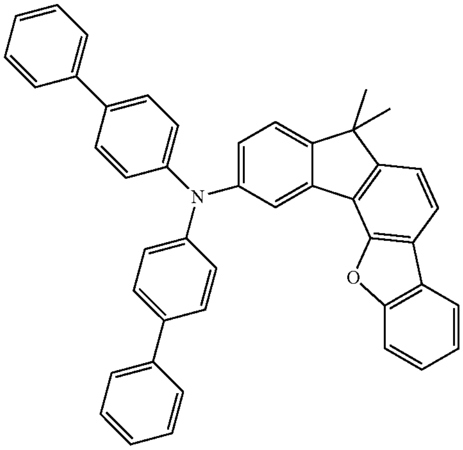
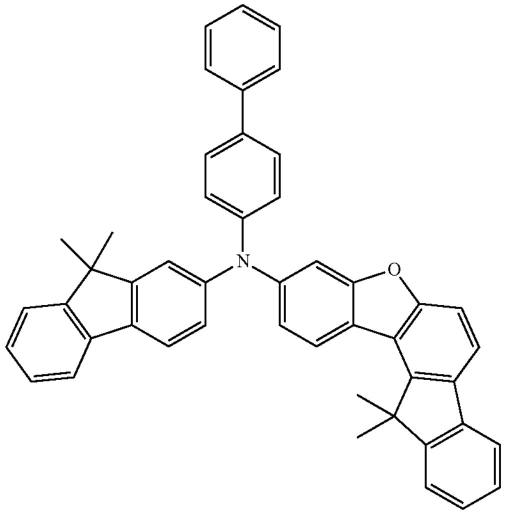
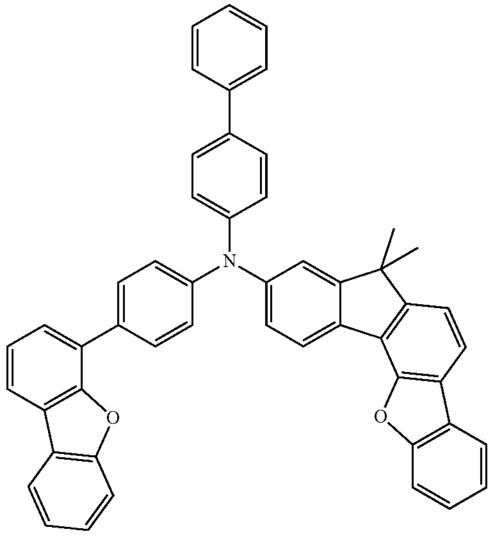
-continued
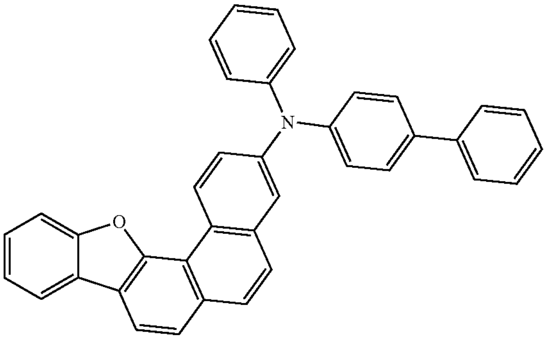
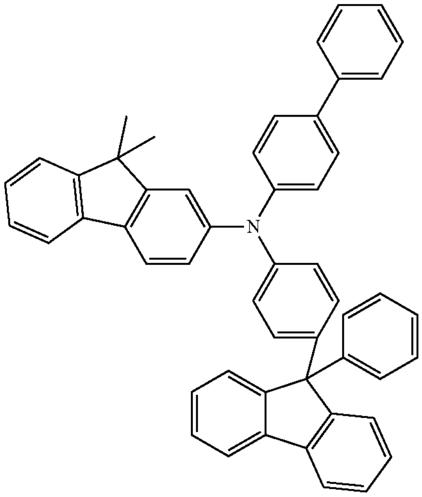
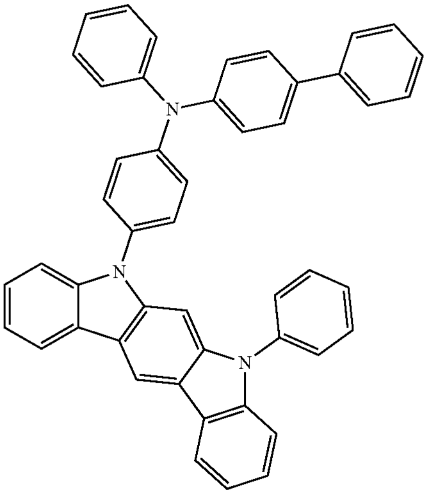

-continued

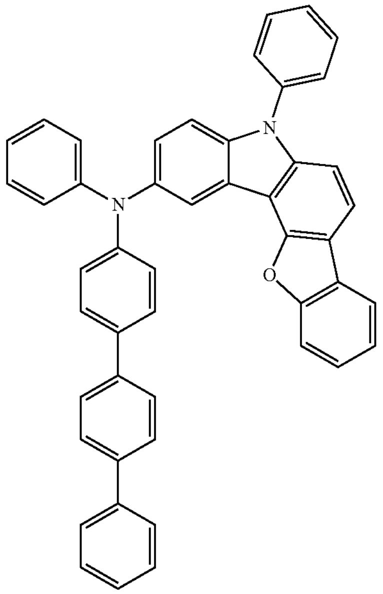

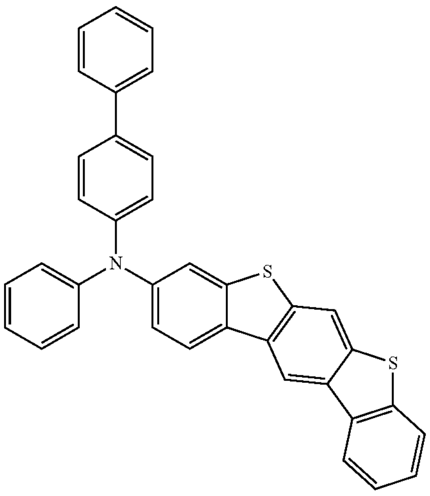

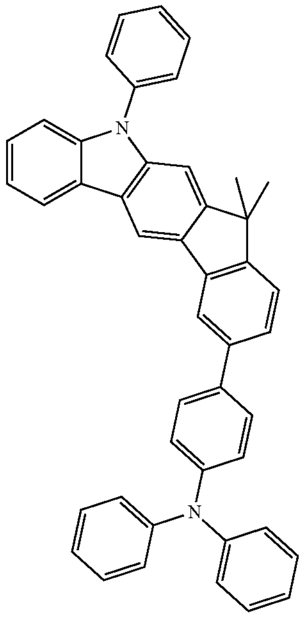

-continued

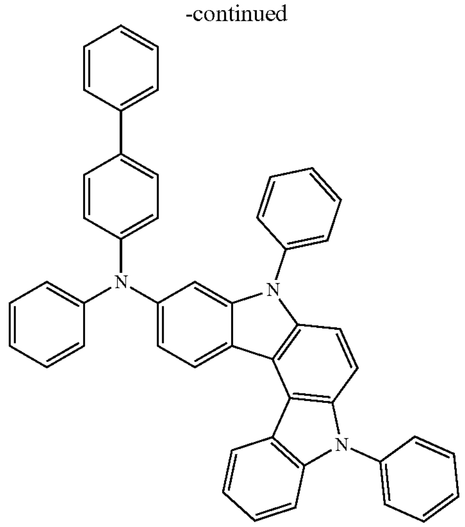

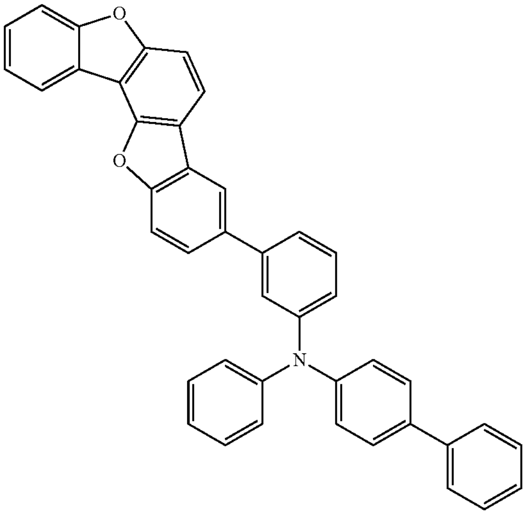

In an implementation, in the hole transport auxiliary layer, other suitable compounds may be included, in addition to the aforementioned compounds.

In an implementation, an organic light emitting diode may further include an electron transport layer, an electron injection layer, or a hole injection layer as the organic layer 105.

The organic light emitting diodes 100 and 200 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo chemical industry or P&H tech as far as there is no particular comment or were synthesized by suitable methods.

Preparation of Compound for Organic Optoelectronic Device

Synthesis of First Compound

Synthesis Example 1: Synthesis of Compound 1-1

Reaction Scheme 1

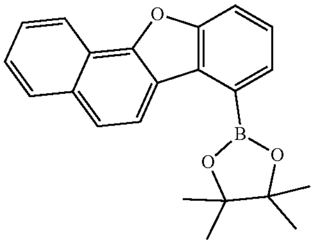

Int-1

+

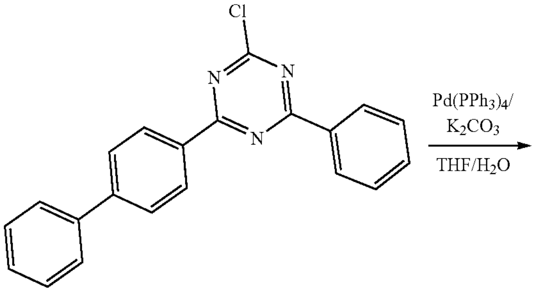

Int-2

-continued

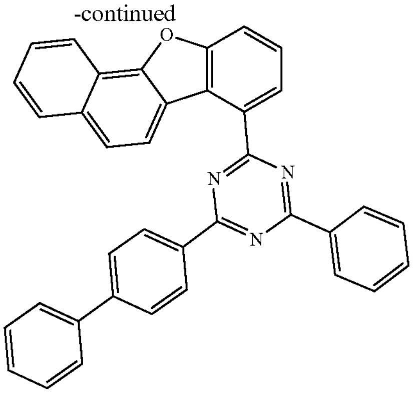

1-1

11.01 g (31.99 mmol) of Int-1, 11.00 g (31.99 mmol) of Int-2, 1.11 g (0.96 mmol) of tetrakis(triphenylphosphine) palladium, and 8.84 g (63.99 mmol) of potassium carbonate were put in a round-bottomed flask and dissolved in 150 mL of tetrahydrofuran and 75 mL of distilled water and then, heated and refluxed under a nitrogen atmosphere. After 12 hours, the reaction solution was cooled down, and after removing an aqueous layer, an organic layer therefrom was dried under a reduced pressure. A solid obtained therefrom was washed with water and methanol and then, recrystallized with 200 mL of toluene, obtaining 14.7 g (Yield: 87%) of Compound 1-1.

LC/MS calculated for: $C_{37}H_{23}N_3O$ Exact Mass: 525.18 found for 525.20 [M+H]

Synthesis Examples 2 to 7

Compounds were synthesized according to the same method as used to synthesize Compound 1-1 in Synthesis Example 1, except that Int-2 was changed into Int-A shown in Table 1.

TABLE 1

| Synthesis Examples | Int-A | Final product |
|---|---|---|
| Synthesis Example 2 | 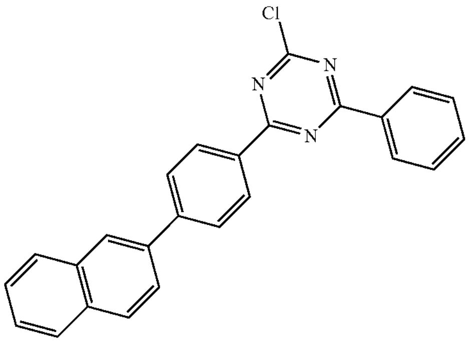 Int-3 | 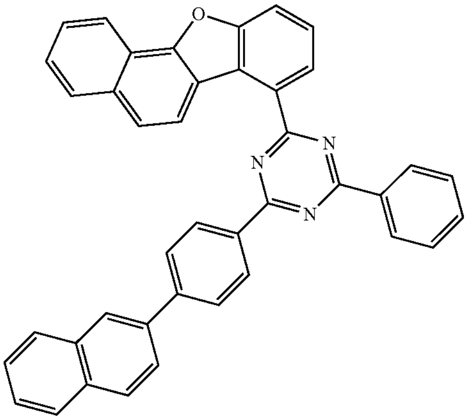 1-2 |

TABLE 1-continued
| | | |
|---|---|---|
| Synthesis Example 3 | 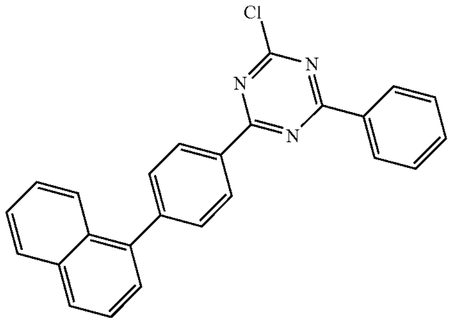<br>Int-4 | 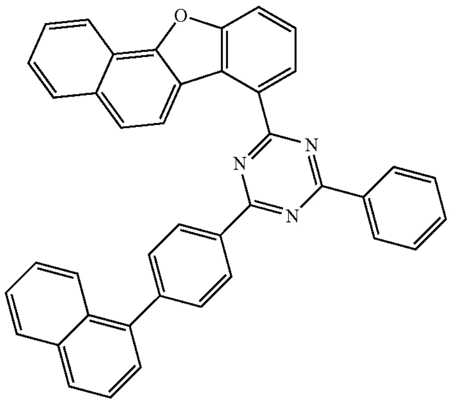<br>1-3 |
| Synthesis Example 4 | 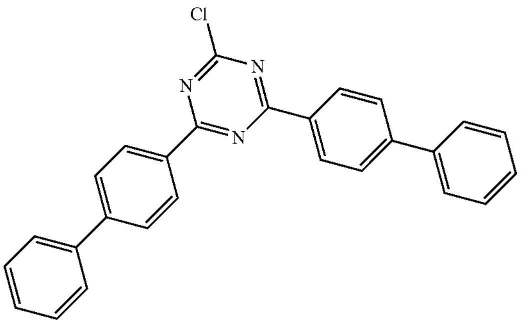<br>Int-5 | 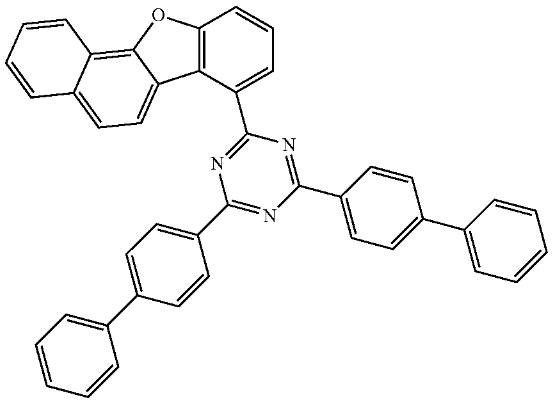<br>1-4 |
| Synthesis Example 5 | 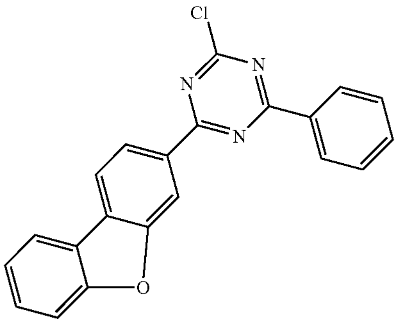<br>Int-6 | 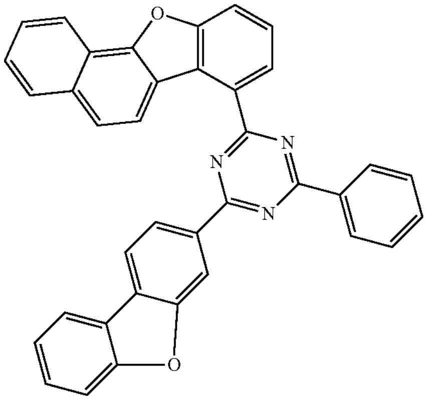<br>1-7 |

TABLE 1-continued

| | | |
|---|---|---|
| Synthesis Example 6 | 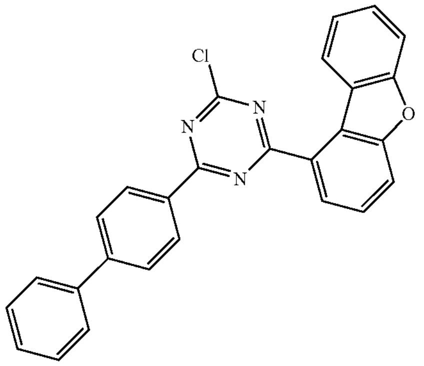<br>Int-7 | 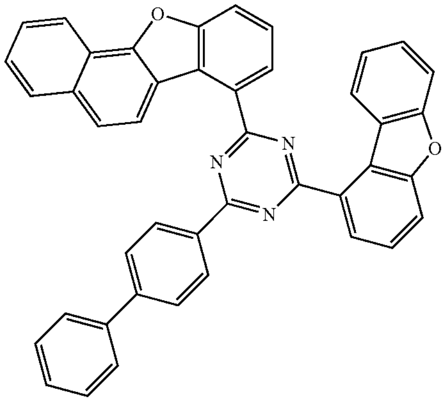<br>1-12 |
| Synthesis Example 7 | 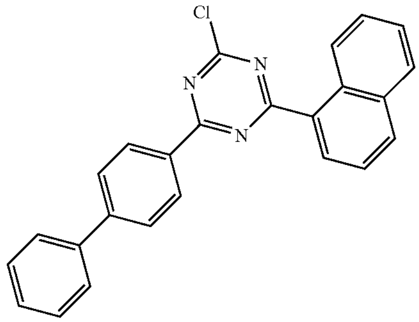<br>Int-8 | 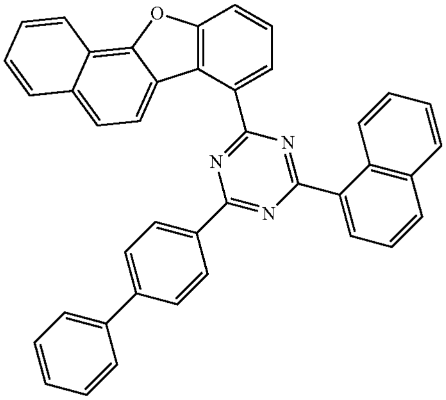<br>1-5 |

| Synthesis Examples | Amount (Yield) | Property data of final product |
|---|---|---|
| Synthesis Example 2 | 8.33 g (74%) | LC/MS calculated for: C41H25N3O Exact Mass: 575.20 found for 525.35 [M + H] |
| Synthesis Example 3 | 6.29 g (71%) | LC/MS calculated for: C37H23N3O Exact Mass: 575.20 found for 525.45 [M + H] |
| Synthesis Example 4 | 7.67 g (71%) | LC/MS calculated for: C43H27N3O Exact Mass: 601.22 found for 601.29 [M + H] |
| Synthesis Example 5 | 8.99 g (70%) | LC/MS calculated for: C37H21N3O2 Exact Mass: 539.16 found for 539.32 [M + H] |
| Synthesis Example 6 | 8.37 g (75%) | LC/MS calculated for: C43H25N3O2 Exact Mass: 615.19 found for 615.23 [M + H] |
| Synthesis Example 7 | 10.22 g (85%) | LC/MS calculated for: C41H25N3O Exact Mass: 575.20 found for 525.26 [M + H] |

Comparative Synthesis Examples 1 to 4

Compounds were synthesized according to the same method as used to synthesize Compound 1-1 in Synthesis Example 1 except that Int-1 and Int-2 were changed into Int-B or Int-A shown in Table 2.

TABLE 2

| Synthesis Examples | Int-B | Int-A |
|---|---|---|
| Comparative Synthesis Example 1 | 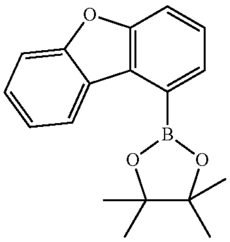 Int-9 | 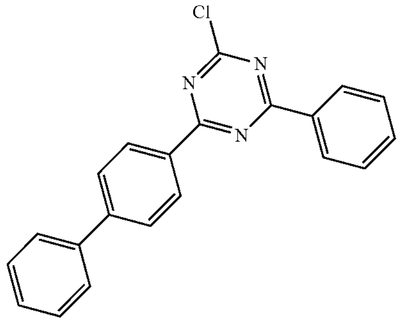 Int-2 |
| Comparative Synthesis Example 2 | Int-9 | 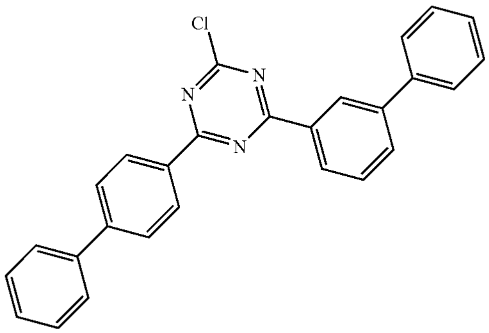 Int-10 |
| Comparative Synthesis Example 3 | Int-9 | 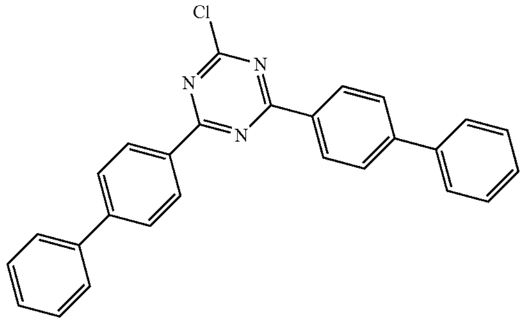 Int-5 |
| Comparative Synthesis Example 4 | Int-9 | 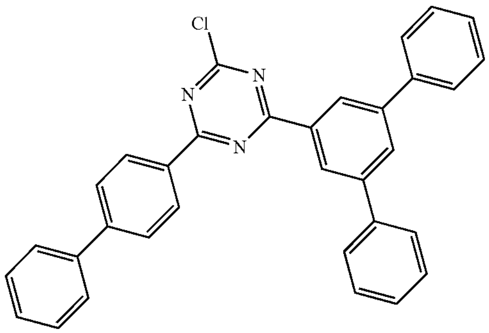 Int-11 |

TABLE 2-continued
| Synthesis Examples | Final product | Amount (Yield) | Property data of final product |
|---|---|---|---|
| Comparative Synthesis Example 1 | 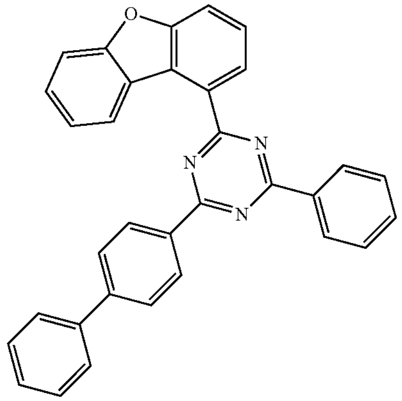 D-1 | 5.42 g (72%) | LC/MS calculated for: C33H21N3O Exact Mass: 475.17 found for 475.25 [M + H] |
| Comparative Synthesis Example 2 | 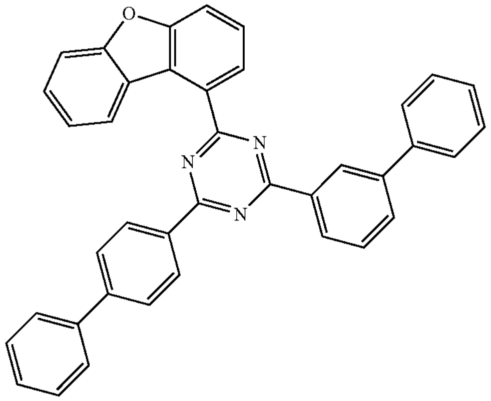 D-2 | 6.24 g (71%) | LC/MS calculated for: C39H25N3O Exact Mass: 551.20 found for 551.27 [M + H] |
| Comparative Synthesis Example 3 | 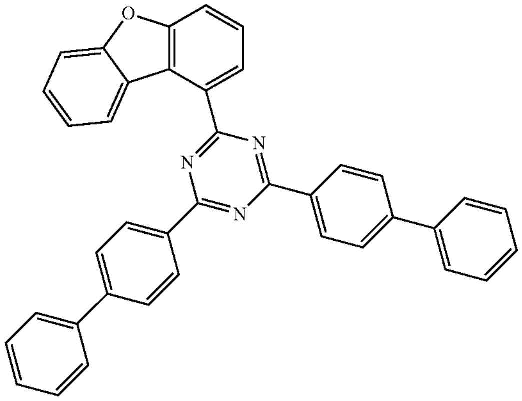 D-3 | 5.85 g (71%) | LC/MS calculated for: C39H25N3O Exact Mass: 551.20 found for 551.27 [M + H] |

TABLE 2-continued
| | | | |
|---|---|---|---|
| Comparative Synthesis Example 4 | 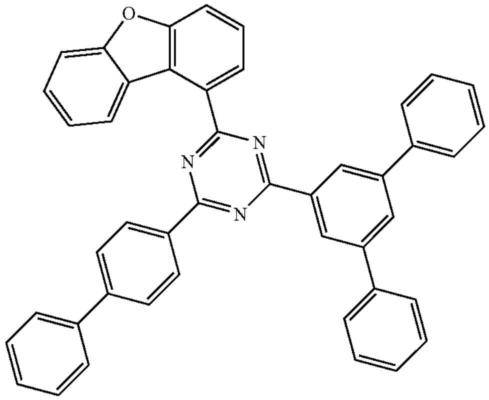<br>D-4 | 5.66 g (70%) | LC/MS calculated for: C45H29N3O Exact Mass: 627.23 found for 627.31 [M + H] |
Synthesis of Second Compound
The following intermediates were synthesized as described in KR10-1423173 B1.
M-3
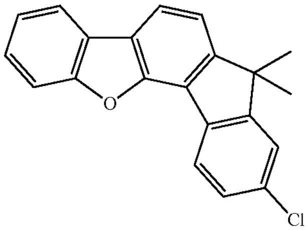
M-6
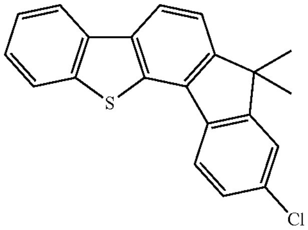
M-10
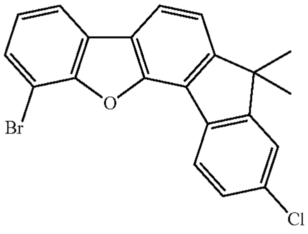
M-11
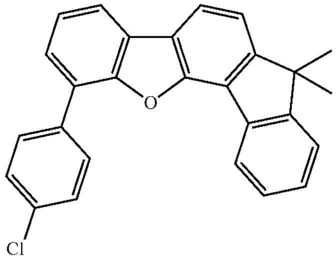
-continued
M-15
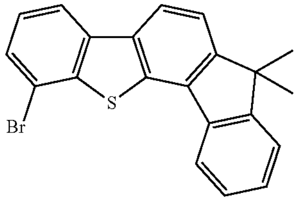
M-16
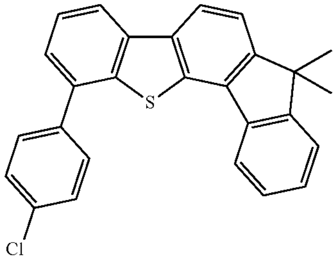
M-40
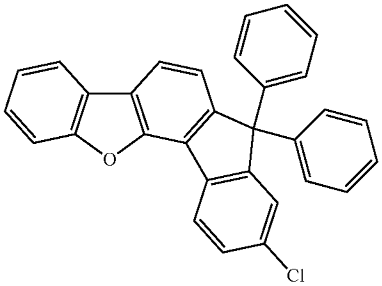

Synthesis Example 8: Synthesis of Compound A-51

Reaction Scheme 2

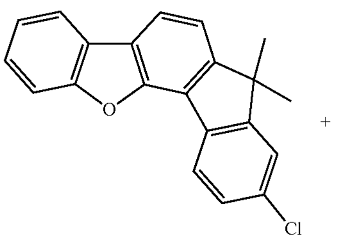

M-3

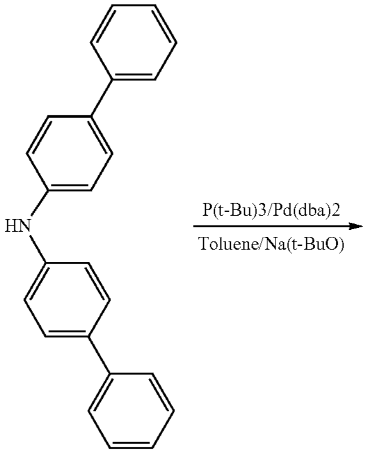

A

-continued

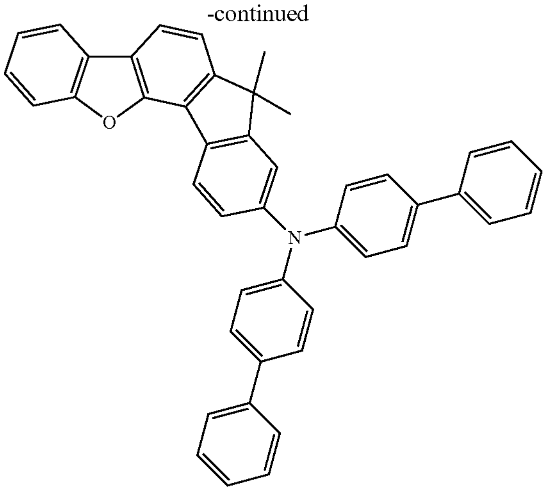

5.0 g (15.68 mmol) of Intermediate M-3, 5.04 g (15.68 mmol) of Intermediate A, 4.52 g (47.95 mmol) of sodium t-butoxide, and 0.1 g (0.47 mmol) of tri-tert-butylphosphine were dissolved in 200 ml of toluene, and 0.27 g (0.47 mmol) of $Pd(dba)_2$ was added thereto and then, stirred under reflux under a nitrogen atmosphere for 12 hours. When a reaction was completed, the resultant was extracted with toluene and distilled water, and an organic layer therefrom was dried with anhydrous magnesium sulfate and filtered, and a filtrate therefrom was concentrated under a reduced pressure. A product therefrom was purified with n-hexane/dichloromethane (in a volume ratio of 2:1) through silica gel column chromatography to obtain 7.8 g (Yield: 82.3%) of Compound A-51 as a white solid.

LC/MS calculated for: C45H33NO Exact Mass: 603.26 found for 603.87 [M+H]

Synthesis Examples 9 to 14

Compounds were synthesized according to the same method as used to synthesize Compound A-51 in Synthesis Example 8 except that M-3 and A were respectively changed into Int-C or Int-D shown in Table 3.

TABLE 3

| Synthesis Examples | Int-C | Int-D |
|---|---|---|
| Synthesis Example 9 | M-3 | 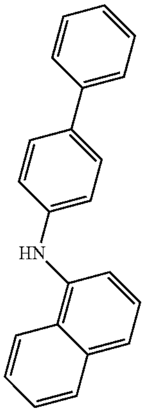 B |

TABLE 3-continued
| | | |
|---|---|---|
| Synthesis Example 10 | M-3 | 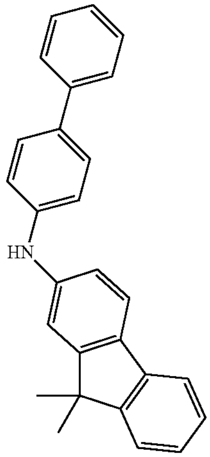 C |
| Synthesis Example 11 | M-3 | 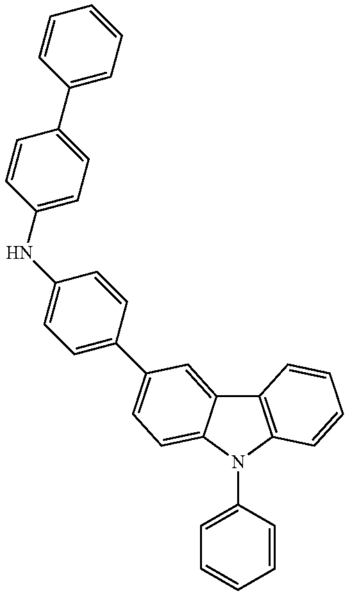 D |

TABLE 3-continued
| | | |
|---|---|---|
| Synthesis Example 12 | M-3 | 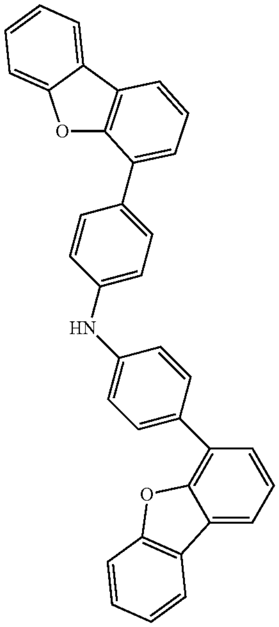<br>E |
| Synthesis Example 13 | M-3 | 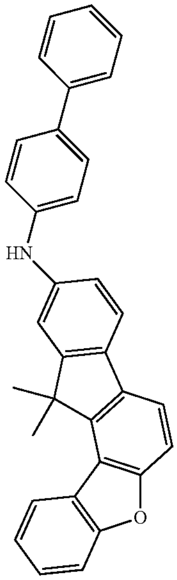<br>F |
| Synthesis Example 14 | 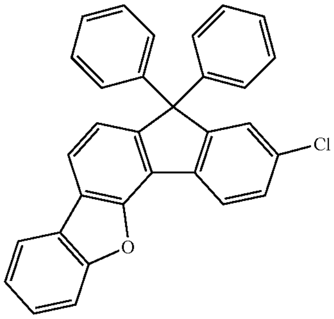<br>M-40 | A |

TABLE 3-continued
| | | |
|---|---|---|
| Synthesis Example 15 | 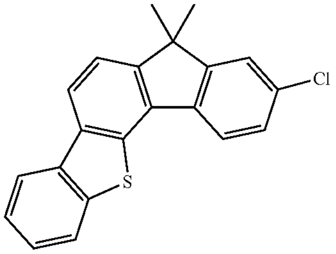 M-6 | A |
| Synthesis Example 16 | 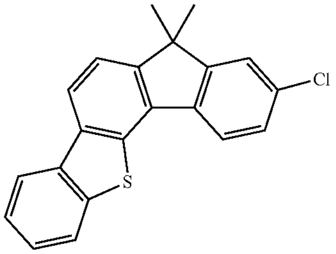 M-6 | B |
| Synthesis Example 17 | 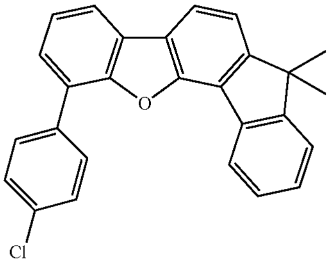 M-11 | A |
| Synthesis Example 18 | M-3 | 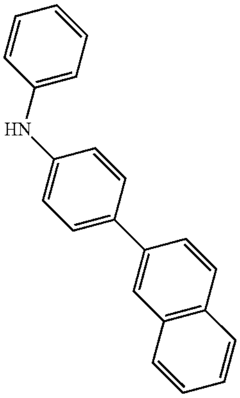 G |

TABLE 3-continued
| | | | |
|---|---|---|---|
| Synthesis Example 19 | M-6 | | G |
| Synthesis Examples | Final product | Amount (Yield) | Property data of final product |
|---|---|---|---|
| Synthesis Example 9 | 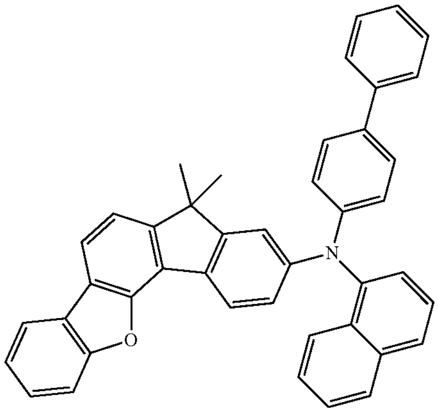 A-81 | 10.22 g (78%) | LC/MS calculated for: C43H31NO Exact Mass: 577.24 found for 577.87 [M + H] |
| Synthesis Example 10 | 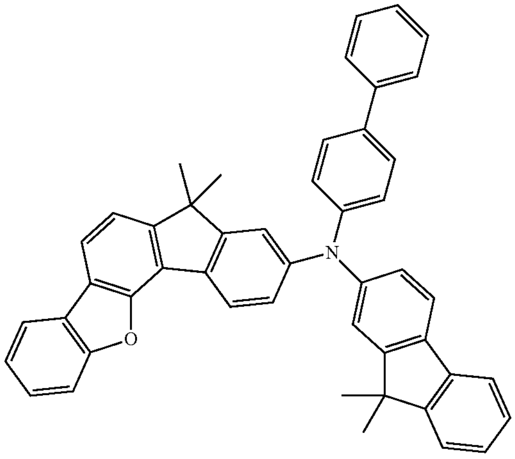 A-55 | 6.50 g (80%) | LC/MS calculated for: C48H37NO Exact Mass: 643.29 found for 643.89 [M + H] |

TABLE 3-continued
| | | | |
|---|---|---|---|
| Synthesis Example 11 | 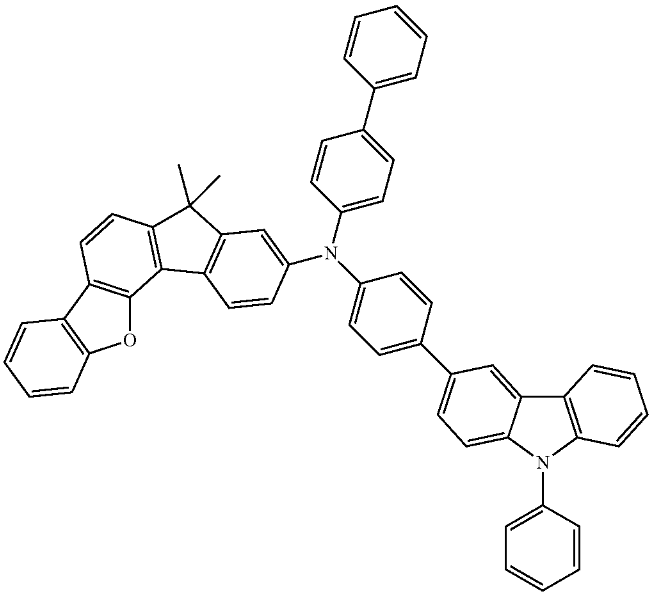<br>A-69 | 8.26 g (75%) | LC/MS calculated for: C57H40N2O Exact Mass: 768.31 found for 768.78 [M + H] |
| Synthesis Example 12 | 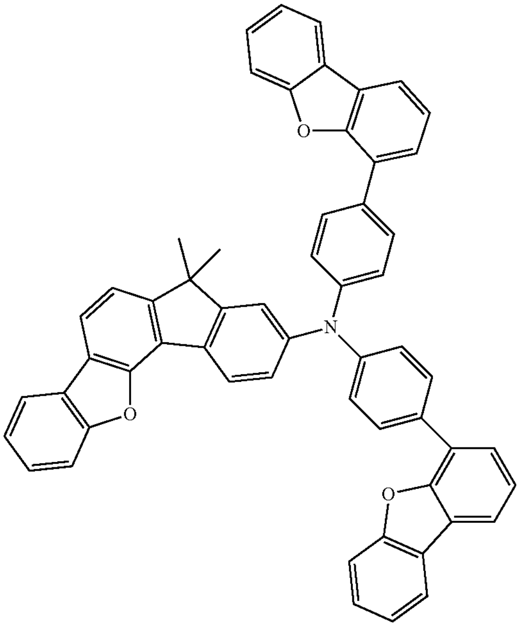<br>A-75 | 6.53 g (70%) | LC/MS calculated for: C57H37NO3 Exact Mass: 783.28 found for 783.65 [M + H] |

TABLE 3-continued
| | | | |
|---|---|---|---|
| Synthesis Example 13 | 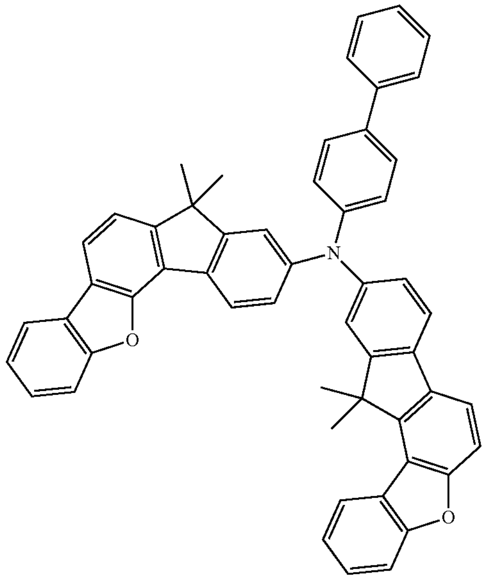 A-83 | 7.24 g (85%) | LC/MS calculated for: C54H39NO2 Exact Mass: 733.30 found for 733.76 [M + H] |
| Synthesis Example 14 | 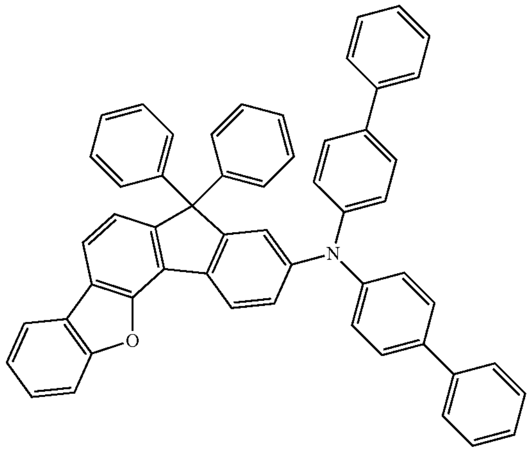 A-52 | 8.45 g (85%) | LC/MS calculated for: C55H37NO Exact Mass: 727.29 found for 727.57 [M + H] |
| Synthesis Example 15 | 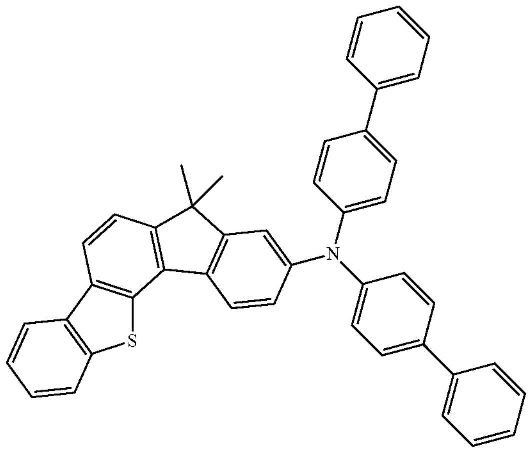 A-53 | 8.65 g (80%) | LC/MS calculated for: C45H33NS Exact Mass: 619.23 found for 619.23 [M + H] |

TABLE 3-continued
| | | | |
|---|---|---|---|
| Synthesis Example 16 | 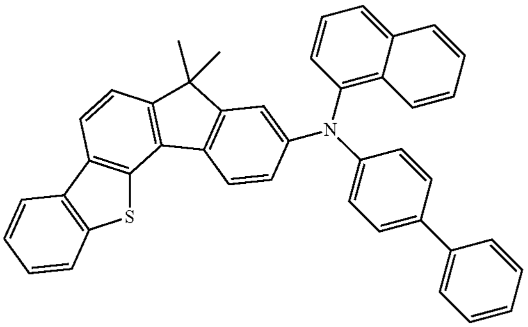<br>A-86 | 7.24 g (82%) | LC/MS calculated for: C43H31NS Exact Mass: 593.22 found for 593.77 [M + H] |
| Synthesis Example 17 | 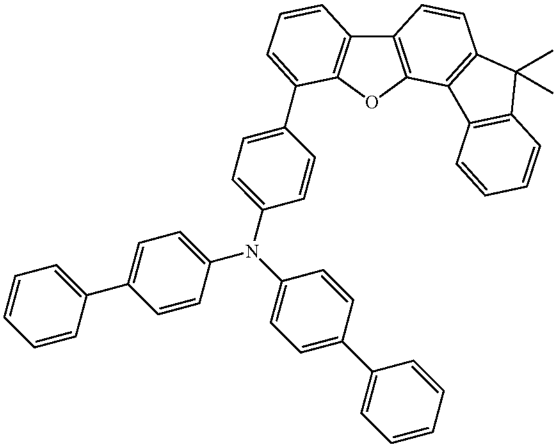<br>A-27 | 9.65 g (85%) | LC/MS calculated for: C51H37NO Exact Mass: 679.29 found for 679.75 [M + H] |
| Synthesis Example 18 | 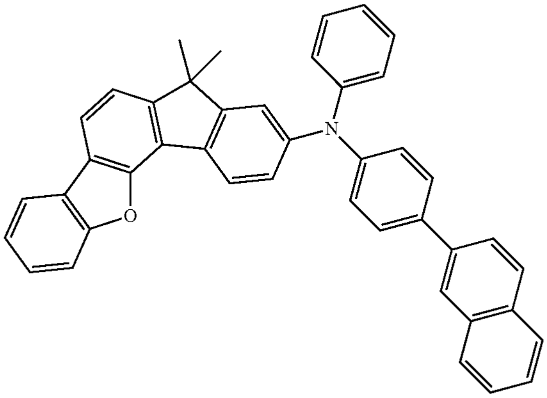<br>A-92 | 7.95 g (81%) | LC/MS calculated for: C43H31NO Exact Mass: 577.24 found for 577.64 [M + H] |

TABLE 3-continued

| | | | |
|---|---|---|---|
| Synthesis Example 19 | 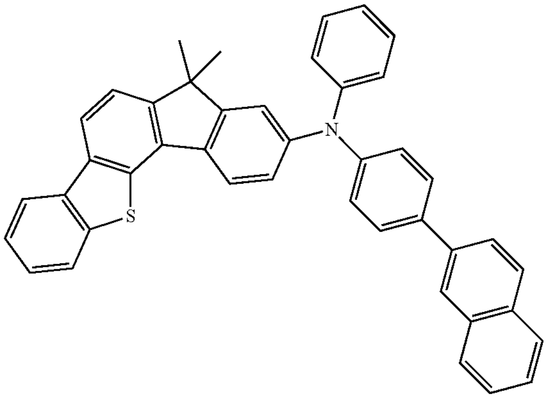 A-93 | 10.24 g (85%) | LC/MS calculated for: C43H31NS Exact Mass: 593.22 found for 593.72 [M + H] |

Comparative Synthesis Example 5: Synthesis of Compound D-5

Reaction Scheme 3

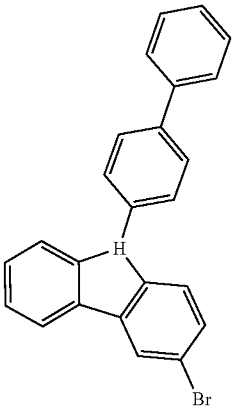

Int-22

+

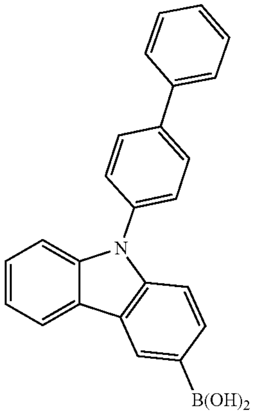

Int-23

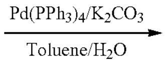

-continued

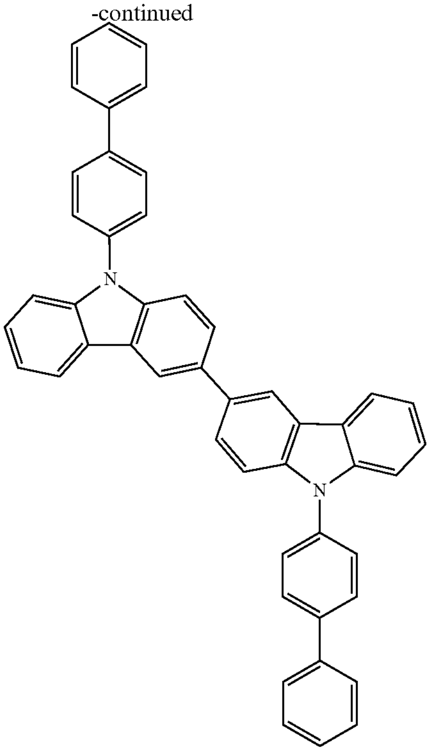

D-5

Int-22 (12.33 g, 30.95 mmol) was dissolved in 200 mL of toluene under a nitrogen atmosphere, and Int-23 (12.37 g, 34.05 mmol) and tetrakis(triphenylphosphine) palladium (1.07 g, 0.93 mmol) were added thereto and then, stirred. Subsequently, potassium carbonate (12.83 g, 92.86 mmol) saturated in water was added thereto and then, heated and refluxed at 90° C. for 12 hours. When a reaction was completed, after removing an aqueous layer therefrom, a solid formed therein was filtered. The obtained solid was recrystallized in monochlorobenzene (MCB) and purified to obtain Compound D-5 (18.7 g, 92%).

LC/MS calculated for: C48H32N2 Exact Mass: 636.26 found for 636.30 [M+H]

Comparative Synthesis Example 6: Synthesis of Compound D-6

Reaction Scheme 4

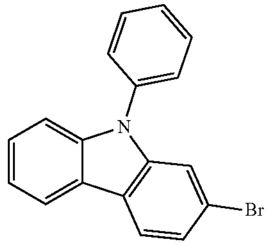

+

Int-24

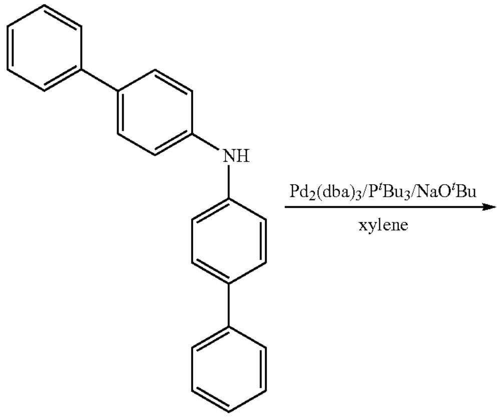

A

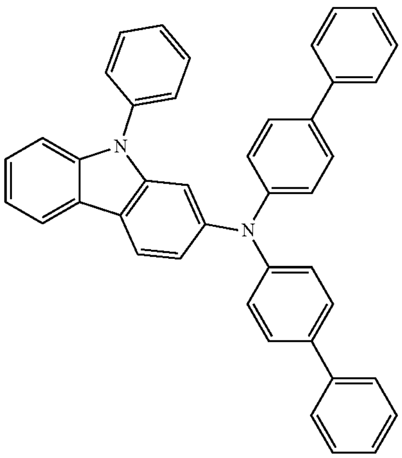

D-6

Compound D-6 was synthesized according to the same method as Synthesis Example 8 except that Intermediate Int-24 and Intermediate A were used in an equivalent ratio of 1:1.

LC/MS calculated for: C42H30N2 Exact Mass: 562.24 found for 562.35 [M+H]

Comparative Synthesis Example 7: Synthesis of Compound D-7

Reaction Scheme 5

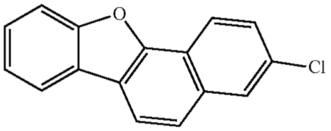

+

Int-25

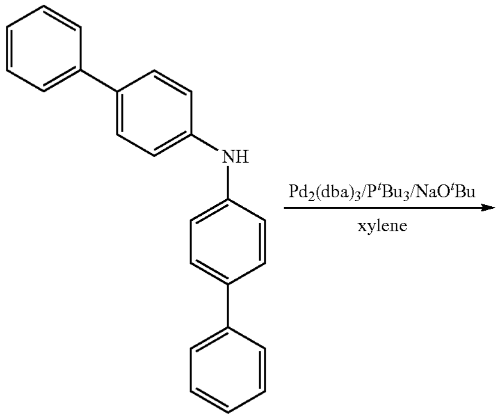

A

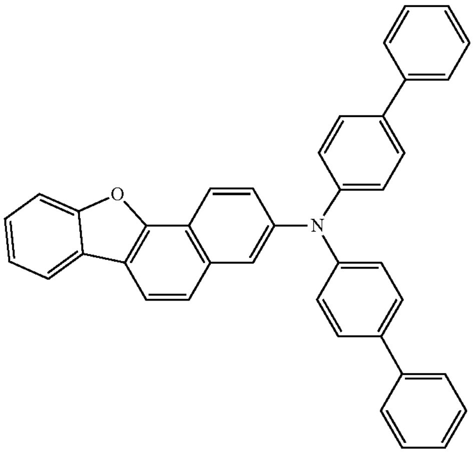

D-7

Compound D-7 was synthesized according to the same method as Synthesis Example 8 except that Intermediate Int-25 and Intermediate A were used in an equivalent ratio of 1:1.

LC/MS calculated for: C40H27NO Exact Mass: 537.21 found for 537.35 [M+H]

Comparative Synthesis Example 8: Synthesis of Compound D-8

Reaction Scheme 6

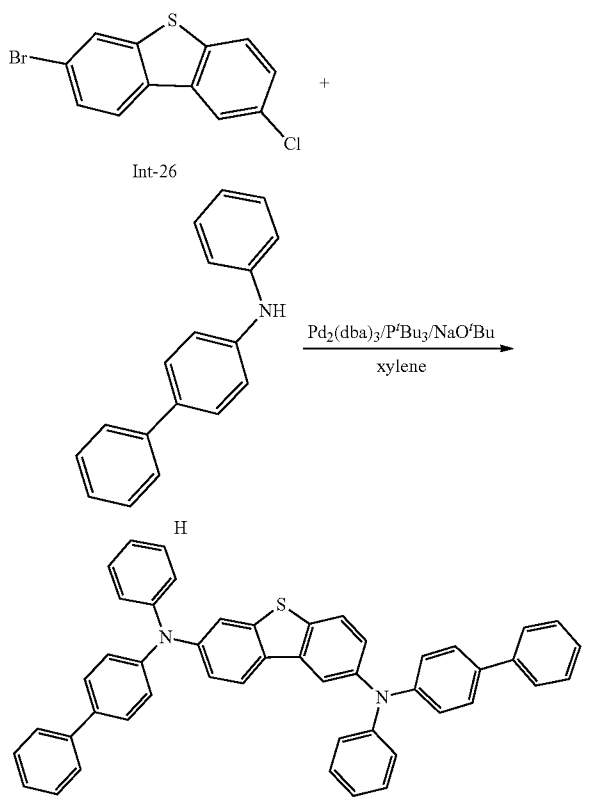

Int-26

H

D-8

Compound D-8 was synthesized according to the same method as used in Synthesis Example 8 except that Intermediate Int-26 and Intermediate H were used in an equivalent ratio of 1:2.

LC/MS calculated for: C48H34N2S Exact Mass: 670.24 found for 670.37 [M+H]

Manufacture of Organic Light Emitting Diode

Example 1

A glass substrate coated with ITO (indium tin oxide) was washed with distilled water. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 1% NDP-9 (available from Novaled) was vacuum-deposited on the ITO substrate to form a 1,400 Å-thick hole transport layer, and Compound B was deposited on the hole transport layer to form a 600 Å-thick hole transport auxiliary layer. On the hole transport auxiliary layer, a 400 Å-thick light emitting layer was formed by vacuum-depositing Compound 1-1 and Compound A-92 as a host simultaneously and doping 2 wt % of $[Ir(piq)_2acac]$ as a dopant. Herein, Compound 1-1 and Compound A-92 were used in a weight ratio of 5:5. Subsequently, Compound C was deposited on the light emitting layer to form a 50 Å-thick electron transport auxiliary layer, and Compound D and LiQ were simultaneously vacuum deposited at a weight ratio of 1:1 to form a 300 Å-thick electron transport layer. On the electron transport layer, Liq and Al were sequentially vacuum-deposited to be 15 Å thick and 1,200 Å thick, manufacturing an organic light emitting diode having the following structure.

ITO/Compound A (1% NDP-9 doping, 1,400 Å)/Compound B (600 Å)/EML [98 wt % of host (Compound 1-1 (50%): Compound A-92 (50%)): 2 wt % of $[Ir(piq)_2acac]$] (400 Å)/Compound C (50 Å)/Compound D: Liq (300 Å)/LiQ (15 Å) /Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Examples 2 to 9 and Comparative Examples 1 to 8

Diodes of Examples 2 to 9, and Comparative Examples 1 to 8 were manufactured in the same manner as in Example 1, except that the host was changed as described in Table 4.

Evaluation: Effect of Life-span Synergy Effect

Life-span characteristics of the organic light emitting diodes according to Examples 1 to 9 and Comparative Examples 1 to 8 were evaluated. Specific measurement methods are as follows, and the results are shown in Table 4.

(1) Measurement of Current Density Change Depending on Voltage Change

The obtained organic light emitting diodes were measured regarding a current value flowing in the unit diode, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminous efficiency (cd/A) of the same current density (10 $mA/cm^2$) was calculated using the luminance and current density measured from the (1) and (2).

(4) Measurement of T90 Life-Span

While maintaining the luminance ($cd/m^2$) at 6,000 $cd/m^2$, the time for the luminous efficiency (cd/A) to decrease to 90% was measured to obtain the results.

(5) Calculation of Life-Span Ratio (%)

The relative comparison values with the measured T90(h) life-span of Comparative Example 1 are shown in Table 4.

TABLE 4

| | First host | Second host | T90 life-span ratio (%) |
|---|---|---|---|
| Example 1 | 1-1 | A-92 | 185 |
| Example 2 | 1-2 | A-92 | 165 |
| Example 3 | 1-3 | A-92 | 180 |
| Example 4 | 1-7 | A-92 | 140 |
| Example 5 | 1-12 | A-92 | 122 |
| Example 6 | 1-5 | A-92 | 140 |
| Example 7 | 1-1 | A-51 | 175 |

TABLE 4-continued

| | First host | Second host | T90 life-span ratio (%) |
|---|---|---|---|
| Example 8 | 1-1 | A-53 | 168 |
| Example 9 | 1-1 | A-93 | 180 |
| Comparative Example 1 | D-1 | A-92 | 100 |
| Comparative Example 2 | D-2 | A-92 | 97 |
| Comparative Example 3 | D-3 | A-92 | 95 |
| Comparative Example 4 | D-4 | A-92 | 80 |
| Comparative Example 5 | 1-1 | D-5 | 18 |
| Comparative Example 6 | 1-1 | D-6 | 30 |
| Comparative Example 7 | 1-1 | D-7 | 10 |
| Comparative Example 8 | 1-1 | D-8 | 25 |

Referring to Table 4, the composition according to the Examples exhibited significantly improved life-span compared with the Comparative Examples.

One or more embodiments may provide a composition for an organic optoelectronic device capable of implementing an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:

a first compound represented by Chemical Formula 1, and a second compound represented by a combination of Chemical Formula 2 and Chemical Formula 3:

[Chemical Formula 1]

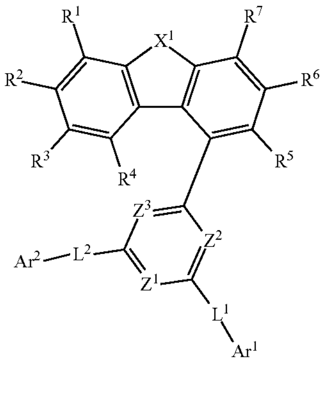

wherein, in Chemical Formula 1, $X^1$ is O or S, $Z^1$ to $Z^3$ are each independently N or $CR^a$, at least two of $Z^1$ to $Z^3$ being N, $L^1$ and $L^2$ are each independently a single bond, a substituted or unsubstituted C6 to C20 arylene group, a substituted or unsubstituted C2 to C20 heterocyclic group, or a combination thereof, $Ar^1$ and $Ar^2$ are each independently a substituted or unsubstituted C6 to C30 aryl group or a substituted or unsubstituted C2 to C30 heterocyclic group, $R^a$ and $R^1$ to $R^7$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and at least one pair of $R^1$ and $R^2$; $R^2$ and $R^3$; $R^3$ and $R^4$; $R^5$ and $R^6$; and $R^6$ and $R^7$ are linked to each other to provide a substituted or unsubstituted aromatic ring or a substituted or unsubstituted heteroaromatic ring,

[Chemical Formula 2]

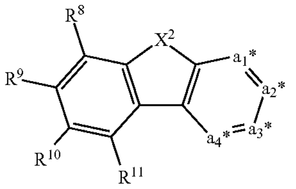

[Chemical Formula 3]

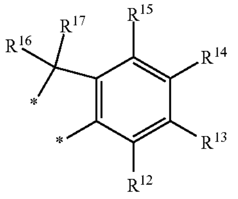

wherein, in Chemical Formula 2 and Chemical Formula 3, $X^2$ is O or S, two adjacent ones of a1* to a4* of Chemical Formula 2 are linking carbons linked at * of Chemical Formula 3, the remaining two of a1* to a4* of Chemical Formula 2, not linked at * of Chemical Formula 3, are $CR^b$, $R^b$ and $R^8$ to $R^{15}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, at least one of $R^8$ to $R^{15}$ being a group represented by Chemical Formula A, and $R^{16}$ and $R^{17}$ are each independently a substituted or unsubstituted C1 to C30 alkyl group or a substituted or unsubstituted C6 to C30 aryl group,

[Chemical Formula A]

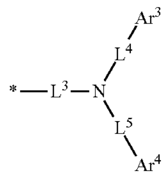

wherein, in Chemical Formula A, $L^3$ to $L^5$ are each independently a single bond or a substituted or unsubstituted C6 to C30 arylene group, $Ar^3$ and $Ar^4$ are each independently a substituted or unsubstituted C6 to C30 aryl group or a substituted or unsubstituted C2 to C30 heterocyclic group, and

* is linking point.

2. The composition as claimed in claim 1, wherein the first compound is represented by one of Chemical Formula 1-I to Chemical Formula 1-XI:
[Chemical Formula 1-I]
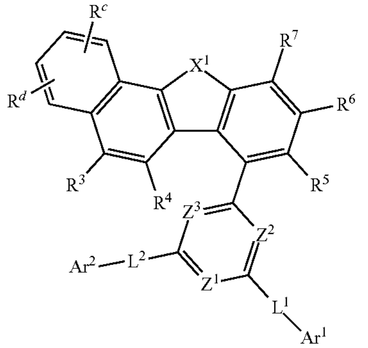
[Chemical Formula 1-II]
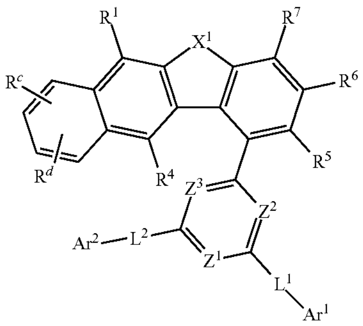
[Chemical Formula 1-III]
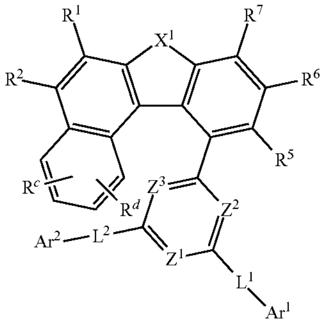
[Chemical Formula 1-IV]
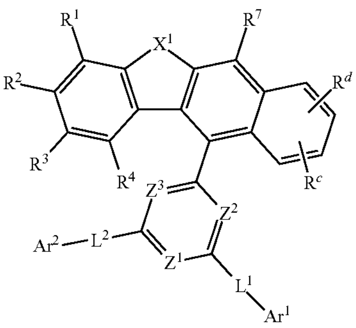
-continued
[Chemical Formula 1-V]
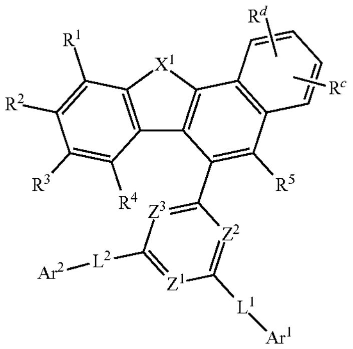
[Chemical Formula 1-VI]
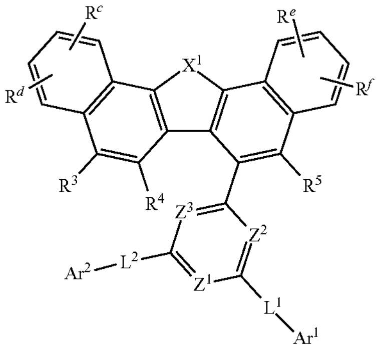
[Chemical Formula 1-VII]
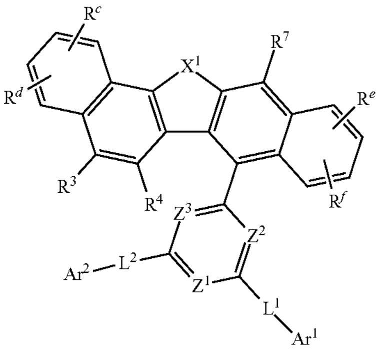
[Chemical Formula 1-VIII]
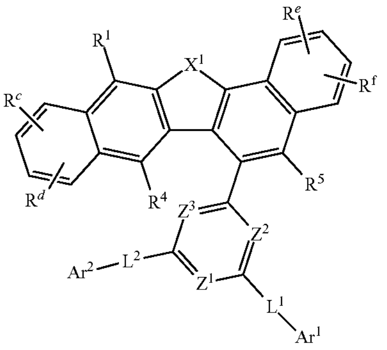

-continued

[Chemical Formula 1-IX]

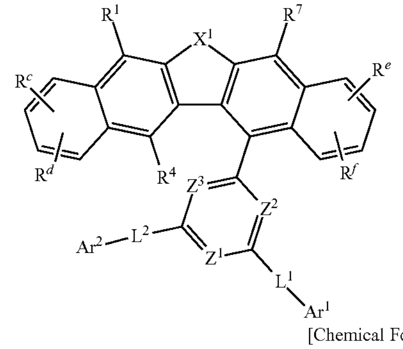

[Chemical Formula 1-X]

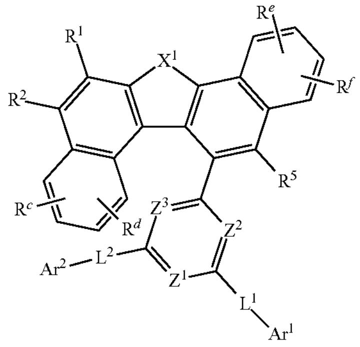

[Chemical Formula 1-XI]

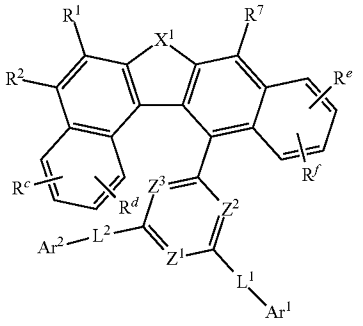

wherein, in Chemical Formula 1-I to Chemical Formula 1-XI, $X^1$, $Z^1$ to $Z^3$, $L^1$ and $L^2$, $Ar^1$ and $Ar^2$ are defined the same as those of Chemical Formula 1, and $R^c$, $R^d$, $R^e$, $R^f$, and $R^1$ to $R^7$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group or a combination thereof.

3. The composition as claimed in claim 2, wherein the first compound is represented by Chemical Formula 1-I, Chemical Formula 1-II, Chemical Formula 1-III, Chemical Formula 1-VI, Chemical Formula 1-VII, Chemical Formula 1-VIII, or Chemical Formula 1-X.

4. The composition as claimed in claim 1, wherein $Ar^1$ and $Ar^2$ in Chemical Formula 1 are each independently a substituted or unsubstituted phenyl group, a substituted or unsubstituted biphenyl group, a substituted or unsubstituted naphthyl group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuran, or a substituted or unsubstituted benzonaphthothiophene.

5. The composition as claimed in claim 1, wherein:

$Ar^1$ and $Ar^2$ in Chemical Formula 1 are each independently a group of Group I:

[Group I]

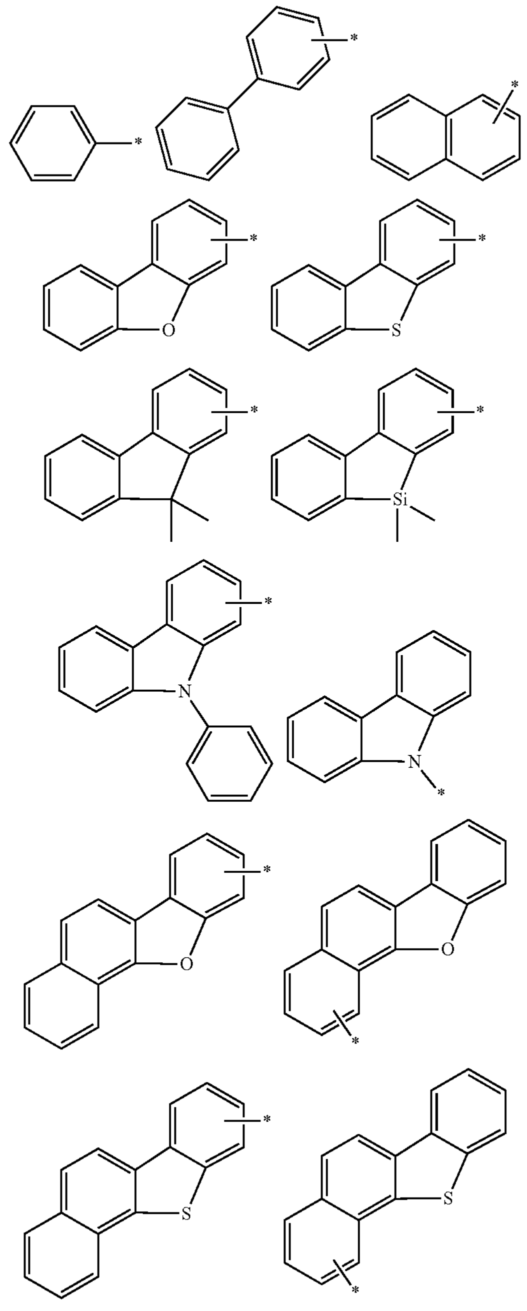

in Group I, * is a linking point.

6. The composition as claimed in claim 1, wherein the first compound is a compound of Group 1:

[Group 1]
[1-1]
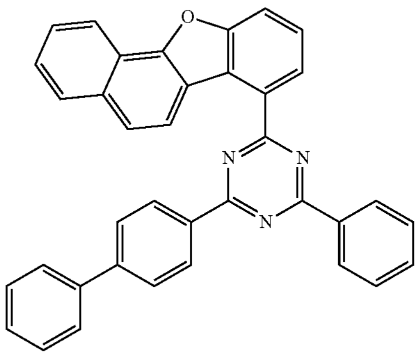
[1-2]
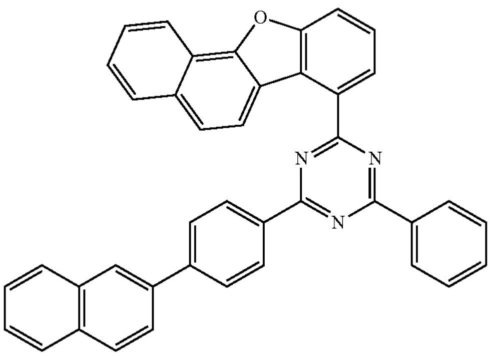
[1-3]
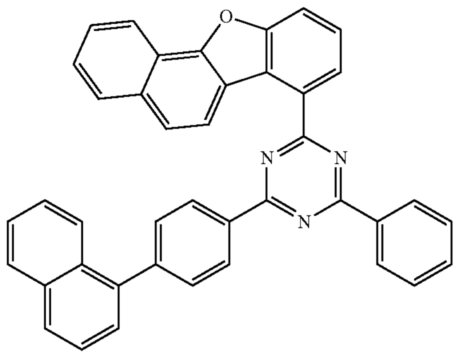
[1-4]
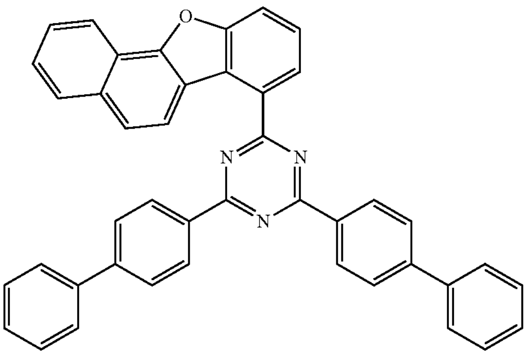
-continued
[1-5]
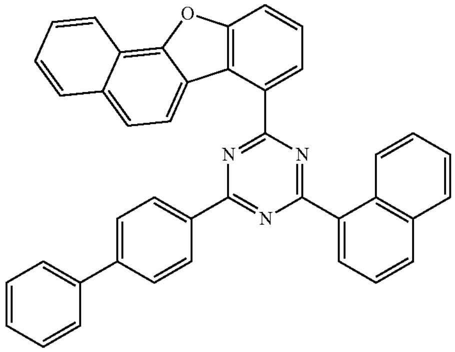
[1-6]
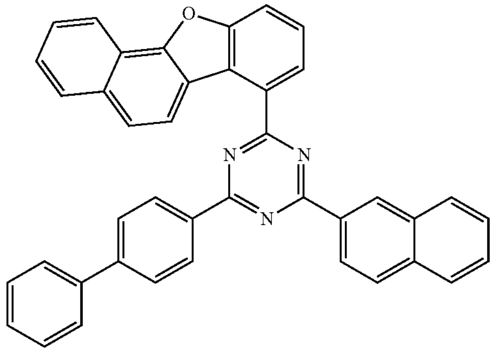
[1-7]
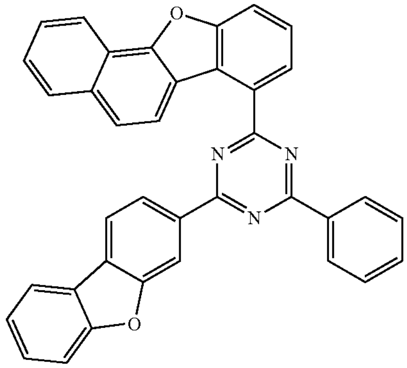
[1-8]
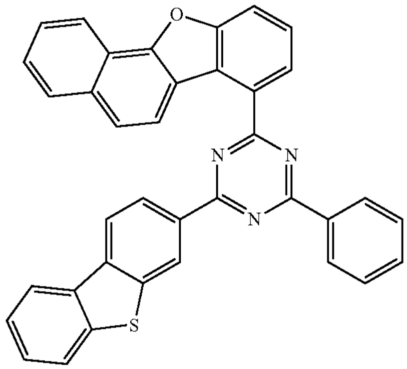

-continued
[1-9]
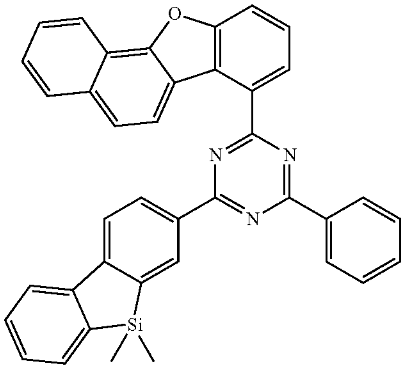
[1-10]
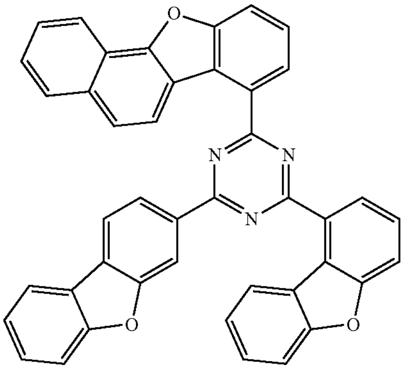
[1-11]
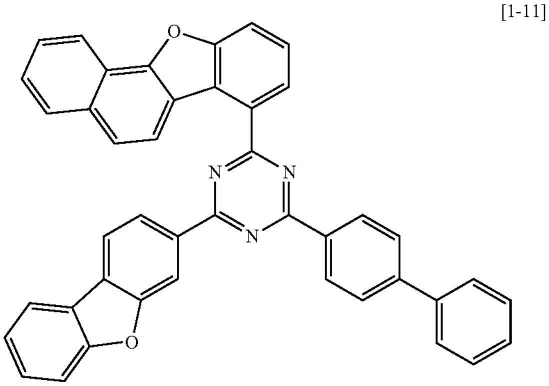
[1-12]
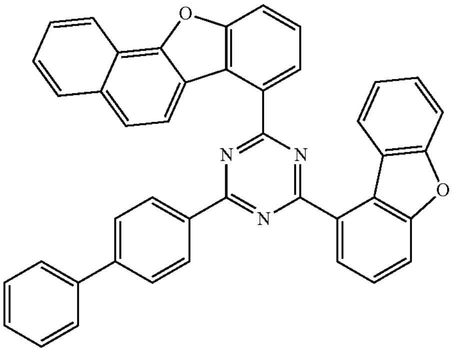
-continued
[1-13]
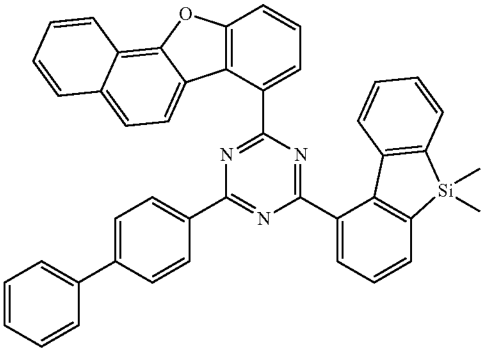
[1-14]
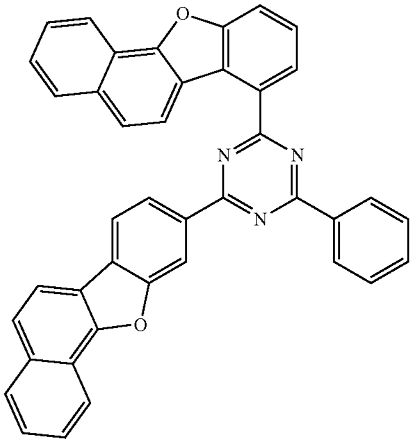
[1-15]
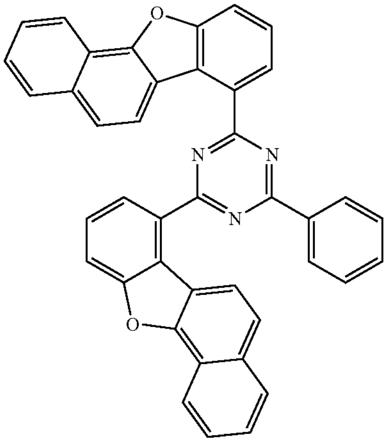
[1-16]
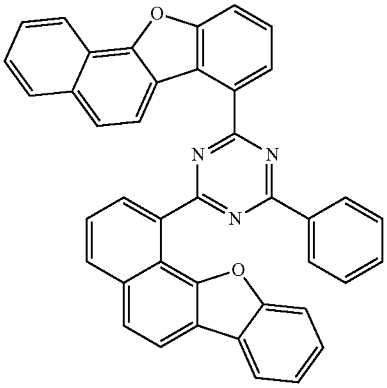

-continued
[1-17]
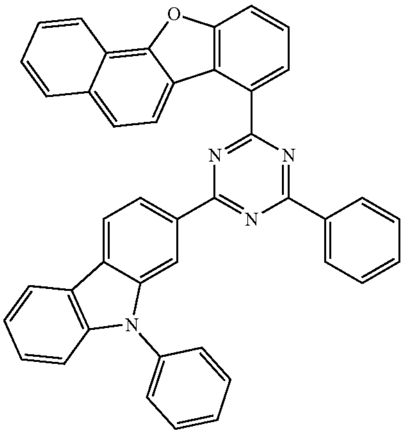
[1-18]
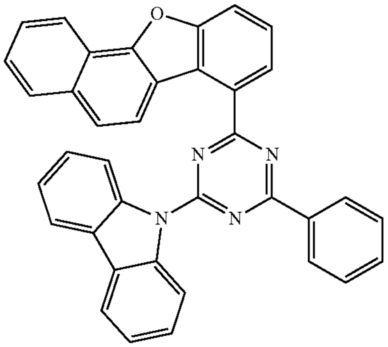
[1-19]
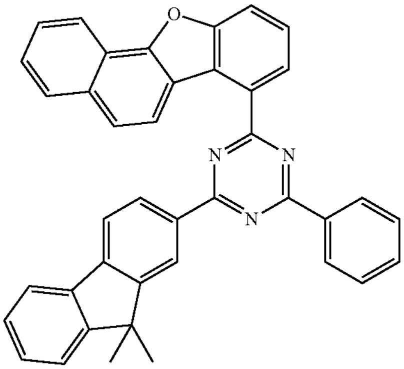
[1-20]
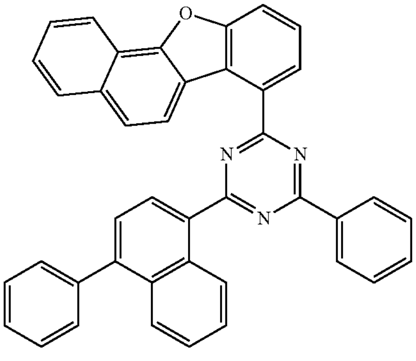
-continued
[1-21]
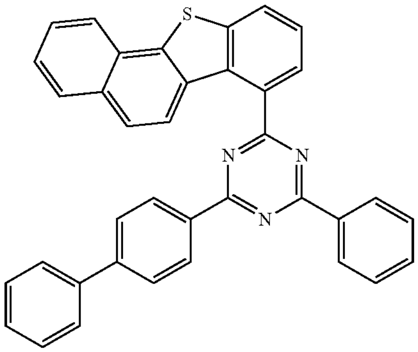
[1-22]
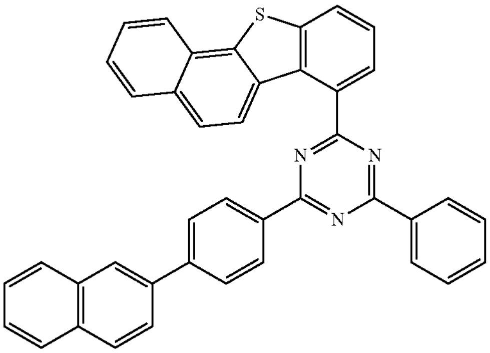
[1-23]
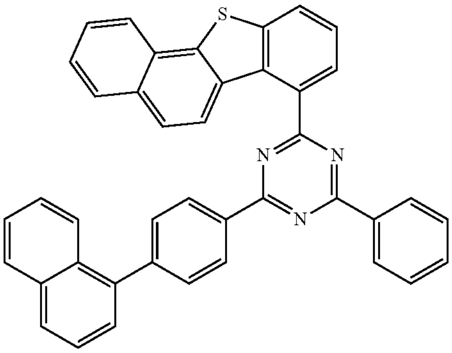
[1-24]
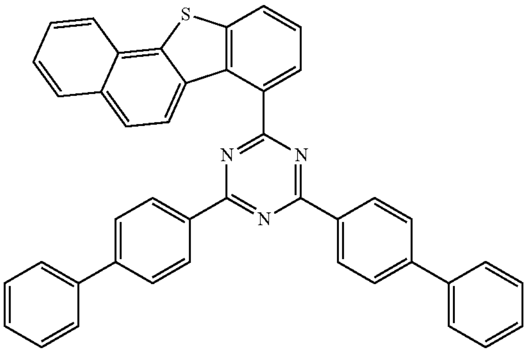

-continued
[1-25]
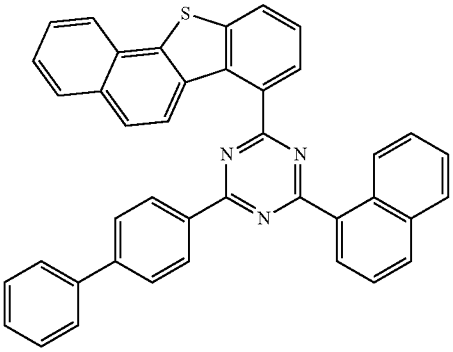
[1-26]
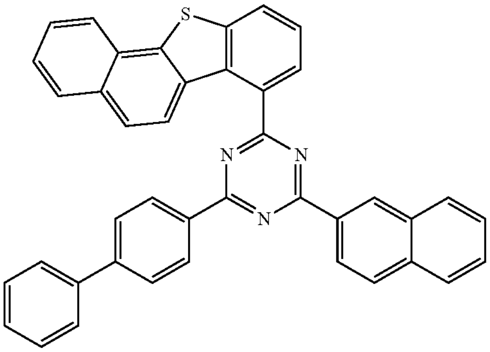
[1-27]
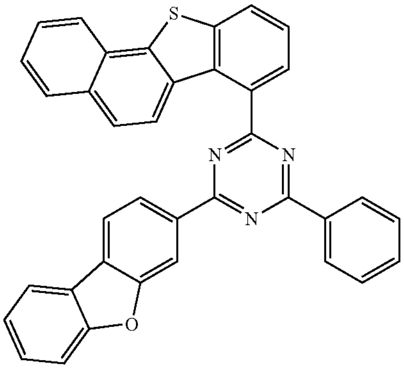
[1-28]
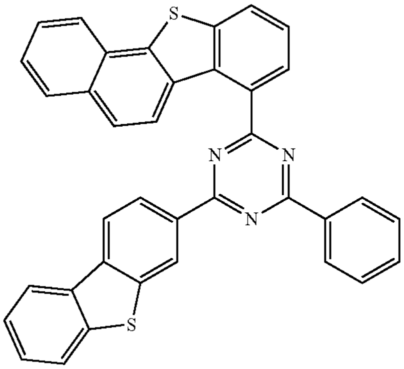
-continued
[1-29]
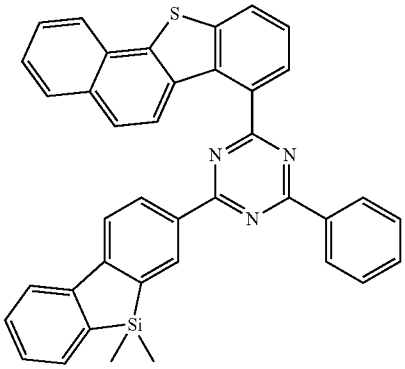
[1-30]
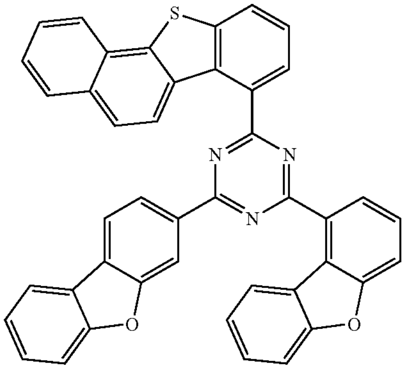
[1-31]
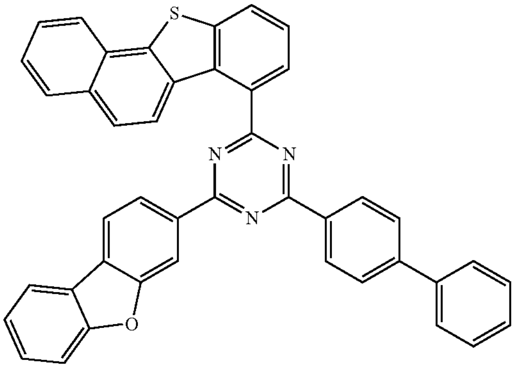
[1-32]
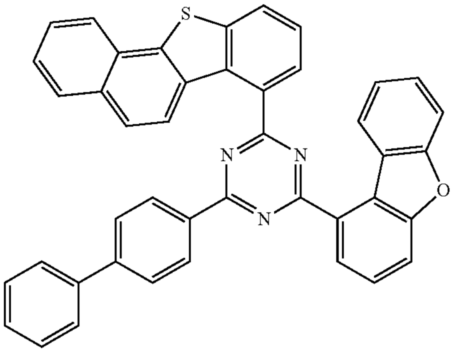

-continued
[1-33]
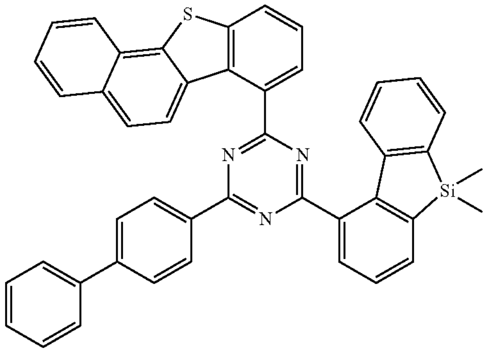
[1-34]
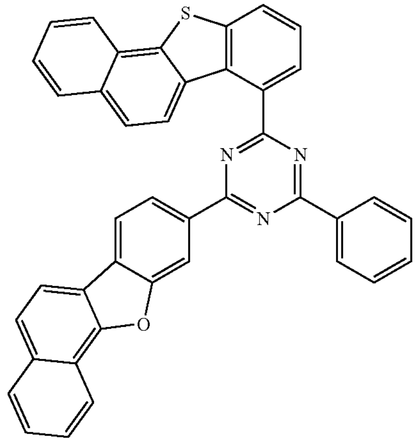
[1-35]
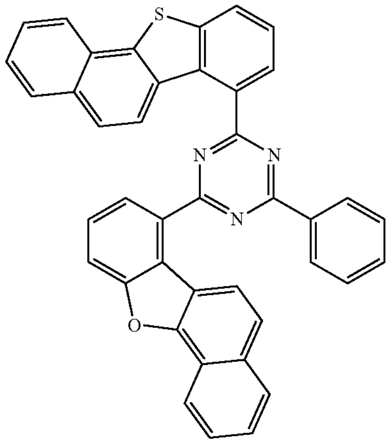
[1-36]
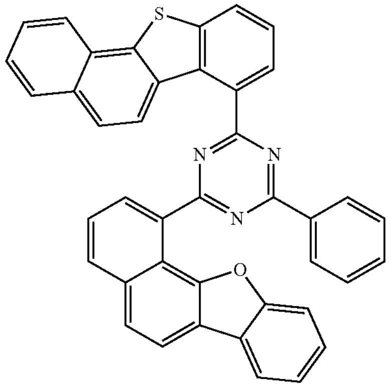
-continued
[1-37]
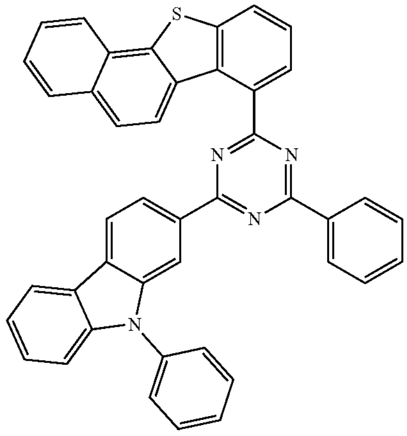
[1-38]
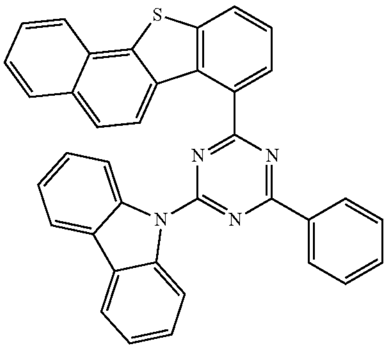
[1-39]
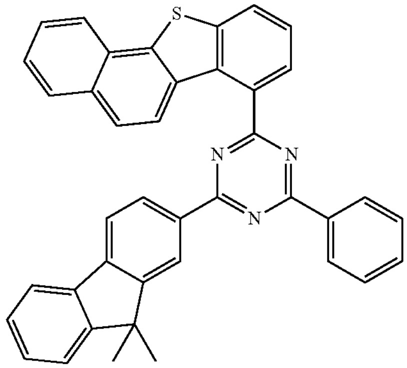
[1-40]
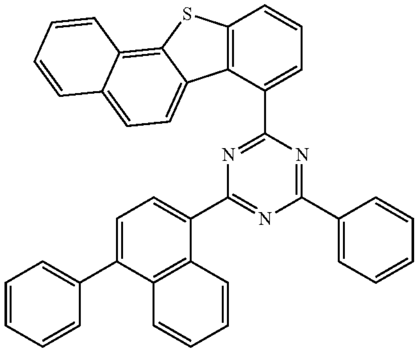

-continued
[1-41]
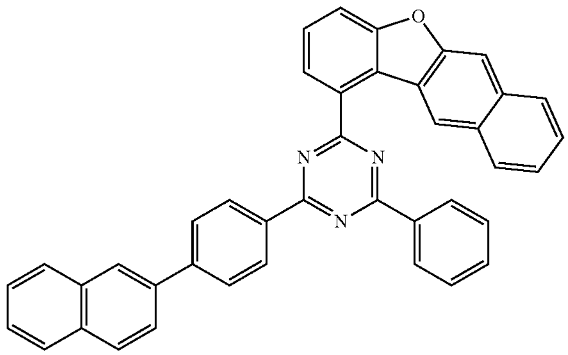
[1-42]
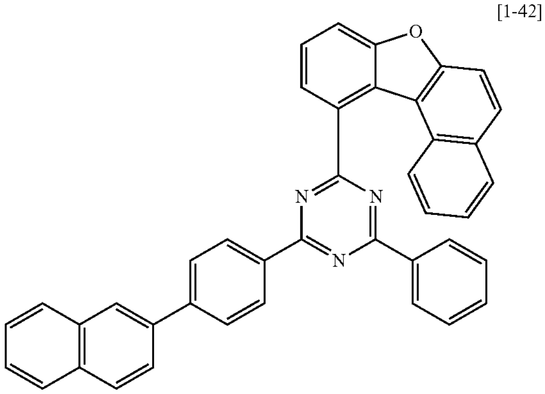
[1-43]
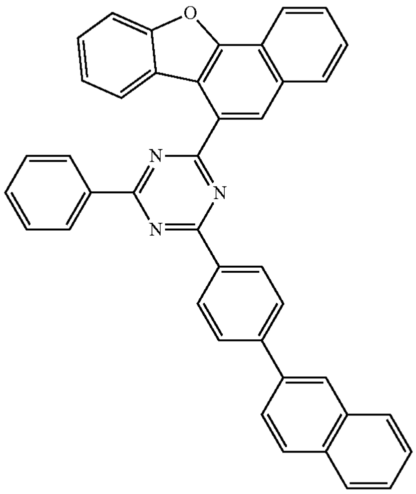
-continued
[1-44]
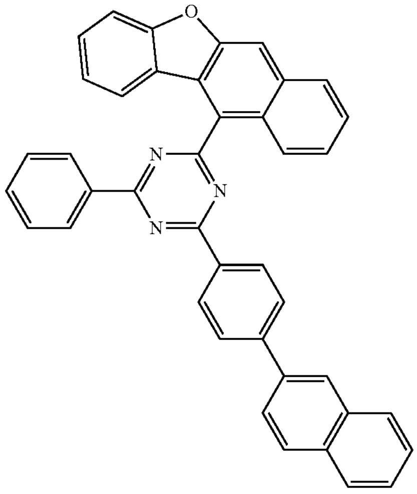
[1-45]
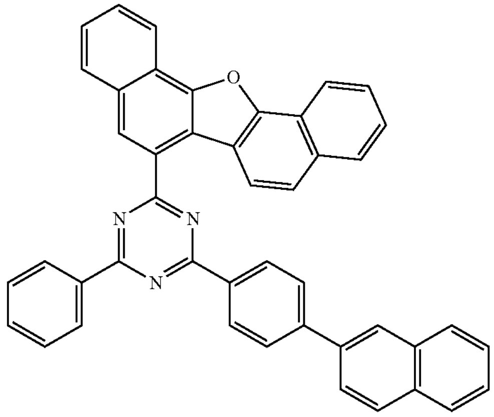
[1-46]
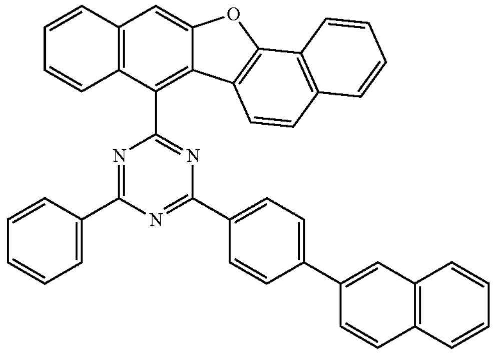

-continued
[1-47]
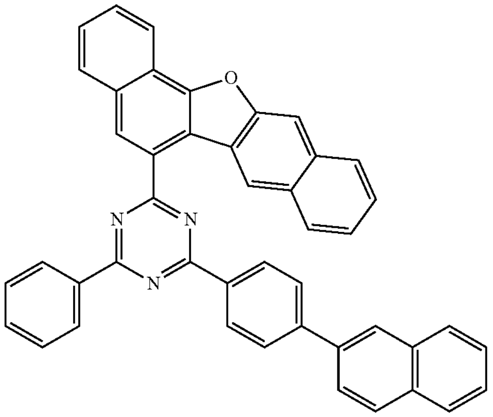
[1-48]
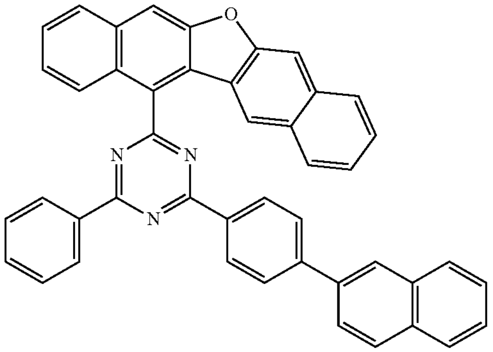
[1-49]
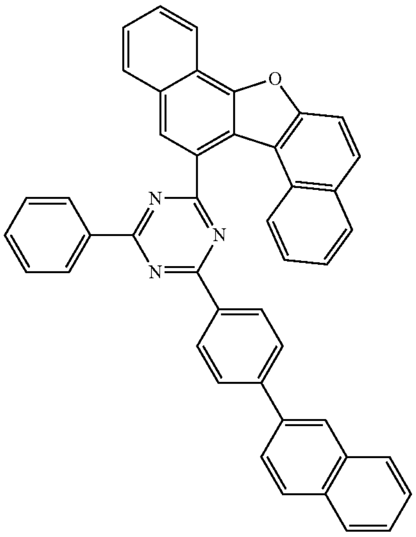
[1-50]
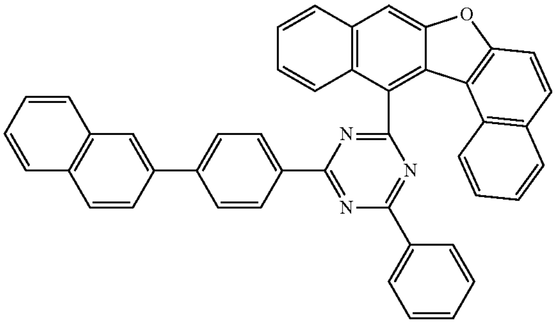
-continued
[1-51]
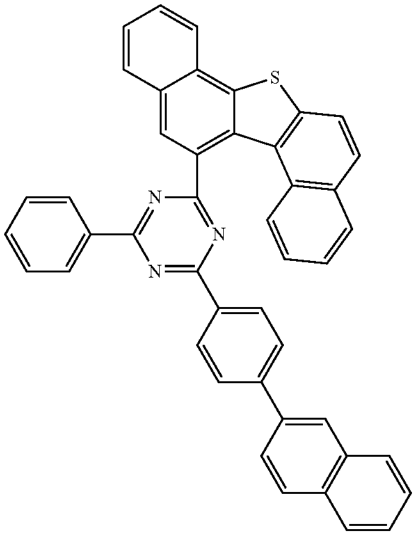
[1-52]
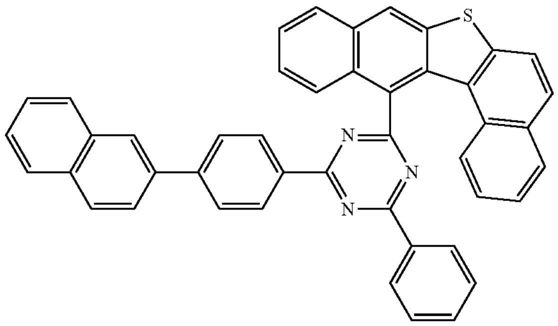
[1-53]
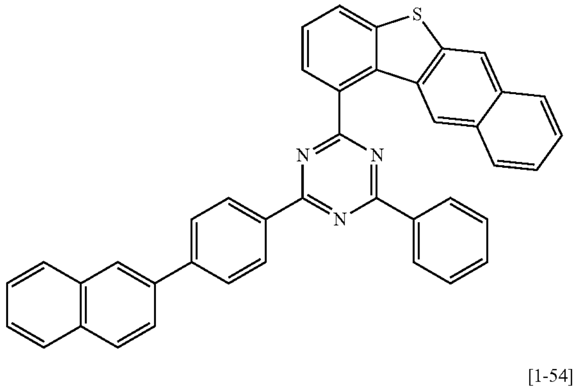
[1-54]
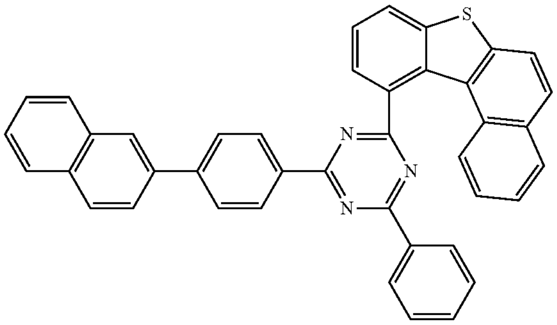

-continued
[1-55]
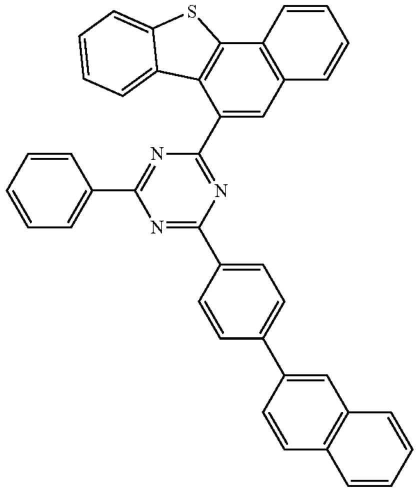
[1-56]
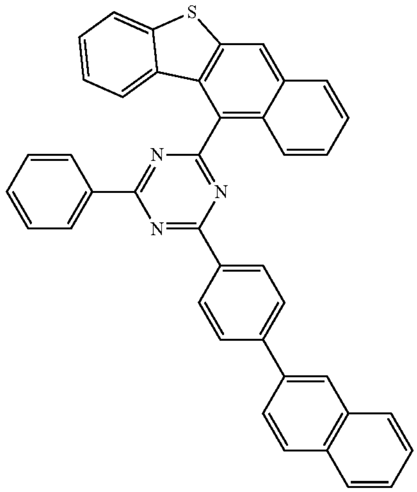
[1-57]
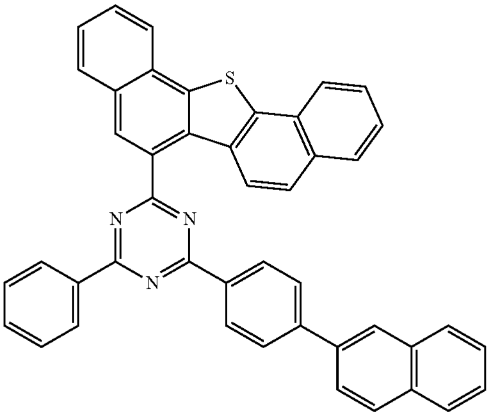
-continued
[1-58]
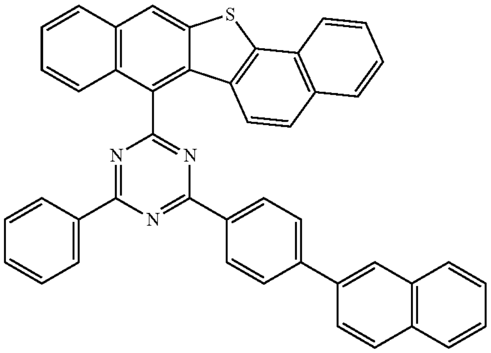
[1-59]
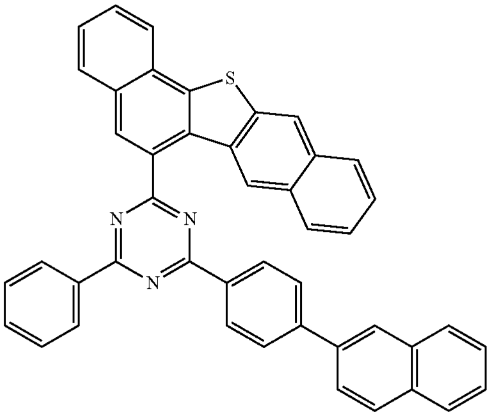
[1-60]
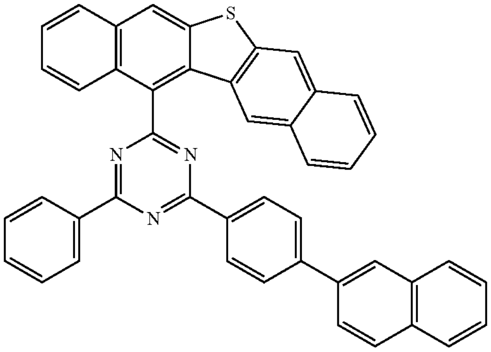
.
7. The composition as claimed in claim 1, wherein the second compound is represented by Chemical Formula 2-IA, Chemical Formula 2-IB, Chemical Formula 2-IC, Chemical Formula 2-ID, Chemical Formula 2-IE, Chemical Formula 2-IF, Chemical Formula 2-IIA, Chemical Formula 2-IIB, Chemical Formula 2-IIC, Chemical Formula 2-TID, Chemical Formula 2-TIE, or Chemical Formula 2-IIF:

[Chemical Formula 2-IA]
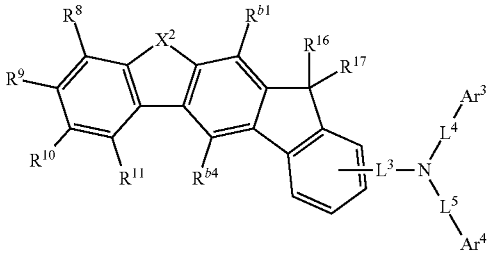
[Chemical Formula 2-IB]
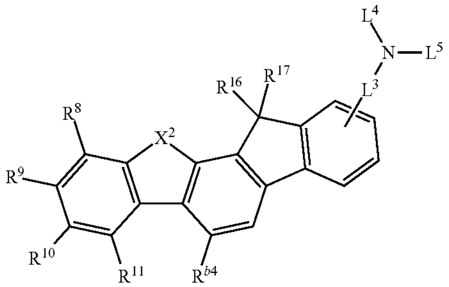
[Chemical Formula 2-IC]
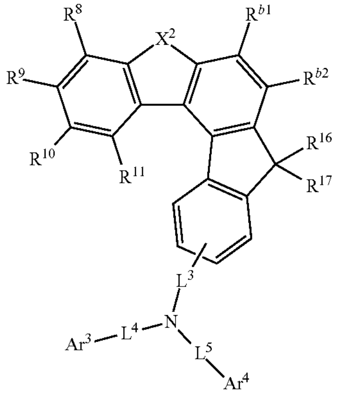
[Chemical Formula 2-ID]
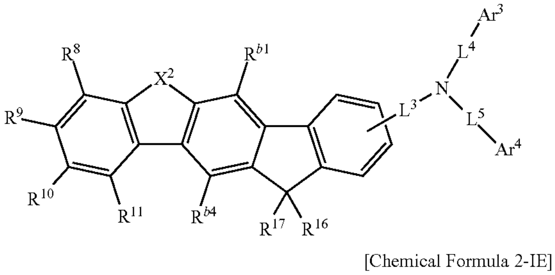
[Chemical Formula 2-IE]
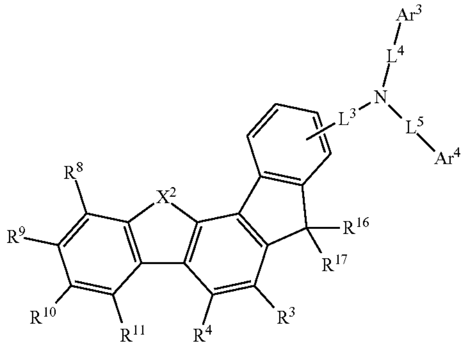
-continued
[Chemical Formula 2-IF]
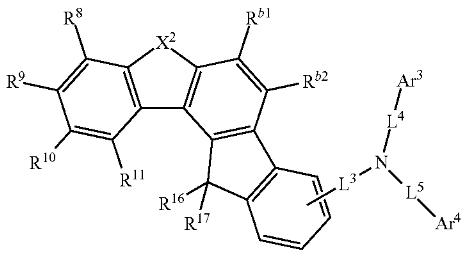
[Chemical Formula 2-IIA]
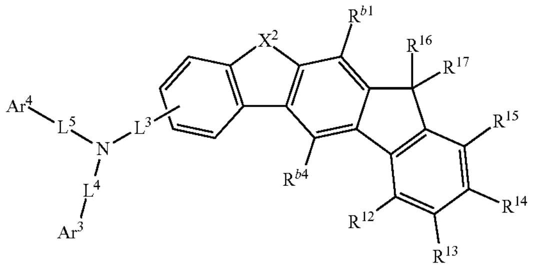
[Chemical Formula 2-IIB]
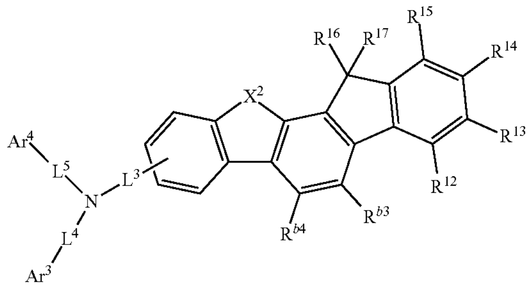
[Chemical Formula 2-IIC]
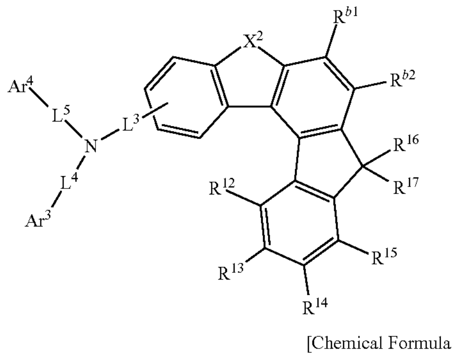
[Chemical Formula 2-IID]
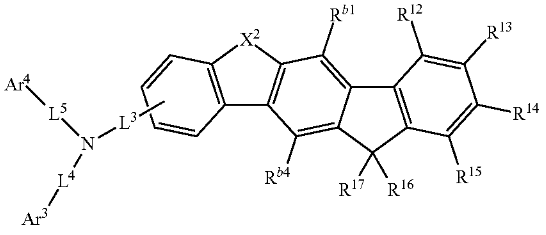

-continued

[Chemical Formula 2-IIE]

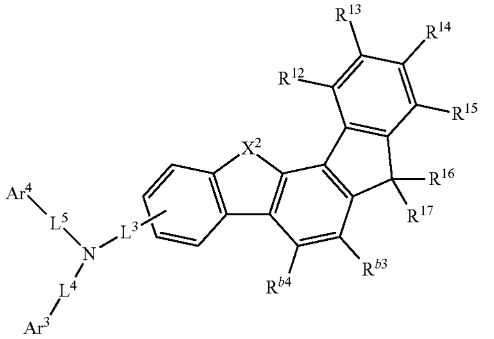

[Chemical Formula 2-IIF]

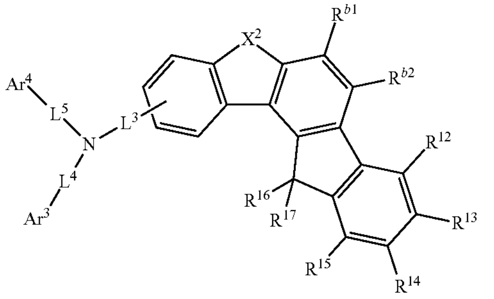

wherein, in Chemical Formula 2-IA to Chemical Formula 2-IF and Chemical Formula 2-IIA to Chemical Formula 2-IIF, $X^2$, $Ar^3$, $Ar^4$, $L^3$ to $L^5$, $R^8$ to $R^{17}$ are defined the same as those of Chemical Formulae 2 and 3, and $R^{b1}$ to $R^{b4}$ are each independently defined the same as $R^b$ of Chemical Formulae 2 and 3.

8. The composition as claimed in claim 1, wherein the second compound is represented by Chemical Formula 2-IA-2, Chemical Formula 2-IA-3, Chemical Formula 2-IB-2, Chemical Formula 2-IB-3, Chemical Formula 2-IC-2, Chemical Formula 2-IC-3, Chemical Formula 2-ID-2, Chemical Formula 2-ID-3, Chemical Formula 2-IE-1, Chemical Formula 2-IE-2, Chemical Formula 2-IE-3, Chemical Formula 2-IE-4, Chemical Formula 2-IF-2, Chemical Formula 2-IF-3, Chemical Formula 2-IIA-4, Chemical Formula 2-IIB-4, Chemical Formula 2-IIC-4, Chemical Formula 2-IID-4, Chemical Formula 2-IIE-1, Chemical Formula 2-IIE-2, Chemical Formula 2-IIE-3, Chemical Formula 2-IIE-4, or Chemical Formula 2-IIF-4:

[Chemical Formula 2-IA-2]

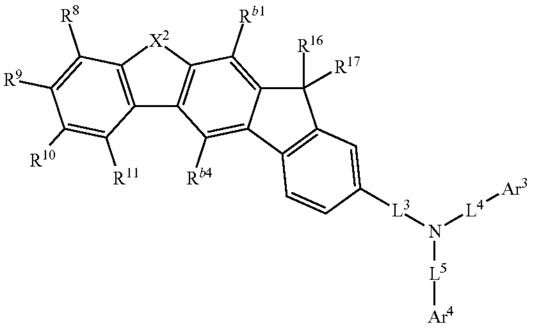

-continued

[Chemical Formula 2-IA-3]

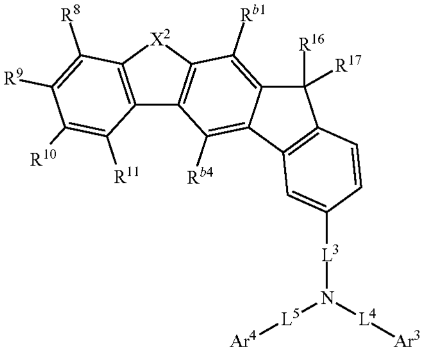

[Chemical Formula 2-IB-2]

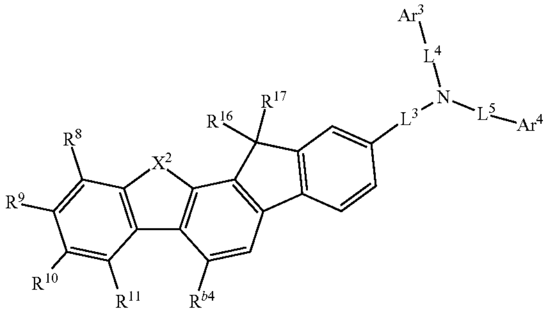

[Chemical Formula 2-IB-3]

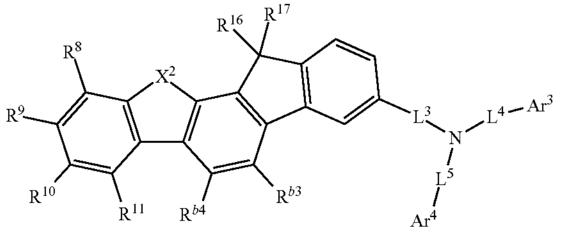

[Chemical Formula 2-IC-2]

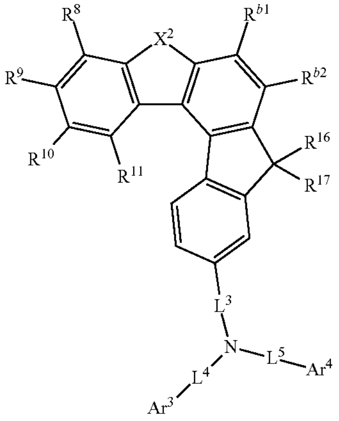

-continued
[Chemical Formula 2-IC-3]
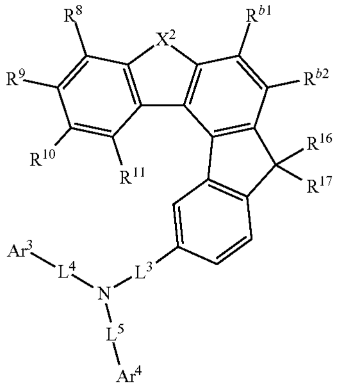
[Chemical Formula 2-ID-2]
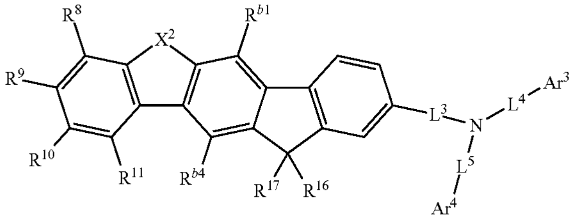
[Chemical Formula 2-ID-3]
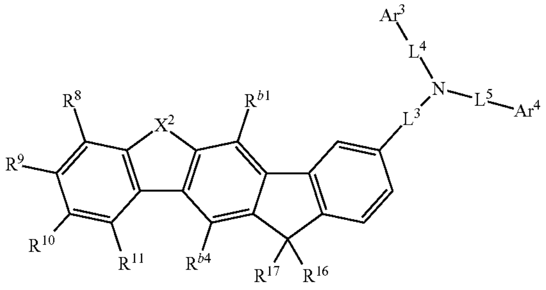
[Chemical Formula 2-IE-1]
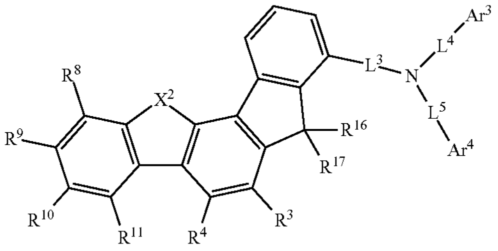
[Chemical Formula 2-IE-2]
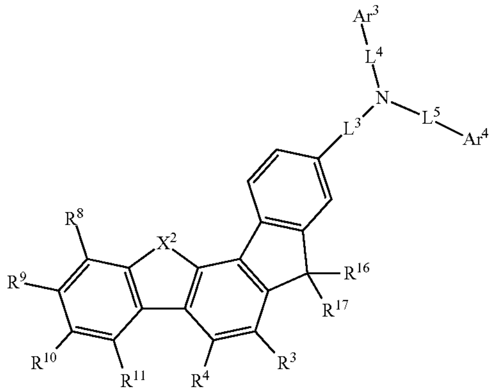
-continued
[Chemical Formula 2-IE-3]
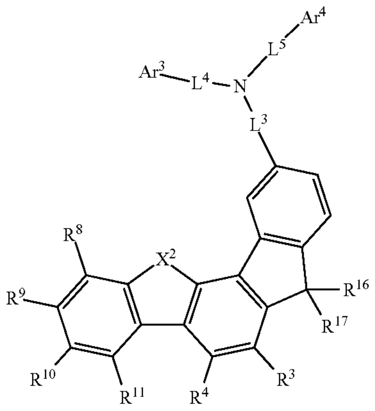
[Chemical Formula 2-IE-4]
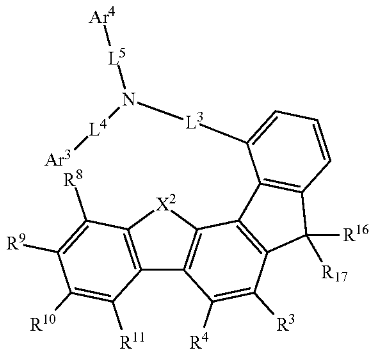
[Chemical Formula 2-IF-2]
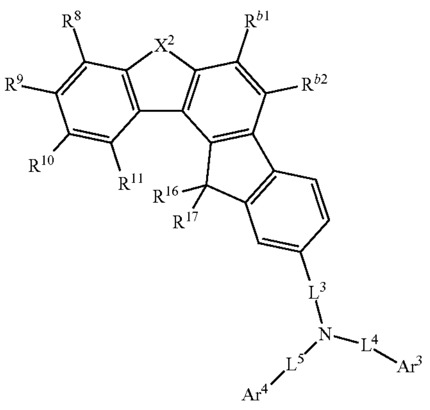
[Chemical Formula 2-IF-3]
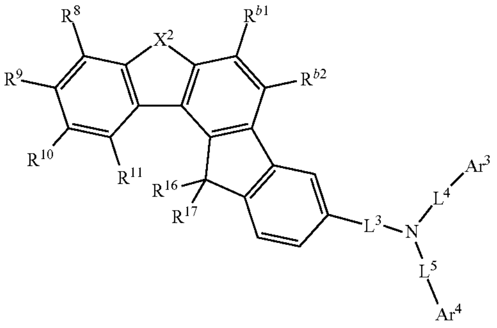

-continued
[Chemical Formula 2-IIA-4]
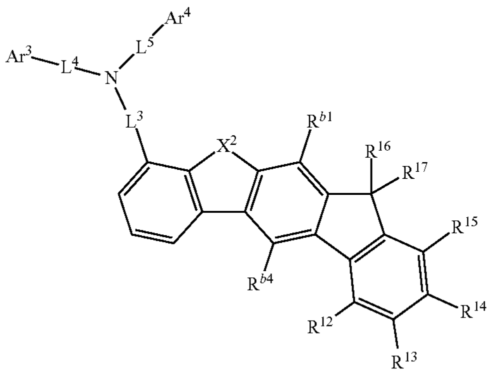
[Chemical Formula 2-IIB-4]
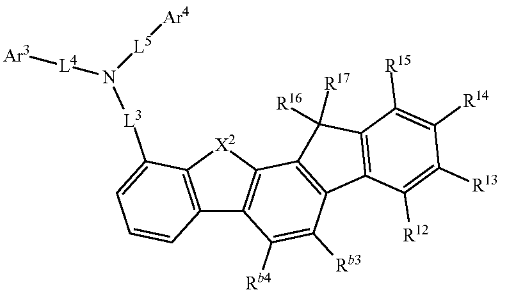
[Chemical Formula 2-IIC-4]
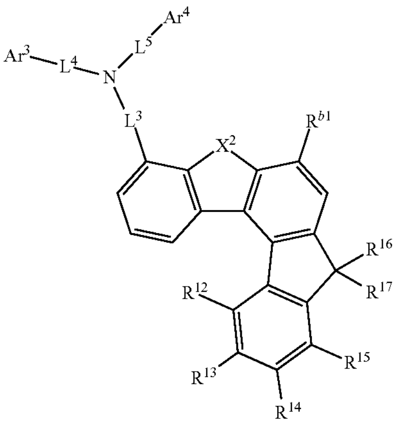
[Chemical Formula 2-IID-4]
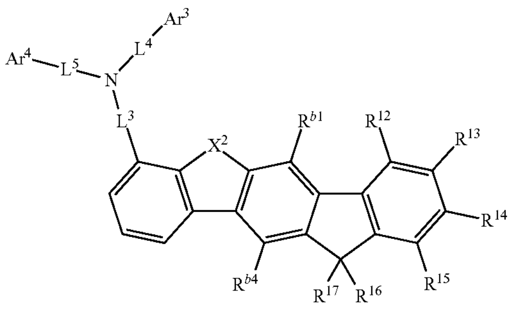
-continued
[Chemical Formula 2-IIE-1]
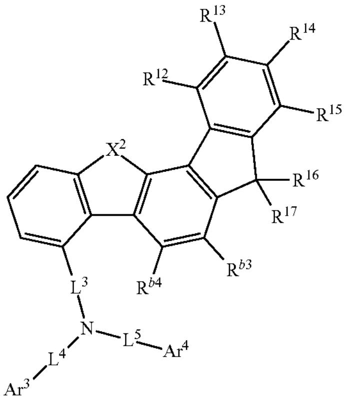
[Chemical Formula 2-IIE-2]
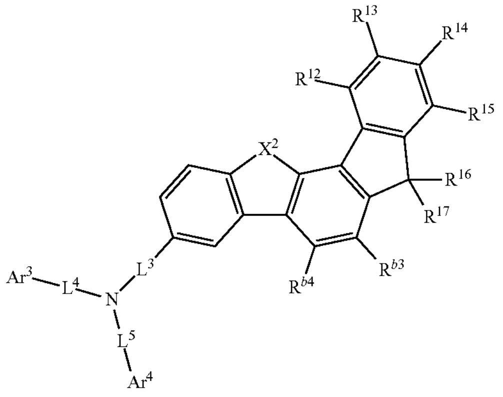
[Chemical Formula 2-IIE-3]
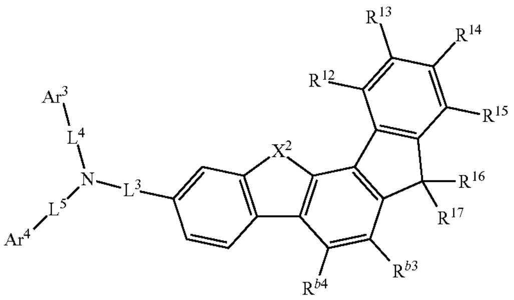
[Chemical Formula 2-IIE-4]
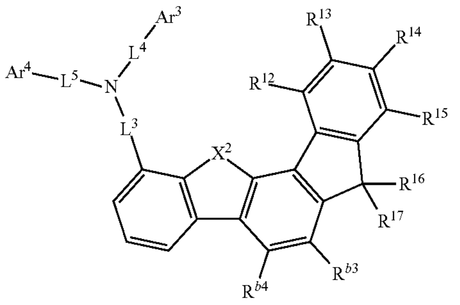

-continued

[Chemical Formula 2-IIF-4]

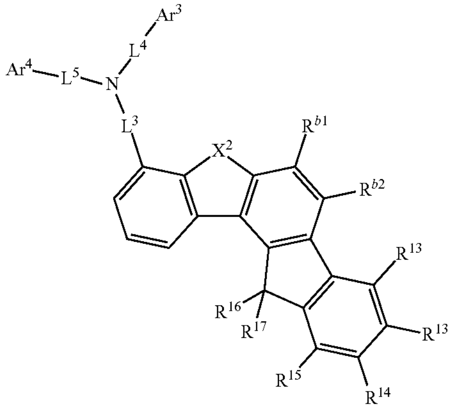

wherein, in Chemical Formula 2-IA-2, Chemical Formula 2-IA-3, Chemical Formula 2-IB-2, Chemical Formula 2-IB-3, Chemical Formula 2-IC-2, Chemical Formula 2-IC-3, Chemical Formula 2-ID-2, Chemical Formula 2-ID-3, Chemical Formula 2-IE-1, Chemical Formula 2-IE-2, Chemical Formula 2-IE-3, Chemical Formula 2-IE-4, Chemical Formula 2-IF-2, Chemical Formula 2-IF-3, Chemical Formula 2-IIA-4, Chemical Formula 2-IIB-4, Chemical Formula 2-IIC-4, Chemical Formula 2-IID-4, Chemical Formula 2-IIE-1, Chemical Formula 2-IIE-2, Chemical Formula 2-IIE-3, Chemical Formula 2-IIE-4, and Chemical Formula 2-IIF-4, $X^2$, $Ar^3$, $Ar^4$, $L^3$ to $L^5$, $R^8$ to $R^{17}$ are defined the same as those of Chemical Formulae 2 and 3, and $R^{b1}$ to $R^{b4}$ are each independently defined the same as $R^b$ of Chemical Formulae 2 and 3.

9. The composition as claimed in claim 8, wherein the second compound is represented by Chemical Formula 2-IE-2 or Chemical Formula 2-IIE-4.

10. The composition as claimed in claim 8, wherein:

$Ar^3$ and $Ar^4$ are each independently a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group, $L^3$ to $L^5$ are each independently a single bond, a substituted or unsubstituted phenylene group, or a substituted or unsubstituted biphenylene group, $R^{b1}$ to $R^{b4}$ and $R^8$ to $R^{15}$ are each independently hydrogen, deuterium, a substituted or unsubstituted C1 to C10 alkyl group, or a substituted or unsubstituted C6 to C12 aryl group, and $R^{16}$ and $R^{17}$ are each independently a substituted or unsubstituted C1 to C10 alkyl group, or a substituted or unsubstituted C6 to C10 aryl group.

11. The composition as claimed in claim 1, wherein the second compound is a compound of Group 2:

[Group 2]

[A-1]

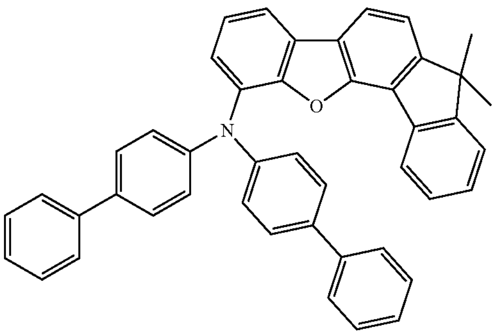

[A-2]

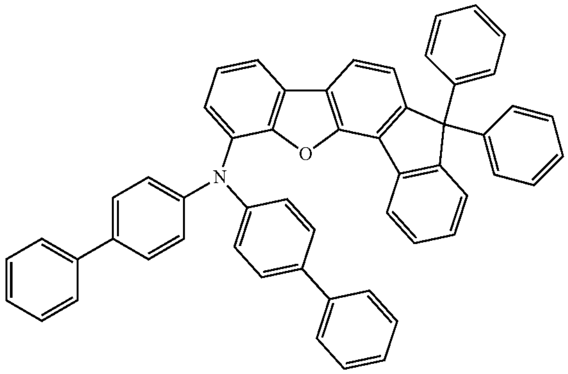

[A-3]

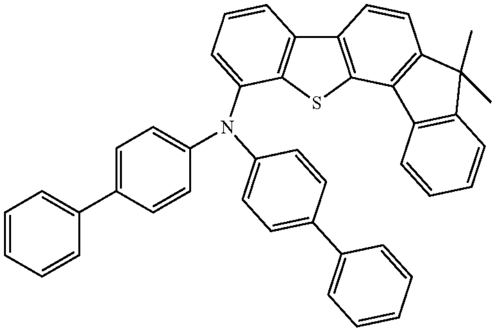

[A-4]

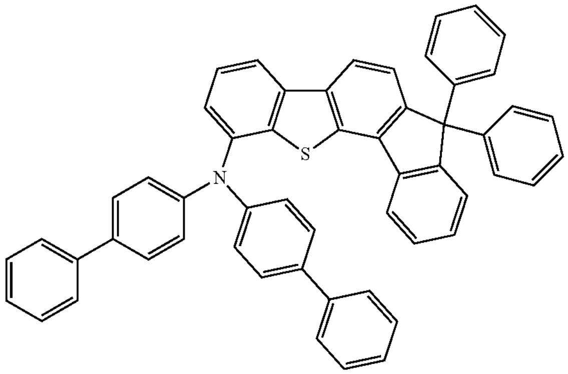

-continued
[A-5]
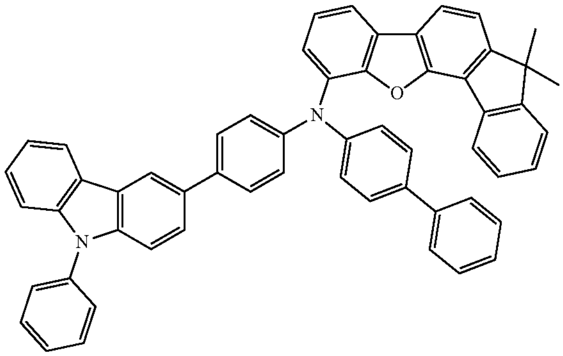
[A-6]
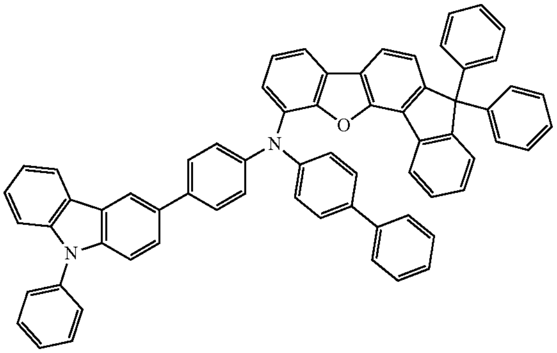
[A-7]
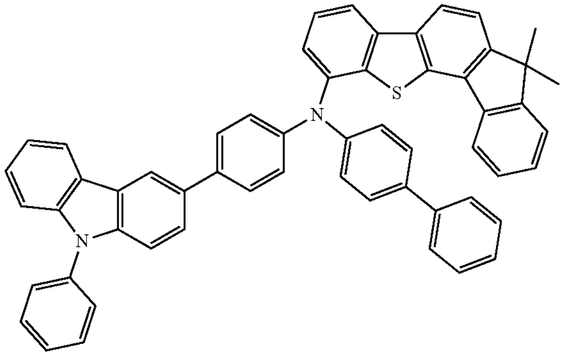
[A-8]
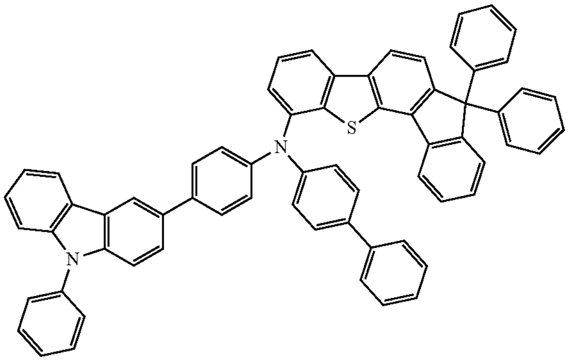
-continued
[A-9]
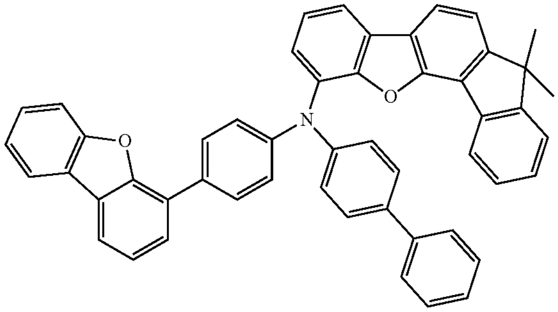
[A-10]
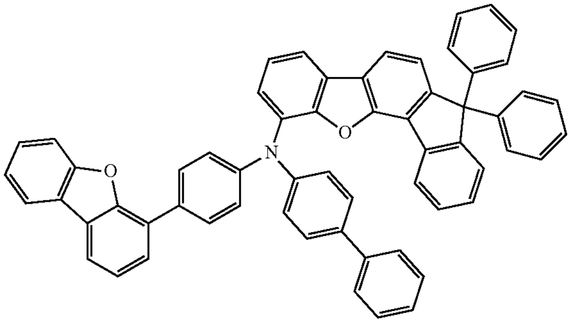
[A-11]
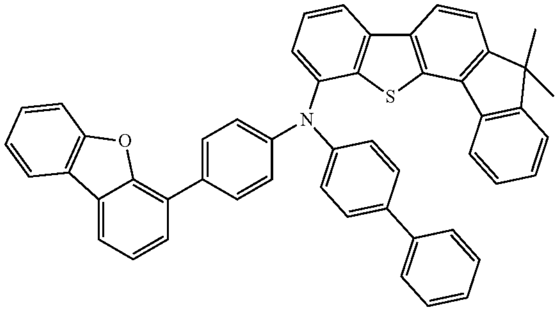
[A-12]
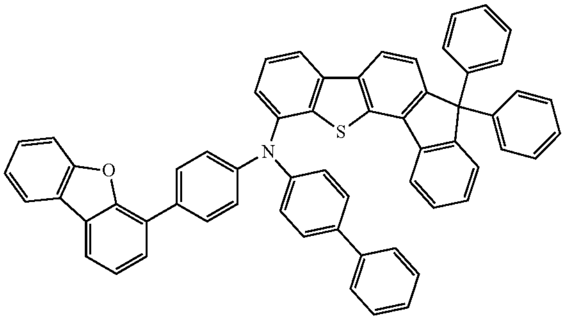

-continued
[A-13]
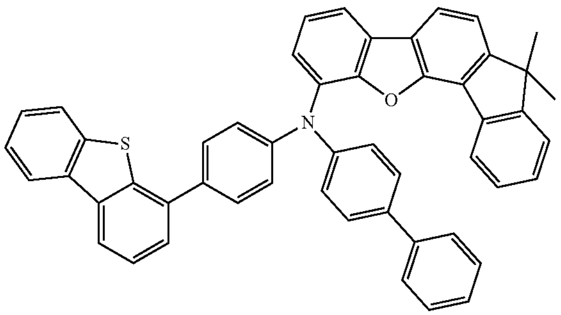
[A-14]
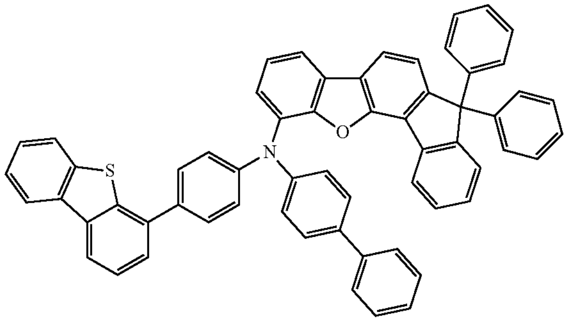
[A-15]
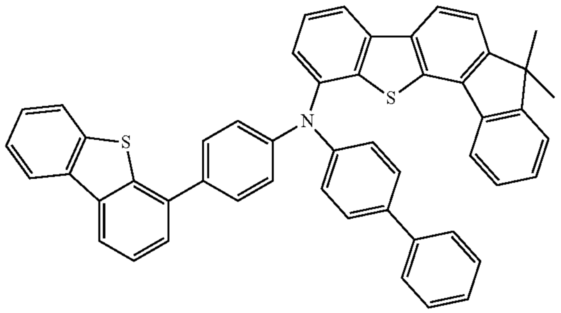
[A-16]
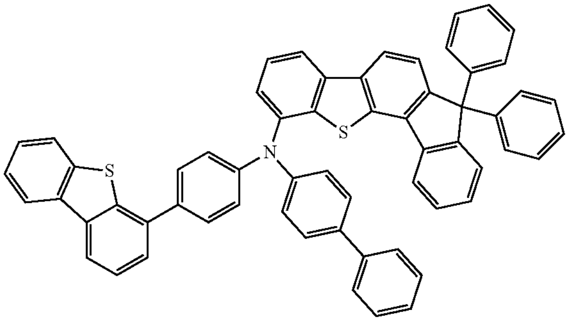
-continued
[A-17]
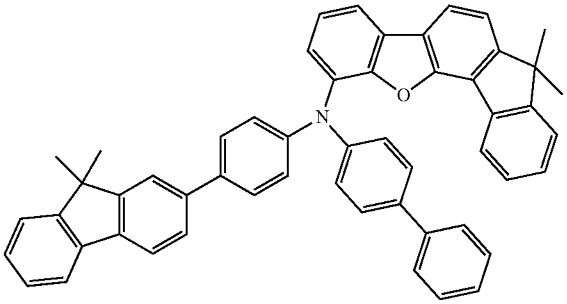
[A-18]
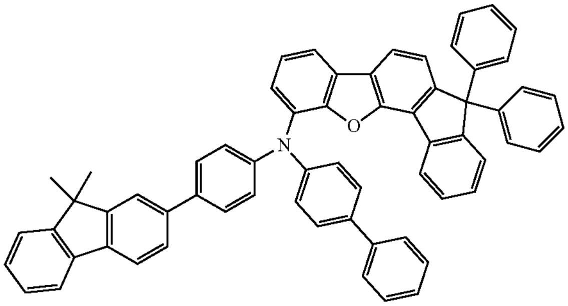
[A-19]
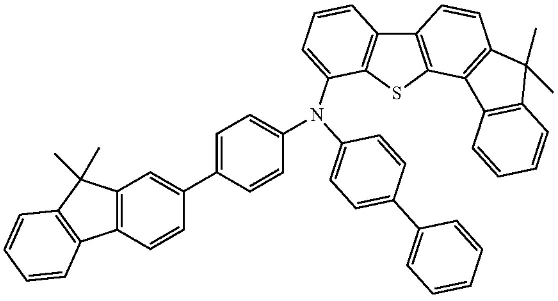
[A-20]
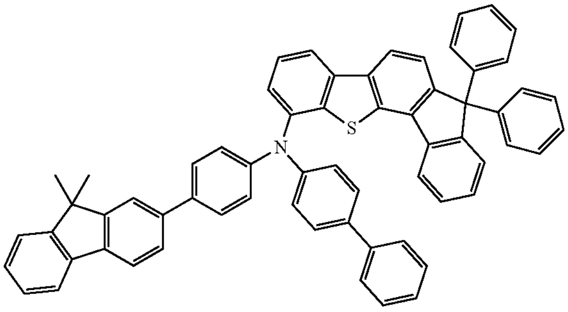

-continued
[A-21]
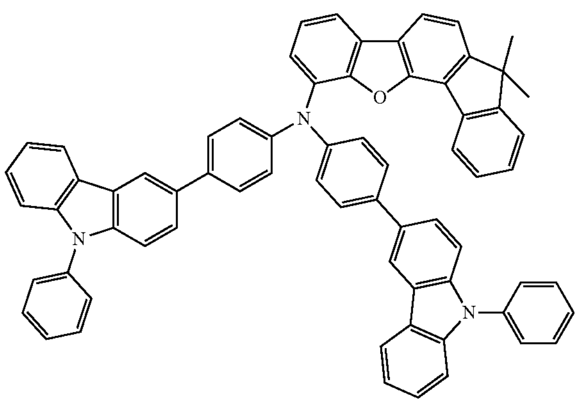
[A-22]
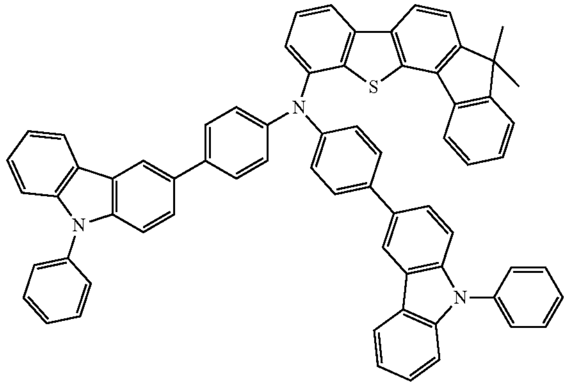
[A-23]
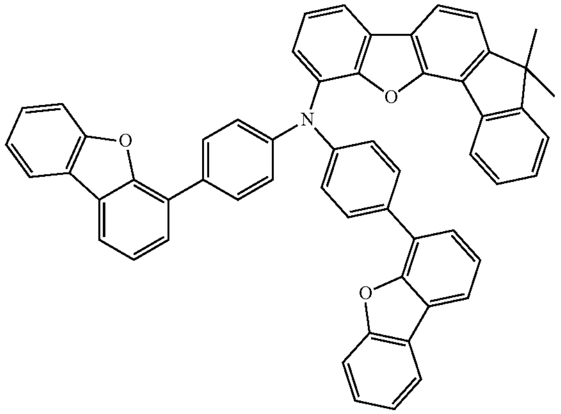
-continued
[A-24]
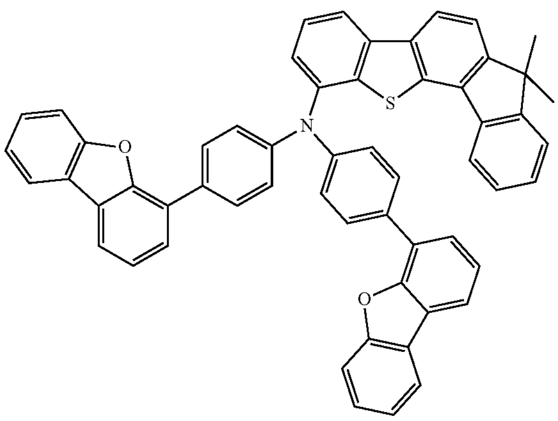
[A-25]
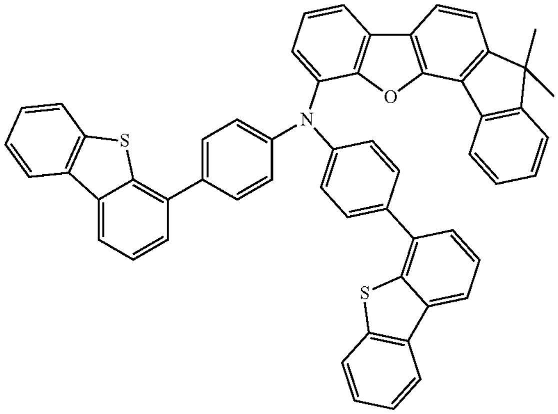
[A-26]
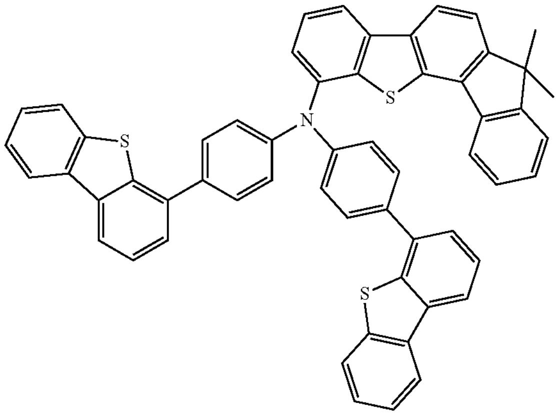

-continued
[A-27]
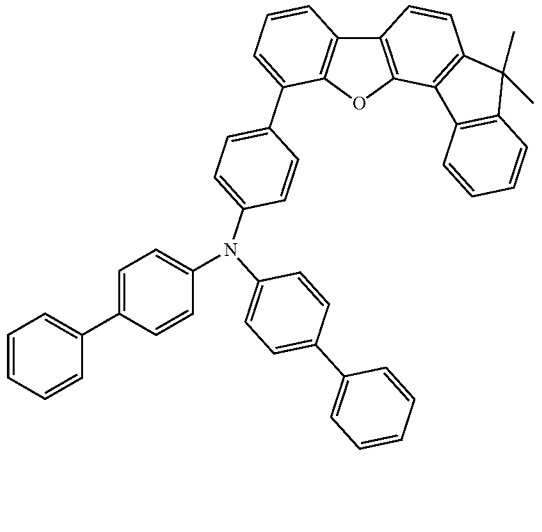
[A-28]
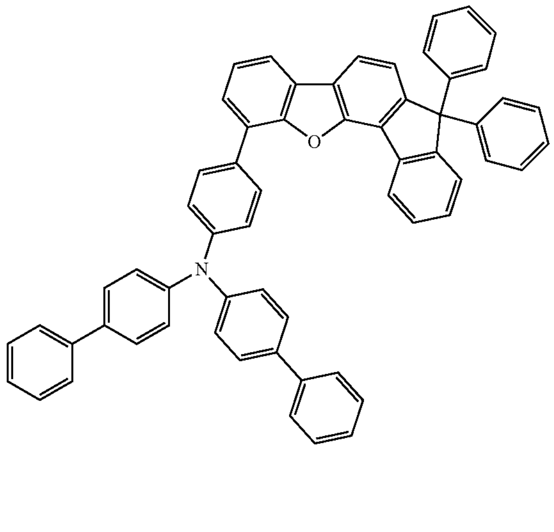
[A-29]
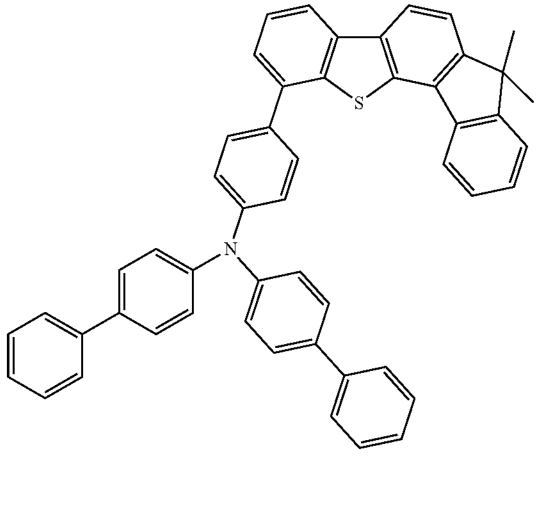
-continued
[A-30]
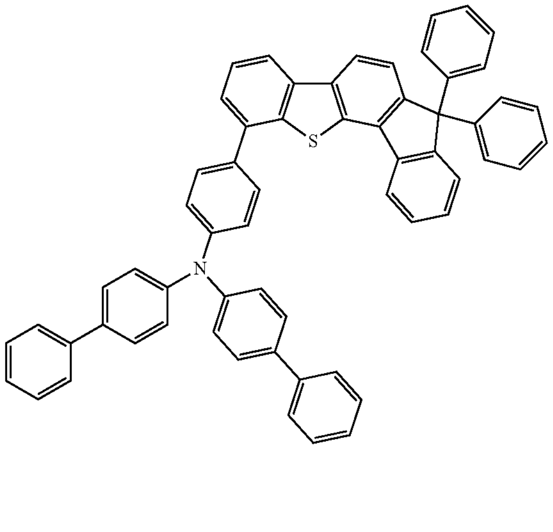
[A-31]
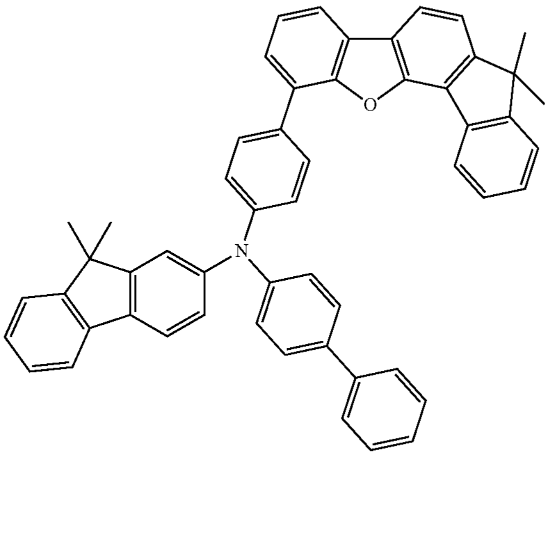
[A-32]
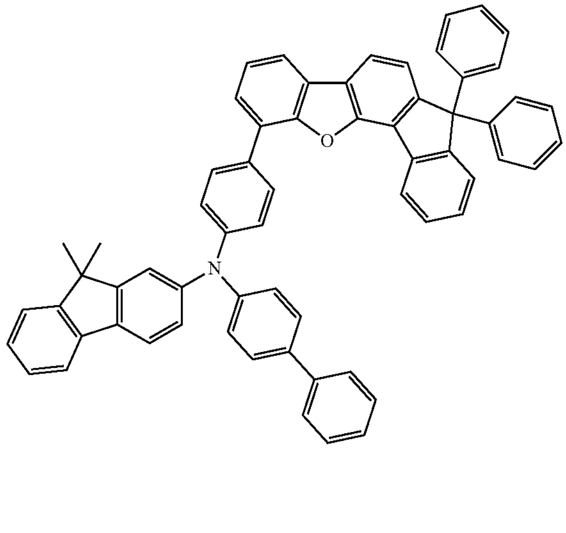

-continued
[A-33]
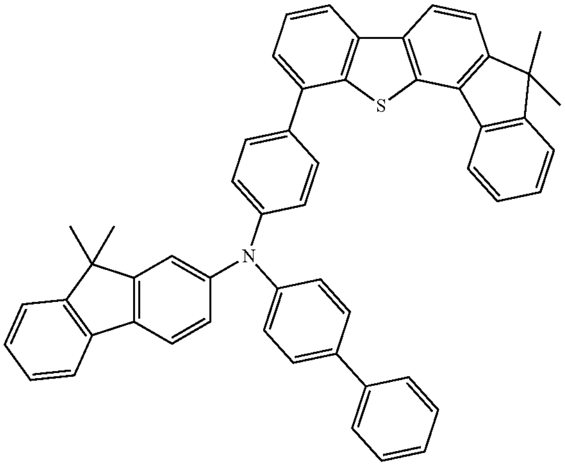
[A-34]
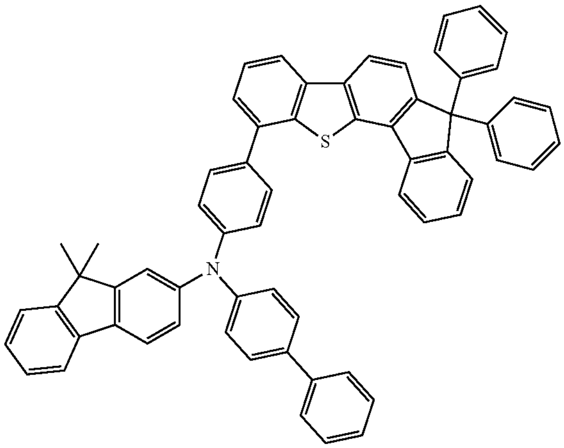
[A-35]
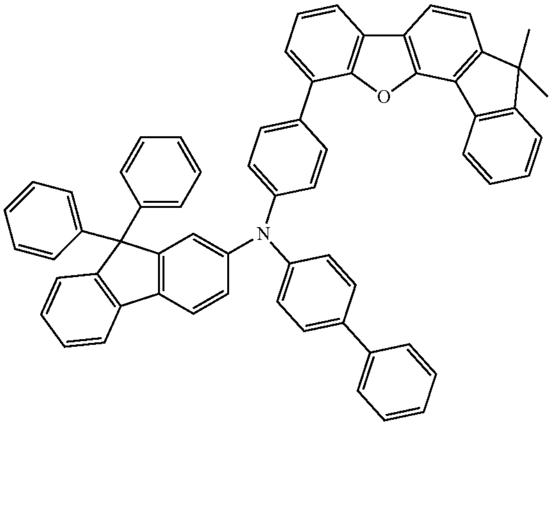
-continued
[A-36]
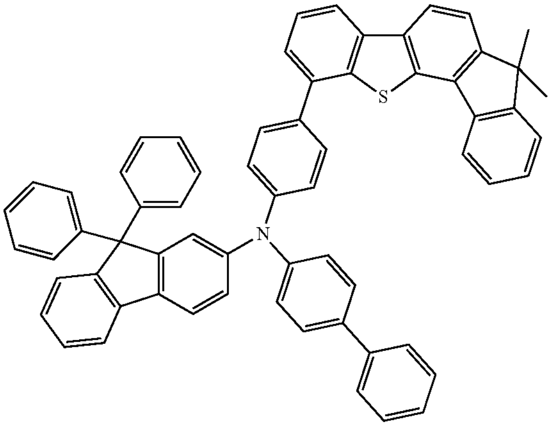
[A-37]
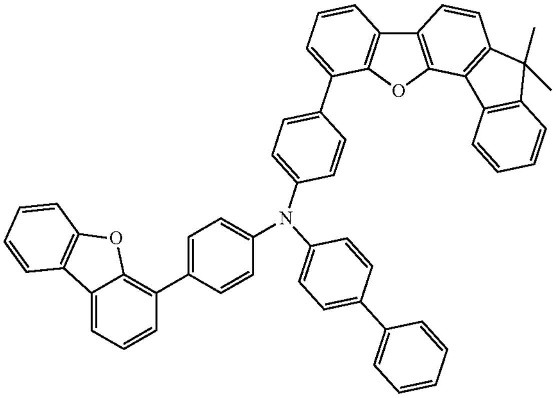
[A-38]
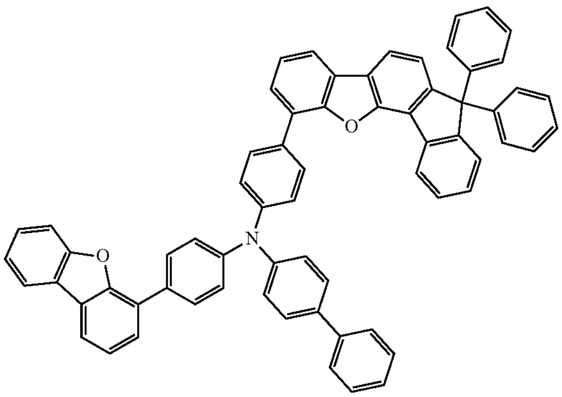

[A-39]
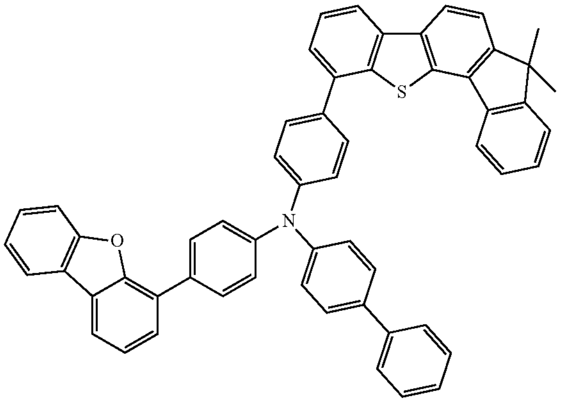
[A-40]
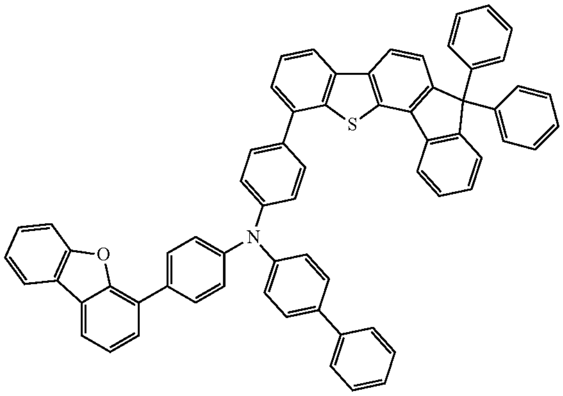
[A-41]
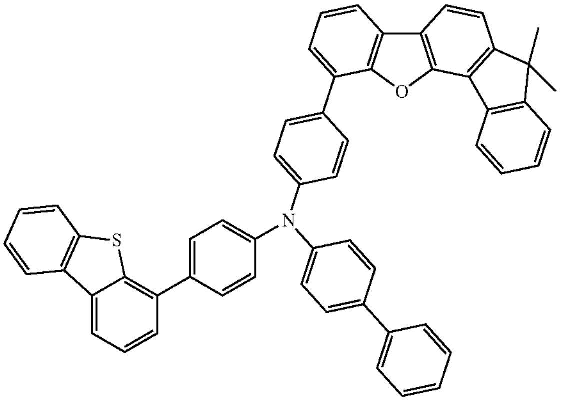
[A-42]
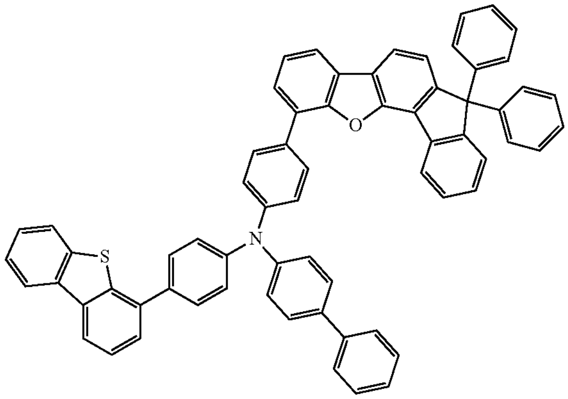
[A-43]
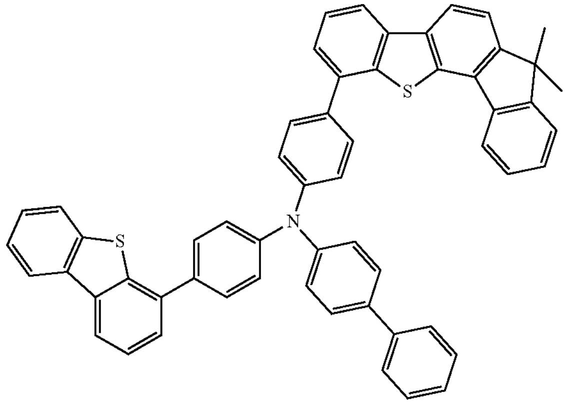
[A-44]
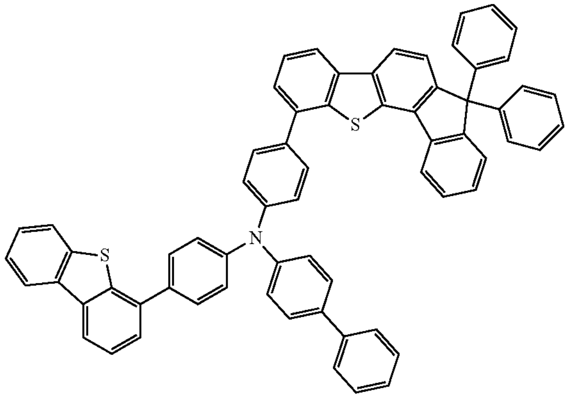

-continued
[A-45]
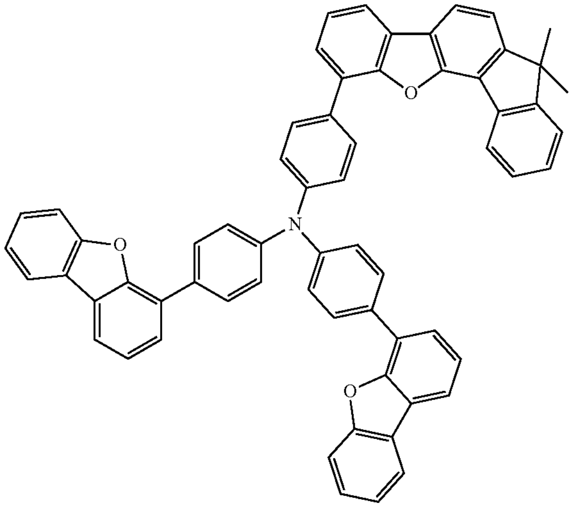
[A-46]
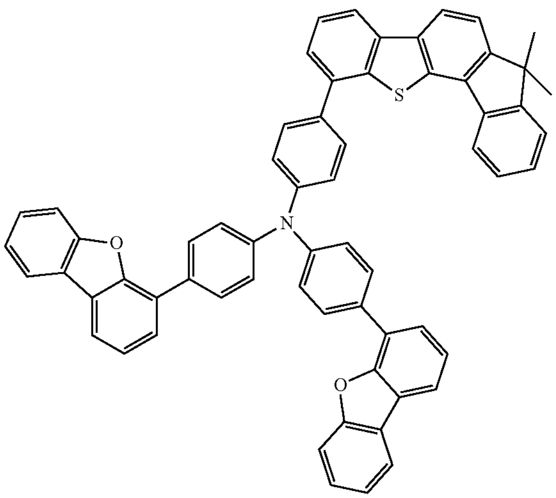
[A-47]
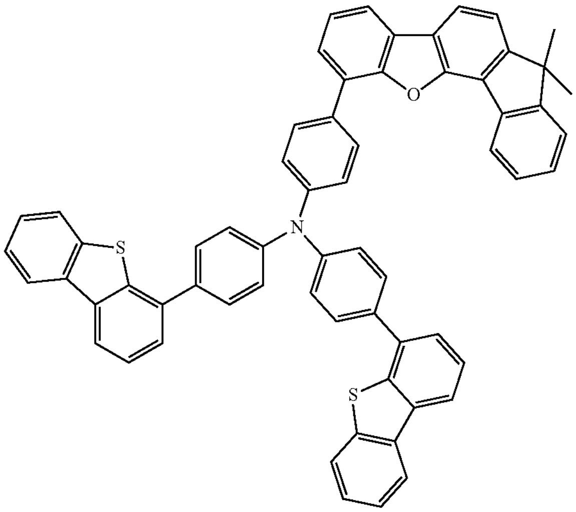
-continued
[A-48]
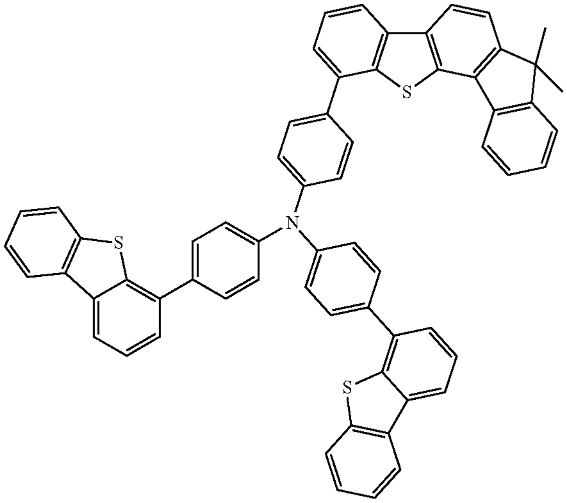
[A-49]
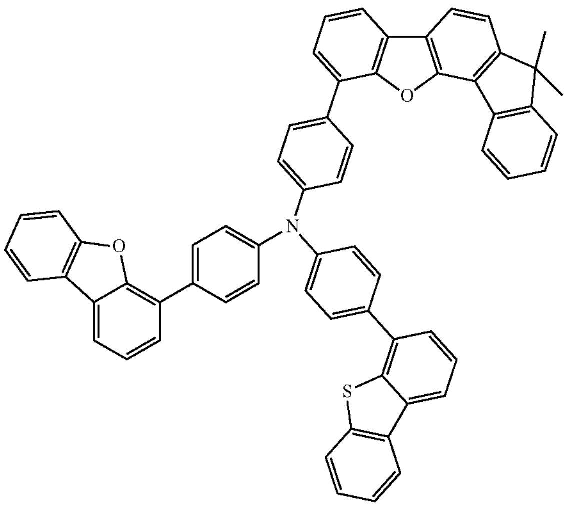
[A-50]
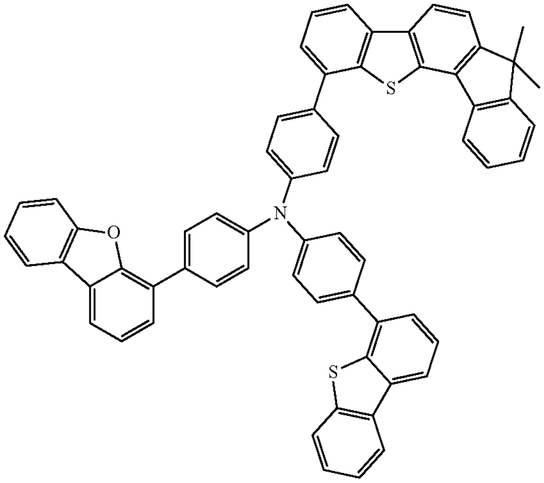

-continued
[A-51]
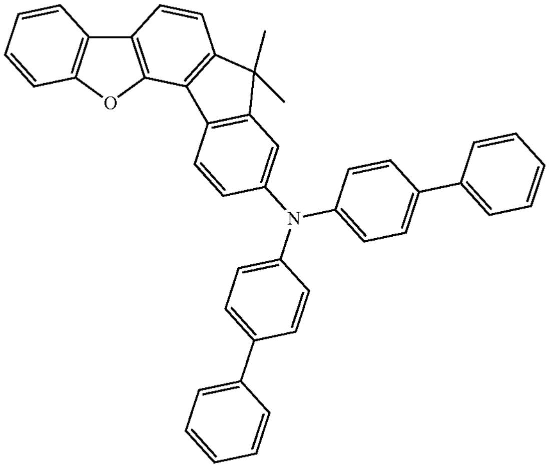
[A-52]
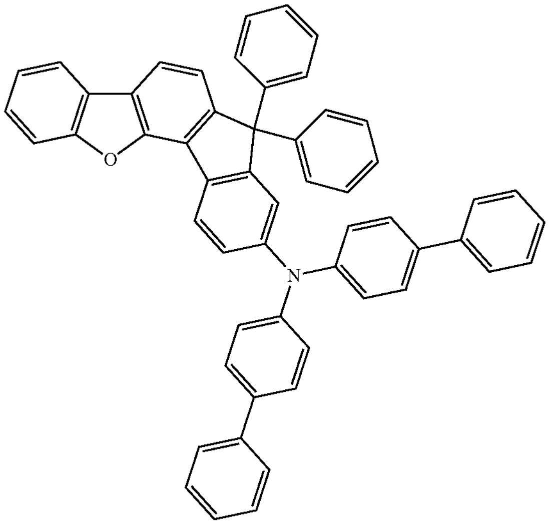
[A-53]
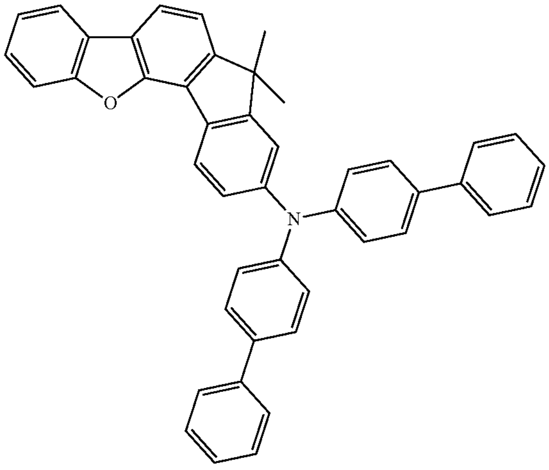
-continued
[A-54]
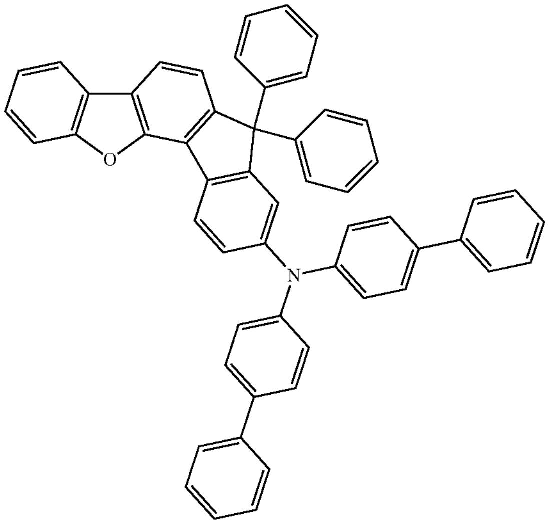
[A-55]
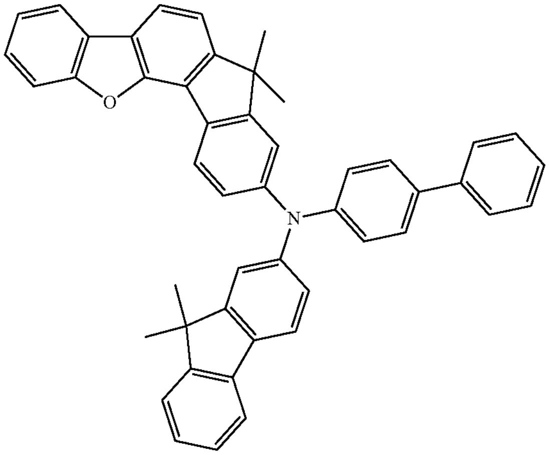
[A-56]
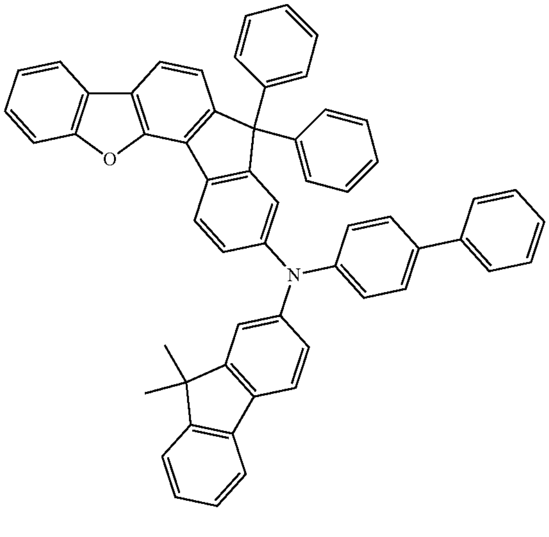

-continued
[A-57]
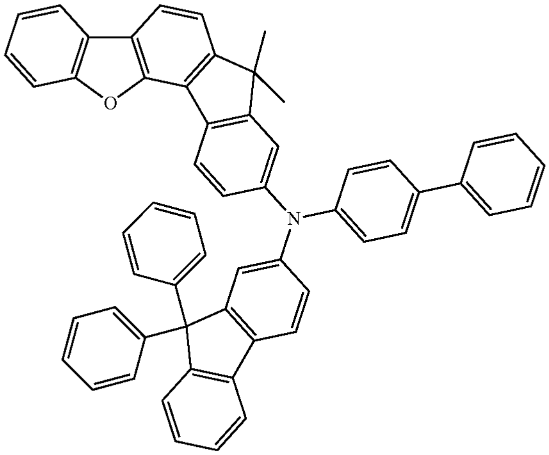
[A-58]
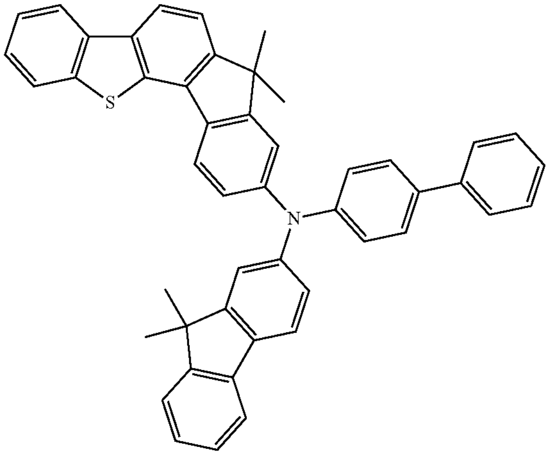
[A-59]
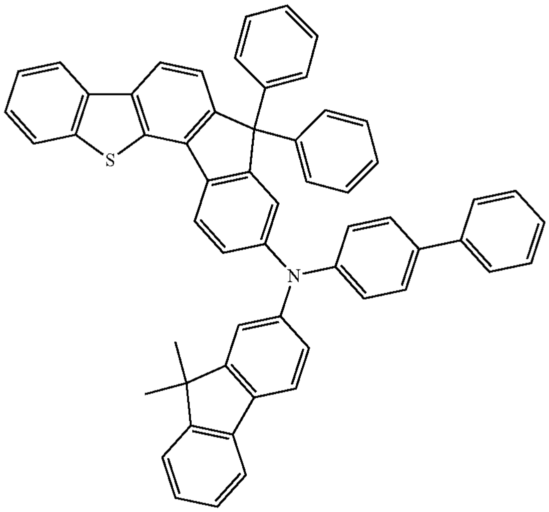
-continued
[A-60]
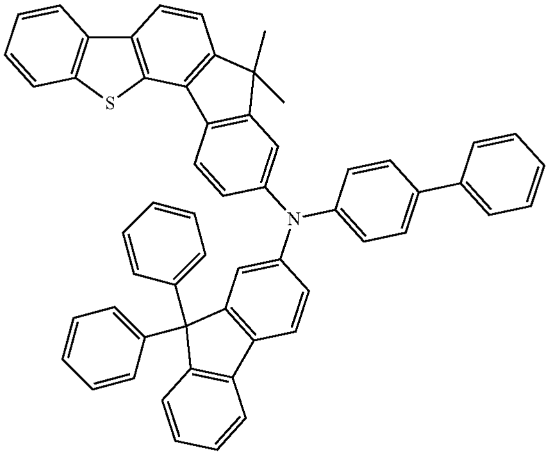
[A-61]
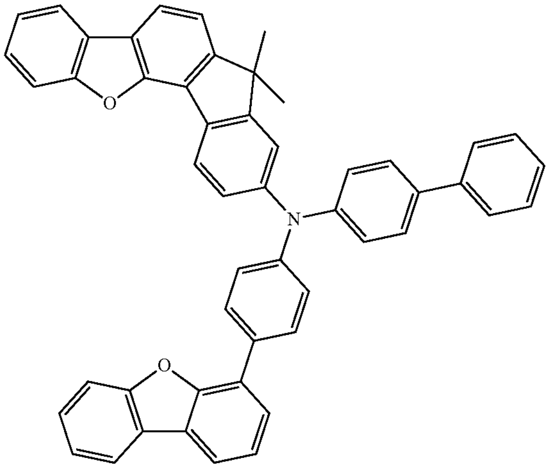
[A-62]
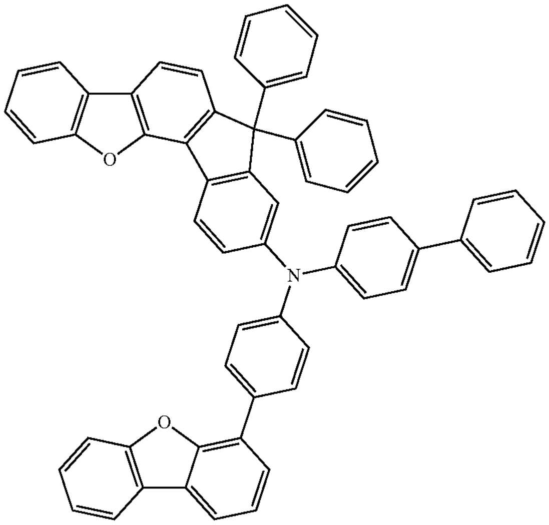

-continued
[A-63]
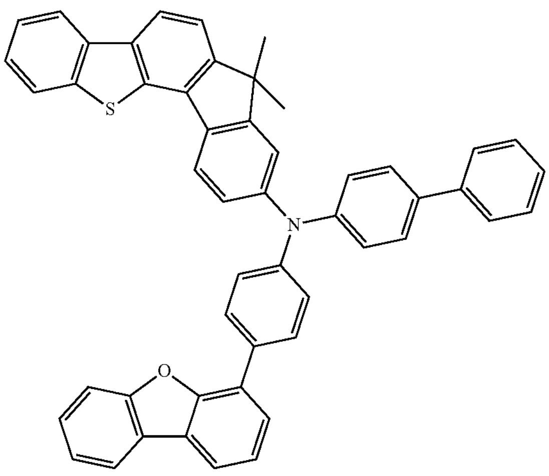
[A-64]
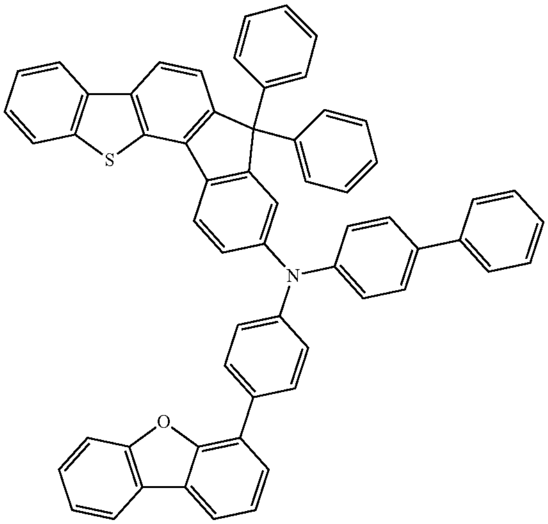
[A-65]
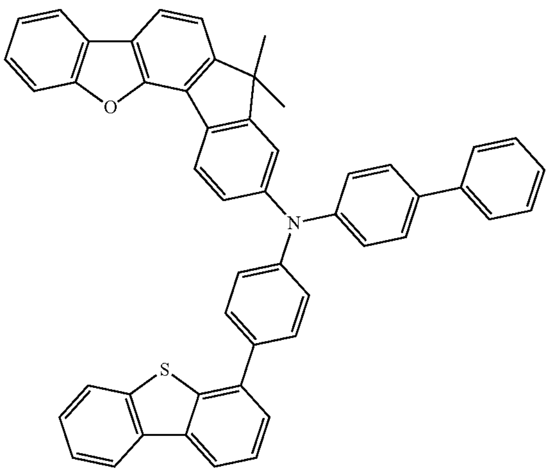
-continued
[A-66]
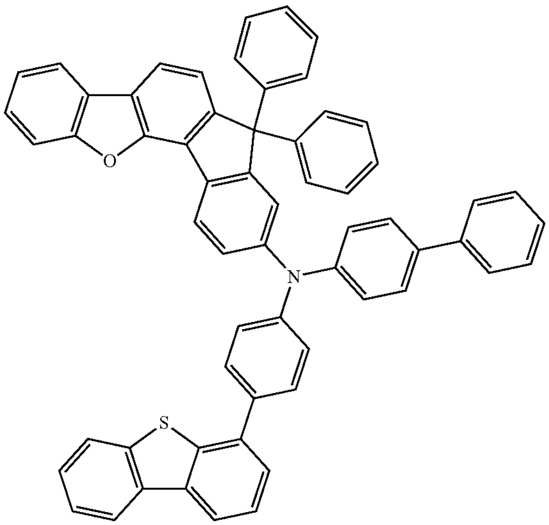
[A-67]
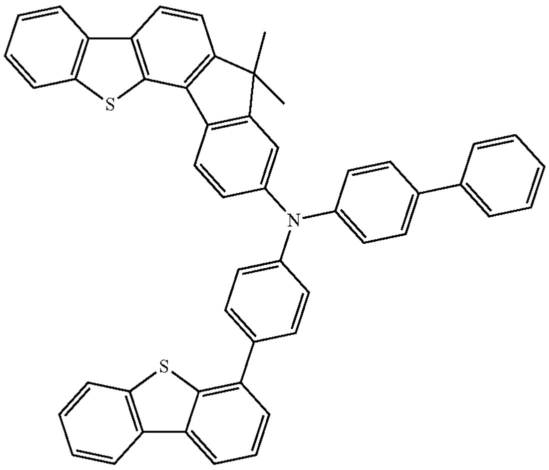
[A-68]
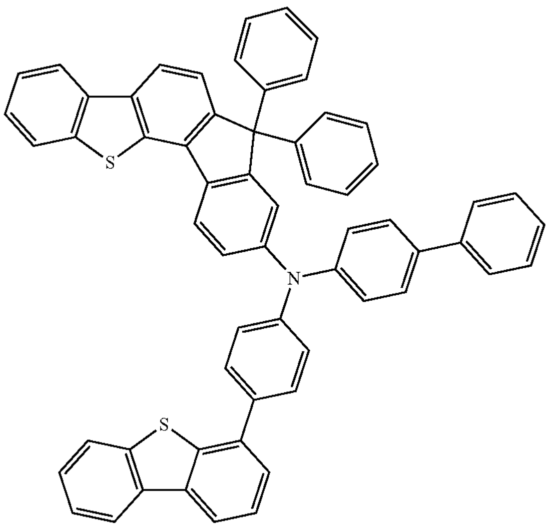

-continued
[A-69]
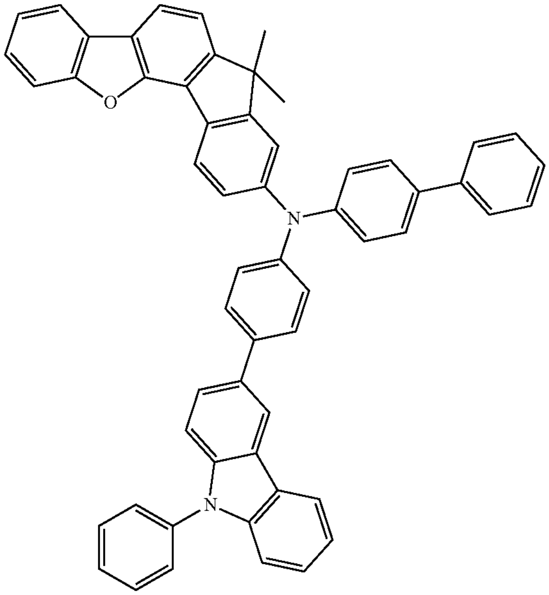
[A-70]
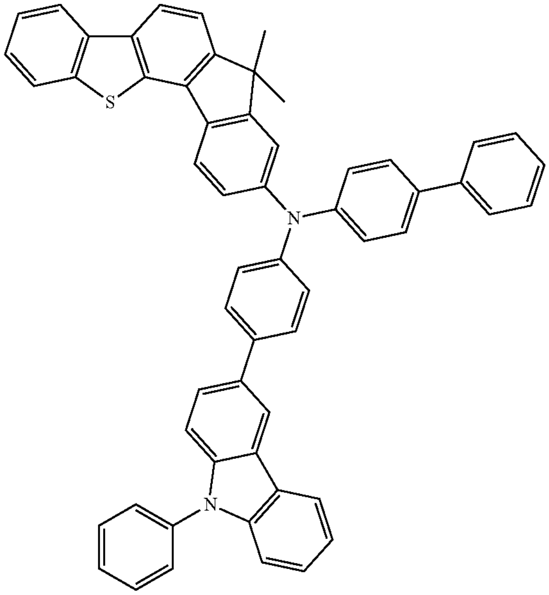
-continued
[A-71]
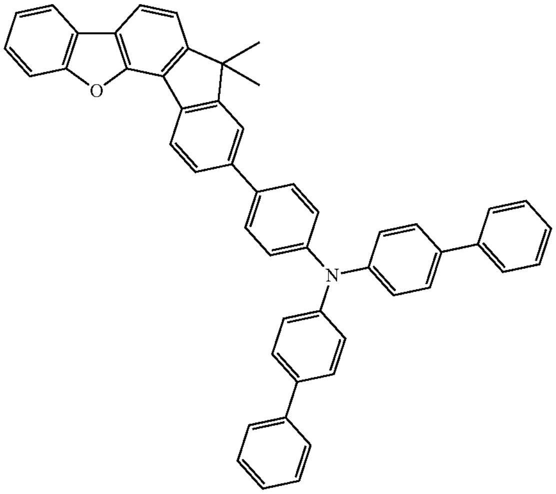
[A-72]
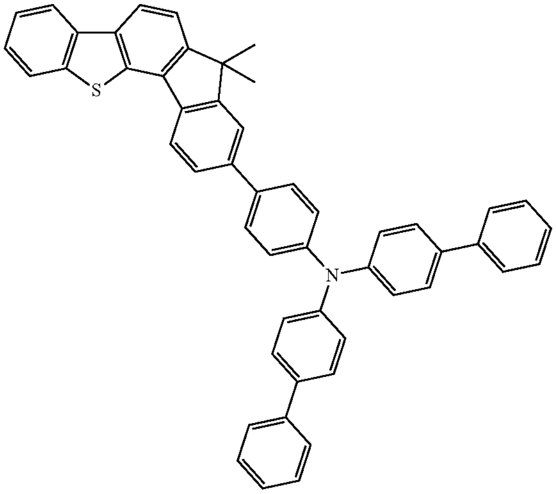
[A-73]
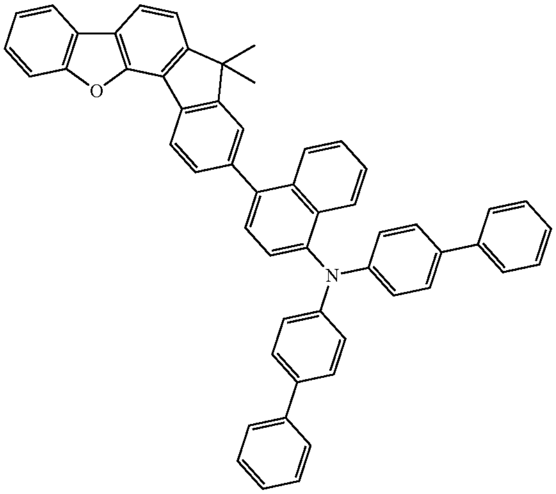

-continued
[A-74]
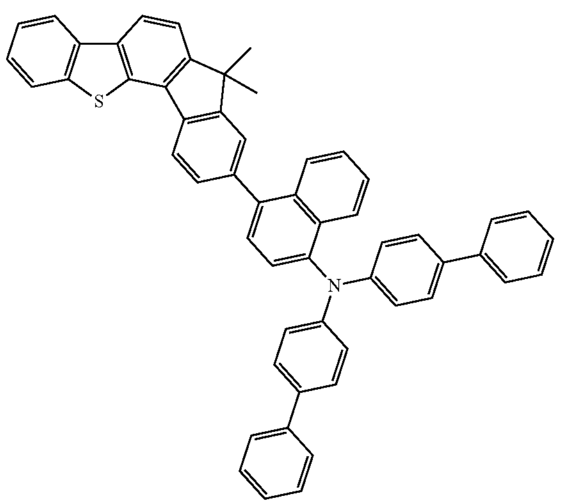
[A-75]
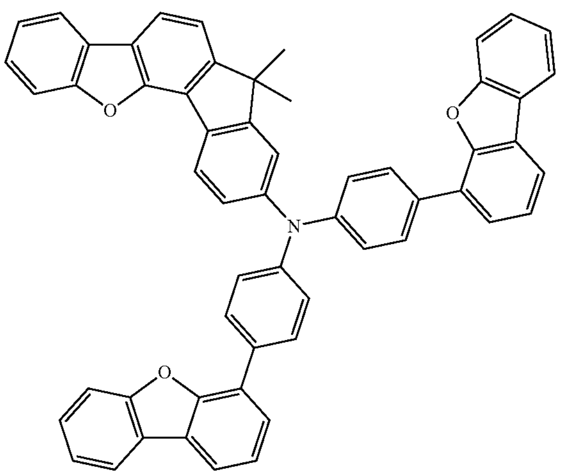
[A-76]
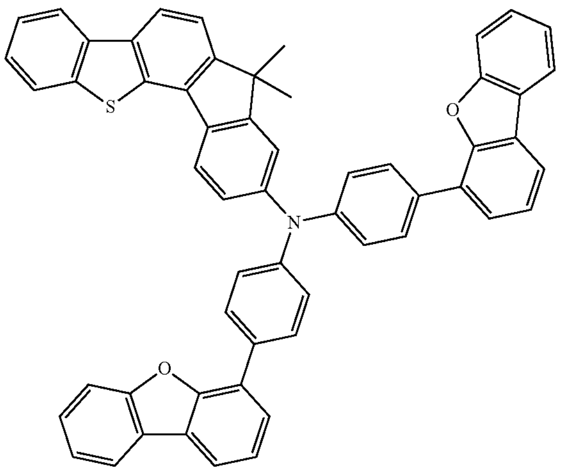
-continued
[A-77]
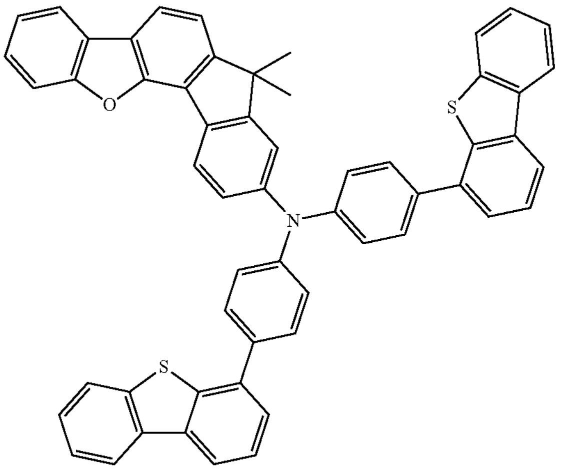
[A-78]
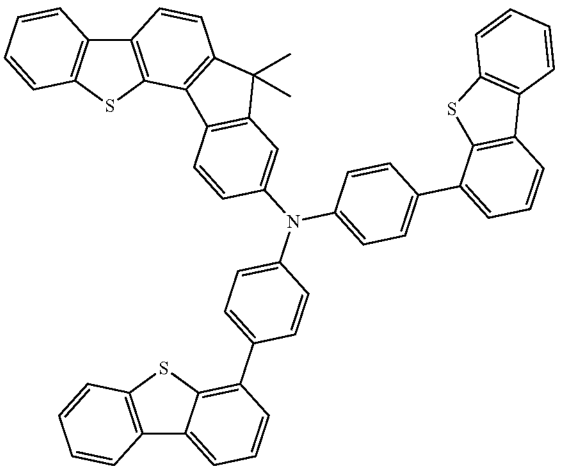
[A-79]
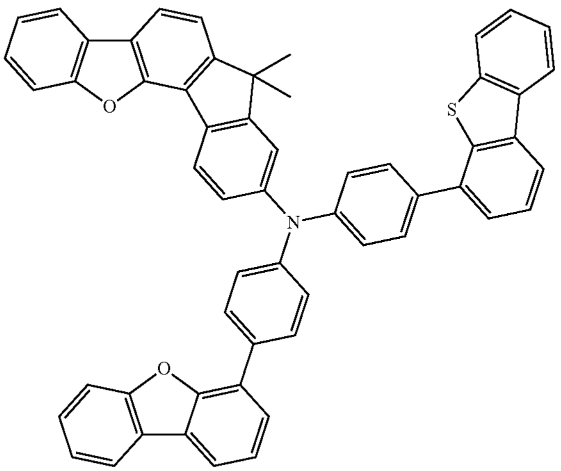

-continued
[A-80]
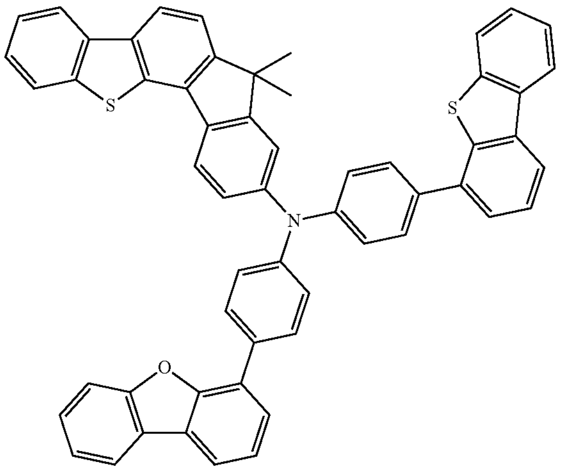
[A-81]
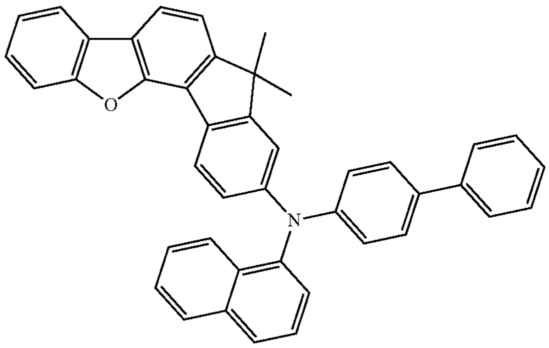
[A-82]
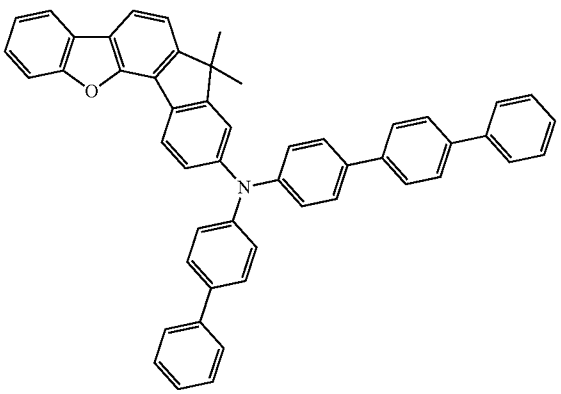
-continued
[A-83]
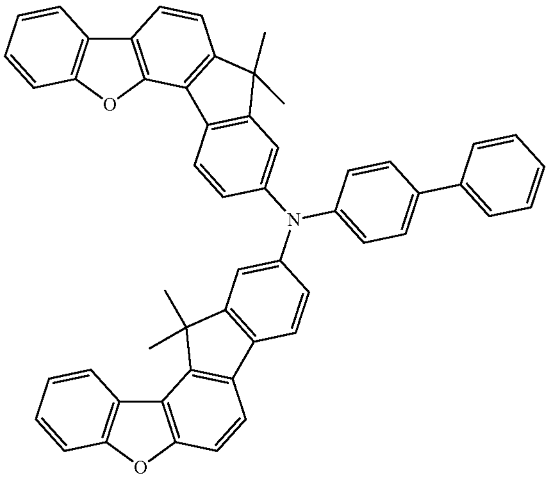
[A-84]
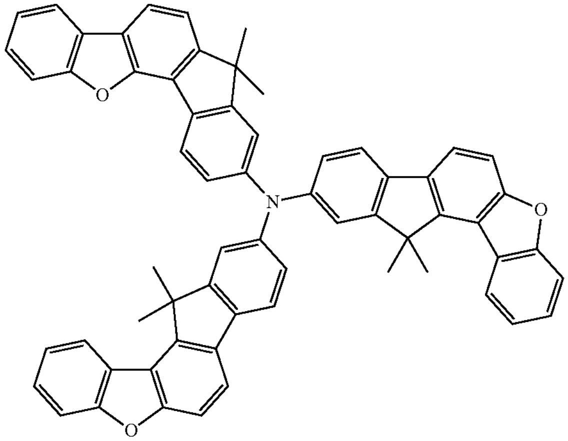
[A-85]
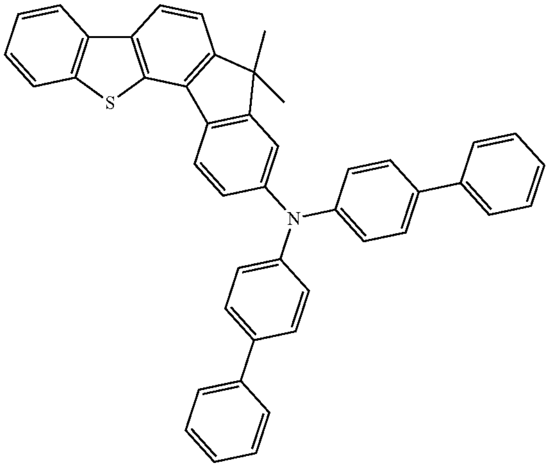

-continued
[A-86]
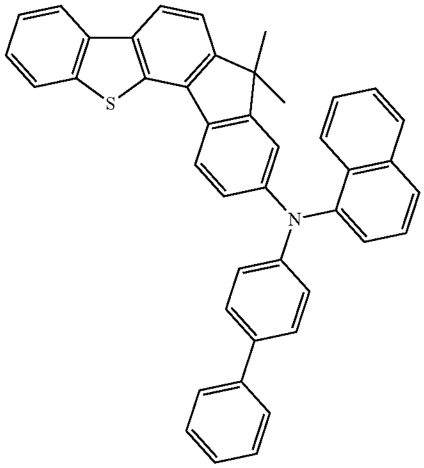
[A-87]
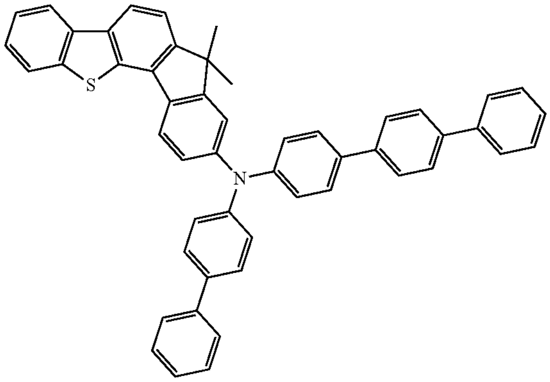
[A-88]
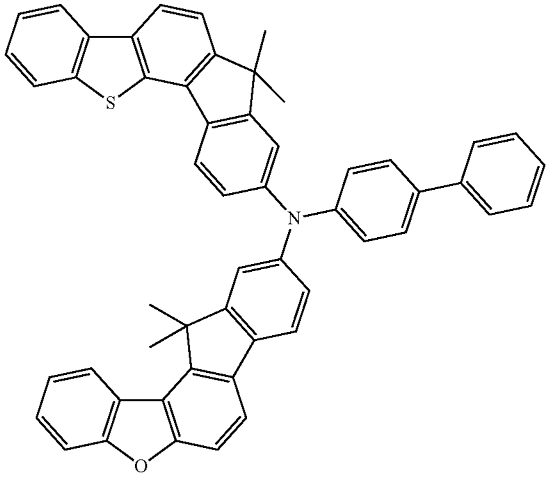
-continued
[A-89]
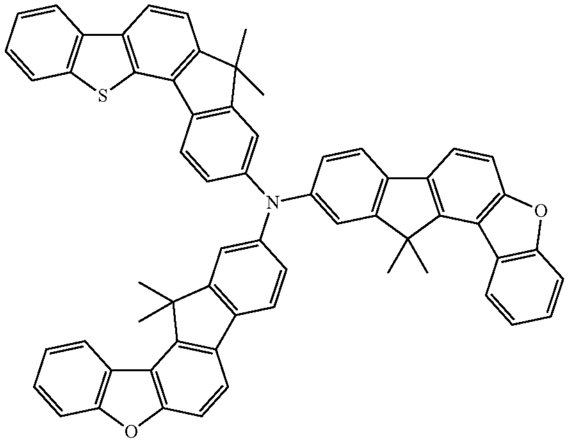
[A-90]
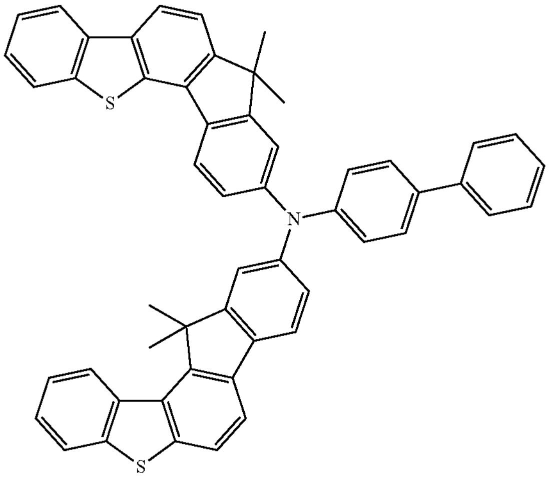
[A-91]
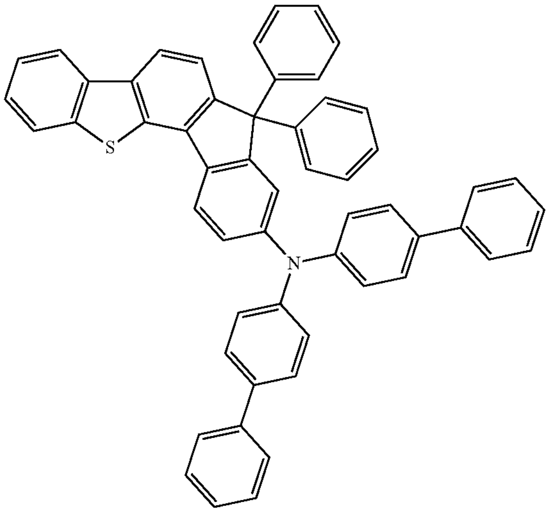

-continued
[A-92]
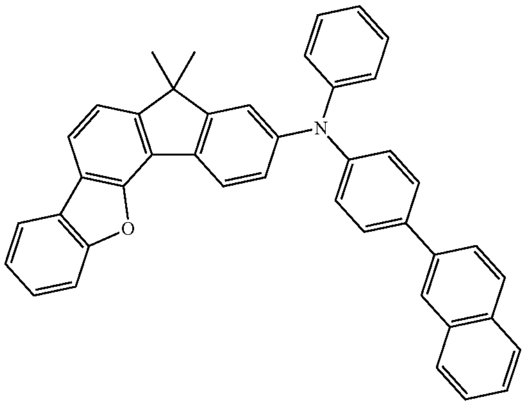
[A-93]
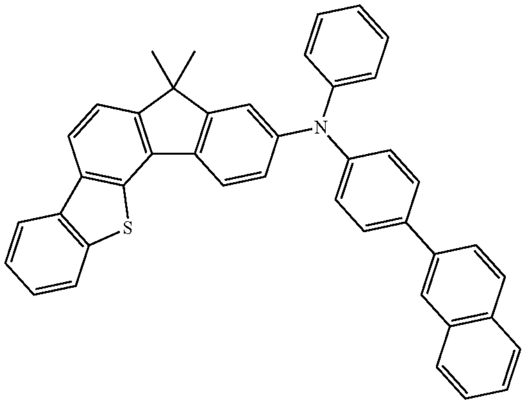
[A-94]
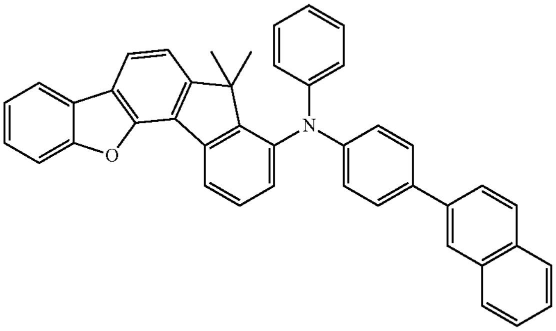
[A-95]
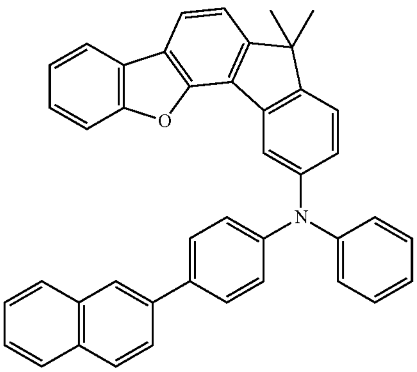
-continued
[A-96]
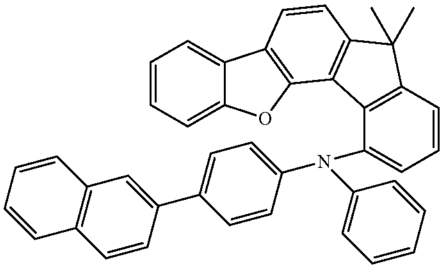
[A-97]
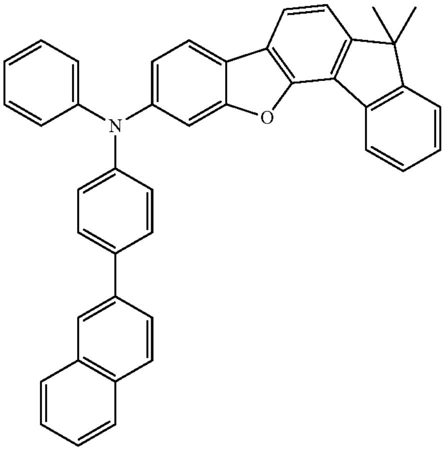
[A-98]
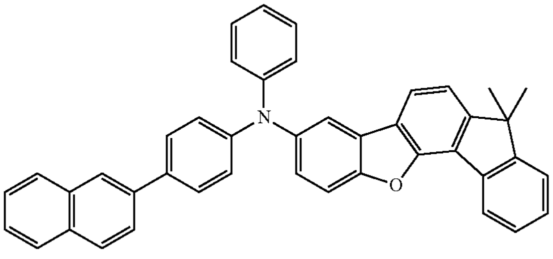
[A-99]
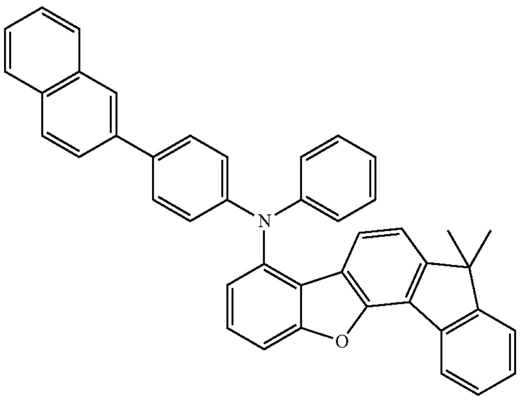

-continued
[A-100]
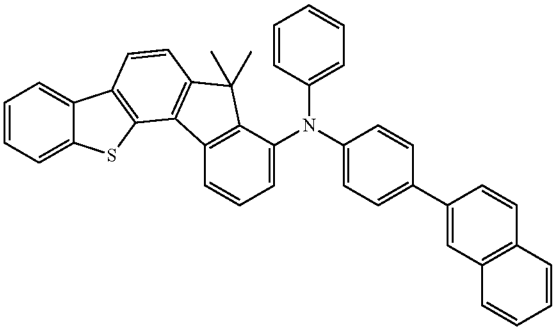
[A-101]
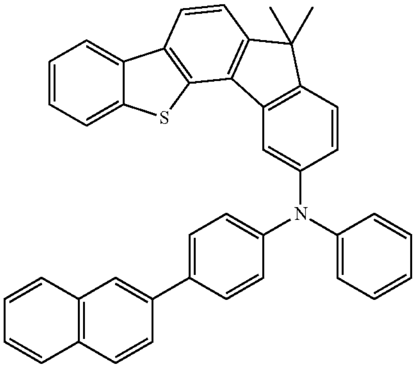
[A-102]
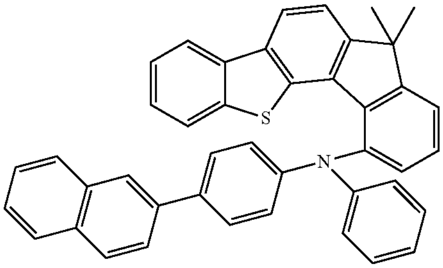
[A-103]
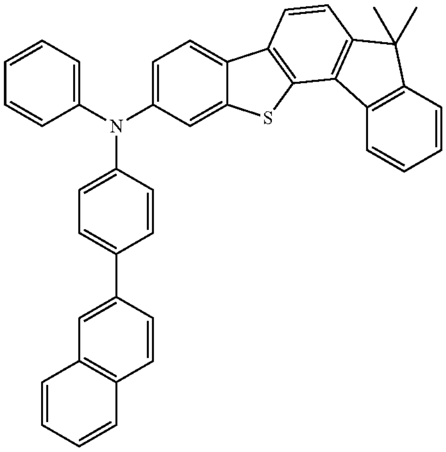
-continued
[A-104]
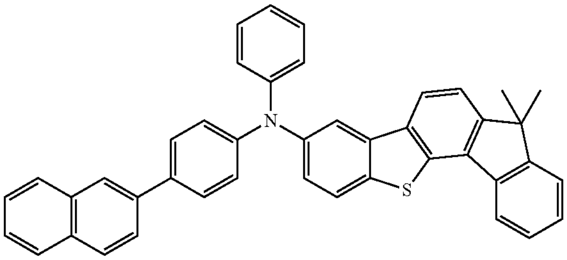
[A-105]
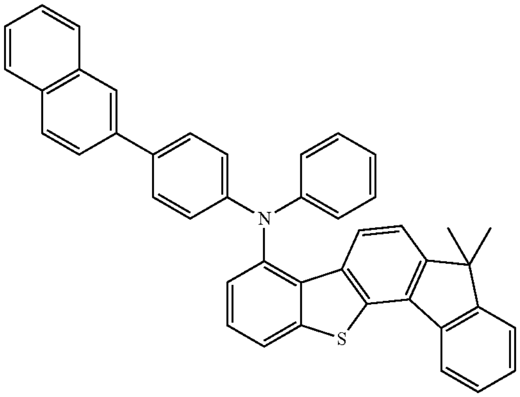
[A-106]
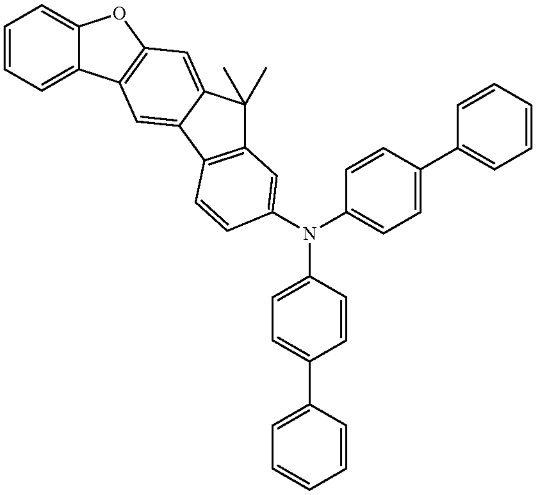

-continued
[A-107]
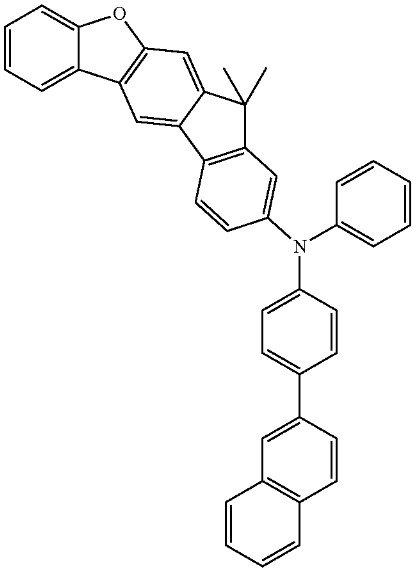
[A-108]
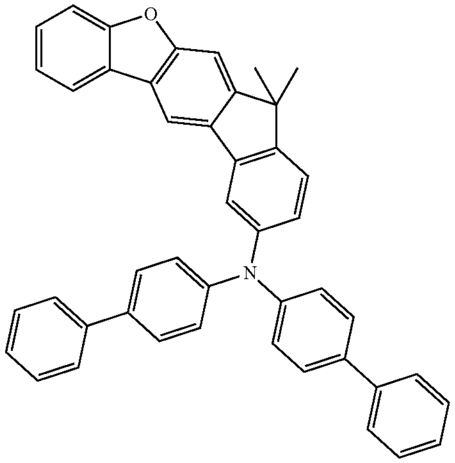
[A-109]
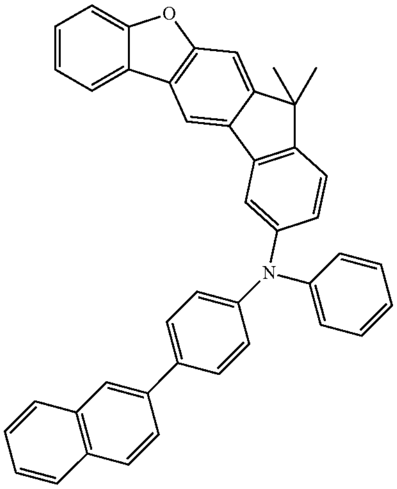
-continued
[A-110]
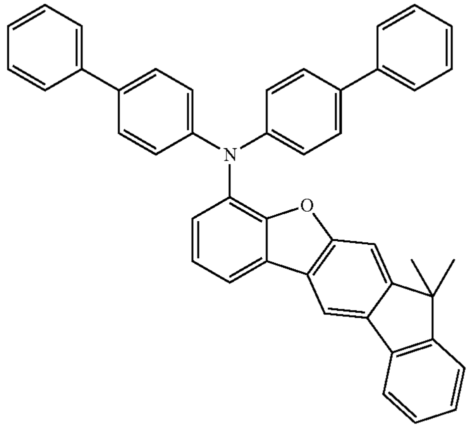
[A-111]
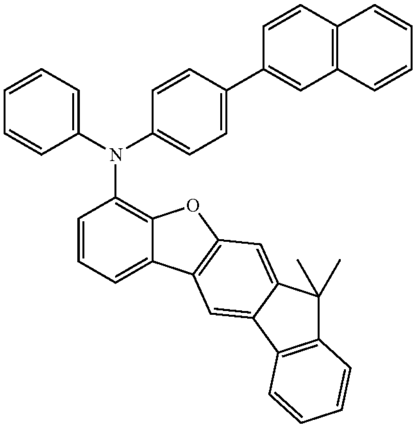
[A-112]
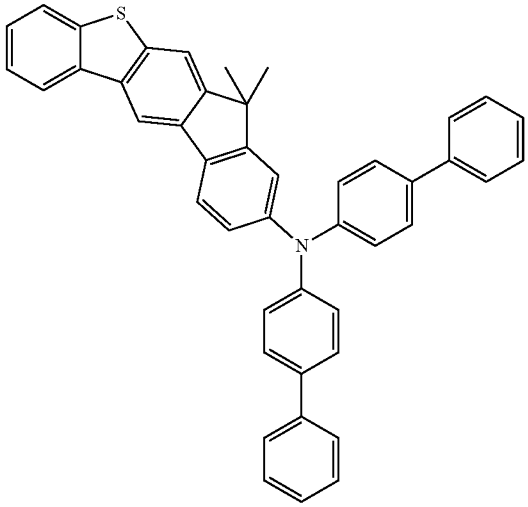

-continued
[A-113]
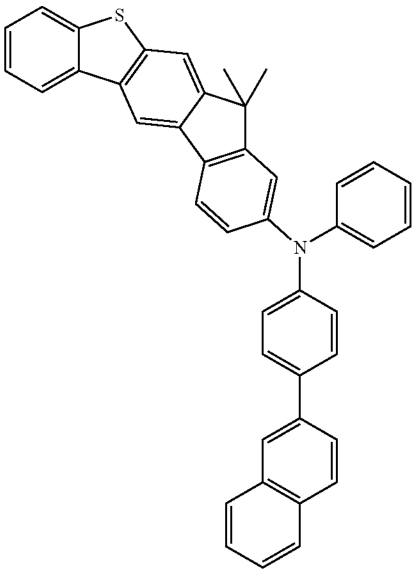
[A-114]
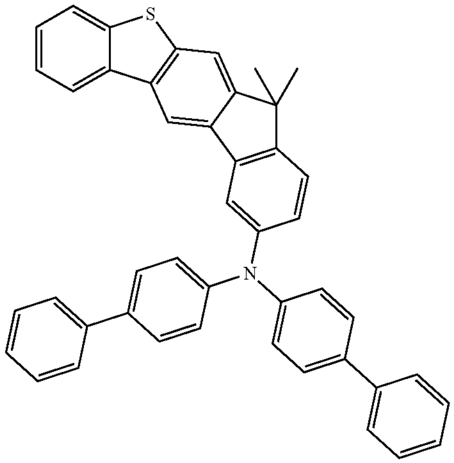
[A-115]
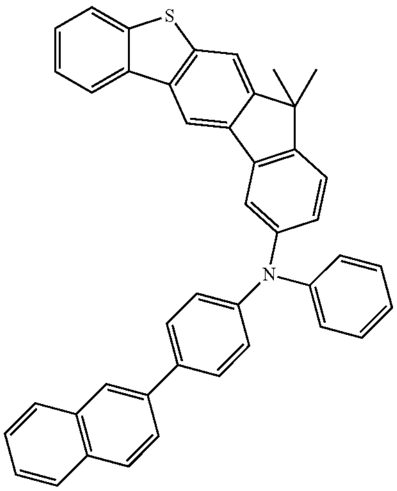
-continued
[A-116]
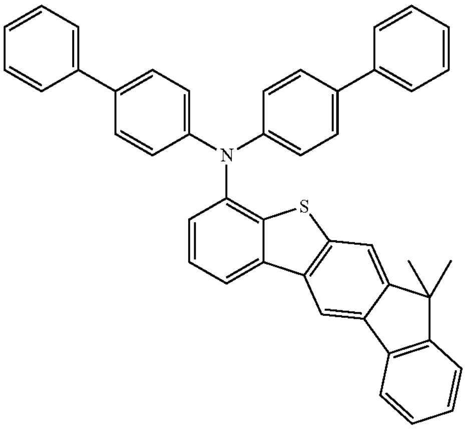
[A-117]
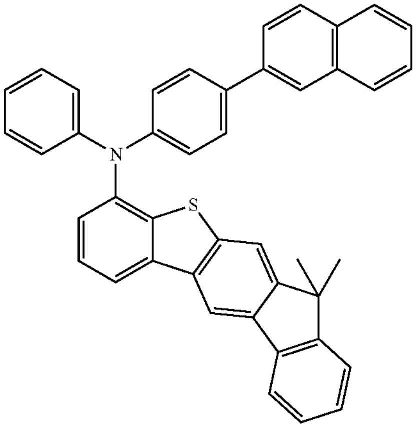
[A-118]
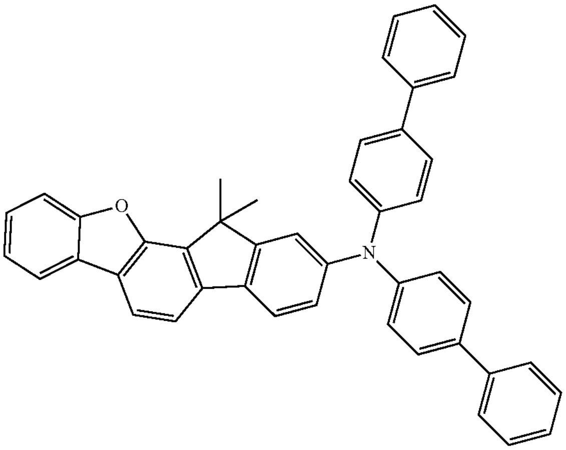

-continued
[A-119]
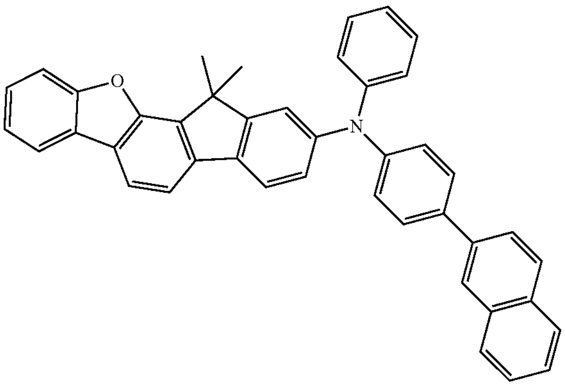
[A-120]
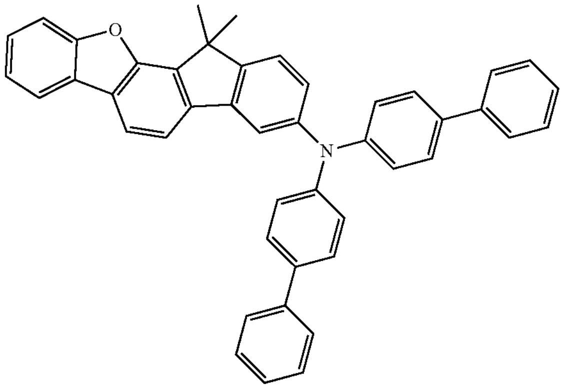
[A-121]
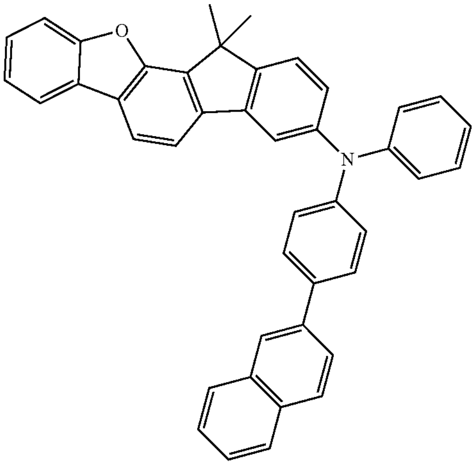
[A-122]
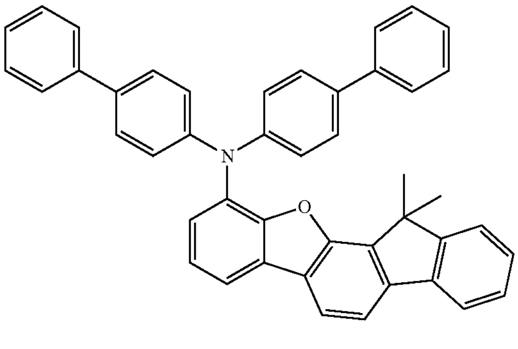
-continued
[A-123]
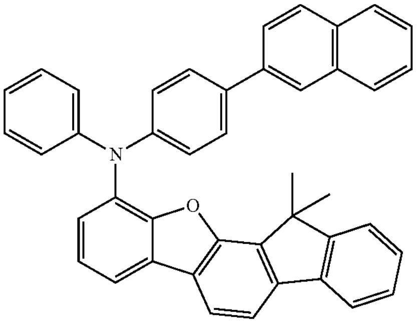
[A-124]
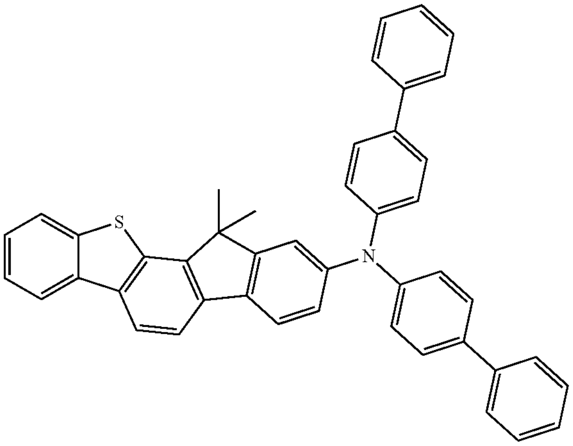
[A-125]
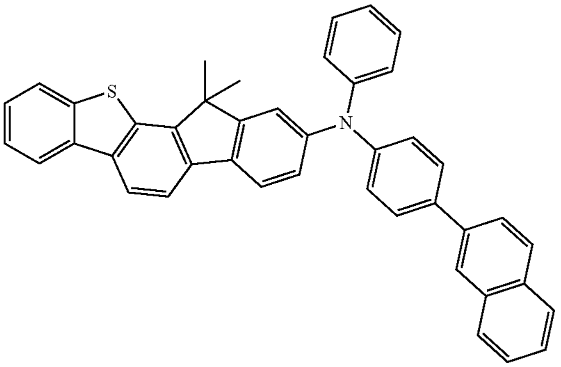
[A-126]
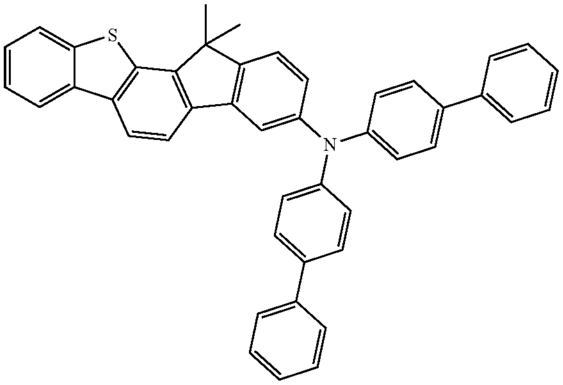

-continued
[A-127]
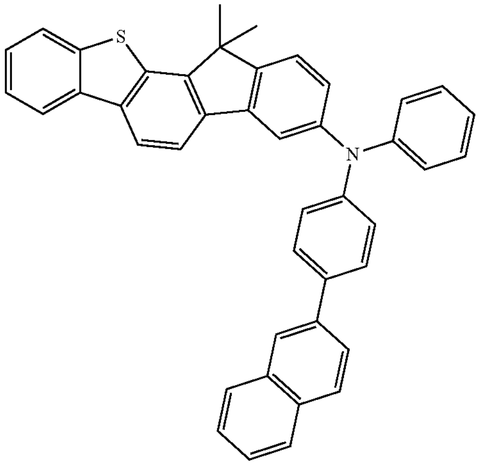
[A-128]
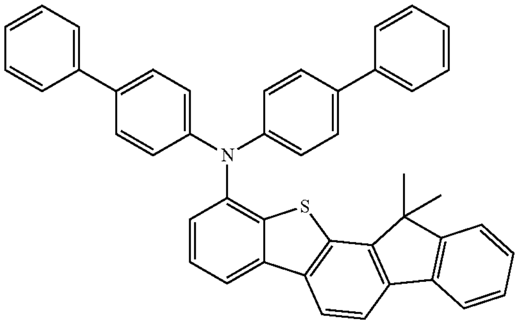
[A-129]
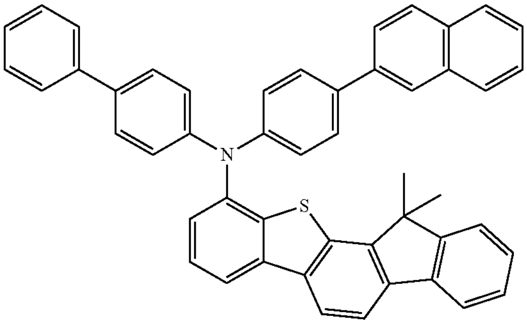
[A-130]
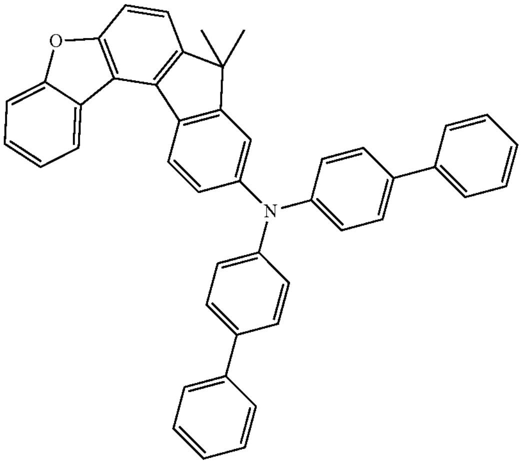
-continued
[A-131]
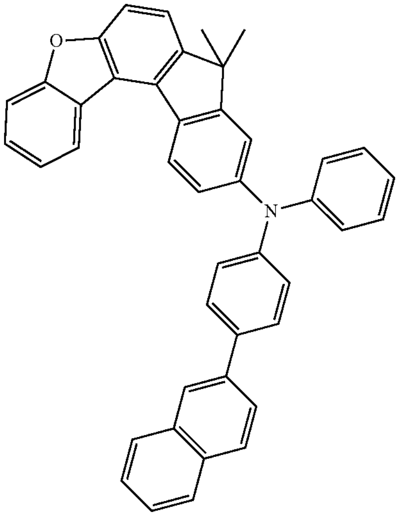
[A-132]
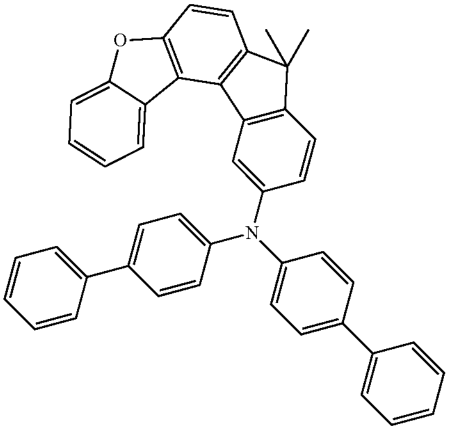
[A-133]
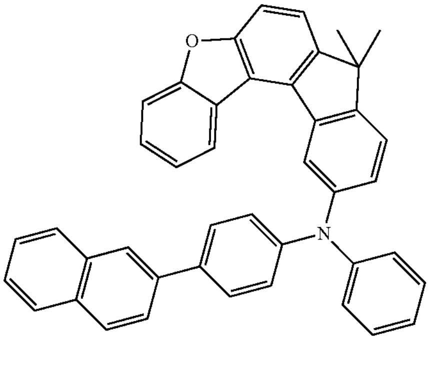

-continued
[A-134]
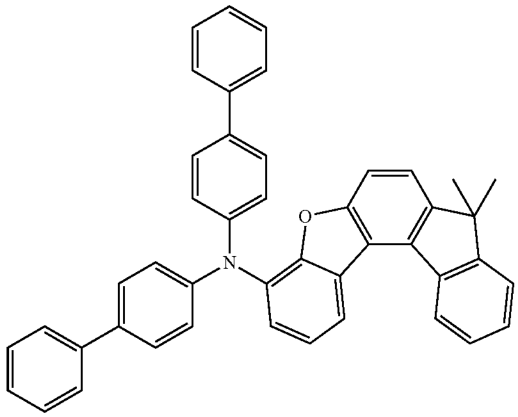
[A-135]
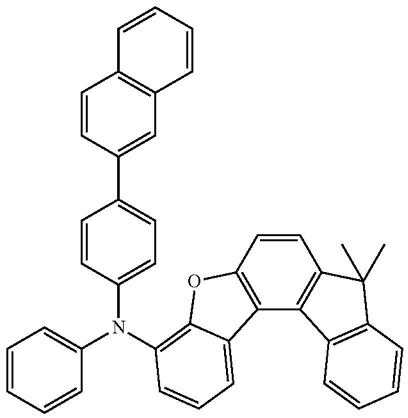
[A-136]
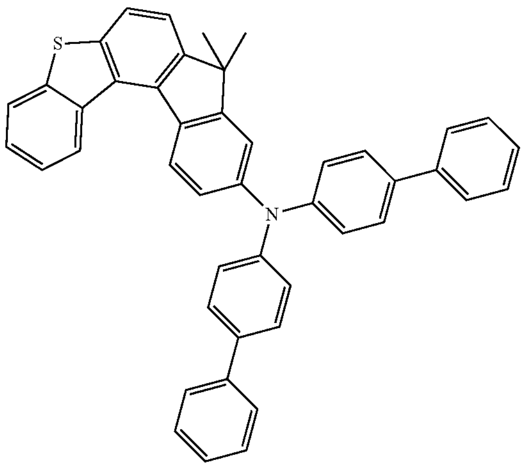
-continued
[A-137]
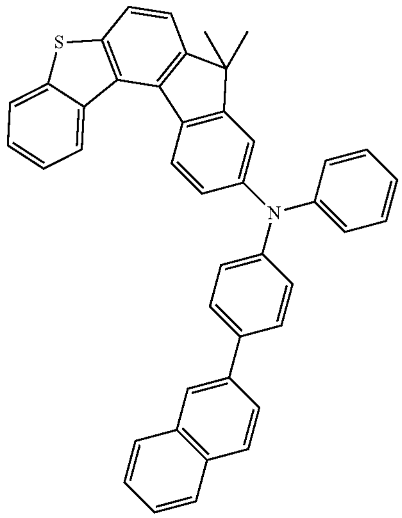
[A-138]
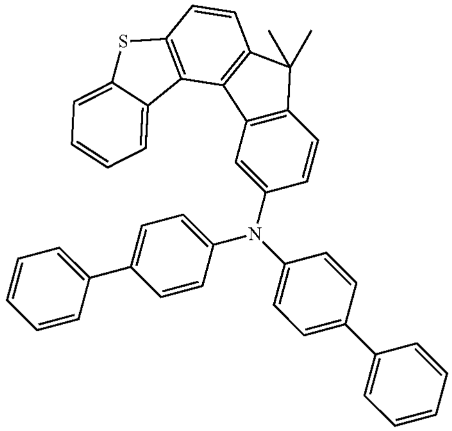
[A-139]
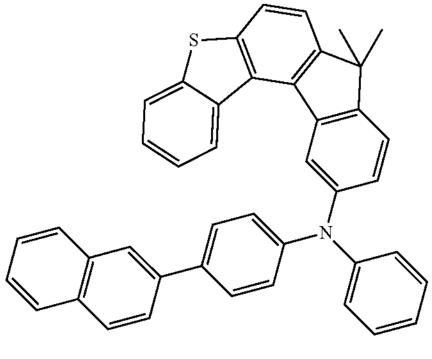

-continued
[A-140]
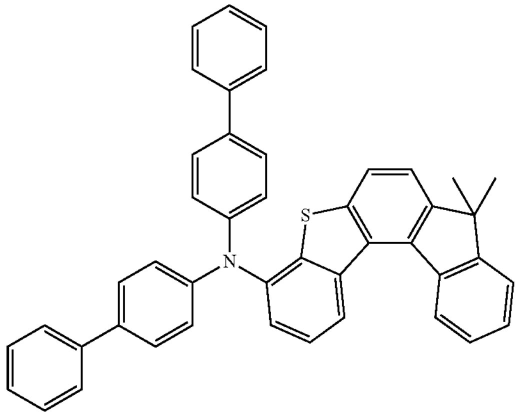
[A-141]
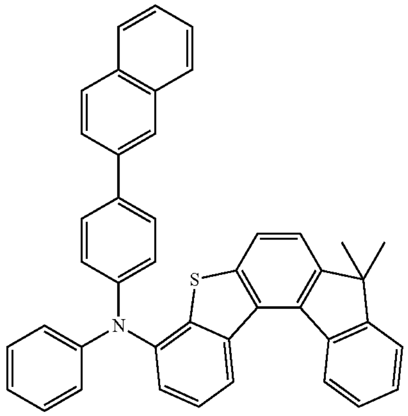
[A-142]
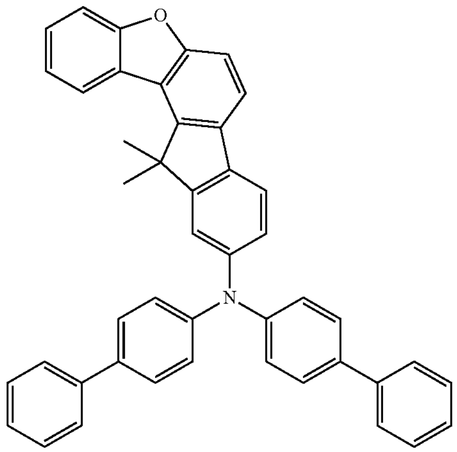
-continued
[A-143]
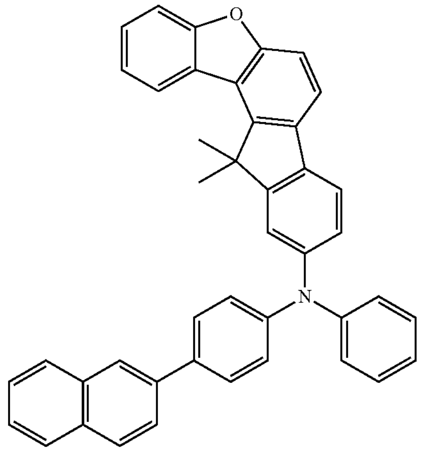
[A-144]
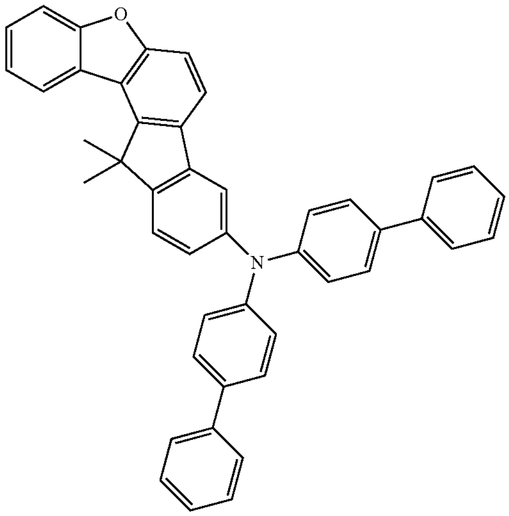
[A-145]
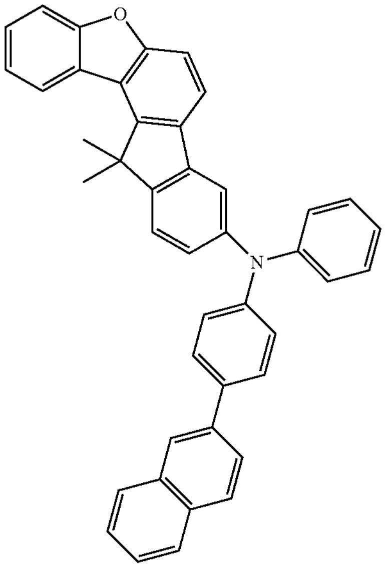

-continued
[A-146]
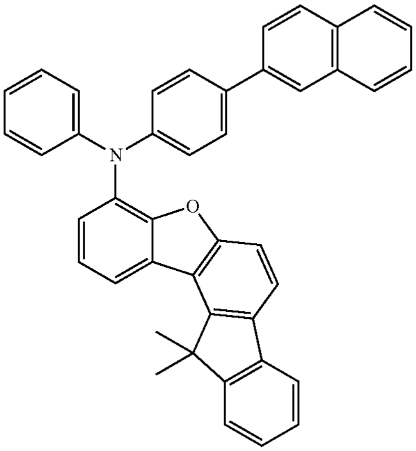
[A-147]
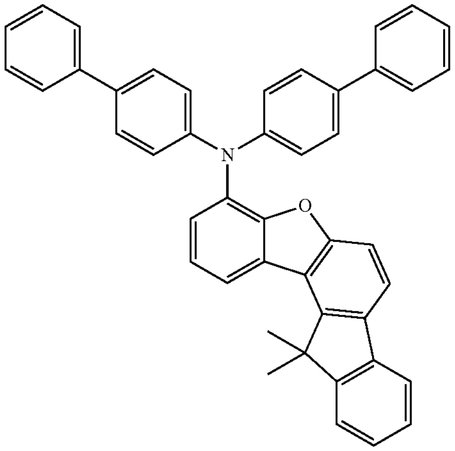
[A-148]
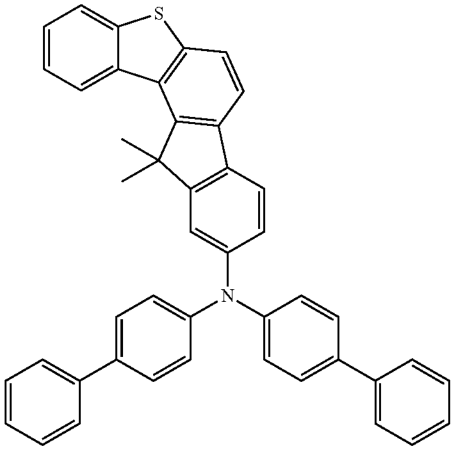
-continued
[A-149]
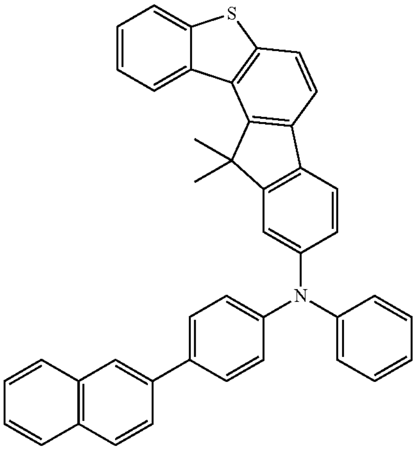
[A-150]
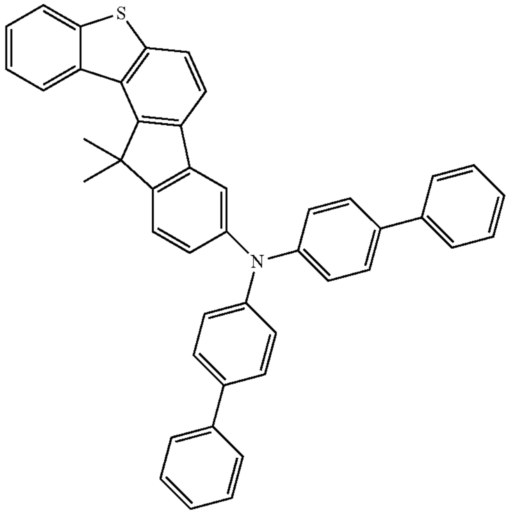
[A-151]
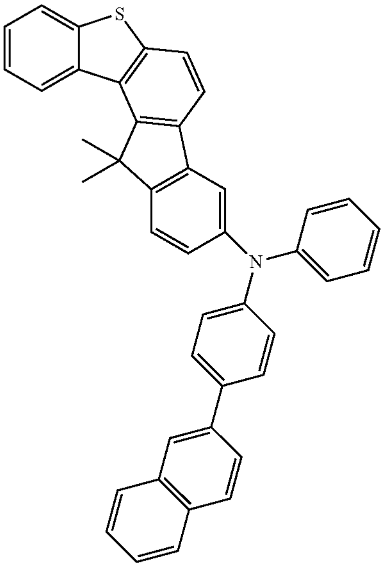

-continued
[A-152]
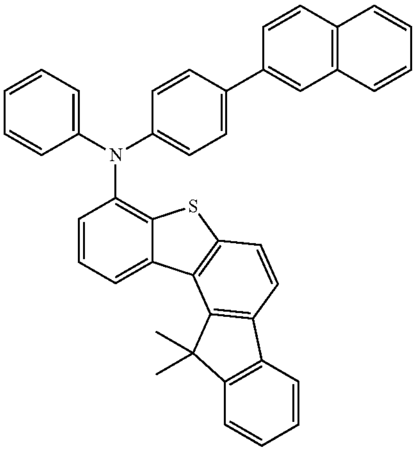
[A-153]
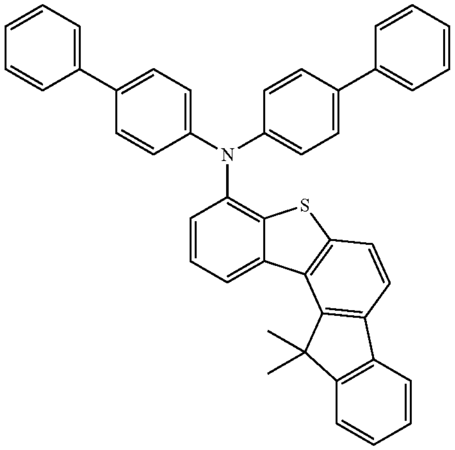
[A-154]
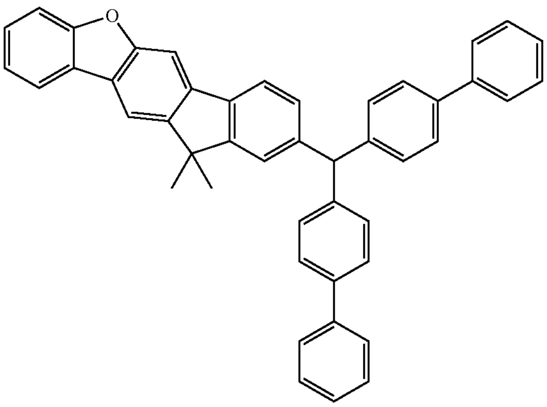
-continued
[A-155]
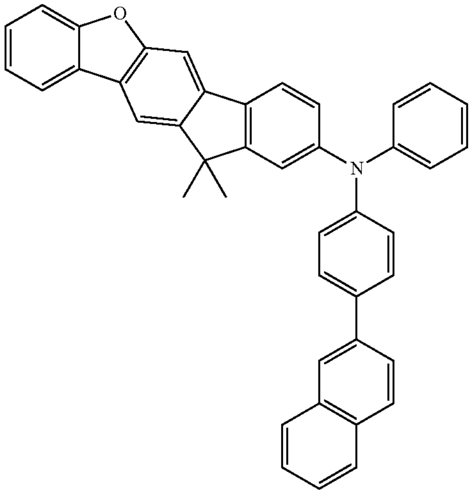
[A-156]
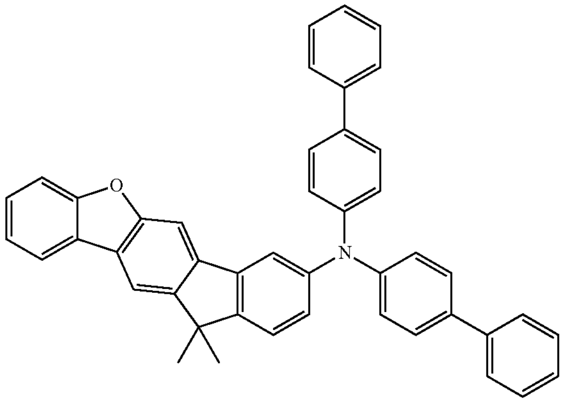
[A-157]
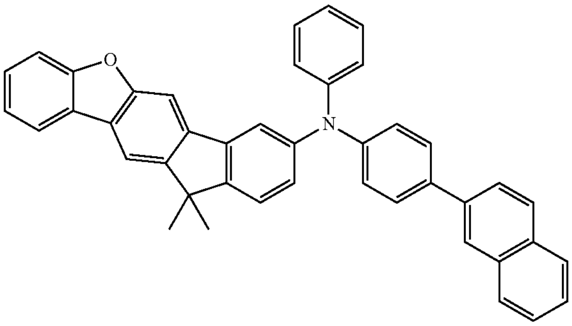

-continued
[A-158]
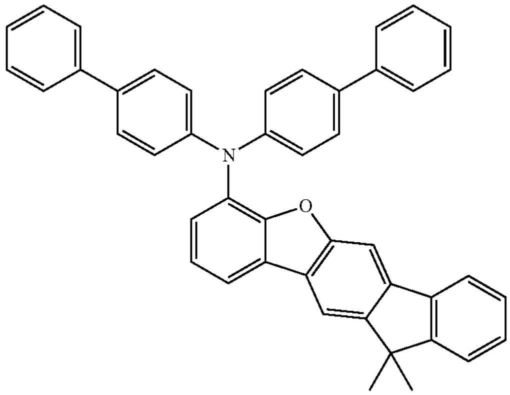
[A-159]
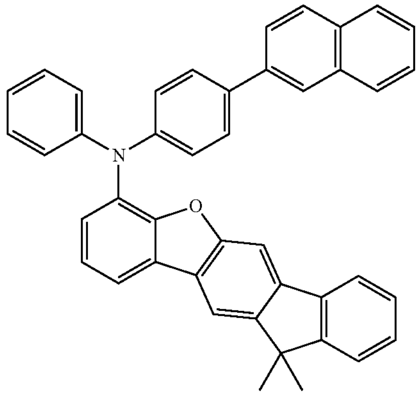
[A-160]
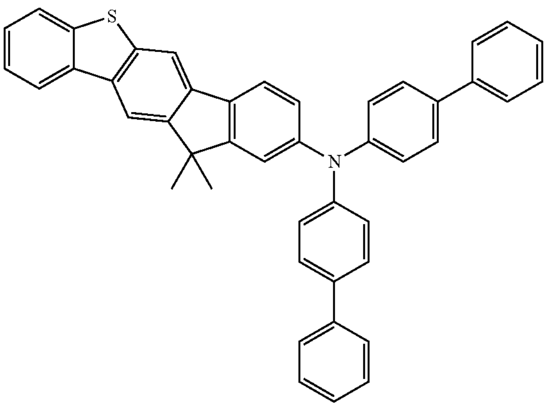
-continued
[A-161]
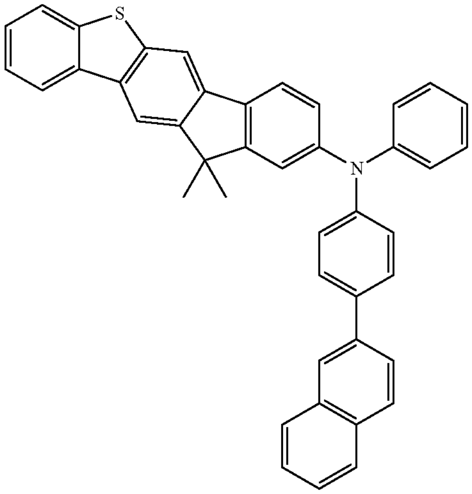
[A-162]
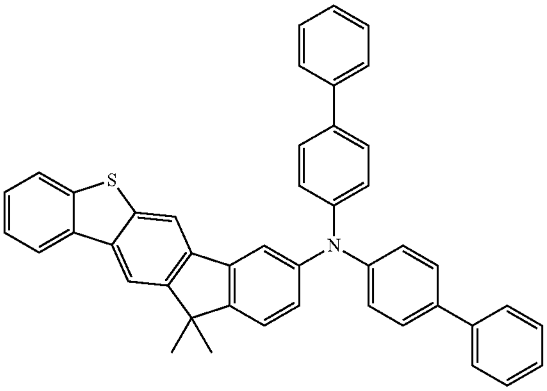

-continued

[A-163]

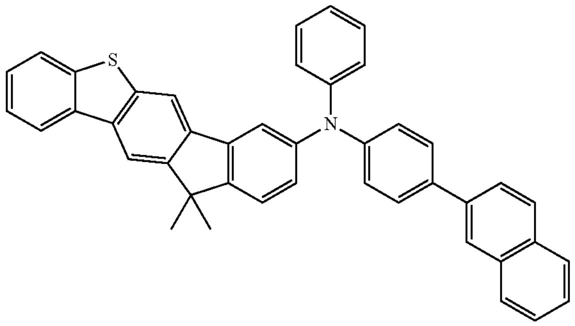

[A-164]

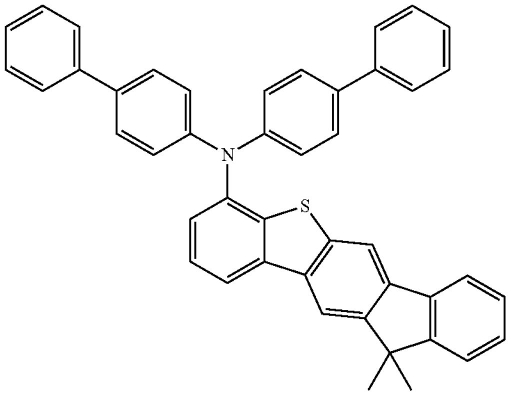

-continued

[A-165]

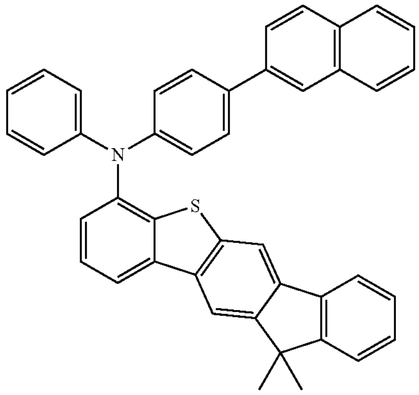

.

12. An organic optoelectronic device, comprising:

an anode and a cathode facing each other, and at least one organic layer between the anode and the cathode, wherein:

the at least one organic layer includes a light emitting layer, and the light emitting layer includes the composition for an organic optoelectronic device as claimed in claim 1.

13. The organic optoelectronic device as claimed in claim 12, wherein the composition for an organic optoelectronic device is a host of the light emitting layer.

14. The organic optoelectronic device as claimed in claim 13, wherein the composition for an organic optoelectronic device includes the first compound and the second compound in a weight ratio of about 70:30 to about 30:70.

15. A display device comprising the organic optoelectronic device as claimed in claim 12.

* * * * *